(12) United States Patent
Yu et al.

(10) Patent No.: US 6,506,738 B1
(45) Date of Patent: Jan. 14, 2003

(54) BENZIMIDAZOLONE ANTIVIRAL AGENTS

(75) Inventors: Kuo-Long Yu, Zionsville, IN (US); Rita Civiello, Killingworth, CT (US); Keith Combrink, Wallingford, CT (US); Hatice Belgin Gulgeze, Middletown, CT (US); Bradley C. Pearce, East Hampton, CT (US); Xiangdong Wang, Guilford, CT (US); Nicholas A. Meanwell, East Hampton, CT (US); Yi Zhang, Evansville, IN (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/952,736

(22) Filed: Sep. 14, 2001

Related U.S. Application Data

(60) Provisional application No. 60/235,804, filed on Sep. 27, 2000.

(51) Int. Cl.[7] .................... C07D 401/14; C07D 403/06; C07D 403/14; A61K 31/4184; A61K 31/443
(52) U.S. Cl. .................... 514/80; 514/254.06; 514/269; 514/322; 514/363; 514/364; 514/370; 514/381; 514/387; 544/139; 544/310; 544/370; 546/199; 546/273.7; 548/113; 548/139; 548/132; 548/181; 548/250; 548/350.7
(58) Field of Search ................ 544/139, 310, 544/370; 546/199, 273.7; 548/113, 139, 132, 181, 250, 305.7; 514/80, 254.06, 269, 322, 363, 364, 370, 381, 387

(56) References Cited

U.S. PATENT DOCUMENTS

| | | | |
|---|---|---|---|
| 3,394,141 A | 7/1968 | Sparatore | 260/294.7 |
| 4,324,794 A | 4/1982 | Tidwell et al. | 424/273 |
| 5,256,668 A | 10/1993 | Hsu et al. | 514/269 |

FOREIGN PATENT DOCUMENTS

| | | |
|---|---|---|
| EP | 058146 A1 | 8/1982 |
| WO | WO 00/04900 | 2/2000 |
| WO | WO 00/38508 | 7/2000 |
| WO | WO 01/00611 | 1/2001 |
| WO | WO 01/00612 | 1/2001 |
| WO | WO 01/00615 | 1/2001 |

OTHER PUBLICATIONS

E. J. Dubovi, et al, Antimicrobial Agents and Chemotherapy, 19(4), pp. 649–656, 1981.
P. R. Wyde, et al, Antiviral Research, 38, pp. 31–42, 1998.
F. Pagani, et al, Boll. Chim. Farm., 104, pp. 427, 1965.
G. Paglietti, et al, IL. Farmaco–Ed. Sc., 30, pp. 505–511, 1975.
S. Shigeta, et al, Antiviral Chemistry & Chemotherapy, 3(3), pp. 171–177, 1992.
W. R. Roderick, et al, J. Med. Chem., 15(6), pp. 655–658, 1972.
B. Cakir, et al, Gazi Eczacilik Fak. Der., 5(1), pp. 71–77, 1988.
H. R. Howard, et al, Eur. J. Med. Chem., 27, pp. 779–789, 1992.
F. Sparatore, et al, IL Farmaco Ed. Sci., 33, pp. 901–923, 1978.
N. A. Meanwell, et al, "Regiospecific Functionalization of 1,3–Dihydro–2H–benzimidazol–2–one and Structurally Related Cyclic Urea Derivatives," Journal of Organic Chemistry, 60(6), pp. 1565–1582, 1995.

*Primary Examiner*—Deepak R. Rao
(74) *Attorney, Agent, or Firm*—Samuel J. DuBoff

(57) ABSTRACT

The present invention concerns antiviral compounds, their compositions, and use in the treatment of viral infections. More particularly, the invention provides benzimidazolone derivatives for the treatment of respiratory syncytial virus infection.

10 Claims, No Drawings

BENZIMIDAZOLONE ANTIVIRAL AGENTS

CROSS REFERENCE TO RELATED APPLICATION

This application claims the benefit of U.S. Provisional Application Ser. No. 60/235,804 filed on Sep. 27, 2000.

BACKGROUND OF THE INVENTION

1. Field of the Invention

The present invention concerns antiviral compounds, their methods of preparation and their compositions, and use in the treatment of viral infections. More particularly, the invention provides benzimidazolone derivatives for the treatment of respiratory syncytial virus infection.

2. Background Art

Respiratory syncytial virus (RSV) is the leading cause of serious lower respiratory tract infection in infants, children, elderly and immunocompromised persons. Severe infection of the virus may result in bronchiolitis or pneumonia which may require hospitalization or result in death. (*JAMA*, 1997, 277, 12). Currently only Ribavirin is approved for the treatment of this viral infection. Ribavirin is a nucleoside analogue which is administered intranasally as an aerosol. The agent is quite toxic, and its efficacy has remained controversial. RespiGam, approved for prophylaxis in high risk pediatric patients, is an intravenous immunoglobulin which effectively neutralizes the virus. Recently, Synagis, a monoclonal antibody administered through intramuscular injection has also been approved for use in high risk pediatric patients. However, both drugs are very expensive. Accordingly, inexpensive, safe and effective antiviral agents against respiratory syncytial virus will be beneficial for patients.

Many agents are known to inhibit respiratory syncytial virus (De Clercq, Int. *J Antiviral Agents*, 1996, 7, 193). Y. Tao et al. (EP 0 058 146 A1, 1998) disclosed that Ceterizine, a known antihistamine, exhibited anti-RSV activity. Tidwell et al., *J. Med Chem.* 1983, 26, 294 (U.S. Pat. No. 4,324,794, 1982), and Dubovi et al., *Antimicrobial Agents and Chemotherapy*, 1981, 19, 649, reported a series of amidino compounds with the formula shown below as inhibitors of RSV.

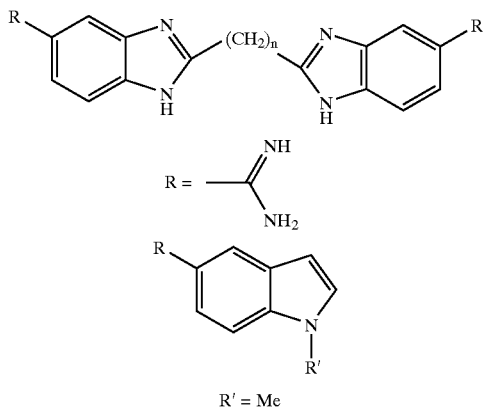

Hsu et al., U.S. Pat. No. 5,256,668 (1993) also disclosed a series of 6-aminopyrimidones that possess anti-viral activity against RSV.

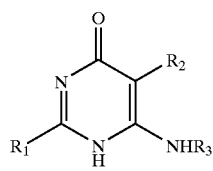

Y. Gluzman, et al., (AU Patent, Au-A-14,704, 1997) and P. R. Wyde et al. (*Antiviral Res.* 1998, 38, 31) disclosed a series of triazine containing compounds that were useful for the treatment and/or prevention of RSV infection.

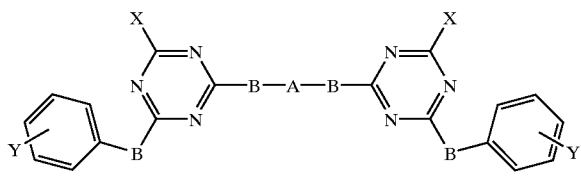

In addition, T. Nitz, et al., (WO Patent, WO 00/38508, 1999) disclosed a series of triaryl containing compounds that were useful for the treatment and/or prevention of RSV and related pneumoviral infections.

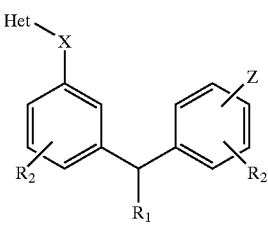

A related series of compounds were first disclosed by F. Pagani and F. Sparatore in *Boll Chim Farm.* 1965, 104, 427 and by G. Paglietti, et al. in *Il Farmaco, Ed. Sci.* 1975, 30, 505, and found to possess analgesic and anti-arrhythmic activity. The structural formula for these compounds are depicted in Formula Ia and Ib.

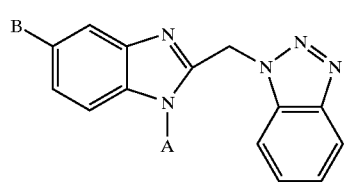
Formula Ia

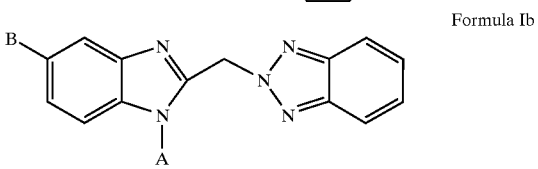
Formula Ib

In Formula Ia and Ib, A is —(CH$_2$)n-N(R)$_2$, n=2 or 3, R=Me or Et,

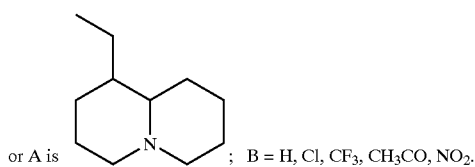

or A is [structure]; B = H, Cl, CF₃, CH₃CO, NO₂.

Another series of closely related compounds that Sparatore had disclosed were in *Il Farmaco Ed. Sci.* 1967, 23, 344 (U.S. Pat. No 3,394, 141, 1968). Some of the compounds were reported to have analgesic, anti-inflammatory or antipyretic activities. The structure of these compounds is depicted in formula Ic. In Formula Ic, C=H, CF$_3$, or N$_2$. D is —(CH$_2$)n-NR$_2$, n=2 or 3, R=Me or Et, or

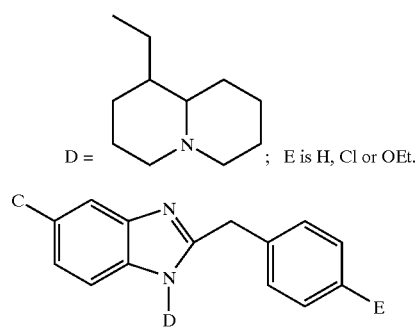

D = [structure]; E is H, Cl or OEt.

Formula Ic

Another series of compounds structurally related to this invention are pyrido[1,2-a]benzoazoles and pyrimidio[1,2a] benzimidazoles disclosed by S. Shigeta et al in *Antiviral Chem. & Chemother.* 1992, 3, 171. These compounds have demonstrated inhibition of orthomyxovirus and paramyxovirus replication in HeLa cells. The structures of these compounds are shown in formulas Id and Ie, in which R=NH, S, or O; Q=—NHCOPh, —COOH, COOEt, or CN; T=COMe, CN, or COOEt; G=O or NH.

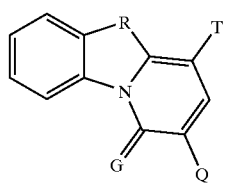

Formula Id

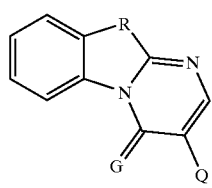

Formula Ie

Another series of 2-aminobenzimidazoles have been reported by E. Janssens, et al. as inhibitors of RSV in a series of recent publications and representative examples formula 1f–1h are shown below from PCT WO 01/0061 1 A1; PCT WO 01/00612 and PCT WO 01/00615, respectively all published on Jan. 4, 2001.

Formula 1f

Formula 1g

Formula 1h

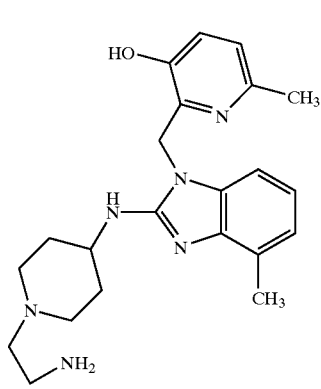

A bis-benzimidazole with an ethylenediol linker shown below has also been reported as a potent inhibitor of rhinoviruses (Roderick, et al. *J. Med Chem.* 1972, 15, 655.

Other structurally related compounds are bis-benzimidazoles which possess antifungal activity (B. Cakir, et al. *Eczacilik Fak. Derg.* 1988, 5, 71.

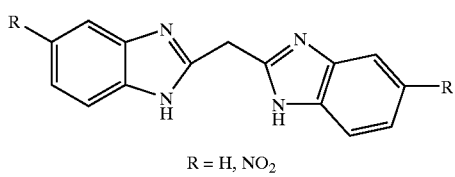

R = H, NO$_2$

Also, H. R. Howard et al. reported a series of benzimidazolone-1-acetic acids that possessed aldolase reductase inhibitory activity (*Eur. J. Med. Chem.* 1992, 27, 779–789).

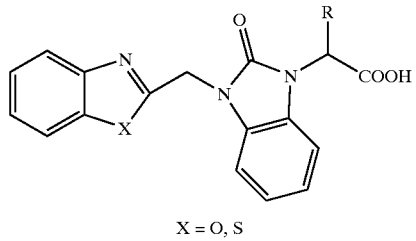

X = O, S

Other prior art related to the chemical structure of the present invention:
(1) F. Sparatore, et al, "Derivati Benzotriazolici Attivi Sull'accrescimento Delle Piante," *Il Farmaco Ed. Sci.* 1978, 33, 901.
(2) Katritzky, A. R. et al, "Synthesis and Transformations Of Substituted Benzazolyl- and Tetrazolyl(benzotriazol-1-yl) methanes," *J. Heterocyclic Chem.* 1996,33,1107.
(3) Terri A. Fairley, et al. "Structure, DNA Minor Groove Binding, And Base Pair Specificity of Alkyl and Aryl-Linked Bis(amidinobenzimidazoles) and Bis (amidinoindoles), *J. Med Chem.* 1993, 36, 1746.
(4) R. K. Upadhyay et al, "New Synthesis and Biological Evaluation," *Indian J Heterocyclic Chem.* 1994, 4, 121.
(5) A. R. Katritzky, et al, "A New Route to N-substituted Heterocycles," *Tetrahedron,* 1993, 49, 2829.
(6) K. Yu et al. in Substituted Benzimidazole Anti-viral Agents, PCT WO 00/04900 published February 3, 2000.

SUMMARY OF THE INVENTION

This invention relates to the antiviral activity against RSV found in a series of 1-substituted 2-(3'-N-substituted 2-oxo-benzimidazolylmethyl)-benzimidazoles. The structural formula for these compounds are depicted in Formula 1, and includes pharmaceutically acceptable salts thereof.

Formula I

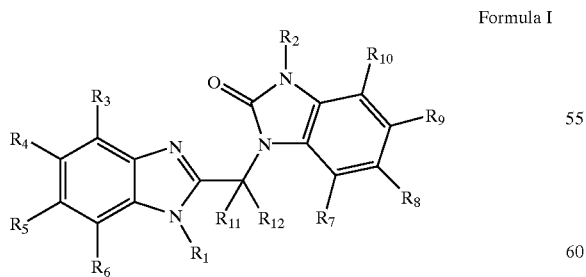

wherein:
$R_1$ is —$(CR^vR^w)_n$—X;
$R^v$ and $R^w$ are independently selected from the group consisting of H, $C_{1-6}$alkyl, and $C_{2-6}$alkenyl; optionally substituted with 1–6 of the same or different halogen;

X is H, $C_{1-6}$alkyl, $C_{2-6}$alkenyl; each of said $C_{1-6}$alkyl, $C_{2-6}$alkenyl being optionally substituted with (1) one to six same or different halogen or hydroxy; (2) a member selected from the group consisting of phenyl, —C(=NOH)NH$_2$, —CH(OH)-Ph, -Ph-S(O)$_2$C$_{1-6}$alkyl,

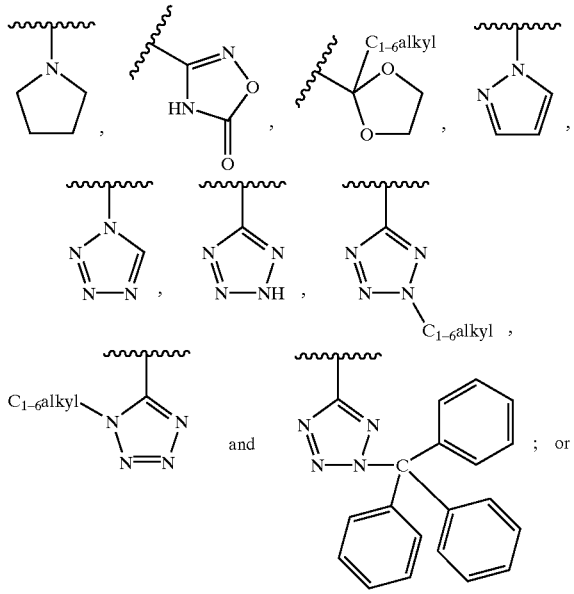

(3) a member from Group A1;
Group A1 is CN, OR', NR'R", R'NCOR", NR'CONR"R"', NR'SO$_2$R", NR'COOR", COR', COOR', OS(O)$_2$R', S(O)$_t$R' or PO(OR')$_2$;
n is 1–6;
t is 0–2;
$R_2$ is
(i) H, $C_1$ alkyl, $C_{2-6}$alkenyl, phenyl, or a functionality selected from Group A2 or Group B; each of said $C_{1-6}$alkyl, $C_{2-6}$ alkenyl, and phenyl being optionally substituted with (1) one to six same or different halogen or hydroxy or (2) one to two same or different members of Group A or Group B;
(ii) —(CR$^x$R$^Y$)$_{n'}$, —(CO)$_p$—C$_6$H$_4$-(Z$_1$)(Z$_2$), wherein Z$_1$ and Z$_2$ are each independently selected from the group consisting of Group A, Group B, and —(CH$_2$)$_{n'}$—Z'; wherein said Z' is heterocycle or —(NR$_d$R$_e$R$_f$)+ (halogen)-; and the Z$_1$ and Z$_2$ groups may each be in the ortho, meta or para position relative to the —(CR$^x$R$^Y$)$_{n'}$—(CO)$_p$-group; wherein R$_d$, R$_e$ and R$_f$ are independently $C_{1-6}$alkyl, $C_{2-6}$alkenyl, OH or $C_{1-6}$alkyl COOH;
p is 0 or 1;
n' is 1–6; or
(iii) —(CR$^x$R$^y$)$_{n''}$—heterocycle;
n" is 0–6;
$R_3$, $R_6$, $R_7$ and $R_{10}$ are each independently H;
$R_5$, $R_8$ and $R_9$ are each independently H, halogen or CF$_3$;
$R_4$ is selected from the group consisting of H, halogen, CN, —C(O)C$_{1-6}$alkyl and

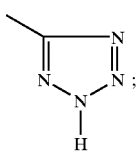

$R_{11}$, $R_{12}$ are each independently H;

$R^x$, $R^y$ are each independently H or $C_{1-6}$alkyl;

Group A2 is COR', COOR', CONRR"" or CONR'SO$_2$R";

Group A3 is CN, N$_2$, OR', OCONR'R", NR'R", N(R') COR", N(R')CONR"R"',

NR'SO$_2$R", NR'COOR", SO$_m$R', SO$_2$NR'R", SO$_2$NR'COR" or PO(OR')$_2$;

Group A is a member selected from Group A2 and Group A3;

R', R", R'" are each independently selected from the group consisting of H, $C_{1-6}$alkyl, phenyl and heterocycle; and each of said $C_{1-6}$alkyl, phenyl and heterocycle being optionally substituted with (1) one to six of same or different halogen or hydroxy; (2) one to two of the same or different members of Group A' or Group B; or (3) heterocycle; or R'and R" taken together form a 5 to 6 membered aromatic or non-aromatic ring containing one to four of the same or different heteroatoms selected from the group consisting of N, S and O;

Group A' is halogen, CN, NO$_2$, OR$^a$, OCONR$^a$R$^b$, NR$^a$R$^b$, R$^a$NCOR$^b$, NR$^a$CONR$^b$R$^c$, NR$^a$SO$_2$R$^b$, NR$^a$COOR$^b$, COR', CR$^c$NNR$^a$R$^b$, CR$^a$NOR$^b$, COOR$^a$, CONR$^a$R$^b$, CONR$^a$ SO$_2$R$^b$, SO$^m$'R$^a$, SO$_2$NR$^{aRb}$, SO$_2$NR$^a$COR$^b$ or PO(OR$^a$)$_2$;

R$^a$, R$^b$, R$^c$ are each independently selected from the group consisting of H and $C_{1-6}$alkyl;

Group B is —(CH$_2$)$_{n'''Q}$, —(CH$_2$)$_n$"SO$_m$"—R$_{13}$ or —COQ;

Q is an N-linked amino acid selected from the group consisting of alanine, asparagine, aspartic acid, glutamic acid, glutamine, glycine, pipecolic acid, α-amino-butyric acid, α-amino-propanoic acid, 2-amino-3-phosphonopropionic acid and iminodiacetic acid; wherein Q is linked to the adjacent carbon atom in Group B through a nitrogen atom of said N-linked amino acid; wherein said N-linked amino acid includes D- or L-enantiomers or mixtures thereof;

$R_{13}$ is selected from a group consisting of H and $C_{1-6}$alkyl; said C, alkyl being optionally substituted with (1) one to five hydroxy groups or (2) two of the same or different functionalities selected from the group consisting of COOR$^x$ and CONR$^x$R$^y$;

m, m and m are independently 0–2;

n'" is 1–6;

heterocycle is a 5–6 membered aromatic or non-aromatic ring which contains one to four heteroatoms independently selected from the group consisting of O, N and S; wherein said aromatic or non-aromatic ring is optionally fused to a phenyl ring; wherein the aromatic or non-aromatic ring is optionally substituted with one to five of the same or different substituents selected from the group consisting of $C_{1-6}$alkyl, Group A and Group B; and halogen is bromine, chlorine, fluorine or iodine.

In a preferred embodiment, the heterocycle is an aromatic ring selected from the group consisting of furyl, thienyl, pyridyl, pyrrolyl, oxazolyl, thiazolyl, imidazolyl, pyrazolyl, isoxazolyl, isothiazolyl, 1,2,3-oxadiazolyl, 1,2,4-oxadiazolyl, 1,2,4-oxadiazol-5-one, 1,2,3-triazolyl, 1,3,4-thiadiazolyl, pyridazinyl, pyrimidinyl, pyrazinyl, 1,3,5-triazinyl, indolizinyl, indolyl, isoindolyl, 3 H-indolyl, indolinyl, benzo[b]furanyl, benzo[b]thiophenyl, 1 H-indazolyl, benzimidazolyl, tetrazole, uridinyl and cytosinyl.

In another preferred embodiment, the heterocycle is a non-aromatic ring selected from the group consisting of pyrrolidine, imidazoline, 2-imidazolidone, 2-pyrrolidone, pyrrolin-2-one, tetrahydrofuran, 1,3-dioxolane, piperidine, tetrahydropyran, oxazoline, 1,3-dioxane, 1,4-piperazine, morpholine and thiomorpholine.

In another preferred embodiment in $R_2$, substituents $R^x$ and $R^y$ are each hydrogen. Also preferred is $R_{11}$, and $R_{12}$ each being hydrogen. Still more preferred are compounds wherein n is 1 and n" is 3–4.

In another preferred embodiment, n is 1–4.

In another preferred embodiment are compounds wherein:

$R_1$ is vinyl, allyl, 3-methyl-2-butene or —(CH$_2$)n-X, wherein n is 2–4, and X is a functionality selected from the group consisting of

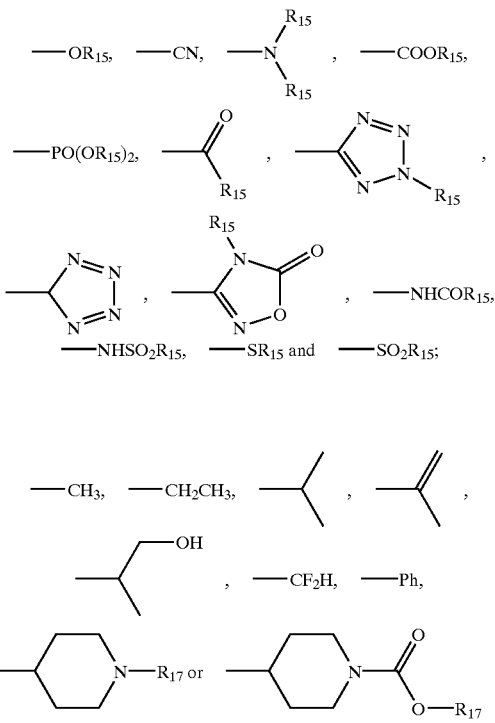

$R_2$ is (i)

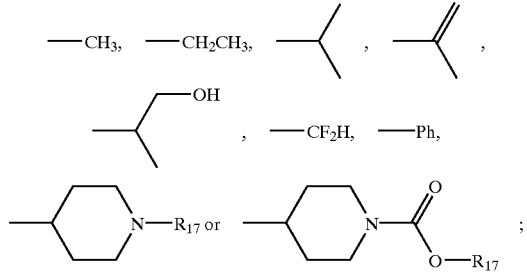

wherein $R_{17}$ is H or $C_{1-4}$alkyl;

(ii) —CH$_2$—C$_6$H$_4$-Z;

(iii) —(CH$_2$)$_k$-Z", wherein k is 1–6; wherein Z and Z" are each independently selected from the group consisting of:

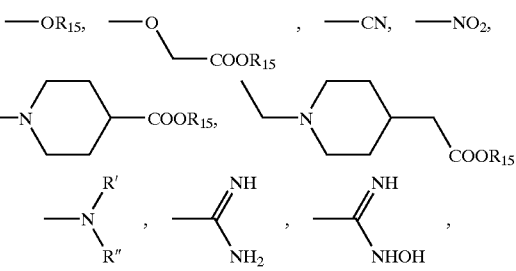

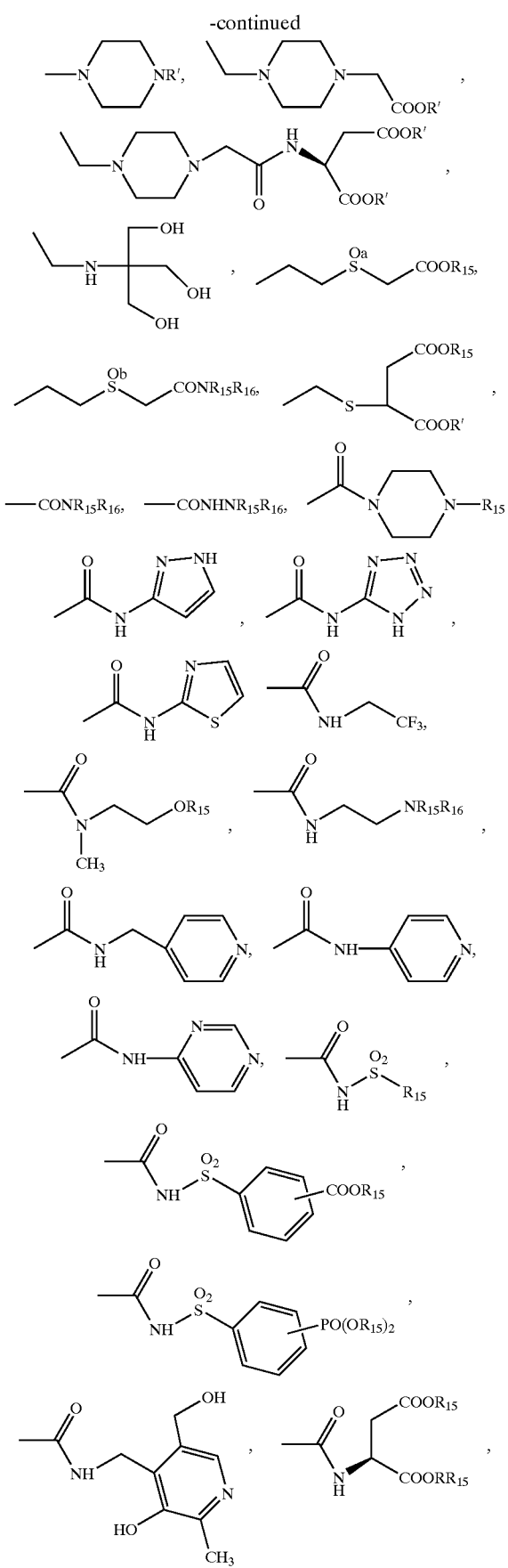
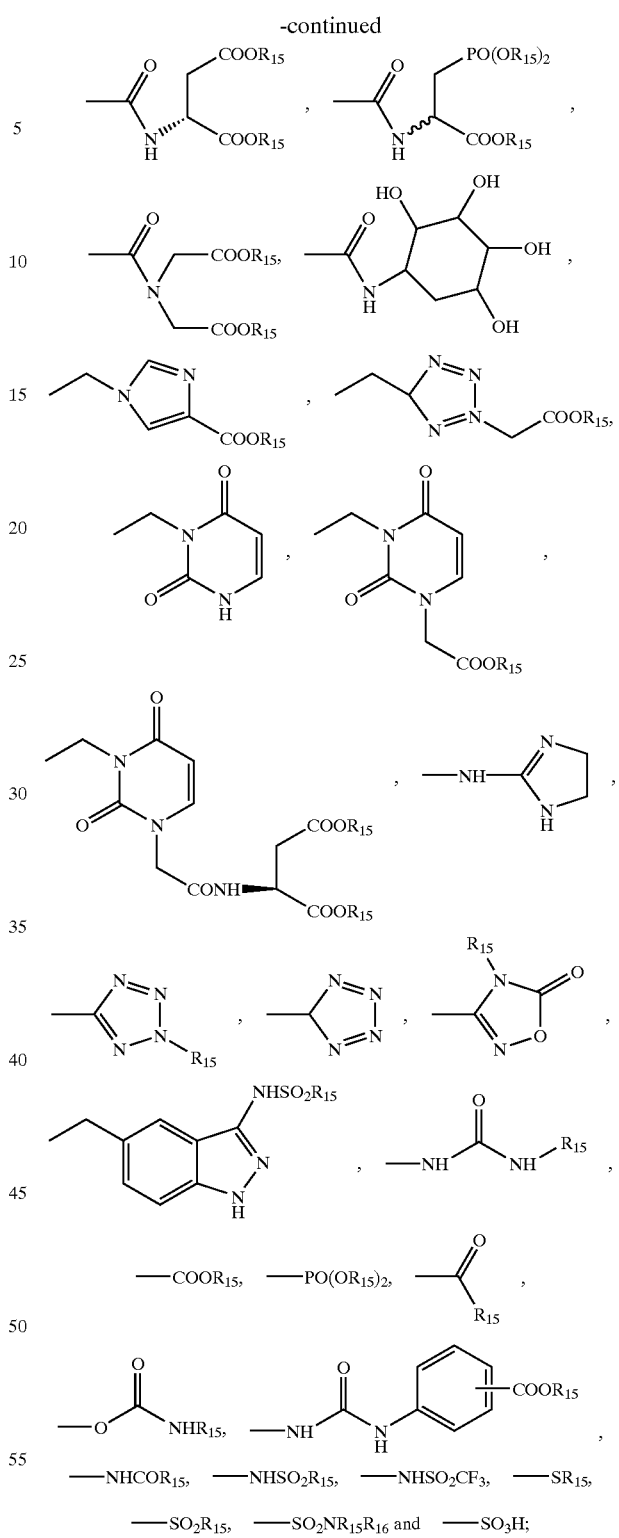
a and b are each independently 0–2; and
$R_{15}$ and $R_{16}$ are each independently H, $C_{1-4}$alkyl, wherein said $C_{1-4}$ alkyl is optionally substituted with 1–3 same or different halogens.

In another embodiment of the invention there is provided a method for treating mammals infected with RSV, and in need thereof, which comprises administering to said mammal a therapeutically effective amount of one or more of the aforementioned compounds of having Formula I, including pharmaceutically acceptable salts thereof.

Another embodiment includes a pharmaceutical composition which comprises a therapeutically effective amount of one or more of the aforementioned anti-RSV compounds of having Formula I, including pharmaceutically acceptable salts thereof, and a pharmaceutically acceptable carrier.

The term pharmaceutically acceptable salt includes solvates, hydrates, acid addition salts, base addition salts, and the salts of quaternary amines and pyridiniums. The acid addition salts are formed from a compound of Formula I and a pharmaceutically acceptable inorganic or organic acid including but not limited to hydrochloric, hydrobromic, sulfuric, phosphoric, methanesulfonic, acetic, citric, malonic, fumaric, maleic, sulfamic, or tartaric acids. The counter ion of quaternary amines and pyridiniums include chloride, bromide, iodide, sulfate, phosphate, methansulfonate, citrate, acetate, malonate, fumarate, sulfamate, and tartrate. The base addition salts include but are not limited to salts such as sodium, potassium, calcium, lithium and magnesium.

Halogen means bromine, chlorine, iodine and fluorine.

DETAILED DESCRIPTION OF THE INVENTION

Compounds of Formula I may be prepared using the procedures outlined in Schemes I–V.

Compounds of Formula I can be prepared as shown in Scheme I. Starting from the methansulfonamide of IV, alkylation with N-isopropylidenebenzimidazolone V in the presence of an appropriate base, such as NaH or a phosphazene base such as BTPP, followed by cleavage of the methanesulfonamide with tetrabutylammonium fluoride (TBAF) gives compounds of Formula VI. Alkylation of compounds of Formula VI with $R_1$-LG where LG is a leaving group, preferably halide or sulfonate such as mesylate using an appropriate base such as NaH or $Cs_2CO_3$ provides compounds of Formula VII. Alternatively, compounds with Formula VII can be obtained through Michael addition of VI with acrylonitrile, vinyl sulfone, or an ester of acrylic acid. Alkylation of VI may give mixtures of regioisomers when $R_3$–$R_6$ are non-equivalent. These mixtures may be purified by various chromatographic techniques. Alternatively, single regioisomers can be obtained by employing a reaction sequence like that described in Scheme IVa. Cleavage of the isopropylidene moiety with acid such as hydrochloric acid or acetic acid followed by a second alkylation step with $R_2$-LG provides compounds of Formula I.

Scheme I

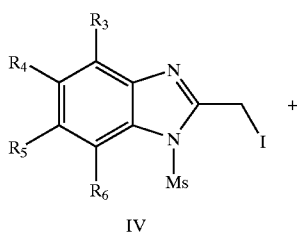

IV

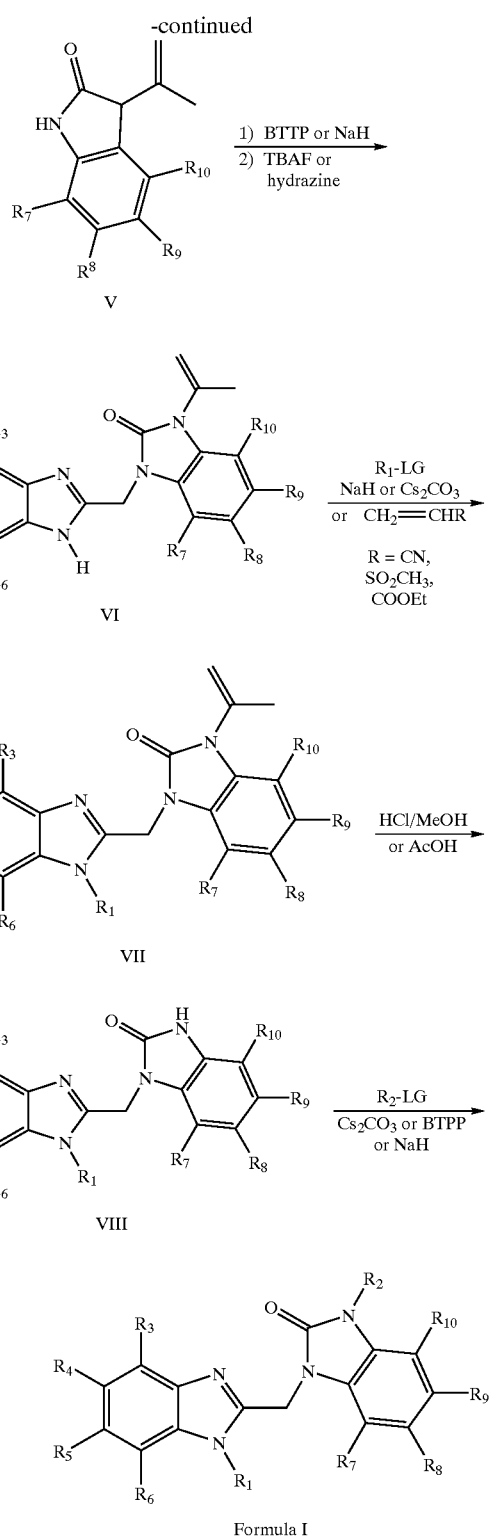

Compound IV can be prepared using the reaction sequence depicted in Scheme Ia. When R4 and R5 are equivalent reaction of 2-chloromethylbenzimidazole (II) with methanesulfonyl chloride (MsCl) and triethylamine gives compounds of Formula III. The chloride can be refluxed with potassium iodide in acetone to produce IV, as described in PCT WO 00/04900.

Scheme Ia

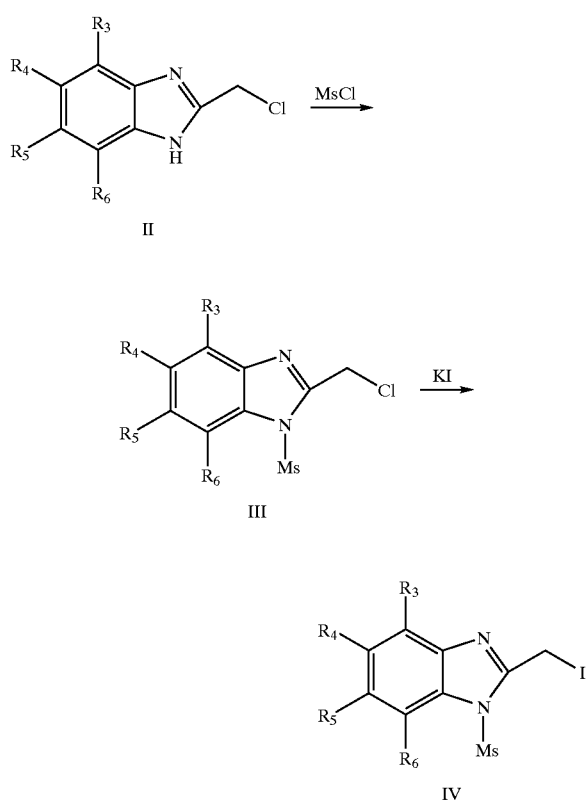

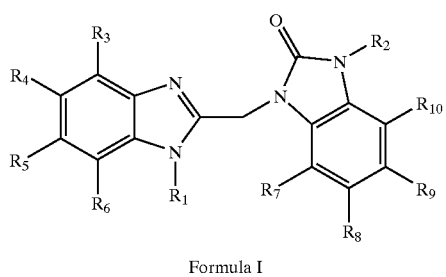

Formula I

Compounds of Formula I can also be prepared as shown in Scheme II. Alkylation of the substituted benzimidazolone of Formula XIII with a chloride XI in the presence of an appropriate base such as BTPP, $Cs_2CO_3$, or NaH, gives compounds of Formula I.

Scheme II

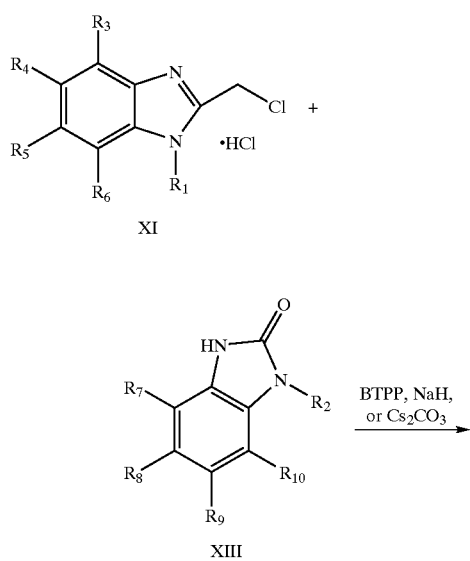

The synthesis of intermediates XI and XIII are depicted below in Schemes IIa and IIb, respectively. When $R_4$ and $R_5$ are equivalent selective N-alkylation of 2-hydroxybenzimidazole (IX) with $R_1$-LG or a Michael acceptor, such as acrylonitrile (R=CN), followed by conversion of the hydroxyl group of X to the chloride with $SOCl_2$ affords intermediate of Formula XI. Reaction of N-isopropylidenebenzimidazolone V with $R_2$-LG in the presence of an appropriate base such as NaH, BTPP, or $Cs_2CO_3$ affords intermediate XII. Cleavage of the isopropylidene moiety with acid gives compounds of Formula XIII.

Scheme IIa

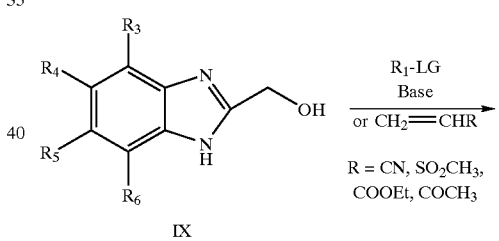

R = CN, $SO_2CH_3$, COOEt, $COCH_3$

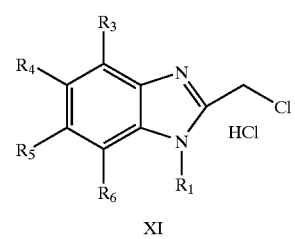

Scheme IIb

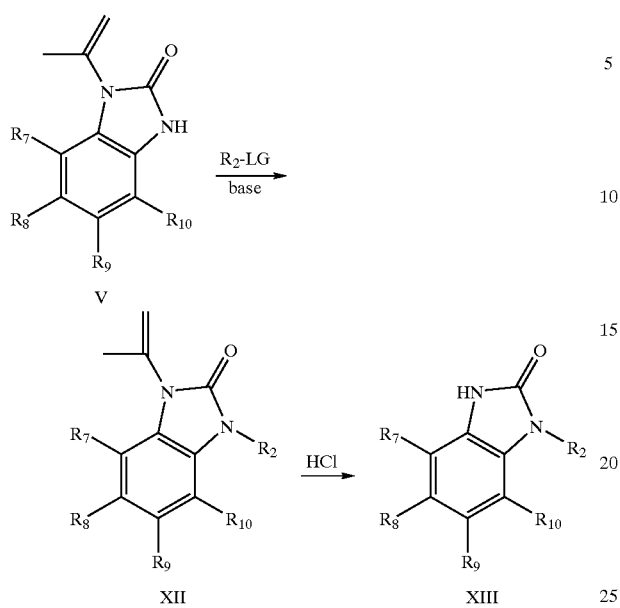

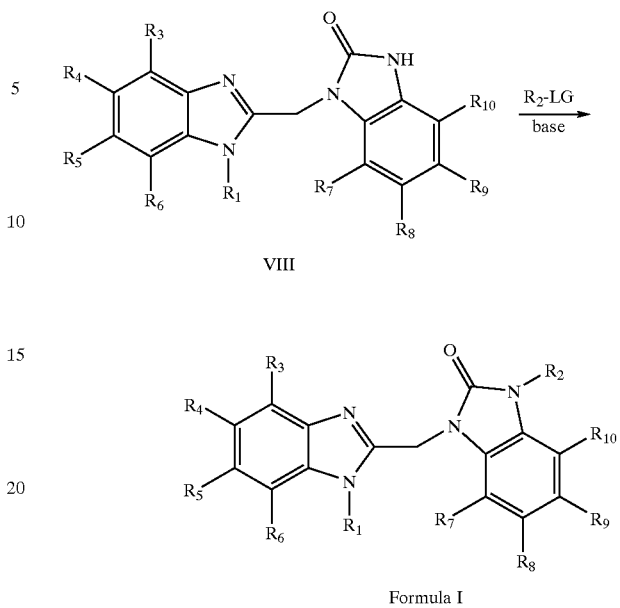

Additionally, a hybrid method from Schemes I and II may be employed for the preparation of compounds of Formula I as depicted in Scheme III. Coupling of intermediates XI and V in the presence of an appropriate base affords compounds of Formula VII. Cleavage of the isopropylidene moiety and reaction with R₂-LG utilizing the same procedures described in Scheme I gives compounds of Formula I

Scheme III

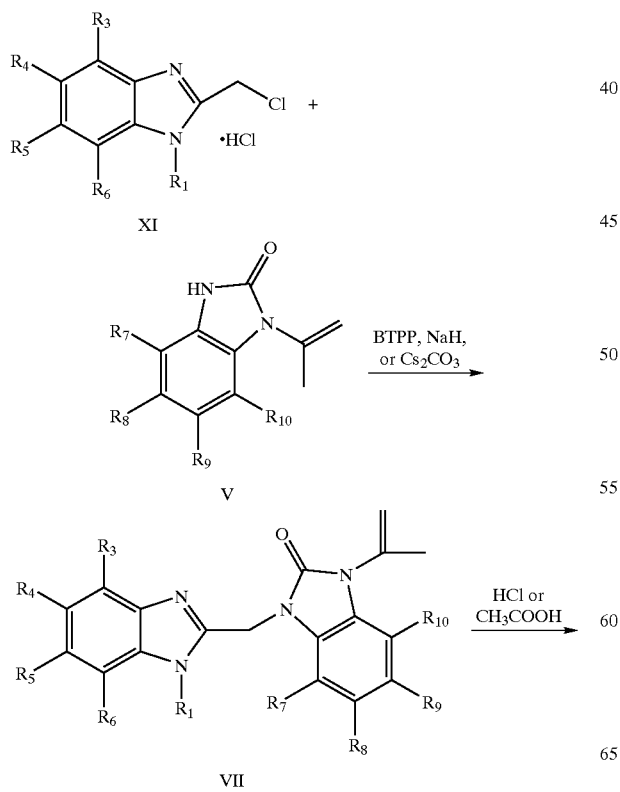

In a different approach, compounds of Formula I were prepared using the synthetic route illustrated in Scheme IV. Substituted phenylenediamine XIV can be coupled with either the acid XV through an amide coupling agent, such as a carbodiimide, or with the acid chloride XVI and a base. The crude material is directly cyclized to the benzimidazole in warm acetic acid to give compounds of Formula I. Alternatively, the phenylenediamine XIV can directly react with acid XV in the presence of EEDQ or the acid chloride XVI to give compounds of Formula I. In a slightly modified procedure depicted in Scheme IV, phenylenediamine XIV can be coupled with acid XV or acid chloride XVI in the same manner described above to give compounds of Formula XXIII which then can react with R₁LG in the presence of an appropriate base to afford compounds of Formula I.

Scheme IV

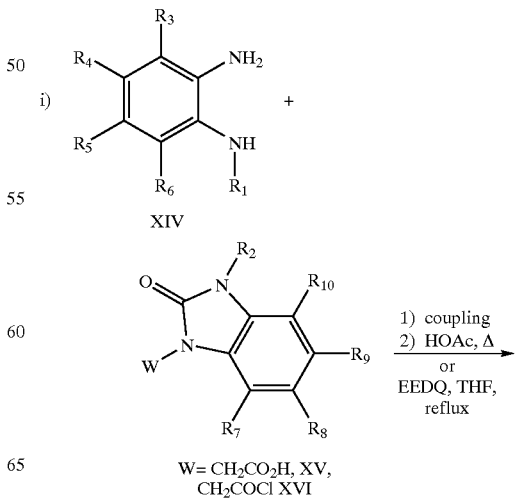

-continued

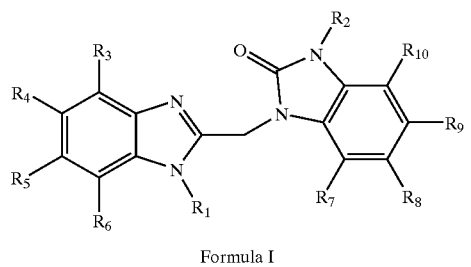

Formula I ii) 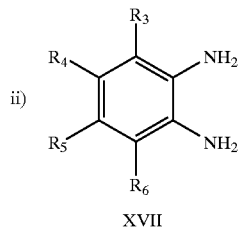

XVII

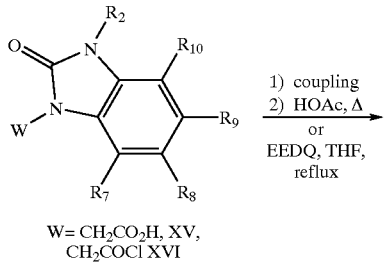

W= CH$_2$CO$_2$H, XV,
CH$_2$COCl XVI

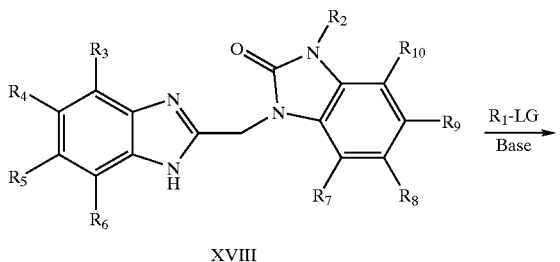

XVIII

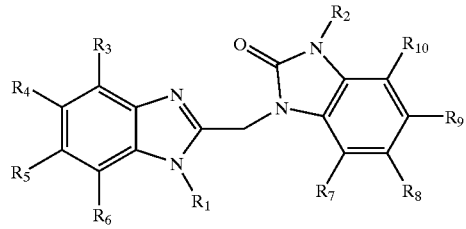

Formula I

The preparation of pheneylenediamines XXI is described in Scheme IVa. Coupling of a 1-fluoro-2-nitrobenzene derivative XIX and the appropriate amine produces compounds of Formula XX. Reduction of compound XX under catalytic hydrogenation conditions to give phenylenediamine XXI.

Scheme IVa

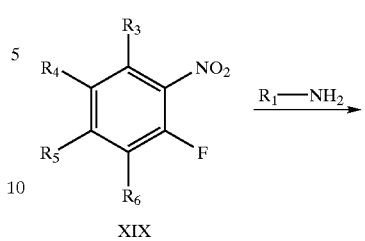

XIX

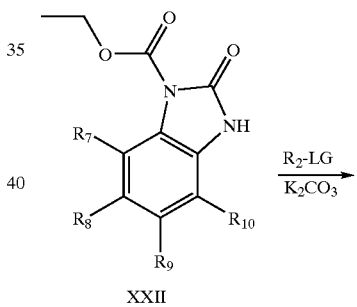

XX  XXI

The right-hand benzimidazolone intermediates XXII and XXIII can be prepared using standard alkylation chemistry and deprotection procedures as depicted in Scheme IVb starting with the known compound of Formula XXII.

Scheme IVb

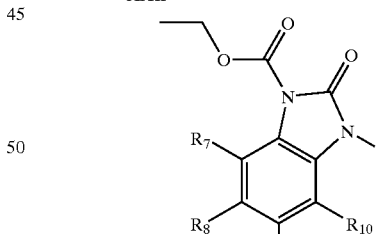

XXII

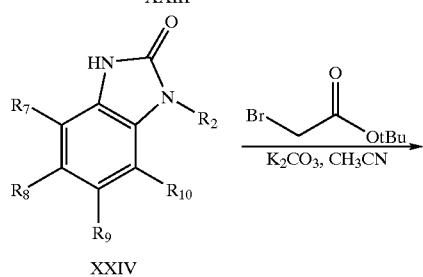

XXIII

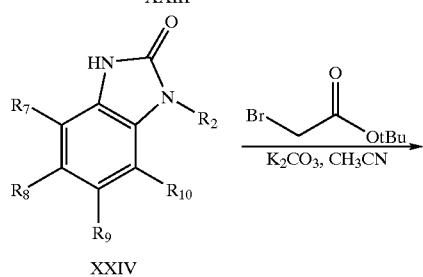

XXIV

-continued

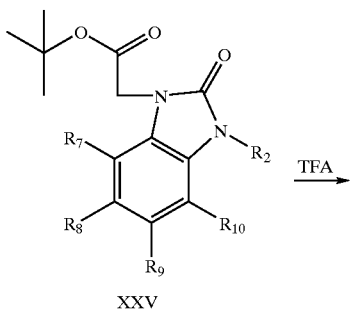

XXV

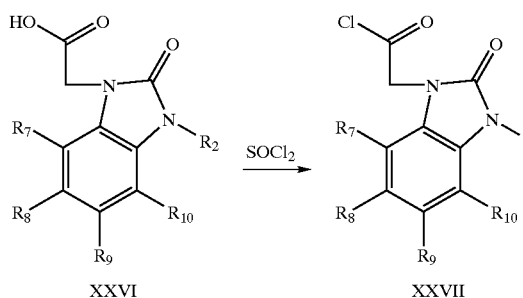

XXVI   XXVII

Further modification of compounds at the $R_2$ side-chain can be accomplished by extension of the side-chain with one or more linkers as described in Scheme V. Alkylation of compounds of Formula VIII with a linker (Y-LG) in the presence of an appropriate base such as $Cs_2CO_3$, NaH, or BTPP affords intermediates XXIV. Intermediate XXIV is then extended through standard coupling and alkylation reactions to give compounds of Formula I.

Scheme V

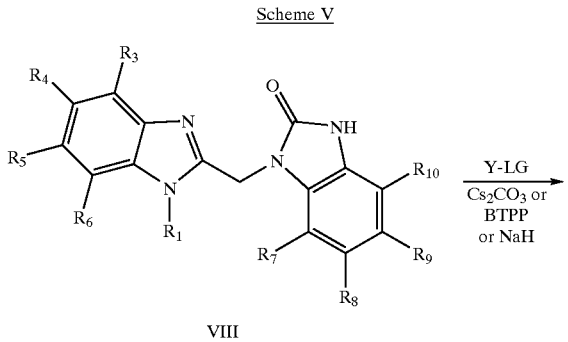

VIII

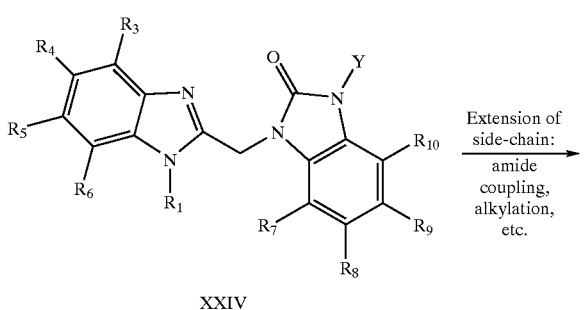

XXIV

-continued

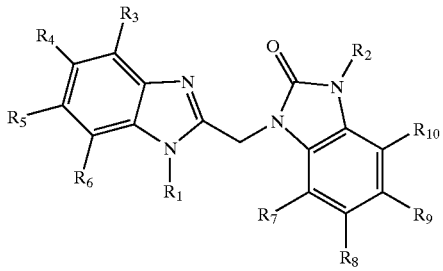

Formula I

Abbreviations Used Herein, Including in Schemes I-V, Experimental Section Unless Indicated Otherwise:

AcOH: acetic acid
AIBN: azobisisobutyronitrile
BEMP: 2-t-butylimino-2-diethylamino- 1,3-dimethyl-perhydro-1,3,2-diazaphosphorane
BTPP: t-butylimino-tri(pyrrolidino)phosphorane
DEAD: diethyl azodicarboxylate
DMF: dimethylformamide
EDC: 1-ethyl-3-(3-dimethylaminopropyl)carbodiimide
EEDQ: 2-ethoxy-1-ethoxycarbonyl-1,2-dihydroquinoline
Et: ethyl
$Et_2O$: diethyl ether
EtOAc: ethyl acetate
EtOH: ethyl alcohol
HOAc: glacial acetic acid
Me: methyl
MeOH: methyl alcohol
MTBD: 1,3,4,6,7,8-hexahydro-l-methyl-2 H-pyrimido[1,2-a]pyrimidine
Ph: phenyl
Prep HPLC: preparative high performance liquid chromatography
PyBroP: bromotripyrrolidinophosphonium hexafluorophosphate
TBAF: tetrabutylammonium fluoride
TEA: triethylamine
TFA: trifluoroacetic acid
THF: tetrahydrofuran
Tr: triphenylmethyl (trityl) group It will be appreciated by those skilled in the art that reference herein to treatment extends to prophylaxis as well as the treatment of established infections or symptoms.

It will be further appreciated that the amount of a compound of the invention required for use in treatment will vary not only with the particular compound selected but also with the route of administration, the nature of the condition being treated and the age and condition of the patient, and will ultimately be at the discretion of the attendant physician or veterinarian. In general however, a suitable dose will be in the range of from about 0.01 to 750 mg/kg of body weight per day preferably in the range of 0.1 to 100 mg/kg/day, most preferably in the range of 0.5 to 25 mg/kg/day.

Treatment is preferably commenced before or at the time of infection and continued until virus is no longer present in the respiratory tract. However, the treatment can also be commenced when given post-infection, for example after the appearance of established symptoms.

Suitable treatment is to administer the compound 1–4 times daily and continue for 3–7 days, e.g. 5 days, post infection, depending upon the particular compound used.

The desired dose may be administered as a single dose or in divided doses administered at appropriate intervals, for example as two, three, four or more sub-doses per day.

The compound is conveniently administered in unit dosage form, for example, containing 10 to 1500 mg, conveniently 20 to 1000 mg, most conveniently 50 to 700 mg of active ingredient per unit dosage form.

While it is possible that, for use in therapy, a compound of the invention may be administered as the raw chemical, it is preferable to present the active ingredient as a pharmaceutical formulation.

The invention thus further provides a pharmaceutical formulation comprising a compound of the formula I, but not subject to the proviso thereto, or a pharmaceutically acceptable salt or derivative thereof together with a pharmaceutically acceptable carrier thereof.

The carrier must be "acceptable" in the sense of being compatible with the other ingredients of the formulation and not deleterious to the recipient thereof.

The pharmaceutical formulations may be in the form of conventional formulations for the intended mode of administration.

For intranasal administration according to the method of the invention the compounds of the invention may be administered by any of the methods and formulations employed in the art for intranasal administration.

Thus in general the compounds may be administered in the form of a solution or a suspension or as a dry powder. Solid carriers include, for example, starch, lactose, dicalcium phosphate, microcrystalline cellulose, sucrose and kaolin.

Solutions and suspensions will generally be aqueous, for example prepared from water alone (for example sterile or pyrogen-free water), or water and a physiologically acceptable co-solvent (for example ethanol, propylene glycol, and polyethylene glycols such as PEG 400).

Such solutions or suspensions may additionally contain other excipients, for example, preservatives (such as benzalkonium chloride), solubilizing agents/surfactants such as polysorbates (e.g. Tween 80, Span 80, benzalkonium chloride), buffering agents, isotonicity-adjusting agents (for example sodium chloride), absorption enhancers and viscosity enhancers. Suspensions may additionally contain suspending agents (for example microcrystalline cellulose, carboxymethyl cellulose sodium).

Solutions or suspensions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the patient administering an appropriate, predetermined volume of the solution or suspension. In the case of a spray this may be achieved for example by means of a metering atomizing spray pump.

Intranasal administration may also be achieved by means of an aerosol formulation in which the compound is provided in a pressurized pack with a suitable propellant such as a chlorofluorocarbon (CFC), for example dichlorodifluoromethane, trichlorofluoromethane or dichlorotetrafluroroethane, carbon dioxide or other suitable gas. The aerosol may conveniently also contain a surfactant such as lecithin. The dose of drug may be controlled by provision of a metered valve.

Experimental Section

Proton nuclear magnetic resonance ($^1$H NMR) spectra were recorded on a Bruker Advance 500, AC-300, Bruker DPX-300 or a Varian Gemini 300 spectrometer. All spectra were determined in $CDCl_3$, $CD_3OD$, or DMSO-$d_6$ and chemical shifts are reported in δ units relative to tetramethylsilane (TMS). Splitting patterns are designated as follows: s, singlet; d, doublet; t, triplet; m, multiplet; b, broad peak; dd, doublet of doublets; dt, doublet of triplets. Mass spectroscopy was performed on a Finnigan SSQ 7000 quadrupole mass spectrometer in both positive and negative electrospray ionization (ESI) modes or on a LC-MS using Shimadzu LC-10AS with micromass platform LC single quadrupole mass spectrometer in positive electrospray ionization. High resolution mass spectroscopy was recorded using a Finnigan MAT 900. Infrared (IR) spectra were recorded on a Perkin-Elmer system 2000 FT-IR. Elemental analysis was performed with a Perkin-Elmer series II, model 2400 CHN/O/S analyzer. Column chromatography was performed on silica gel from VWR Scientific. Preparative HPLC was performed using a Shimadzu LC-8A on a C18 column eluted with mixture of MeOH in water with 0.1% trifluoroacetic acid.

Preparation of Compounds as depicted in Scheme I

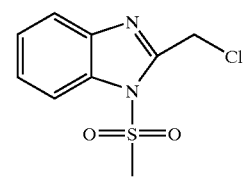

1

To a solution of 2-(chloromethyl)benzimidazole (80 g, 0.48 mol) and methanesulfonyl chloride (58.3 mL, 0.75 mol) in $CH_2Cl_2$ (0.5 L), triethylamine (136 mL, 0.97 mol) was added dropwise under nitrogen. The resulting mixture was stirred at room temperature for 6 hours. The mixture was filtered and the filtrate was evaporated. The residue was triturated with MeOH and filtered to afford 74.9 g (64% yield) of compound I as a brown solid:

$^1$H NMR ($CDCl_3$) δ8 3.44 (s, 3 H), 5.11 (s, 2 H), 7.40–7.49 (m, 2 H), 7.76–7.82 (m 1 H), 7.85–7.91 (m, 1H); IR (KBr, cm$^{-1}$) 3027, 2920, 1371, 1349, 1177, 1144, 1059; MS m/e 245 (MH$^+$); Anal. Calcd for $C_9$ $H_9ClN_2O_2S$: C, 44.18; H, 3.71; N, 11.45 Found: C, 44.09; H, 3.57; N, 11.49.

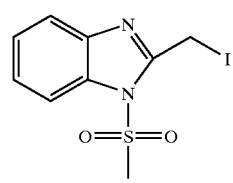

2

A solution of potassium iodide (206 g, 1.24 mol) and compound 1 (74.8 g, 0.414 mol) in acetone (1 L) was stirred at reflux under nitrogen for 4 hours. The solid was filtered and the filtrate was evaporated. The crude product was triturated in MeOH and filtered to give 83 g (60% yield) of compound 2 as a solid:

$^1$H NMR (CDCl$_3$) δ6 3.48 (s, 3 H), 4.97 (s, 2 H), 7.40–7.50 (m, 2 H), 7.75–7.85 (m, 2 H); IR (KBr, cm$^{-1}$) 3022, 2916, 1366, 1173, 1055, 966, 763, 745; MS m/e 336 (MH$^+$); Anal. Calcd for C$_9$H$_9$IN$_2$O$_2$S: C, 32.16; H, 2.70; N, 8.33 Found: C, 32.05; H, 2.63; N, 8.22.

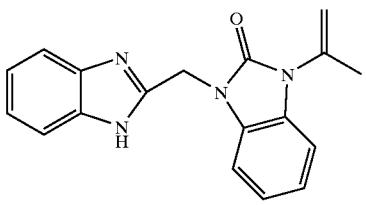

3

2-(Iodomethyl)-1-(methanesulfonyl) benzimidazole, 2, (160 g, 0.476 mol) and 1-isopropenyl-2-benzimidazolone (prepared using the procedure described by J. Davoll, J. Chem. Soc. 1960, p308) were dissolved in 2 L of anhydrous THF and the solution cooled in a ice bath. To the solution, BTPP (223 g, 0.714 mol) was slowly added. The ice bath was removed, and the mixture was stirred at room temperature for 1.5 hours. The solution was evaporated. The residue was dissolved in ethyl acetate, washed with water, brine, dried over magnesium sulfate and evaporated. The residue was dissolved in THF (1 L) and tetrabutylammonium fluoride hydrate (130.7 g, 0.5 mol) was added. The mixture was stirred at reflux for 5 hours. The solvent was evaporated. The residue was dissolved in EtOAc, washed with water, brine, dried over magnesium sulfate, and evaporated. The residue was purified through a short silica gel column with EtOAc in CH$_2$Cl$_2$ (10 to 100%) to give 92.0 g (72% yield) of compound 3 as a solid:

$^1$H NMR (CDCl$_3$) δ2.24 (s, 3 H), 5.22 (s, 1H), 5.41 (s, 3 H), 7.09–7.17 (m, 3 H), 7.26–7.30 (m, 2 H), 7.39 (d, J=6.9 Hz, 1 H), 7.60 (dd, J=3.3, 6.0 Hz, 2 H); MS m/e 305 (MH$^+$).

(Scheme I)

Compound 4

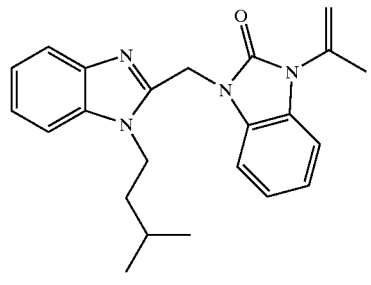

4

To compound 3 (30.4 g, 100 mmol) in DMF (200 mL) was added NaH (60% in mineral oil, 5.2 g, 130 mmol) in several portions at room temperature. After stirring for 30 minutes, 1-bromo-3-methylbutane (16.62 g, 110 mmol) was added to the suspension and the mixture was stirred at 70° C. overnight. The crude product was purified by flash chromatography to give 33.7 g (90% yield) of compound 4 as a white solid:

$^1$H NMR (CDCl$_3$) δ0.94 (d, J=6.6 Hz, 6 H), 1.37–1.45 (m, 2 H), 1.64–1.75 (m, 1 H), 2.25 (s, 3 H), 4.31 (bt, J=8.1 Hz, 2 H), 5.21 (s, 1H), 5.38 (s, 1 H), 5.40 (s, 2 H), 7.01–7.10 (m, 3 H), 7.25–7.35 (m, 3 H), 7.46–7.47 (m, 1 H), 7.79–7.82 (m, 1 H); IR (KBr, cm$^{-1}$) 2962, 1702, 1491, 1471, 1395, 1331, 740, 734; MS m/e 375 (MH$^+$); Anal. Calcd for C$_{23}$H$_{26}$N$_4$O: C, 73.77; H, 7.00; N, 14.96 Found: C, 73.82; H, 6.94; N, 14.91.

(Scheme I)

Compound 5

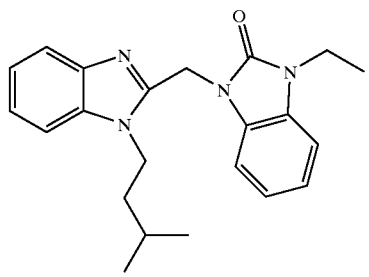

Compound 5 was prepared as described for compound 4 using 1-ethyl-1,3-dihydro-benzoimidazol-2-one.

$^1$H NMR (CDCl$_3$) δ0.92 (d, J=6.6 Hz, 6 H), 1.32–1.40 (m, 5 H), 1.63–1.72 (m, 1H), 3.90–4.01 (m, 2H), 4.27–4.33 (m, 2H), 5.43 (s, 2H), 6.90–7.12 (m, 4H), 7.26–7.29 (m, 2H), 7.44 (d, J=7.6 Hz, 1H), 7.79–7.82 (m, 1H), 8.46 (bs, 1H); MS m/e 363 (MH$^+$).

(Scheme I)

Compound 6

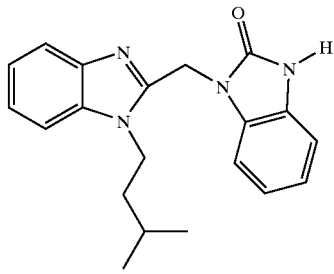

To compound 4 (33.7 g, 90 mmol) was added to 10% conc. HCl in MeOH (100 mL) and the reaction mixture was stirred at 75 ° C. for 1 h. The solvent was evaporated, and to the residue was added saturated NaHCO$_3$ The mixture was extracted with CH$_2$Cl$_2$. The combined extracts were washed with water and brine, and then dried over MgSO$_4$. The solvent was evaporated, and the residue was passed through a short silica gel column to give a product which crystallized from CH$_2$Cl$_2$/EtOAc to give 22.83 g (84% yield) of compound 6 as white solid:

$^1$H NMR (CDCl$_3$) δ1.89 (d, J=6.6 Hz, 6 H), 1.38–1.46 (m, 2 H), 1.67–1.74 (m, 1 H), 4.29–4.35 (m, 2 H), 5.46 (s, 2 H), 7.01–7.08 (m, 3 H), 7.28–7.31 (m, 3 H) 7.42–7.44 (m, 1 H), 7.81–7.84 (m, 1 H), 9.78 (bs, 1 H); IR (KBr, cm$^{-1}$) 2957, 1696, 1489, 1458, 1390, 1332, 749, 737; MS m/e 335 (MH$^+$); Anal. Calcd for C$_{20}$H$_{22}$N$_4$O: C, 70.69; H, 6.70; N, 16.49 Found: C, 70.43; H, 6.69; N, 16.25.

(Scheme I)

Compound 7

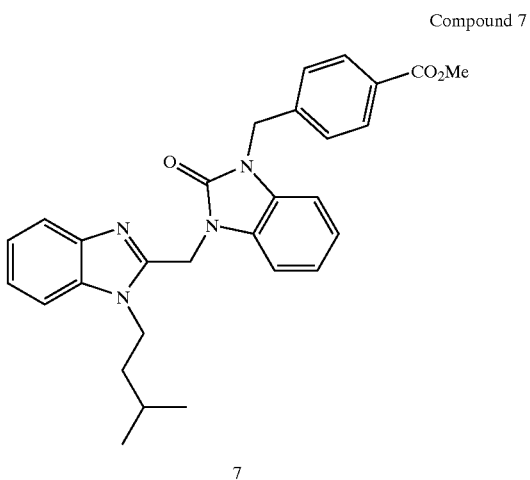

7

A solution of compound 6 (212 mg, 0.63 mmol) and methyl 4-(bromomethyl)-benzoate (160 mg, 0.70 mmol) in THF (2 mL) was cooled to 0° and BTPP (219 mg, 0.7 mmol) was added dropwise under nitrogen. The resulting mixture was stirred at 0° for 0.5 h then at room temperature for 2 hours. The mixture was diluted with EtOAc and washed with water. The organic extracts were dried with $MgSO_4$ and evaporated. The residue was purified by flash chromatography (gradient, hexanes:EtOAc 2:1 to 1:2) to give (219 mg, 71% yield) of compound 7 as a white solid:

$^1$H NMR (CDCl$_3$) δ 0.94 (d, J=6.6 Hz, 6 H), 1.47 (m, 2 H), 1.70 (m, 1 H), 3.91 (s, 3 H), 4.34 (m, 2 H), 5.16 (s, 2 H), 5.49 (s, 2 H), 6.82 (d, J=8.9 Hz, 1 H), 7.02 (m, 2 H), 7.29 (m, 3 H), 7.38 (d, J=8.3 Hz, 2 H), 7.50 (d, J=7.3 Hz, 1 H), 7.82 (m, 1 H), 7.99 (d, J=8.3 Hz, 2 H); IR (KBr, cm$^{-1}$) 3418, 2952, 1707, 1495, 1406, 1279, 748; MS m/e 483 (MH$^+$); Anal. Calcd for C$_{29}$H$_{30}$N$_4$O$_3$: C, 72.18; H, 6.27; N, 11.61 Found: C, 71.95; H, 6.20; N, 11.41.

Compound 8

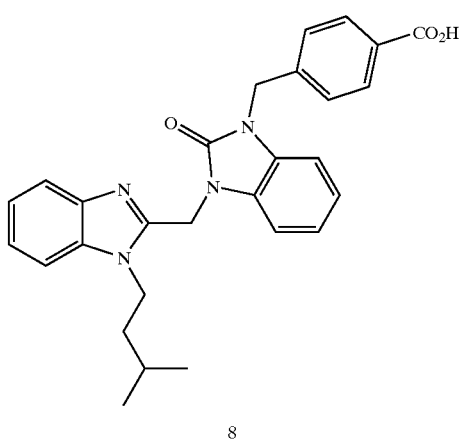

8

Compound 7 (130 mg, 0.27 mmol) was dissolved in methanol (2 mL). A solution of 1 N NaOH (0.81 mL, 0.81 mmol) was added and the resulting mixture was heated to reflux for 3 h then cooled to room temperature. The solution was concentrated, and adjusted to pH 5 with 1 N HCl. The precipitate was filtered and dried to give 81 mg (63% yield) of compound 8. The acid was then converted to a sodium salt by adding aqueous NaHCO$_3$, and the resulting solution was adjusted to pH 8 with 1 N HCl. The solution was evaporated to give the sodium salt of compound 8 as a white solid:

$^1$H NMR (DMSO-d$_6$) δ 0.91 (d, J=6.6 Hz, 6 H), 1.46 (m, 2 H), 1.65 (m, 1 H), 4.32 (m, 2 H), 5.09 (s, 2 H), 5.42 (s, 2 H), 6.99 (m, 2 H), 7.10 (m, 1 H), 7.29 (m, 5 H), 7.51 (d, J=7.3 Hz, 1 H), 7.60 (d, J=7.3 Hz, 1 H), 7.78 (d, J=8.3 Hz, 2 H); IR (KBr, cm$^{-1}$) 3396, 2956, 1703, 1612, 1598, 1329, 750; MS m/e 469 (MH$^+$); Anal. Calcd for C$_{28}$H$_{27}$N$_4$O$_3$Na.1.5NaCl.2 H$_2$O: C, 54.79; H, 5.09; N, 9.12 Found: C, 55.08; H, 5.35; N, 8.86.

Compound 9

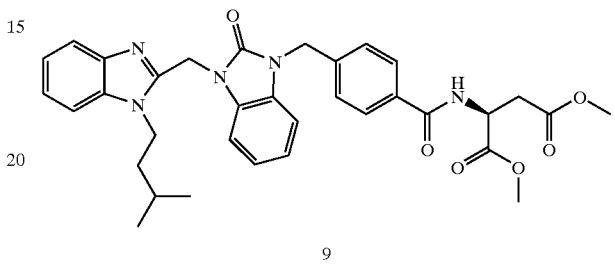

9

To a suspension of acid 8 (6.80 g, 14.5 mmol) in DMF (200 mL) at 0° C. was added PyBroP (7.41 g, 15.9 mmol). The suspension was stirred at 0° C. until it turned to a clear solution (about 30 minutes). Diisopropylethylamine (7.49 g, 57.9 mmol) and (L)-aspartic acid dimethyl ester hydrochloride (3.14 g, 15.9 mmol) were added and the resulting solution was stirred at ambient temperature overnight. The solvent was evaporated and the residue was purified by column chromatography (hexane: EtOAc 3:1 to 1:4) to afford 8.30 g (94% yield) of compound 9 as a white solid:

$^1$HNMR (DMSO-d$_6$) δ 0.90 (d, J=6.6 Hz, 6 H), 1.41–1.48 (m, 2H), 1.59–1.68 (m, 1H), 2.72–2.97 (m, 2H), 3.57 (s, 3H), 3.61 (s, 3H), 4.29 (t, J=7.9 Hz, 2H), 4.76–4.83 (m, 1H), 5.17 (s, 2H), 5.42 (s, 2H), 6.98–7.25 (m, 6H), 7.44 (d, J=8.3 Hz, 2H), 7.50 (d, J=7.5 Hz, 1H), 7.59 (d, J=7.3 Hz, 1 H), 7.78 (d, J=8.3 Hz, 2 H), 8.88 (d, J=7.7 Hz, 1 H); IR (KBr, cm$^{-1}$) 3312, 2953, 1740, 1708, 1495, 1170, 846, 748; MS m/e 612 (MH$^+$);

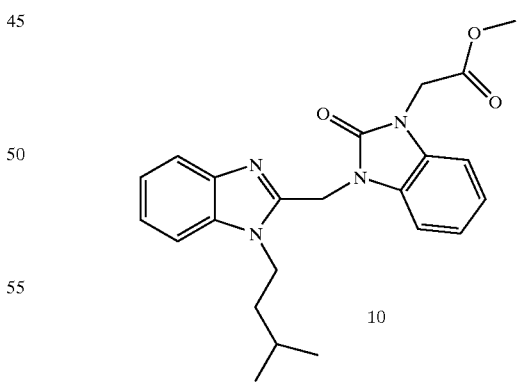

10

Compound 10 was prepared as described for compound 7 using methyl bromoacetate and sodium hydride as the base.

$^1$H NMR (CDCl$_3$) δ 0.94 (d, J=6.6 Hz, 6H), 1.42–1.56 (m, 2H), 1.64–1.73 (m, 1 H), 3.76 (s, 3 H), 4.29 (t, J=8.2 Hz, 2H), 4.66 (s, 2H), 5.44 (s, 2H), 6.84–6.90 (m, 1 H), 7.04–7.10 (m, 3 H), 7.27–7.30 (m, 2 H), 7.44–7.52 (m, 1 H), 7.76–7.82 (m, 1 H); MS m/e 406 (MH$^+$).

TABLE 1

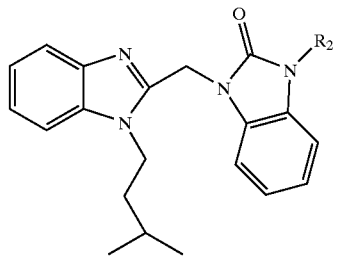

11

Additional examples prepared as described for compound 9.

| # | R₂ | ¹H-NMR Data | MS Data |
|---|---|---|---|
| 11a | ![structure] | (CDCl₃) δ 0.91 (d, J=6.6 Hz, 6H), 0.99–1.13 (m, 2H), 1.43–1.51(m, 4H), 1.56–1.69(m, 2H), 1.84–1.98(m, 4H), 2.00–2.16(m, 1H), 2.80–3.08(m, 2H), 3.28(t, J=6.3 Hz, 2H), 3.70(s, 3H), 3.75(s, 3H), 4.29(t, J=8.2 Hz, 2H), 4.83–4.89(m, 1H), 5.30(s, 2H), 5.45(s, 2H), 6.50(d, J=8.1 Hz, 1H), 6.90–6.96(m, 1H), 7.06–7.09(m, 2H), 7.21–7.24(m, 1H), 7.31–7.34(m, 4H), 7.43–7.50(m, 2H), 7.75–7.78(m, 1H) | 751 (MH⁺) |
| 11b | ![structure] | (DMSO-d₆) δ 0.91(d, J=6.5 Hz, 6H), 1.47–1.54(m, 2H), 1.64–1.70(m, 1H), 1.73–1.77 (m, 1H), 3.07–3.19(m, 2H), 3.45–3.51(m, 2H), 3.57–3.66(m, 2H), 3.70–3.79(m, 2H), 4.38(t, J=8.1 Hz, 2H), 4.58(d, J=8.3 Hz, 2H), 5.04(d, J=3.0 Hz, 1H), 5.17(s, 2H), 5.51(s, 2H), 7.00–7.03(m, 2H), 7.08–7.13(m, 1H), 7.25–7.36(m, 3H), 7.42(d, J=8.4 Hz, 2H), 7.63(t, J=6.7 Hz, 2H), 7.80(d, J=8.3 Hz, 1H), 7.85(d, J=8.3 Hz, 1H), 7.98(d, J= 7.2 Hz, 1H) | 630 (MH⁺) |
| 11c | ![structure] | (CDCl₃) δ 0.90(d, J=6.6 Hz, 6H), 1.03–1.14 (m, 2H), 1.39–1.66(m, 7H), 1.91–2.06(m, 4H), 2.24–2.33(m, 1H), 3.35(t, J=6.4 Hz, 2H), 3.68(s, 3H), 4.27–4.34(m, 2H), 5.32(s, 2H), 5.52(bs, 2H), 7.00–7.13(m, 4H), 7.16–7.19(m, 1H), 7.30–7.35(m, 4H), 7.49–7.62 (m, 2H), 7.82–7.87(m, 1H) | 622 (MH⁺) |

Compound 12

12

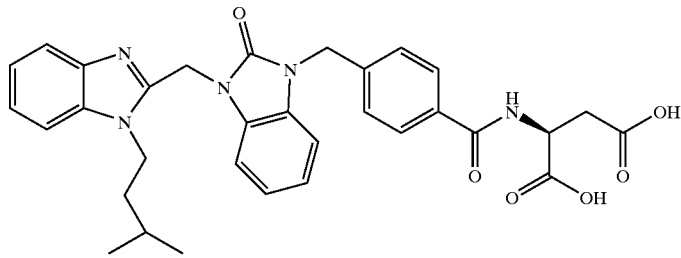

To a solution of compound 9 (3.3 g, 5.39 mmol) in MeOH (100 mL) was added 1 N NaOH (32 mL) and the solution was stirred at 60° C. for 10 min. The solvent was evaporated. The residue was dissolved in water and adjusted to pH 2 with 1 N HCl, extracted with THF and then EtOAc. The combined extracts were washed with brine, dried over MgSO₄, and evaporated. The residue was triturated in EtOAc to give 2.55 g of compound 12 as a free acid. To the acid in methanol (50 mL) was added 2 equivalents of 1 N NaOH and solvent was evaporated. The residue was triturated with Et₂O to give 2.53 g of the disodium salt of compound 12 as a white solid:

¹H NMR (CD₃OD) δ0.95 (d, J=6.6 Hz, 6 H), 1.43–1.51 (m, 2 H), 1.64–1.73 (m, 1 H), 2.82 (d, J=5.9 Hz, 2 H), 4.35–4.40 (m, 2 H), 4.70 (t, J=5.9 Hz, 1 H), 5.24 (s, 2 H), 5.51 (s, 2 H), 7.02–7.06 (m, 3 H), 7.18–7.36 (m, 3 H), 7.45–7.51 (m, 3 H), 7.67 (dd, J=1.7, 7.0 Hz, 1 H), 7.88 (d,

J=8.3 Hz, 2 H); IR (KBr, cm$^{-1}$): 3411, 2956, 1706, 1612, 1494, 1407, 854, 749; MS m/e/e 584 (MH$^+$).

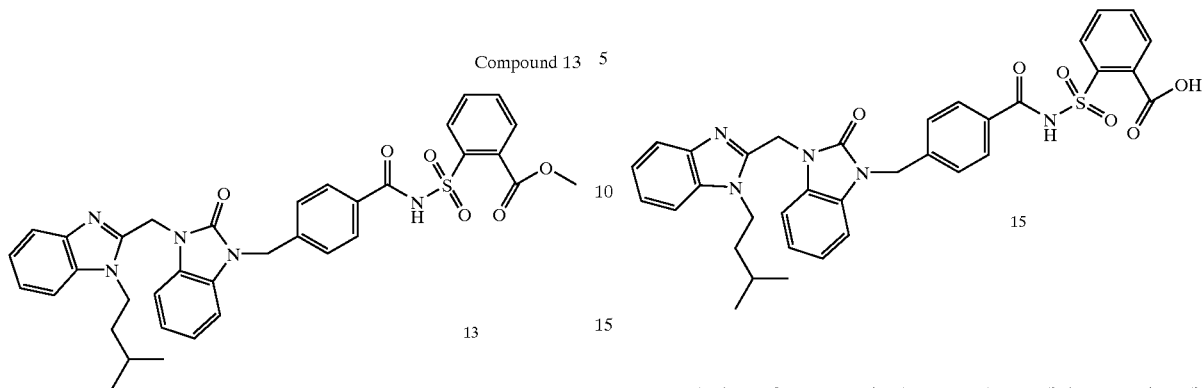

Compound 13

Compound 15

A mixture of acid 8 (3.20 g, 6.82 mmol), 2-carbomethoxybenzenesulfonamide (1.76 g, 8.18 mmol), EDC (1.57 g, 8.18 mmol), and DMAP (1.00 g, 8.18 mmol) in CH$_2$Cl$_2$ (150 ml) was stirred at ambient temperature for 12 hours. The solution was diluted with CH$_2$Cl$_2$ (150 ml), washed with 1 N HCl (200 ml) and brine. The organic phase was dried over MgSO$_4$ and evaporated. The residue was purified on a silica gel column which was pre-treated with 0.1% acetic acid in CH$_2$C$_2$ and eluted with EtOAc, and then 5% to 10% MeOH in EtOAc to afford 4.13 g (91%) of compound 13 as white solid:

$^1$HNMR (CD$_3$OD) δ0.91 (d, J=6.6 Hz, 6 H), 1.40–1.48 (m, 2 H), 1.60–1.69 (m, 1 H), 3.74 (s, 3 H), 4.34 (t, J=8.0 Hz, 2 H), 5.19 (s, 2 H), 5.48 (s, 2 H), 7.03–7.04 m, 3 H), 7.17–7.21 (m, 1 H), 7.27–7.38 (m, 4 H), 7.46–7.58 (m, 4 H), 7.64–7.67 (m, 1 H), 8.00 (d, J=8.2 Hz, 2 H), 8.12–8.15 (m, 1 H); IR (KBr, cm$^{-1}$) 3424, 2955, 1709, 1612, 1590, 1542, 1493, 1435, 1348, 1301, 1258, 750; MS m/e 666 (MH$^+$); Anal. Calcd for C$_{36}$H$_{35}$ N$_5$O$_6$.1.85 H$_2$O: C, 61.85; H, 5.58; N, 10.02 Found: C, 62.24; H, 5.41; N, 9.57.

A solution of ester 13 (0.53 g, 0.85 mmol) in THF (1 ml) and MeOH (5 ml) was treated with IN NaOH (4.23 ml, 4.23 mmol). The solution was stirred at reflux for 12 h. After cooling to room temperature, the solution was acidified with 1 N HCl to pH 4.5 and evaporated. The residue was triturated in hot H$_2$O (10 ml) and filtered. The solid was washed with H$_2$O and dried in vacuum to give 0.49 g (89% yield) of compound 15 as a white solid:

$^1$HNMR (CD$_3$OD) δ0.91 (d, J=6.6 Hz, 6 H), 1.43–1.50 (m, 2 H), 1.60–1.69 (m, 1 H), 4.36 (t, J=8.1 Hz, 2 H), 5.22 (s, 2 H), 5.51 (s, 2 H), 7.03–7.06 (m, 3 H 7.20–7.21 (m, 1 H), 7.28–7.37 (m, 2 H), 7.44–7.52 (m, 3 H), 7.60–7.69 (m, 4 H 7.91 (d, J=8.3 Hz, 2 H), 8.19–8.21 (d, J=7.4 Hz, 1 H); IR (KBr, cm$^{-1}$): 3424, 2957, 1710, 1612, 1591, 1563, 1528, 1512, 1492, 1439, 1406,1348,1173,750; MS m/e 652 (MH$^+$); Anal. Calcd for C$_{35}$ H$_{33}$N$_5$O$_6$. H$_2$O C, 62.77; H, 5.27; N, 10.46 Found: C, 62.61; H, 5.45; N, 10.27.

A suspension of the acid (1.20 g, 1.84 mmol) in MeOH (50 ml) was triturated with IN NaOH (3.67 ml, 3.67 mmol) to pH 7.8 and filtered. The filtrate was lyophilized to yield 1.20 g (94% yield) of a white solid as a disodium salt of compound 15:

Compound 14

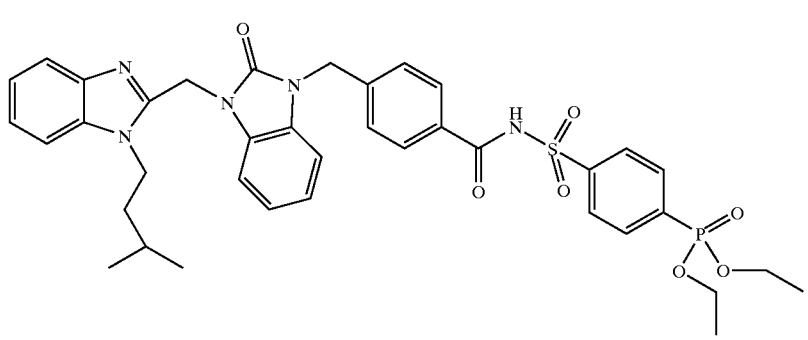

Prepared as described for compound 13.

$^1$H-NMR (CD$_3$OD) 6 0.95 (d, J=6.4 Hz, 6H), 1.35 (t, J=7.1 Hz, 6 H), 1.59–1.72 (m, 3H), 4.12–4.23 (m, 4H), 4.47–4.52 (m, 2H), 5.24 (s, 2H), 5.67 (s, 2H), 7.12–7.14 (m, 3H), 7.24–7.27 (m, 1H), 7.49–7.57 (m, 4H), 7.73 (t, J=7.1 Hz, 2 (d, J=8.3 Hz, 2 H), 7.97–8.01 (m, 2H), 8.23 (dd, J=3.4, 8.4 Hz, 2H); MS m/e 744 (MH$^+$);

$^1$HNMR ( CD$_3$OD) δ0.91 (d, J 6.6 Hz, 6 H), 1.41–1.49 (m, 2 H), 1.62–1.69 (m, 1 H), 4.36 (t, J=8.1 Hz, 2 H), 5.20 (s, 2 H), 5.49 (s, 2 H), 7.00–7.04 (m, 3 7.17–7.20 (m, 1 H), 7.25–7.49 (m, 8 H), 7.65–7.68 (m, 1H), 7.99–8.03 (m, 3 H IR (KBr cm$^{-1}$) 3424, 2956, 1707, 1608, 1592, 1565, 1504, 1493, 1403, 1330, 1154, 750; MS m/e 652 (MH$^+$); Anal. Calcd for C$_{35}$ H$_{31}$N$_5$Na$_2$O$_6$. 4 H$_2$O: C, 54.75; H, 5.12; N, 9.12 Found: C, 54.87; H, 5.01; N, 9.11.

Compound 16

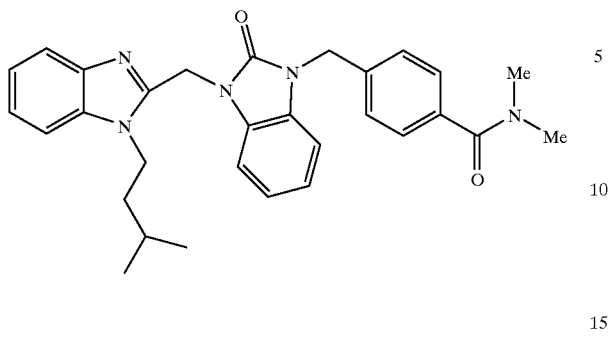

Compound 16 was prepared by the same procedure as compound 9 using acid 8 and dimethylamine hydrochloride:

$^1$HNMR (CD$_3$OD) δ1.66–1.76 (m, 3H), 2.98 (s, 3H), 3.10 (s, 6H), 4.57 (t, J=8.3 Hz, 2H), 5.23 (s, 2H), 5.76 (s, 2H), 7.16–7.21 (m, 2H), 7.29–7.31 (m, 1H), 7.43 (d, J=8.0 Hz, 2H), 7.51 (d, J=8.0 Hz, 2H), 7.59–7.66 (m, 2H), 7.76 (d, J=7.8 HZ, 1 H), 7.86 (d, J=8 Hz, 1 H); MS m/e 496 (MH$^+$); IR (KBr, cm$^{-1}$)3424, 1708, 1634, 1494, 1404, 1190, 751 Anal. Calcd for C$_{30}$H$_{33}$N$_5$O$_2$1.0TFA.H$_2$O: C, 61.24; H, 5.78; N, 11.16 Found: C, 61.10; H, 5.41; N, 10.83

Compound 17

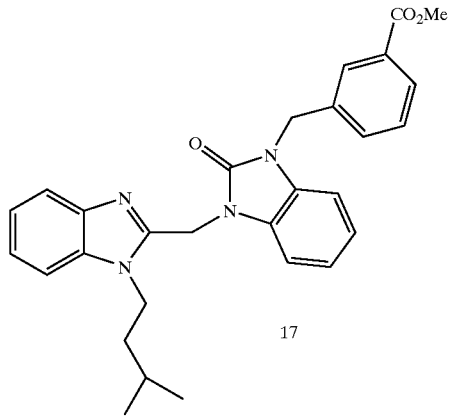

Compound 17 was prepared as a white powder in 87% yield using the same procedure as compound 7 with compound 6 and m-bromomethylbenzoic acid methyl ester:

$^1$H NMR (CDCl$_3$) δ0.94 (d, J=6.6 Hz, 6 H), 1.47 (m, 2 H), 1.69 (m, 1H), 3.91 (s, 3H), 4.32 (m, 2H), 5.15 (s, 2H), 5.46 (s, 2H), 6.84 (d, J=8.9 Hz, 1H), 6.99 2H), 7.31 (m, 3H), 7.40 (m, 2H), 7.52 (d, J=7.3 Hz, 1H), 7.81 (m, 1H), 7.97 (d, J=8.3 Hz, 1H), 8.05 (s, 1H); IR (KBr, cm$^{-1}$) 3405, 2952, 1707, 1497, 1407, 1291, 747. MS m/e 483 (MH$^+$); Anal. Calcd for C$_{29}$H$_{30}$N$_4$O$_3$: C, 72.18; H, 6.27; N, 11.61 Found: C, 72.08; H, 6.32; N, 11.42

Compound 18

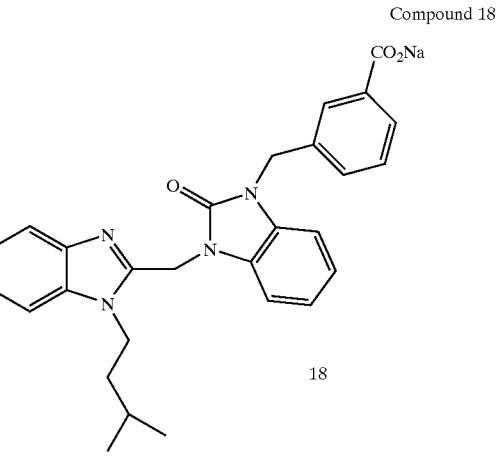

Compound 18 was prepared as a white powder in 77% yield using the same procedure as for compound 8:

$^1$H NMR (DMSO-d$_6$) δ0.90 (d, J=6.6 Hz, 6 H), 1.43 (m, 2 H), 1.64 (m, 1 H), 4.32 (m, 2 H), 5.09 (s, 2H), 5.42 (s, 2H), 6.99 (m, 2H), 7.08 (m, 1H), 7.19 (m, 5H), 7.49 (d, J=7.3 Hz, 1H), 7.59 (d, J=7.3 Hz, 1 H), 7.72 (d, J=8.3 Hz, 1H), 7.81 (s, 1H); IR (KBr, cm$^{-1}$) 3401, 2955, 1702, 1565, 1493, 1391, 750; MS m/e 469 (MH$^+$); Anal. Calcd for C$_{28}$H$_{27}$N$_4$O$_3$Na.2.25 H$_2$O: C, 63.32; H, 5.97; N, 10.55 Found: C, 63.31; H, 5.62; N, 10.41

Compound 19

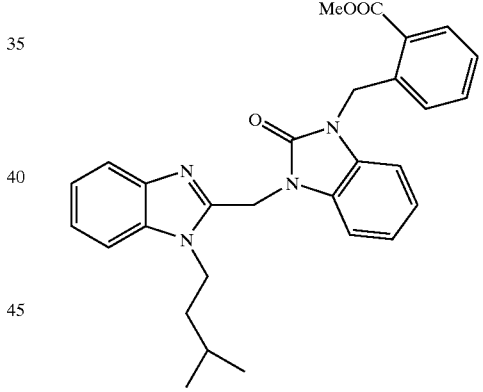

Compound 6 (5.0 g, 14.95 mmol), o-bromomethylbenzoic acid methyl ester (4.43g, 19.44 mmol) and Cs$_2$CO$_3$ (14.62, 44.85 mmol) were stirred at reflux in acetone (200 mL) for 1 hour. The solvent was evaporated and the residue dissolved in CH$_2$Cl$_2$ and filtered. The filtrate was washed with water, dried over MgSO$_4$ and evaporated. The residue was triturated in EtOAc to give 6.37 g (88% yield) of compound 19 as a white solid:

$^1$H NMR (CDCl$_3$) δ0.93 (d, J=6.6 Hz, 6 H), 1.42–1.50 (m, 2 H), 1.65–1.74 (m, 1 H), 3.96 (s, 1 H), 4.29–4.35 (m, 2 H), 5.46 (s, 2 H), 5.58 (s, 2 H), 6.79 (d, J=7.9 Hz, 1 H), 6.95–7.06 (m, 3 H), 7.27–7.38 (m, 4 H), 7.48 (d, J=7.1 Hz, 1H), 7.78–7.81 (m, 1 H), 8.06 (dd, J=1.6, 7.6 Hz, 1 H); IR (KBr, cm$^{-1}$) 1707, 1497, 1403, 1284, 1257, 739; MS m/e 483 (MH$^+$); Anal. Calcd for C$_{29}$H$_{30}$N$_4$O$_3$: C, 72.18; H, 6.27; N, 11.61 C, 71.96; H, 6.21;N, 11.41.

Compound 20

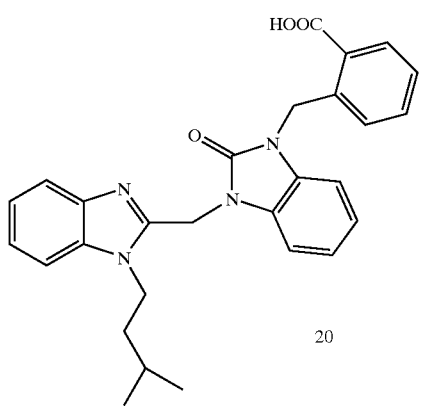

Compound 20 was prepared using the same procedure as for compound 8.

¹H NMR (DMSO-d₆) δ0.91 (d, J=6.7 Hz, 6 H), 1.40–1.47 (m, 2 H), 1.61–1.70 (m, 1 H), 4.30–4.35 (m, 2 H), 5.43 (s, 2 H), 5.55 (s, 2 H), 6.85 (dd, J=1.5, 7.9 Hz, 1 H), 6.89–6.98 (m, 2 H), 7.06–7.26 (m, 6 H), 7.50 (d, J=7.4 Hz, 1 H), 7.61 (d, J=6.8. Hz, 1 H), 7.69 (dd, J=1.9, 7.4 Hz, 1 H); IR (KBr, cm⁻¹) 3403, 2956, 1701, 1609, 1586, 1562, 1493, 1396, 742; MS m/e 469 (MH⁺); Anal. Calcd for $C_{29}H_{27}NaN_4O_3$. 1.85 $H_2O$: C, 64.19; H, 5.90; N, 10.64 Found: C, 63.78; H, 5.49; N, 10.50.

Compound 21

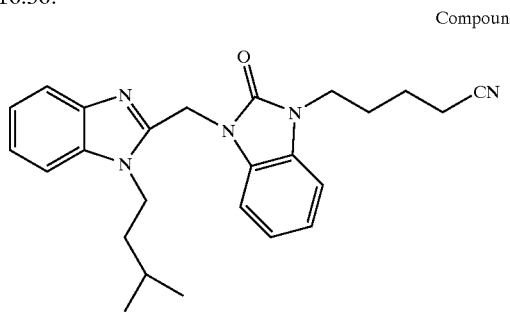

Compound 21 was prepared using the same procedure as for compound 7 with compound 6 and 5-bromovaleronitrile:

¹H NMR (CDCl₃) δ0.94 (d, J=6.6 Hz, 6H), 1.43 (m, 2H), 1.63–1.81 (m, 3H), 1.97 (m, 2H), 2.46 (t, J=7.1 Hz, 2H), 3.99 (t, J=6.8 Hz, 2H), 4.30 (m, 2H 5.40 (s, 2H), 6.96–7.12 (m, 3H), 7.29 (m, 3H), 7.44 (d, J=7.2 Hz, 1H), 7.80 (m, 1H) MS m/e 416 (MH⁺).

Compound 22

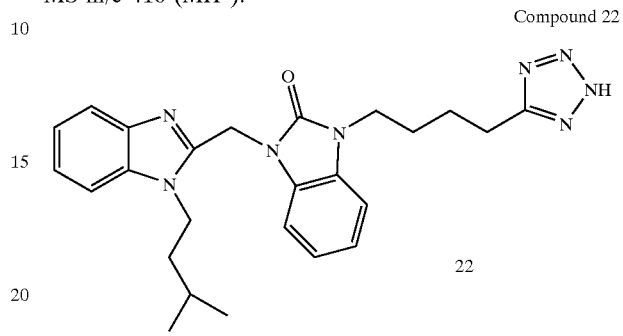

Nitrile 21 (2.89g, 6.96 mmol), ammonium chloride (1.12g, 20.87 mmol) and sodium azide (1.36 g, 20.87 mmol) were mixed in anhydrous DMF (100 mL) and stirred at 110° C. for 1 day. After additional ammonium chloride (1.12 g, 20.87 mmol) and sodium azide (1.36 g, 20.87 mmol) were added, the mixture was stirred for additional 2 days at 110° C. The solvent was evaporated and the residue purified by silica gel column chromatography (gradient, MeOH in EtOAc 0 to 10%). The residue was dissolved in 1 N NaOH and chromatographed on a C18 column using 10 to 40% MeOH/water to give 1.2 g (38% yield) of compound 22:

¹H NMR (CDCl₃) δ0.94 (d, J=6.6 Hz, 6 H), 1.60 (m, 2H), 1.70 (m, 1H), 1.91 (m, 2H), 2.00 (m, 2H), 3.03 (t, J=7.1 Hz, 2H), 4.00 (t, J=6.8 Hz, 2H), 4.29 (m, 2H), 5.40 (s, 2 H), 6.90 (m, 1H), 7.03 (m, 2H), 7.20–7.36 (m, 4H), 7.60 (d, J=7.5 Hz, 1H); 15 MS m/e 459 (MH⁺).

TABLE 2

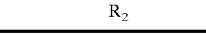

Compounds listed below were prepared by alkylation of compound 6 as described for the preparation of compound 7.

| # | R₂ | ¹H-NMR Data | MS Data |
|---|---|---|---|
| 23a[a] | 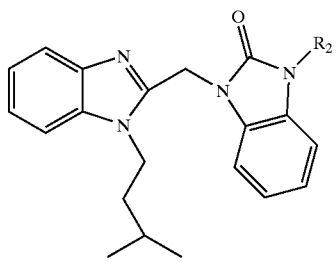 | (CDCl₃) δ 0.97(d, J=6.6 Hz, 6H), 1.46–1.54(m, 2H), 1.67–1.74(m, 1H), 4.38–4.43(m, 2H), 5.21(s, 2H), 5.58 (s, 2H), 6.82(d, J=7.4 Hz, 1H), 7.02–7.14(m, 2H), 7.38(bs, 3H), 7.49(d, J= 8.7 Hz, 2H), 7.64–7.7 1(m, 1H), 7.84–7.92(m, 1H), 8.20(d, J=8.8 Hz, 2H) | 470 (MH⁺) |

TABLE 2-continued

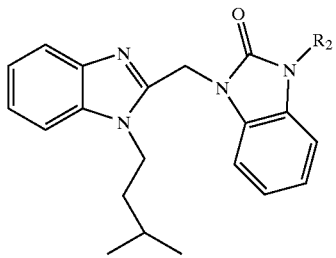

23

Compounds listed below were prepared by alkylation of compound 6 as described for the preparation of compound 7.

| # | R$_2$ | $^1$H-NMR Data | MS Data |
|---|---|---|---|
| 23b[b] | 4-ethylphenyl-P(O)(OEt)$_2$ | (CDCl$_3$) δ 0.96(d, J=6.5 Hz, 6H), 1.32(t, J=7.1 Hz, 6H), 1.45–1.74(m, 3H), 4.03–4.19(m, 4H), 4.38(t, J=7.9 Hz, 2H), 5.16(s, 2H), 5.54(s, 2H), 6.84–6.87(m, 1H), 7.03–7.08(m, 2H), 7.41–7.45(m, 5H), 7.53–7.59(m, 1H), 7.75–7.86(m, 3H) | 561 (MH$^+$) |
| 23c[c] | 4-ethylphenyl-O-CH$_2$-CO$_2$tBu | (DMSO-d$_6$) δ 0.90(d, J=6.6 Hz, 6H), 1.40(s, 9H), 1.39–1.47(m, 2H), 1.61–1.65(m, 1H), 4.20–4.33(m, 2H), 4.59 (s, 2H), 5.03(s, 2H), 5.40(s, 2H), 6.85 (d, J=8.6 Hz, 2H), 6.97–7.00(m, 2H), 7.14–7.26(m, 4H), 7.29(d, J=14.7 Hz, 2H), 7.50(d, J=7.7 Hz, 1H), 7.59 (d, J=7.6 Hz, 1H) | 554 (MH$^+$) |
| 23d[c] | 2-ethylphenyl-O-CH$_2$-CO$_2$tBu | (DMSO-d$_6$) δ 0.91(d, J=6.6 Hz, 6H), 1.44(s, 11H), 1.54–1.68(m, 1H), 4.31–4.38(m, 2H), 4.81(s, 2H), 5.16(s, 2H), 5.43(s, 2H), 6.82–7.08(m, 4H), 7.10–7.12(m, 2H), 7.15–7.31(m, 4H), 7.51–7.58(m, 1H), 7.59–7.64(m, 1H) | 554 (MH$^+$) |
| 23e[c] | 3-ethylphenyl-O-CH$_2$-CO$_2$Et | (DMSO-d$_6$) δ 0.90(d, J=6.6 Hz, 6H), 1.37(s, 9H), 1.41–1.48(m, 2H), 1.59–1.66(m, 1H), 4.28–4.34(m, 2H), 4.59 (s, 2H), 5.05(s, 2H), 5.40(s, 2H), 6.76–6.80(dd, J=2.2, 7.9 Hz, 1H), 6.90–7.01(m, 4H), 7.09–7.26(m, 5H), 7.48 (d, J=7.4 Hz, 1H), 7.58(d, J=7.3 Hz, 1H) | 554 (MH$^+$) |
| 23f[a] | 4-ethyl-2-(OCH$_2$CO$_2$Et)-phenyl-CO$_2$Et | (DMSO-d$_6$) δ 0.91(d, J=5.3 Hz, 6H), 1.17(d, J=7.1 Hz, 3H), 1.30(d, J=7.1 Hz, 3H), 1.48–1.60(m,2H), 1.61–1.75(m, 1H), 4.07(q, J=7.2 Hz, 2H), 4.22(q, J=6.9 Hz, 2H), 4.43(t, J=7.8 Hz, 2H), 4.82(s, 2H), 5.12(s, 2H), 5.58(s, 2H), 7.00–7.01(m, 2H), 7.10–7.23(m, 2H), 7.30–7.43(m, 5H), 7.60 (d, J=7.5 Hz, 1H), 7.68–7.73(m, 2H) | 641 (MH$^+$) |
| 23g[a] | 4-ethyl-2-OMe-phenyl-CO$_2$Me | (DMSO-d$_6$) δ 0.90(d, J=6.5 Hz, 6H), 1.41–1.55(m, 2H), 1.49–1.67(m, 1H), 3.75(s, 3H), 3.79(s, 3H), 4.82(t, J=7.6 Hz, 2H), 5.16(s, 2H), 5.43(s, 2H), 6.88(d, J=8.0 Hz, 1H), 6.99–7.04(m, 2H), 7.15–7.26(m, 5H), 7.53(d, J=8.4 Hz, 1H), 7.58(d, J=7.9 Hz, 2H) | 512 (MH$^+$) |

TABLE 2-continued

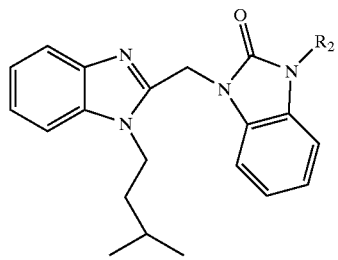

Compounds listed below were prepared by alkylation of compound 6 as described for the preparation of compound 7.

| # | $R_2$ | $^1$H-NMR Data | MS Data |
|---|---|---|---|
| 23h[a] | 2-ethyl-3-nitro-6-(methoxycarbonyl)phenyl | (DMSO-$d_6$) δ 0.89(d, J=6.6 Hz, 6H), 1.38–1.45(m, 2H), 1.56–1.64(m, 1H), 3.64(s, 3H), 4,24(t, J=7.8 Hz, 2H), 5.30(s, 2H), 5.49(s, 2H), 6.88–6.91 (m, 1H), 6.91–7.02(m, 2H), 7.15–7.27 (m, 3H), 7.50(d, J=7.8 Hz, 1H), 7.60 (d, J=8.1 Hz, 1H), 7.71(t, J=7.8 Hz, 1H), 7.99(d, J=6.9 Hz, 1H), 8.08(d, J= 8.4 Hz, 1H) | 527 (MH$^+$) |
| 23i[a] | 4-ethyl-3-nitro-(methoxycarbonyl)phenyl | (DMSO-$d_6$) δ 0.93(d, J=6.3 Hz, 6H), 1.42–1.58(m, 2H), 1.60–1.78(m, 1H), 3.91(s, 3H), 4.36(t, J=7.5 Hz, 2H), 5.48(s, 2H), 5.59(s, 2H), 6.99–7.10 (m, 2H), 7.12–7.30(m, 4H), 7.35(d, J= 7.2 Hz, 1H), 7.55(d, J=7.5 Hz, 1H), 7.63(d, J=7.8 Hz, 1H), 8.18(dd, J= 1.5, 7.9 Hz, 1H), 8.63(d, J=1.5 Hz, 1H) | 527 (MH$^+$) |
| 23j[a] | 4-ethyl-cyanophenyl | (DMSO-$d_6$) δ 0.89(d, J=6.6 Hz, 6H), 1.40–1.50(m, 2H), 1.58–1.65(m, 1H), 4.31(t, J=7.8 Hz, 2H), 5.22(s, 2H), 5.43(s, 2H), 6.95–7.10(m, 2H), 7.10–7.18(m, 4H), 7.42–7.56(m, 3H), 7.60 (d, J=7.5 Hz, 1H), 7.83(d, J=8.4 Hz, 2H) | 449 (MH$^+$) |
| 23k[d] | 3-ethyl-benzaldehyde | (CDCl$_3$) δ 0.95(d, J=6.5 Hz, 6H), 1.42–1.51(m, 2H), 1.63–1.78(m, 1H), 4.41(t, J=8.4 Hz, 2H), 5.18(s, 2H), 5.59(s, 2H), 6.88–6.89(m, 1H), 7.02–7.08(m, 2M), 7.36–7.38(m, 3H), 7.51–7.62(m, 3H), 7.80–7.87(m, 3H), 10.0 (s, 1H) | 453 (MH$^+$) |
| 23l[d] | 4-ethyl-N,N-dimethylsulfonamidophenyl | (CD$_3$OD) δ 0.95(d, J=6.5 Hz, 6H), 1.61–1.66(m, 3H), 2.65(s, 6H), 4.50–4.53(m, 2H), 5.27(s, 2H), 5.70(s, 2H), 7.14–7.17(m, 3H), 7.25–7.28(m, 1H), 7.53–7.64(m, 4H), 7.71–7.79(m, 4H) | 532 (MH$^+$) |
| 23m[d] | 4-ethyl-methylsulfonylphenyl | (CD$_3$OD) δ 0.95(d, J=6.5 Hz, 6H), 1.61–1.66(m, 3H), 2.65(s, 6H), 4.50–4.53(m, 2H), 5.27(s, 2H), 5.70(s, 2H), 7.14–7.17(m, 3H), 7.25–7.28(m, 1H), 7.53–7.64(m, 4 H), 7.71–7.79(m, 4H) | 503 (MH$^+$) |
| 23n[c] | ethyl-P(O)(OiPr)$_2$ | (DMSO-$d_6$) δ 0.93(d, J=5.5 Hz, 6H), 1.15(d, J 6.2Hz, 6H), 1.19(d, J= 6.2 Hz, 6H), 1.46–1.53(m, 2H), 1.61–1.67(m, 1H), 4.29–4.34(s, 2H), 4.35 (s, 2H), 4.52–4.62(m, 2H), 5.37(s, 2H), 6.98–7.07(m, 2H), 7.09–7.26(m, 4H), 7.48–7.56(m, 2H) | 512 (MH$^+$) |

TABLE 2-continued

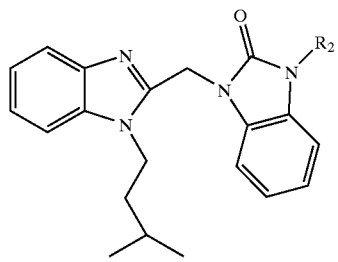

23

Compounds listed below were prepared by alkylation of compound 6 as described for the preparation of compound 7.

| # | R₂ | ¹H-NMR Data | MS Data |
|---|---|---|---|
| 23o[c] | (phenylpentyl) | (DMSO-d₆) δ 0.89(d, J=6.6 Hz, 6H), 1.22–1.42(m, 4H), 1.58–1.74(m, 3H), 1.91–2.01(m, 2H), 3.88(t, J=6.9 Hz, 2H), 4.29(t, J=8.1Hz, 2H), 4.58(t, J=8.1 Hz, 2H), 5.35(s, 2H), 6.98–7.07 (m, 2H), 7.14–7.30(m, 4H), 7.49(d, J=7.7 Hz, 1H), 7.58(d, J=7.4 Hz, 1H), 8.12(t, J=7.1Hz, 2H), 8.56(t, J =7.9 Hz, 1H), 9.04(d, J=5.5 Hz, 2H) | 482 (MH⁺) |
| 23p[c] | ∼∼CH₃ | (CDCl₃) δ 0.85(d, J=6.6Hz, 6H), 1.06(t, J=7.4 Hz, 3H), 1.34–1.41(m, 2H), 1.61–1.86(m, 3H), 3.87(t, J=7.3 Hz, 2H), 4.25–4.31(m, 2H), 5.53(s, 2H), 6.95–7.08(m, 3H), 7.23–7.31(m, 3H), 7.40(dd, J=0.6, 1.6 Hz, 1H), 7.77–7.80(m, 1H) | 377 (MH⁺) |
| 23q[e] | ∼∼N(CH₃)₂ | (CDCl₃) δ 0.93(d, J=6.6 Hz, 6H), 1.36–1.43(m, 2H), 1.60–1.73(m, 1H), 2.08–2.20(m, 2H), 2.40(s, 6H), 2.54(t, J=6.9 Hz, 2H), 4.00(t, J=6.9 Hz, 2H), 4.26(t, J=6.9 Hz, 2H), 5.38(s, 2H), 6.90–7.10(m, 3H), 7.22–7.31(m, 3H), 7.37–7.40(m, 1H), 7.74–7.80(m, 1H) | 420 (MH⁺) |
| 23r[b] | ∼∼N(CH₃)₂ | (CDCl₃) δ 0.95(d, J=6.6 Hz, 6H), 1.35–1.43(m, 2H), 1.64–1.75(m, 1H), 2.36(s, 6H), 2.67(t, J=7.2 Hz, 2H), 4.05(t, J=7.2 Hz, 2H), 4.27–4.32(m, 2H), 5.42(s, 2H), 7.00–7.11(m, 3H), 7.28–7.34(m, 3H), 7.40–7.43(m, 1H), 7.79–7.83(m, 1H) | 406 (MH⁺) |
| 23s[b] | ∼∼CO₂tBu | (CDCl₃) δ 0.96(d, J=6.6 Hz, 6H), 1.41(s, 9H), 1.65–1.74(m, 1H), 2.72(t, J=7.5 Hz, 2H), 4.18(t, J=7.4 Hz, 2H), 4.27–4.33(m, 2H), 5.40(s, 2H), 6.99–7.09(m, 3H), 7.25–7.31(m, 3H), 7.43(d, J=7.4 Hz, 1H), 7.78–7.81(m, 1H) | 463 (MH⁺) |
| 23t[b] | ∼∼CO₂Me | (CDCl₃) δ 0.95(d, J=6.6 Hz, 6H), 1.26(t, J=7.1 Hz, 3H), 1.36–1.44(m, 2H), 1.65–1.74(m, 1H), 2.06–2.15(m, 2H), 2.43(t, J=7.2 Hz, 2H), 3.98(t, J= 7.2 Hz, 2H), 4.14(q, J=7.1 Hz, 2H), 4.28–4.33(m, 2H), 5.42(s, 2H), 7.00–7.11(m, 3H), 7.28–7.34(m, 3H), 7.44 (d, J=7.2 Hz, 1H), 7.79–7.82(m, 1H) | 449 (MH⁺) |
| 23u[b] | ∼∼CO₂Me | (CD₃OD) δ 1.66–1.72(m, 2H), 1.83–1.88(m, 2H), 2.41(t, J=7.2 Hz, 2H), 3.14(s, 6H), 3.62(s, 3H), 3.87(t, J= 8.0 Hz, 2H), 4.02(t, J=6.8 Hz, 2H), 5.19(t, J=7.8 Hz, 2H), 5.86(s, 2H), 7.22–7.34(m, 3H), 7.45–7.48(m, 1H), 7.67–7.79(m, 3H), 8.11(d, J=8.0 Hz, 1H) | 450 (MH⁺) |

TABLE 2-continued

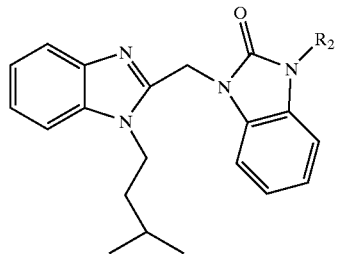

23

Compounds listed below were prepared by alkylation of compound 6 as described for the preparation of compound 7.

| # | R₂ | ¹H-NMR Data | MS Data |
|---|---|---|---|
| 23v[b] | ~~~~CN | (CDCl₃) δ 0.95(d, J=6.56 Hz, 6H), 1.26–1.88(m, 9H), 2.36(t, J=6.99, 2H), 3.94(t, d=7.05 Hz, 2H), 4.29(m, 2H), 5.41(s, 2H), 6.95–7.81(m, 8H) | 430 (MH⁺) |
| 23w[b] | (oxazolidinone-CH₂-CO₂Me) | (CD₃OD) δ 0.97(dd, J=2.8, 6.6 Hz, 6H), 1.36–1.64(m, 2H), 1.68–1.78(m, 1H), 3.67–3.72(m, 1H), 3.70(s, 3H), 3.84–3.87(m, 1H), 4.02(dd, J=18.0 Hz, 2H), 4.28–4.87(m, 2H), 5.01–5.12(m, 1H), 5.47(dd, J=16.3, 22.1 Hz, 2H), 7.05–7.17(m, 3H), 7.28–7.33(m, 3H), 7.49(d, J=7.3 Hz, 1H), 7.65 (d, J=7.1 Hz, 1H) | 506 (MH⁺) |

[a]Cs₂CO₃ used as base;
[b]BEMP used as base;
[c]BTPP used as base;
[d]prepared as described in J. Am. Chem. Soc. 1991, 4208;
[e]NaH used as base.

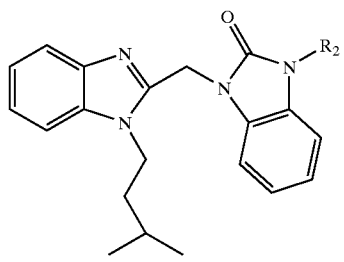

24

TABLE 3

Compounds were prepared by convering the acetic acid or benzoic acid to an acid chloride with SOCl₂ or oxalyl chloride and treating the acid chloride with corresponding amine unless otherwise noted.

| # | R₂ | ¹H-NMR Data | MS Data |
|---|---|---|---|
| 24a | (piperidine-CO-CH(CO₂Et)-propyl) | (DMSO-d₆) δ 0.92(d, J=6.5 Hz, 6H), 1.15–1.28(m, 5H), 1.38–1.60(m, 2H), 1.60–1.75(m, 3H), 1.99–2.20(m, 1H), 2.20–2.30(m, 1H), 3.98–4.04(m, 1H), 4.11 (q, J=7.0 Hz, 2H), 4.18–4.31(m, 2H), 4.62–4.84(m, 1H), 4.91–5.00(m, 2H), 5.37 (s, 2H), 6.95–7.10(m, 3H), 7.15–7.26(m, 3H), 7.50(d, J=8.0 Hz, 1H), 7.60(d, J=7.4 Hz, 1H) | 531 (MH⁺) |

TABLE 3-continued

Compounds were prepared by convering the acetic acid or benzoic acid to an acid chloride with SOCl$_2$ or oxalyl chloride and treating the acid chloride with corresponding amine unless otherwise noted.

| # | R$_2$ | $^1$H-NMR Data | MS Data |
|---|---|---|---|
| 24b | | (DMSO-d$_6$) δ 0.90(dd, J=2.8, 6.5 Hz, 6H), 1.35–1.45(m, 2H), 1.47–1.71(m, 1H), 3.17(s, 3H), 4.00–4.21(m, 1H), 4.32 (t, J=7.2 Hz, 2H), 4.71(s, 1H), 4.86(s, 1H), 5.40(d, J=4.9 Hz, 2H), 6.92(t, J= 7.0 Hz, 1H), 6.99–7.07(m, 2H), 7.16–7.34 (m, 3H), 7.50(d, J=7.9 Hz, 1H), 7.59–7.65(m, 1H), 7.88(d, J=6.5 Hz, 1H), 7.95(d, J=7.6 Hz, 1H), 8.19(d, J=8.1 Hz, 1H), 8.35(d, J=7.4 Hz, 1H) | 525 (MH$^+$) |
| 24c | | (DMSO-d$_6$) δ 0.90(d, J=6.6 Hz, 6H), 1.30(t, J=7.1 Hz, 3H), 1.35–1.55(m, 2H), 1.61–1.75(m, 1H), 4.26–4.33(m, 4H), 4.79 (m, 2H), 5.39(m, 2H), 7.02–7.06(m, 2H), 7.16–7.28(m, 5H), 7.40–7.55(m, 2H), 7.56–7.72(m, 2H), 7.80–7.81(m, 1H), 8.26 (s, 1H) | 539 (MH$^+$) |
| 24d | | (DMSO-d$_6$) δ 0.90(d, J=6.6 Hz, 6H), 1.30(t, J=7.1 Hz, 3H), 1.40–1.44(m, 2H), 1.51–1.67(m, 1H), 4.24–4.34(m, 3H), 4.81 (s, 2H), 5.40(s, 2H), 7.03–7.05(m, 2H), 7.08–7.26(m, 4H), 7.50(d, J=7.6 Hz, 1H), 7.62(d, J=7.5 Hz, 1H), 7.72(d, J= 8.7 Hz, 2H), 7.92(d, J=8.7 Hz, 2H) | 540 (MH$^+$) |
| 24e | | (CDCl$_3$) δ 0.94(d, J=6.54 Hz, 6H), 1.48 (m, 1H), 1.66(m, 1H), 3.17(s, 3H), 4.03 (m, 1H), 4.42(m, 3H), 5.34(m, 2H), 6.55 (m, 1H), 6.69(d, J=7.68 Hz, 1H), 7.11 (m, 1H), 7.34(m, 5H), 7.55(t, J=7.65 Hz, 1H), 7.66(t, J=7.56 Hz, 1H), 7.88(d, J=9.06 Hz, 1H), 8.29(d, J=7.65 Hz, 1H) | 526 (MH$^+$) |
| 24f | | (CDCl$_3$) δ 0.95(d, J=8.78 Hz, 6H), 1.48 (m, 2H), 1.64(m, 1H), 4.32(m, 2H), 4.76 (s, 2H), 5.44(s, 2H), 7.07–7.76(m, 11H), 8.24(d, J=Hz, 1H), 8.66(s, 1H) | 493 (MH$^+$) |
| 24g | | (CDCl$_3$) δ 0.96(d, J=6.6 Hz, 6H, 1.52–1.69(m, 3H), 3.28(s, 3H), 4.37(m, 4H), 5.52(s, 2H), 6.83–7.89(m, 12H) | 516 (MH$^+$) |
| 24h | | (CDCl$_3$) δ 0.80(d, J=6.6 Hz, 6H), 1.37 (m, 2H), 1.56(m, 1H), 4.18(m, 2H), 4.61 (s, 1H), 5.33(s, 1H), 6.29(m, 1H), 6.46 (m, 1H), 6.58(m, 1H), 6.89–7.33(m, 8H),7.65(m, 1H) | 524 (MH$^+$) |
| 24i | | (CDCl$_3$) δ 0.97(d, J=6.57 Hz, 6H), 1.29–1.69(m, 3H), 3.84(s, 3H), 4.32(m, 2H), 4.72(s, 1H), 5.46(s, 1H), 6.55(d, J=3.66 Hz, 1H), 6.91–7.43(m, 8H, 7.77(m, 1H) | 516 (MH$^+$) |
| 24j | | (CDCl$_3$) δ 0.96(d, J=6.51 Hz, 6H), 1.25 J=7.14 Hz, 3H), 1.38(m, 2H), 1.55 (m, 1H), 3.65(s, 2H), 4.06(q, J=7.14 Hz, 2H), 4.30(m, 2H), 4.81(s, 2H), 5.42(s, 2H), 6.80(s, 1H), 7.00–7.61(m, 4H), 7.74(m, 1H) | 561 (MH$^+$) |

TABLE 3-continued

Compounds were prepared by convering the acetic acid or benzoic acid to an acid chloride with SOCl₂ or oxalyl chloride and treating the acid chloride with corresponding amine unless otherwise noted.

| # | R₂ | ¹H-NMR Data | MS Data |
|---|---|---|---|
| 24k | [propionamide-thiadiazole structure] | (CDCl₃) δ 0.99(d, J=6.6 Hz, 6H), 1.57 (m, 2H), 1.74(m, 1 H), 4.35(m, 2H), 5.08 (s, 2H), 5.52(s, 2H), 7.00–7.45(m, 7H), 7.82(m, 1H), 8.82(s, 1H) | 476 (MH⁺) |
| 24l[a] | [propionamide-tetrazole structure] | (DMSO-d₆) δ 0.90–0.98(m, 6H), 1.15–1.23 (m, 2H), 1.60–1.72(m, 1H), 4.28–4.35(m, 2H), 5.38(s, 2H), 6.95–7.03(m, 3H), 7.15–7.29(m, 3H), 7.47–7.51(m, 1H), 7.51–7.63 (m, 1H) | 459 (MH⁺) |
| 24m | [propionamide-benzyl phosphonate diethyl ester structure] | (CDCl₃) δ 0.96(d, J=6.57 Hz, 6H), 1.25 (t, J=7.05 Hz, 6H), 1.56(m, 1H), 1.72 1H), 3.10(d, J=21.45 Hz, 2H), 3.99 (m, 4H), 4.29(m, 2H), 4.59(s, 2H), 5.40 (s, 2H), 7.05–7.37(m, 9H), 7.46(d, J= 8.19 Hz, 2H), 7.73(m, 1H), 8.83(s, 1H) | 618 (MH⁺) |

[a]prepared using EDC as coupling reagent.

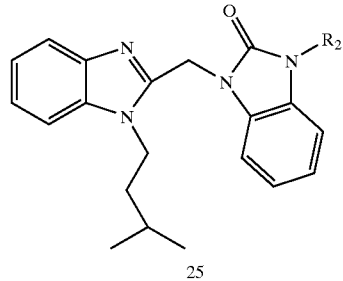

25

TABLE 4

Acids were prepared by hydrolysis of the corresponding ester using NaOH/MeOH as previously described for compound 8.

| # | R₂ | ¹H-NMH Data | MS Data |
|---|---|---|---|
| 25a | [aspartate-ethylbenzamide structure] | (DMSO-d₆) δ 0.87(d, J=6.5 Hz, 6H), 1.38–1.52(m, 2H), 1.58–1.63(m, 1H), 3.38–3.48(m, 1H), 4.24–4.33(m, 2H), 4.38(s, 2H), 5.29(s, 2H), 5.41(d, J=4.3 Hz, 2H), 6.89–7.00(m, 2H), 7.06–7.10(m, 2H), 7.12–7.24(m, 5H), 2H), 5.41(d, J=4.3 Hz, 2H), 6.89–7.00(m, 7.46–7.58(m, 3H) | 629 (MH⁺) |
| 25b | [cyclohexane carboxylic acid-ethylbenzamide structure] | (DMSO-d₆) δ 0.90(d, J=6.5 Hz, 6H), 0.97–1.06(m, 2H), 1.14–1.29(m, 2H), 1.46–1.53(m, 3H), 1.62–1.69(m, 1H), 1.80–1.98(m, 4H), 2.09–2.17(m, 1H), 3.13(t, J=6.2 Hz, 2H), 4.40(t, J=8.0 Hz, 2H), 5.22(s, 2H), 5.56(s, 2H), 7.00–7.09(m, 4H), 7.28–7.38(m, 5H), 7.46–7.49(m, 1H), 7.68(d, J=7.8 Hz, 2H), 8.58(t, J=5.7 Hz, 1H) | 608 (MH⁺) |

TABLE 4-continued

Acids were prepared by hydrolysis of the corresponding ester using NaOH/MeOH as previously described for compound 8.

| # | R$_2$ | $^1$H-NMH Data | MS Data |
|---|---|---|---|
| 25c | 4-ethylbenzoyl-NH-CH(CO$_2$H)-CH$_2$-P(O)(OH)$_2$ | (CD$_3$OD) δ 0.90(d, J=6.6 Hz), 1.36–1.43(m, 2H), 1.59–1.69(m, 1H), 1.99–2.18(m, 2H), 4.30–4.37(m, 2 ), 4.46–4.57(m, 1H), 5.22(s, 2 H), 5.49(s, 2H), 6.98–7.09(m, 3H), 7.15–7.19 (m, 1H), 7.25–7.38(m, 2H), 7.42–7.51(m, 3H), 7.64–7.69(m, 1H), 7.89(d, J=8.4 Hz, 2H) | 664 (MH$^+$) |
| 25d | 4-ethyl-2-methoxy-benzoic acid (OMe, CO$_2$H) | (DMSO-d$_6$) δ 0.91(d, J=6.6 Hz, 6H), 1.40–1.45(m, 2H), 1.58–1.65(m, 1H), 3.79(s, 3H), 4.25–4.38(m, 2H), 5.16(s, 2H), 5.44(s, 2H), 6.87(d, J=8.1 Hz, 1H), 7.02–7.12(m, 2H), 7.16–7.30(m, 4H), 7.52(d, J=7.8 Hz, 1H), 7.58(d, J=8.1 Hz, 2H) | 498 (MH$^+$) |
| 25e | 2-ethyl-3-(methanesulfonamido)-benzoic acid | (DMSO-d$_6$) δ 0.89(d, J=6.6 Hz, 6H), 1.35–1.42(m, 2H), 1.58–1.60(m, 1H), 2.98(s, 3H), 4.25–4.39(m, 2H), 5.38(s, 2H), 5.42(s, 1H), 5.81(s, 2H), 6.95–7.12(m, 2H), 7.12–7.32(m, 3H), 7.35–7.73(m, 3H) | 561 (MH$^+$) |
| 25f | 5-ethyl-isophthalic acid | (CD$_3$OD) δ 0.91(d, J=6.6 Hz, 6H), 1.40–1.47 (m, 2H), 1.59–1.65(m, 1H), 4.37(t, J=8.0 Hz, 2H), 5.27(s, 2H), 5.52(s, 2H), 7.01–7.14(m, 3H), 7.18–7.20(m, 1H), 7.28–7.33(m, 2H), 7.48(d, J=7.5 Hz, 1H), 7.66–7.69(m, 1H), 8.12(s, 2H), 8.56(d, J=1.4 Hz, 1H) | 513 (MH$^+$) |
| 25g | 5-ethyl-2-(carboxymethyl)-tetrazole | (DMSO-d$_6$) δ 0.89(d, J=6.6 Hz, 6H), 1.32–1.48(m, 2H), 1.51–1.71(m, 1H), 4.27–4.35(m, 2H), 4.78–4.85(s, 2H), 5.27–5.45(s, 2H), 6.92–7.05(m, 2H), 7.10–7.28(m, 4H), 7.50(d, J=7.9 Hz, 1H), 7.58–7.62(m, 1H) | 474 (MH$^+$) |
| 25h | 1-propanoyl-piperidine-4-carboxylic acid | (DMSO-d$_6$) δ 0.92(d, J=6.6 Hz, 6H), 1.35–1.51(m, 4 H), 1.52–1.68(m, 2H), 1.69–1.82 (m, 2H), 1.92–2.10(m, 1H), 2.62–2.82(m, 1H), 3.08–3.18(m, 1H), 3.71–3.88(m, 1H), 3.90–4.02(m, 1H), 4.29–4.36(m, 2H), 4.77–4.85(m, 1H), 5.36(s, 2H), 7.01–7.16(m, 3H), 7.18–7.28 (m, 3H), 7.49(d, J=7.6 Hz, 1H), 7.61(d, J=7.3 Hz, 1H) | 503 (MH$^+$) |
| 25i | 1-propanoyl-piperidine-3-carboxylic acid | (DMSO-d$_6$) δ 0.89–0.93(m, 6H), 1.34–1.48(m, 4H), 1.58–1.68(m, 2H), 1.72–1.93(m, 1H), 1.95–2.10(m, 1H), 3.10–3.25(m, 1H), 3.25–3.50(m, 2H), 3.70–3.82(m, 1H), 4.20–4.35(m, 2H), 4.61–4.79(m, 2H), 5.20–5.42(m, 2H), 6.82–7.01(m, 3H), 7.15–.26(m, 3H), 7.48(d, J=8.4 Hz, 1H), 7.62(d, J=8.1 Hz, 1H) | 503 (MH$^+$) |
| 25j | 1-propanoyl-piperidine-2-carboxylic acid | (DMSO-d$_6$) δ 0.90–0.93(m, 6H), 1.23–1.65(m, 8H), 2.27–2.32(m, 1H), 2.51–2.71(m, 1H), 4.02–4.15(m, 2H), 4.28–4.38(m, 2H), 4.50–4.59(m, 1H), 4.76–4.83(m, 1H), 5.36(s, 2H), 6.96–6.99(m, 2H), 7.08–7.26(m, 3H), 7.49(d, J=7.4 Hz, 1H), 7.62(d, J=7.4 Hz, 1H), 7.82 (d, J=7.4 Hz, 1H) | 503 (MH$^+$) |
| 25k | pentanoic acid (n-butyl-CO$_2$H) | (DMSO-d$_6$) δ 0.89(d, J=6.6 Hz, 6H), 1.30–1.37(m, 2H), 1.58–1.64(m, 1H), 1.76–1.83(m, 2H), 1.91(t, J=6.9 Hz, 2H), 3.85(t, J=7.2 Hz, 2H), 4.29(t, J=8.0 Hz, 2H), 5.36(s, 2H), 6.95–7.06(m, 2H), 7.15–7.26(m, 3H), 7.34(d, J=7.4 Hz, 1H), 7.48(d, J=7.5 Hz, 1H), 7.61 (d, J=7.4 Hz, 1H) | 421 (MH$^+$) |

TABLE 4-continued

Acids were prepared by hydrolysis of the corresponding ester using NaOH/MeOH as previously described for compound 8.

| # | R$_2$ | $^1$H-NMH Data | MS Data |
|---|---|---|---|
| 25l | ~~~~CO$_2$H | (DMSO-d$_6$) δ 0.89(d J=6.6 Hz, 6H), 1.32–1.42(m, 2H), 1.44–1.52(m, 2H), 1.59–1.67(m, 3H), 1.97(t, J=6.9 Hz, 2H), 3.35(t, J=6.2 Hz, 2H), 3.85(t J=6.9 Hz, 2H), 4.26–4.32(m, 2H), 5.36(s, 2H) 6.96–7.07(m, 2H), 7.15–7.26 (m, 4H), 7.48(d J=7.5 Hz, 1H), 7.60(d, J=7.2 Hz, 1H) | 435 (MH$^+$) |
| 25m | ~~~~CO$_2$H | (CD$_3$OD) δ 0.94(d J=6.6 Hz, 6H), 1.31–1.51 (m, 4H), 1.64–1.74(m 3H), 1.78–1.88(m, 2H), 2.19(t, J=7.6 Hz, 2H) 3.98(t, J=7.3 Hz, 2H), 4.34(t, J=8.2 Hz 2H), 5.45(s, 2H), 7.01–7.06(m, 1H), 7.10–7.35(m, 5H), 7.47 (dd, J=1.7, 6.9 Hz 1H),7.67(dd, J=1.7, 6.8 Hz, 1H) | 449 (MH$^+$) |
| 25n | ethyl-oxazolidinone-CH$_2$CO$_2$H | (CD$_3$OD) δ 0.94(d, J=6.3Hz, 6H), 1.39–1.48 (m, 2H), 1.62–1.70(m, 1H), 3.58–3.63(m, 1H), 3.76(s, 2H), 3.88(t, J=9.3Hz, 1H), 4.19–4.23 (m, 1H), 4.29–4.41(m, 2H), 4.91–5.02(m, 2H), 5.44(s, 2H), 7.03–7.16(m, 3H), 7.26–7.33(m, 2H), 7.37(d, J=7.5 Hz, 1H), 7.46(d, J=7.2 Hz, 1H), 7.63(d, J=7.2 Hz, 1H) | 492 (MH$^+$) |

26

TABLE 5

Phosphonates

| # | R$_2$ | $^1$H-NMR Data | MS Data |
|---|---|---|---|
| 26a[a] | ~~~P(O)(OEt)$_2$ | (DMSO d$_6$) δ 0.92(d, J=6.6 Hz, 6H), 1.15(t, J=7.0 Hz 6H), 1.38–1.46(m, 2H), 1.63–1.68(m, 1H), 2.17–2.28(m, 2H), 3.90–3.98(m, 4H), 4.00–4.11(m, 2H), 4.28 4 34(m, 2H), 5.35(s, 2H), 6.98–7.09(m, 2H) 7.15–7.24(m, 4H), 7.50(d J=7.5 Hz, 1H), 7.59(d, J= 7.4 Hz, 1H) | 498 (MH$^+$) |
| 26b[b] | ~~~O~P(O)(OiPr)$_2$ | (CDCl$_3$) δ 0.96(d, J=6.7 Hz, 6H), 1.21(d J=6.2 Hz, 6H), 1.27(d, J= 6.2 Hz, 6H) 1.31–1.46(m, 2H), 1.66–1.75(m 1H) 3.74(d, J=8.4 Hz, 2H), 3.92(t, J=5.4 Hz, 2H), 4.14(t, J=5.4 Hz, 2H), 4.33(t, J=8.2 Hz, 2H), 4.60–4.71(m, 2H), 5.43(s, 2H), 7.02–7.16 (m, 3H), 7.29–7.32(m, 3H), 7.44(d, J=7.3 Hz, 1H), 7.80–7.84(m, 1H) | 557 (MH$^+$) |

[a]prepared by 1,4-addition to diethylvinyl phosphonate;
[b]alklyation using methanesulfonic acid 2-(diisopropoxy-phosphorylmethoxy)-ethyl ester.

TABLE 5-continued

Phosponates

| # | R$_2$ | $^1$H-NMR Data | MS Data |
|---|---|---|---|

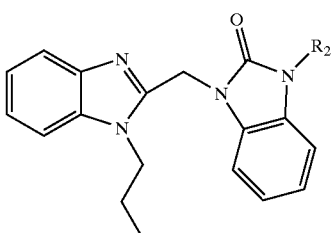

27

TABLE 5

Phosphonate esters were cleaved with TMSBr.

| # | R$_2$ | $^1$H-NMR Data | MS Data |
|---|---|---|---|
| 27a | (propyl-P(O)(OH)$_2$) | (CDCl$_3$) δ 0.80(d, J=6.6 Hz, 6H), 1.12–1.22 (m, 2H), 1.47–1.53(m, 2H), 1.54–1.70(m, 2H), 3.90–4.05(m, 2H), 4.19–4.24(m, 2H), 5.31(s, 2H), 6.95(t, J=8.5 Hz, 1H), 7.05(t, J=7.7 Hz, 1H), 7.12–7.31(m, 4H), 7.43(d, J=7.2 Hz, 1H), 7.58(d, J=7.2 Hz, 1H) | 442 (MH$^+$) |
| 27b | (propyl-O-CH$_2$-P(O)(OH)$_2$) | (CD$_3$OD) δ 0.95(d, J=6.7 Hz, 6H), 1.36–1.44(m, 2H), 1.62–1.74(m, 1H), 3.56(d, J=8.9 Hz, 2H), 3.88(t, J=5.3 Hz, 2H), 4.23(t, J=5.4 Hz, 2H), 4.35(t, J=8.1 Hz, 2H), 5.47(s, 2H), 6.97–7.05(m, 1H), 7.08–7.17 (m, 2H), 7.23–7.34(m, 3H), 7.47(d, J=7.3 Hz, 1H), 7.63–7.68(m, 1H) | 473 (MH$^+$) |

Compound 28

28

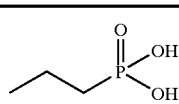

Compound 6 (4.01 g, 12 mmol) in CH$_2$Cl$_2$ (60 mL) was slowly added to a suspension of α,α'-dibromo-p-xylene (15.84, 60 mmol) and BTPP (9.9 g, 18 mmol) in a mixture of methylene chloride and THF (120 mL, 1:1). The resulting mixture was stirred at room temperature for 1 h. The solvent was evaporated and the residue was purified by flash chromatography (EtOAc: hexane=1:4 to 2:1) to give a product which was triturated in EtOAc/Et$_2$O to provide 4.12 g (66% yield) of the compound 28 as a white solid:

$^1$H NMR (DMSO-d$_6$) δ0.91 (d, J=6.6 Hz, 6H), 1.41–1.49 (m, 2H), 1.60–1.67 (m, 1H), 4.32 (t, J=7.5 Hz, 2H), 4.68 (s, 2H), 5.12 (s, 2H), 5.43 (s, 2H), 7.00–7.04 (m, 2H), 7.15–7.22 (m, 4H), 7.35 (d, J=8.1 Hz, 2H), 7.42 (d, J=8.1 Hz, 2H) 7.52 (d, J=7.8 Hz, 1H), 7.61 (d, J=7.8 Hz, 1H); MS m/e 519, 517 (MH$^+$); Anal. Calcd for C$_{28}$H$_{29}$BrN$_4$O: C, 64.99; H, 5.65; N, 10.83 Found: C, 64.97; H, 5.50; N, 10.57

Compound 29

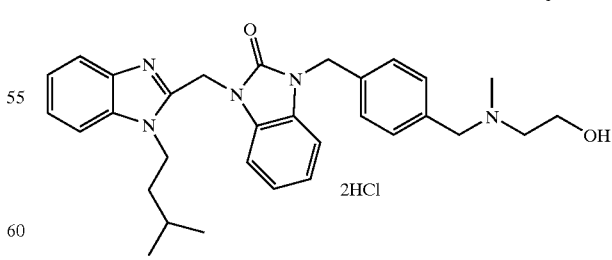

2HCl

Bromide 28 (103 mg, 0.2 mmol) and N-methylaminoethanol (75 mg, 1 mmol) were stirred in methanol (3 mL) overnight. The solvent was evaporated. The residue was diluted with EtOAc, washed with water, dried over MgSO$_4$, and evaporated. To the resulting residue in methanol (2 mL) was added 1N HCl in ether (2 mL). The solvent was evaporated and the residue was dried in vaccum. The solid was triturated in Et$_2$O to give 99 mg (80% yield) of compound 29 as white powder:

$^1$H NMR (DMSO-d$_6$) δ0.90 (d, J=6.5 Hz, 6 H), 1.22–1.38 (m, 2 H), 1.49–1.71 (m, 1 H), 2.66 (d, J=4.8 Hz, 2 H), 2.97–3.08 (m, 2 H), 3.74 (t, J=5.6 Hz, 2 H), 4.24 (dd, J=5.4, 13.0 Hz, 1 H), 4.34 (dd, J=5.1, 13.0 Hz, 1 H), 4.46 (bt, J=7.8 Hz, 2 H), 5.15 (s, 2 H), 5.66 (s, 2 H), 7.03–7.09 (m, 2 H), 7.16–7.21 (m, 1 H), 7.35–7.52 (m, 5 H), 7.57 (d, J=8.1 Hz, 2 H), 7.74 (d, J=7.2 Hz, 1H), 7.81 (d, J=7.7 Hz, 1 H); IR (KBr, cm$^{-1}$) 3307, 2955, 2594, 1706, 1613, 1492, 1461, 1405, 750; MS m/e 512 (MH$^+$); Anal. Calcd for C$_{32}$H$_{40}$N$_5$O$_2$. 2HCl. H$_2$O C, 62.23; H, 7.18; N, 11.34 Found: C, 61.96; H, 6.91; N, 11.48.

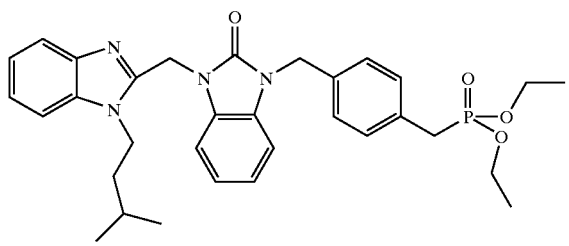

30

A mixture of bromide 28 (160 mg, 0.31 mmol) and triethyl phosphite (536 mg, 3.88 mmol) were stirred at 135° C. for 30 minutes. The mixture was cooled to room temperature, diluted with Et$_2$O, washed with water, dried over MgSO$_4$, and evaporated. The product was initially an oil that slowly crystallized on standing. The solid was filtered and rinsed with Et$_2$O to give 160 mg (90% yield) of compound 30:

$^1$H NMR (CDCl$_3$) δ0.95 (d, J=6.6 Hz, 6H), 1.21 (t, J=7.2 Hz, 6H), 1.41–1.49 (m, 2H), 1.66–1.75 (m, 1H), 3.11 (d, J=21.3 Hz, 2H), 3.93–4.04 (m, 4H), 4.33 (t, J=8.1 Hz, 2H), 5.08 (s, 2H), 5.45 (s, 2H), 6.82 (dd, J=2.1, 6.6 Hz, 1H), 6.94–7.03 (m, 2H), 7.29–7.33 (m, 2H), 7.43–7.46 (m, 1H), 7.79–7.82 (m, 1H) MS m/e 575 (MH$^+$).

Compound 31

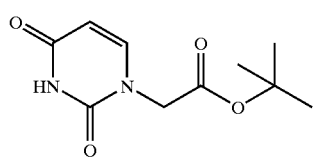

Uracil (5.0 g, 44.6 mmol) and potassium carbonate (7.4 g, 53.5 mmol) were suspended in DMF. t-butyl bromoacetate (9.1 g, 46.8 mmol) was added and the reaction mixture was stirred at 40–50° C. for 18 hours. The solvent was evaporated. The white residue was taken up in water and extracted with EtOAc and CHCl$_3$. The organic extracts were dried over MgSO$_4$ and evaporated. Column chromatography (gradient 2:1 EtOAc/hexanes to 10:1 EtOAc/MeOH) of the residue gave. 8.1 g (80% yield) of compound 31 as a white solid:

$^1$H NMR (CDCl$_3$) δ1.49 (s, 9 H), 4.37 (s, 2 H), 5.75 (dd, J 7.9, 2.0 Hz, 1 H), 7.11 (d, J=7.9 Hz, 1 H), 9.22 (s, 1H); IR (KBr, cm$^{-1}$)3051, 1745, 1715, 1681, 1460, 1234, 1151; MS m/e 325 (MH$^+$). Anal. Calcd for C$_{10}$H$_{14}$N$_2$O$_4$: C, 53.09; H, 6.24; N, 12.38 Found: C, 53.09; H, 6.26; N, 12.43.

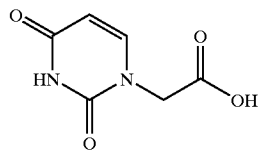

32

To ester 31 (30g, 132.6 mmol) in THF (20 ml) was added 4 N HCl in dioxane (250 mL). The resulting slurry was stirred for 1 day. The solvent was evaporated and the residue was triturated in Et$_2$O to give 21.81 g (97% yield) of compound 32 as a white solid:

$^1$H NMR (DMSO-d$_6$) δ4.41 (s, 2 H), 5.59 (d, J=7.8 Hz, 1 H), 7.61 (d, J=7.8 Hz, 1 H); MS m/e 171 (MH$^+$).

Compound 33

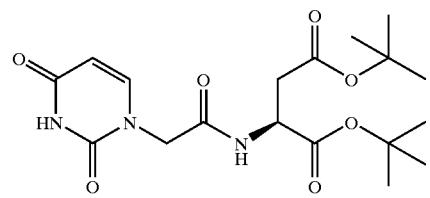

Compound 33 was prepared using the same procedure as for compound 16 with 32 and di-t-butyl aspartate:

$^1$H NMR (CDCl$_3$) δ1.26 (s, 18H), 2.53 (dd, J=4.2, 17.4 Hz, 1H), 2.71 (dd, J=4.8, 17.4 Hz, 1H), 4.20 (d, J=15.9 Hz, 1H), 4.32 (d, J=15.9 Hz, 1H), 4.48–4.50 (m, 1H), 5.55 (dd, J=1.5, 8.1 Hz, 1H), 7.01 (d, J=8.1 Hz, 1H), 8.70 (bs, 1H); MS m/e 398 (MH$^+$).

Compound 34

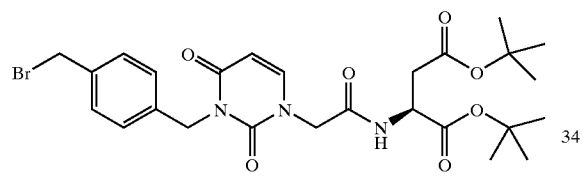

A mixture of 33 (39.0 g, 98.1 mmol), α,α'-dibromo-p-xylene (77.8 g, 294 mmol) and BTPP (36.8 g, 118 mmol) in THF (1 L) was stirred at room temperature for 1 h. After removal of the solvent, the residue was taken up in EtOAc (500 ml), washed with water, 1 N HCl and brine, dried over MgSO$_4$, and evaporated. The residue was purified by column chromatography eluted with EtOAc-hexanes (25% to 75%) to give 38.7 g (68% yield) of compound 34 as a white solid:

$^1$H NMR (DMSO-d$_6$) δ1.39 (s, 9H), 1.40 (s, 9H), 2.58–2.70 (m, 2H), 4.38 (s, 2H), 4.48–4.55 (m, 1H), 4.69 (s, 2H), 4.96 (s, 2H), 5.78–5.80 (m, 1H), 7.20–7.24 (m, 2 H), 7.38–7.40 (m, 2H), 7.64–7.66 (d, J=7.5 Hz, 2H), 8.64–8.66 (d, J=7.5 Hz, 2H); MS m/e 580/582 (MH$^+$); 468/470 [M−(t-Bu)$_2$$^+$].

Compound 35

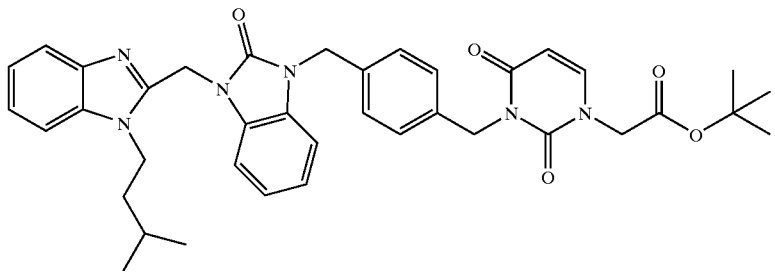

Compound 35 was prepared as described for compound 7 above.

$^1$H NMR (CDCl$_3$) δ0.96 (d, J=6.7 Hz, 6H), 1.44 (s, 9H), 1.51–1.74 (m, 3H), 4.32 (s, 2H), 4.43–4.49 (m, 2H), 5.06 (s, 2H), 5.08 (s, 2H), 5.71 (bs, 2H), 5.78 (d, j=7.9 Hz, 1H), 6.88 (d, J=8.0 Hz, 1H), 6.99–7.09 ((m, 2H), 7.05 (d, J=7.9 Hz, 1H), 7.24–7.28 (m, 4H), 7.39–7.44 (m, 4H), 7.95–8.01 (m, 1H); MS m/e 663 (MH$^+$).

Compound 36

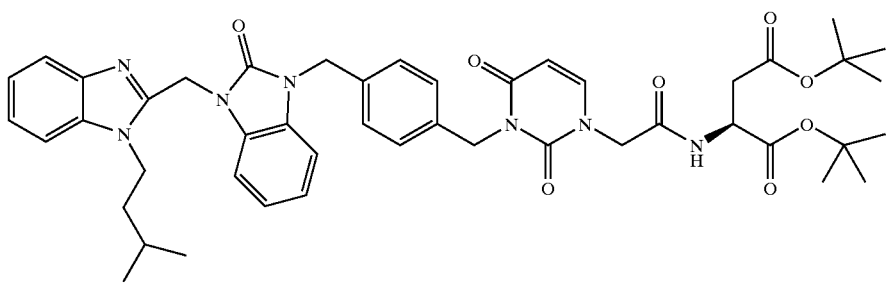

Compound 36 was prepared in 49% yield using the same procedure of compound 19 with compound 7 and bromide 34:

$^1$H NMR (CDCl$_3$) δ0.92 (d, J=6.7 Hz, 6H), 1.30–1.44 (m, 2H), 1.43 (s, 9H), 1.44 (s, 9H), 1.60–1.65 (m, 1H), 2.69 (dd, J=4.3 Hz, 17.1 Hz, 1H), 2.89 (dd, J=4.3, 17.1 Hz), 4.29 (d, J=15.8 Hz, 1H), 4.27–4.35 (m, 2H), 4.43 (d, J=15.8 Hz, 1H), 4.63–4.66 (m, 1H), 5.05 (s, 2H), 5.06 (s, 2H), 5.49 (s, 2H), 5.49 (s, 2H), 5.77 (d, J=7.8 Hz, 1H), 6.85–6.97 (m, 1H), 6.86–7.00 (m, 1H), 7.14 (d, J=7.8 Hz, 1H), 7.24–7.35 (m, 6H), 7.39 (d, J=8.3 Hz, 2H), 7.49 (d, J=7.3 Hz, 1H), 7.82–7.84 (m, 1H); MS m/e 834 (MH$^+$).

TABLE 7

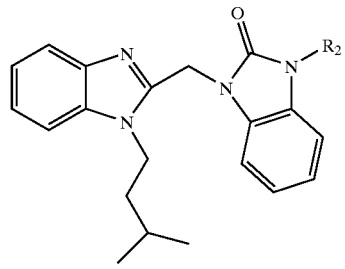

37

Compounds listed below were prepared by treating compound 28 with a nucleophile as described for compound 29.

| # | R$_2$ | $^1$H-NMRData | MSData |
|---|---|---|---|
| 37a | 3) | (DMSO-d$_6$)δ0.93(d, J=6.5Hz, 6H), 1.48–1.53(m, 2H), 1.63–1.69(m, 1H), 3.40–3.50(m, 2H), 4.13–4.19(m, 3H), 4.32–4.38(m, 3H), 5.13(s, 2H), 5.30 (b, 3H), 5.44(s, 2H), 6.99–7.02(m, 2H), 7.12–7.15(m, 1H), 7.18–7.30(m, 3H), 7.39–7.46(m, 4H), 7.54–7.60(m, 2H), 8.38–8.42(m, 2H) | 558(MH$^+$) |

TABLE 7-continued

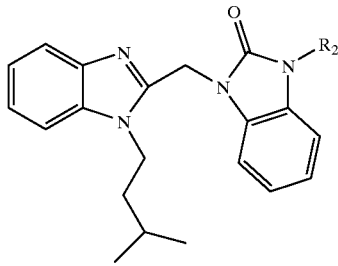

37

Compounds listed below were prepared by treating compound 28 with a nucleophile as described for compound 29.

| # | R$_2$ | $^1$H-NMR Data | MS Data |
|---|---|---|---|
| 37b | 4-ethylbenzyl-N(Et)$_3$$^+$ | (CD$_3$OD) δ 0.99(d, J=6.2Hz, 6H), 1.42(t, J=7.0Hz, 9H), 1.65–1.77(m, 3H), 3.21–3.29(m, 6H), 4.48(s, 2H), 4.58(t, J=7.6Hz, 2H), 5.25(s, 2H), 5.76(s, 2H), 7.17–7.18(m, 3H), 7.30–7.33(m, 1H), 7.56–67(m, 6H), 7.76–7.87(m, 2H) | 538(MH$^+$) |
| 37c | 4-ethylbenzyl-N(Me)$_2$(CH$_2$CH$_2$OH)$^+$ | (DMSO-d$_6$) δ 0.91(d, J=6.6Hz, 6H), 1.43–1.50(m, 2H), 1.60–1.67(m, 1H), 2.97(s, 6H), 3.34–3.40(m, 2H), 3.84–3.93(m, 2H), 4.32(t, J=8.0Hz, 2H), 4.54(s, 2H), 5.17(s, 2H), 5.31(t, J=4.8Hz, 1H), 5.42(s, 2H), 7.00–7.05(m, 2H), 7.15–7.27(m, 4H), 7.47–7.59(m, 4H) | 526(MH$^+$) |
| 37d | 4-ethylbenzyl-N-methylmorpholinium | (DMSO-d$_6$) δ 0.92(d, J=6.6Hz, 6H), 1.44–1.51(m, 2H), 1.61–1.70(m, 1H), 3.01(s, 3H), 3.23–3.28(m, 2H), 3.43–3.55(m, 2H), 3.83–4.01(m, 4H), 4.33(t, J=8.0Hz, 2H), 4.64(s, 2H), 5.18(s, 2H), 5.42(s, 2H), 7.00–7.05(m, 2H), 7.16–7.28(m, 4H), 7.47–7.59(m, 6H) | |
| 37e | 4-ethylbenzyl-N-(2-hydroxyethyl)morpholinium | (DMSO-d$_6$) δ 0.92(d, J=6.6Hz, 6H), 1.45–1.53(m, 2H), 1.59–1.70(m, 1H), 3.56–3.62(m, 8H), 3.84–3.90(m, 2H), 3.97–4.01(m, 2H), 4.35(t, J=7.9Hz, 2H), 4.70(s, 2H), 5.19(s, 2H), 5.45(s, 2H), 7.01–7.05(m, 2H), 7.18–7.29(m, 4H), 7.49–7.60(m, 6H), 8.15(bs, 2H) | 567(MH$^+$) |
| 37f | 4-ethylbenzyl-N(Me)(CH$_2$CO$_2$H)$_2$$^+$ | (DMSO-d$_6$) δ 0.16(d, J=6.6Hz, 6H), 0.73–0.84(m, 2H), 0.86–0.98(m, 1H), 3.52(s, 3H), 3.61–3.69(m, 2H), 4.07(s, 4H), 4.15(bs, 2H), 4.43(bs, 2H), 4.81(bs, 2H), 6.28–6.38(m, 3H), 6.43–6.50(m, 1H), 6.62–6.80(m, 6H), 6.84–6.95(m, 2H) | 584(MH$^+$) |
| 37g | 4-ethylbenzyl-pyridinium | (DMSO-d$_6$) δ 0.88(d, J=6.6Hz, 6H), 1.40–1.48(m, 2H), 1.58–1.67(m, 1H), 4.31(t, J=8.0Hz, 2H), 5.11(s, 2H), 5.41(s, 2H), 5.81(s, 2H), 6.98–7.02(m, 2H), 7.11–7.27(m, 4H), 7.41–7.58(m, 6H), 8.12–8.17(m, 2H), 8.60(t, J=7.8Hz, 1H), 9.17(d, J=5.4Hz, 2H) | 516(MH$^+$) |

TABLE 7-continued

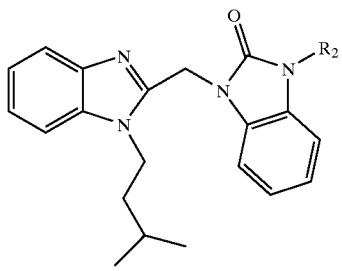

37

Compounds listed below were prepared by treating compound 28 with a nucleophile as described for compound 29.

| # | R$_2$ | $^1$H-NMRData | MSData |
|---|---|---|---|
| 37h | 4-ethylbenzyl-piperazine-NH | (CD$_3$OD)δ0.93(d, J=6.6Hz, 6H), 1.40–1.48(m, 2H), 1.60–1.72(m, 1H), 2.38–2.50(m, 4H), 2.84(t, J=5.0Hz, 4H), 3.50(s, 2H), 4.33–4.39(m, 2H), 5.16(s, 2H), 5.49(s, 2H), 6.99–7.11 (m, 3H), 7.16–7.21(m, 1H), 7.26–7.39 (m, 6H), 7.48(dd, J=1.3, 6.8Hz, 1H), 7.65–7.68(m, 1H) | 523(MH$^+$) |
| 37i | 4-ethylbenzyl-piperazine-CH$_2$CO$_2$tBu | (CDCl$_3$)δ0.95(d, J=6.6Hz, 6H), 1.41–1.49(m, 2H), 1.46(s, 9H), 1.66–1.75(m, 1H), 2.45–2.90(m, 8H), 3.13 (s, 2H), 4.32(t, J=8.1 Hz, 2H), 5.10 (s, 2H), 5.44(s, 2H), 6.86–6.89(m, 1H), 6.98–7.04(m, 2H), 7.25–7.34(m, 2H), 7.43–7.46(m, 1H), 7.77–7.82(m, 1H) | 637(MH$^+$) |
| 37j | 4-ethylbenzyl-piperidine-CO$_2$Et | (CDCl$_3$)δ0.95(d, J=6.6Hz, 6H), 1.25(t, J=7.1Hz, 3H), 1.41–1.49(m, 2H), 1.61–1.87(m, 7H), 2.21–2.34(m, 1H), 2.79–2.90(m, 2H), 3.43–3.54(m, 2H), 4.13(q, J=7.1 Hz, 2H), 4.32(t, J=8.1Hz, 2H), 5.09(s, 2H), 5.44(s, 2H), 6.87–6.90(m, 1H), 6.97–7.02(m, 1H), 7.26–7.34(m, 8H), 7.43–7.47(m, 1H), 7.77–7.82(m, 1H) | 594(MH$^+$) |
| 37k | 4-ethylbenzyl-piperazine-CH$_2$CO$_2$Me | (CD$_3$OD)δ0.99(d, J=6.2Hz, 6H), 1.72–1.74(m, 3H), 3.31–3.47(m, 8H), 3.79(s, 3H), 3.86(s, 2H), 4.39(s, 2H), 4.62(t, J=6.7Hz, 2H), 5.23(s, 2H), 5.83(s, 2H), 7.20–7.21(m, 3H), 7.34–7.36(m, 1H), 7.53–7.61(m, 4H), 7.68–7.73(m, 2H), 7.78–7.82(m, 1H), 7.94–7.97(m, 1H) | 595(MH$^+$) |
| 37l | 4-ethylbenzyl-piperazine-CH$_2$CO$_2$Et | (CDCl$_3$)δ0.95(d, J=6.5Hz, 6H), 1.26(t, J=7.1Hz, 3H), 1.41–1.49(m, 3H), 1.68–1.77(m, 5H), 1.94–2.05(m, 2H), 2.23(d, J=6.9Hz, 2H), 2.79–2.92 (m, 2H), 3.47–3.58(m, 2H), 4.14(q, J= 7.1Hz, 2H), 4.29–4.35(m, 2H), 5.10 (s, 2H), 5.45(s, 2H), 6.88–6.91(m, 1H), 6.99–7.02(m, 1H), 7.28–7.45(m, 7H), 7.80–7.83(m, 1H), 8.52–8.54(m, 1H) | 608*MH$^+$) |
| 37m | 4-ethylbenzyl-S-C(=NH)NH$_2$ | (DMSO-d$_6$)δ0.90(d, J=6.5Hz, 6H), 1.48–1.53(m, 2H), 1.63–1.69(m, 1H), 3.38–3.48(m, 4H), 4.28–4.33(m, 2H), 4.42(s, 2H), 4.57(t, J=5.4Hz, 2H), 5.10(s, 2H), 5.41(s, 2H), 6.98–7.01 (m, 2H), 7.12–7.24(m, 4H), 7.39–7.46 (m, 4H), 7.50–7.54(m, 2H), 7.57–7.59 (m, 2H), 8.99(b, 4H) | 513(MH$^+$) |

TABLE 7-continued

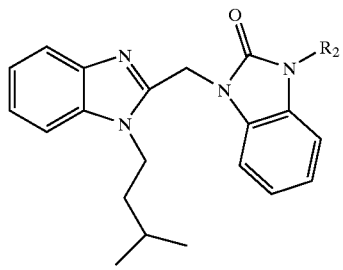

37

Compounds listed below were prepared by treating compound 28 with a nucleophile as described for compound 29.

| # | R₂ | ¹H-NMRData | MSData |
|---|---|---|---|
| 37n | 4-ethylbenzyl-S-CH₂-CO₂Me | (DMSO-d₆)δ0.91(d, J=6.6Hz, 6H), 1.42–1.47(m, 2H), 1.61–1.67(m, 1H), 3.20(s, 2H), 3.57(s, 3H), 3.77(s, 2H), 4.30–4.34(m, 2H), 5.10(s, 2H), 5.42 (s, 2H), 6.98–7.01(m, 2H), 7.14–7.18 (m, 2H), 7.20–7.27(m, 4H), 7.31–7.33 (m, 2H), 7.51(d, J=4.8, 1H), 7.60(d, J=4.7, 1H) | 543(MH⁺) |
| 37o | 4-ethylbenzyl-S-CH₂-C(O)N(Me)₂ | (DMSO-d₆)δ0.91(d, J=3.9, 6H), 1.42–1.46(m, 2H), 1.61–1.69(m, 1H), 2.78(s, 3H), 2.91(s, 3H), 3.73(s, 2H), 4.31–4.33(m, 2H), 5.09(s, 2H), 5.42 (s, 2H), 6.99–7.01(m, 2H), 7.14–7.33 (m, 8H), 7.51(d, J=4.8, 1H), 7.60(d, J=4.7, 1H) | 556(MH⁺) |
| 37p | 4-ethylbenzyl-S-CH(CO₂H)-CH₂-CO₂H | (CD₃OD)δ0.91(d, J=6.5Hz), 1.37–1.44(m, 2H), 1.59–1.71(m, 1H), 2.46–2.55(m, 1H), 2.79–2.87(m, 1H), 3.68(t, J=7.4Hz, 1H), 3.88(s, 2H), 4.34(t, J=8.0Hz, 2H), 5.14(s, 2H), 5.49(s, 2H), 7.01–7.09(m, 3H), 7.16–7.19(m, 1H), 7.28–7.38(m, 6H), 7.45–7.49(m, 1H), 7.65–7.68(m, 1H) | 587(MH⁺) |
| 37q | 4-ethylbenzyl-S-(N-methylpyridinium-2-yl) | (CD₃OD)δ0.95(d, J=6.6Hz, 6H), 1.44–1.52(m, 2H), 1.65–1.73(m, 1H), 4.21(s, 3H), 4.38(t, J=8.2Hz, 2H), 4.71(s, 2H), 5.19(s, 2H), 5.51(s, 2H), 7.04–7.09(m, 3H), 7.17–7.22(m, 1H), 7.28–7.37(m, 2H), 7.45(d, J=8.2Hz, 2H), 7.50-7.55(m, 3H), 7.65–7.73(m, 2H), 8.05(d, J=8.3 Hz, 1H), 8.31(t, J=8.1Hz, 1H), 8.79(d, J=5.8Hz, 1H) | 562(MH⁺) |
| 37r | 4-ethylbenzyl-piperazinyl-CH₂-CO₂H | (DMSO-d₆)δ0.90(d, J=6.5Hz, 6H), 1.51–1.58(m, 2H), 1.63–1.69(m, 1H), 3.11–3.24(m, 2H), 3.27–3.40(m, 2H), 3.75–3.83(m, 2H), 4.20–4.29(m, 2H), 4.41–4.47(m, 2H), 5.14(s, 2H), 5.63 (s, 2H), 7.05–7.07(m, 2H), 7.18–7.21 (m, 1H), 7.31–7.35(m, 1H), 7.42–7.51 (m, 4H), 7.56(d, J=7.4Hz, 2H), 7.72 (d, J=7.6Hz, 1H), 7.77(d, J=6.9Hz, 1H) | 581(MH⁺) |
| 37s | 4-ethylbenzyl-piperazinyl-CH₂-C(O)NH-CH(CO₂H)-CH₂-CO₂H | (CD₃OD)δ0.93(d, J=6.5Hz, 6H), 1.40–1.48(m, 2H), 1.62–1.71(m, 1H), 2.54–2.70(m, 10H), 2.92–3.10(m, 2H), 3.53(s, 2H), 4.36(t, J=8.1Hz, 2H), 4.53(t, J=6.8Hz, 1H), 5.17(s, 2H), 5.50(s, 2H), 7.00–7.10(m, 3H), 7.17–7.20(m, 1H), 7.26–7.40(m, 6H), 7.47–7.50(m, 1H), 7.66–7.68(m, 1H) | 696(MH⁺) |

TABLE 7-continued

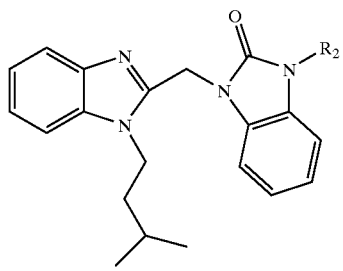

37

Compounds listed below were prepared by treating compound 28 with a nucleophile as described for compound 29.

| # | R$_2$ | $^1$H-NMRData | MSData |
|---|---|---|---|
| 37t | (structure) | (DMSO-d$_6$)δ0.89(d, J=6.6Hz, 6H), 1.42–2.30(10H), 2.64–2.75(m, 2H), 3.31–3.45(m, 2H), 4.31(t, J=8.0Hz, 2H), 5.10(bs, 2H), 5.41(s, 2H), 6.98–7.01(m, 2H), 7.14–7.26(m, 8H), 7.50 (d, J=8.0Hz, 1H), 7.58(d, J=7.5Hz, 1H) | 566(MH$^+$) |
| 37u | (structure) | (CD$_3$OD)δ0.92(d, J=6.6Hz, 6H), 1.38–1.47(m, 2H), 1.63–1.68(m, 1H), 1.70–1.83(m, 4H), 2.00–2.10(m, 2H), 2.16–2.25(m, 1H), 2.66(d, J=6.0Hz, 2H), 2.84–2.93(m, 2H), 3.50(bs, 2H), 4.36(t, J=8.3Hz, 2H), 4 47(t, J=5.8 Hz, 1H), 5.17(s, 2H), 5.50(s, 2H), 7.03–7.09(m, 3H), 7.17–7.20(m, 1H), 7.29–7.38(m, 6H), 7.48(d, J=7.2Hz, 1H), 7.67(d, J=7.1Hz, 1H) | 681(MH$^+$) |
| 37v | (structure) | (DMSO-d$_6$)δ0.89(d, J 6.6Hz, 6H), 1.07–1.23(m, 2H), 1.40–1.47(m, 2H), 1.58–1.69(m, 4H), 1.80–1.94(m, 2H), 2.11(d, J=6.2Hz, 2H), 2.67–2.75(m, 2H), 3.32–3.38(m, 2H), 4.31(t, J=7.9 Hz, 2H), 5.09(s, 2H), 5.41(s, 2H), 6.98–7.01(m, 2H), 7.14–7.32(m, 8H), 7.50(d, J=8.1Hz, 1H), 7.59(d, J= 7.6Hz, 1H) | 580(MH$^+$) |

Compound 38

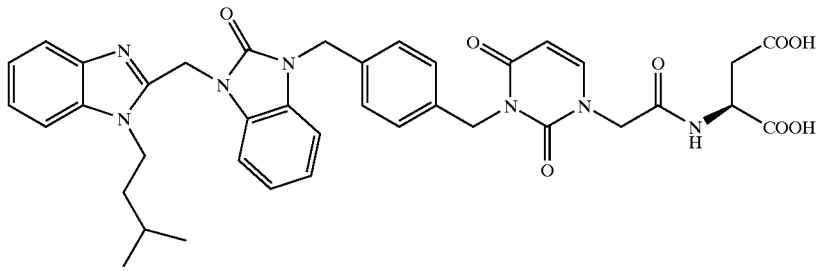

The t-butyl groups of ester 35 were removed with 4N HCl in dioxane using the procedure described for 32. The acid was then treated with 2 equivalents of 1 N NaOH in MeOH to provide a di-sodium salt of 38:
$^1$H NMR (CD$_3$OD) δ0.82 (d, J=6.6 Hz, 6H), 1.29–1.37 (m, 2H), 1.51–1.57 (m, 1H), 2.60–2.63 (m, 2H), 4.23–4.28 (m, 2H), 4.40–4.53 (m, 3H), 5.00 (s, 2H), 5.06 (s, 2H), 5.40 (s, 2H), 5.67 (d, J=8.1 Hz, 1H), 6.93–7.10 (m, 4H), 7.07–7.10 (m, 1H), 7.18–7.30 (m, 6H), 7.40 (d, J=6.9 Hz, 1H), 7.49 (d, J=7.5 Hz, 1H), 7.59 (d, J=6.9 Hz, 1H); IR (KBr, cm$^{-1}$) 3422, 2957, 1705, 1662, 1612, 1493, 1456, 1407, 747; MS m/e 722 (MH$^+$).

Compound 39

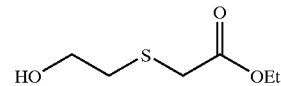

Mercaptoethanol (3 g, 38.39 mmol) and K$_2$CO$_3$ (6.36 g, 46.01 mmol) were suspended in acetone (50 ml). Ethylbromoacetate (7.05 g, 42.21 mmol) was added. The resulting mixture was stirred at room temperature overnight. It was filtered and the filtrate was evaporated to give 6 g (95 % yield) of compound 39 as a yellow oil.

Compound 40

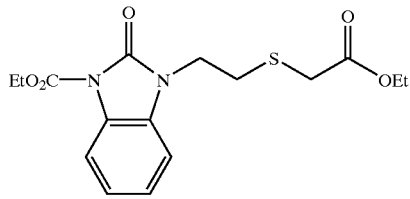

DEAD (506.77 mg, 2.9 mmol) was added to a stirred mixture of 2-oxo-2,3-dihydro-benzoimidazole-1-carboxylic acid ethyl ester (500 mg 2.42 mmol) (Meanwell et al, *J. Org. Chem.* 1995, 60, 1565–1582.), PPh$_3$ (763.21 mg, 2.90 mmol), and (2-hydroxy-ethylsulfanyl)-acetic acid ethyl ester (497.75 mg, 3.03 mmol) in dry THF (20 ml) at room temperature. The mixture was stirred for 48 hours. The solvent was removed and the residue purified by column chromatography (25% EtOAc/Hexane) to give 422 mg (49% yield) of the desired Compound 41

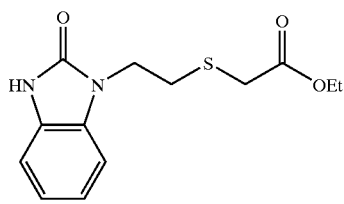

Compound 40 (400 mg, 1.13 mmol) in THF (5 ml) was stirred with 21% NaOEt in EtOH (23.15 mg, 0.43 mmol) at room temperature overnight. The mixture was evaporated to give 284 mg (89% yield) of compound 41.

Compound 42

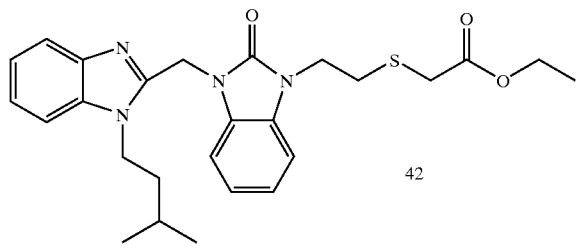

Compound 42 was prepared as with [2-(2-oxo-2,3-dihydro-benzoimidazol-1-yl)-ethylsulfanyl]-acetic acid ethyl ester and compound 6 as described for compound 7.

$^1$H NMR (DMSO-d$_6$) δ0.90 (d, J=6.6, 6 H), 1.18 (t, J=7.1, 3 H), 1.37–1.44 (m, 2 H), 1.59–1.65 (m, 1H), 2.94 (t, J=6.8, 2H), 3.45 (s,2H), 4.01–4.13 (m, 4H), 4.26–4.32 (m, 2H), 5.36 (s, 2H), 6.98–7.08 (m, 2H), 7.14–7.28 (m, 4H), 7.48 (d, J=7.4, 2H), 7.59 (d, J=7.4, 2H); MS m/e 481 (MH$^+$).

Compound 43

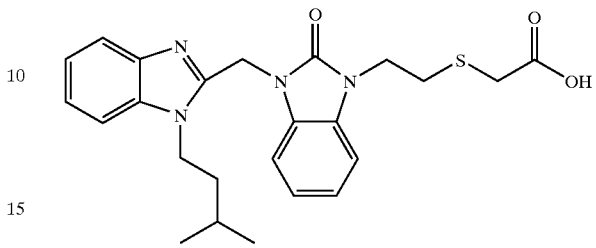

Compound 42 (110 mg, 0.23 mmol) was dissolved in MeOH (10 ml). 1N NaOH (13.73 mg, 0.34 mmol) was added. The reaction was stirred overnight then the solvent was removed. The residue was adjusted to pH 5 with 1N HCl. The white precipitate was filtered, washed with water and dried under vacuum to give 54 mg (52% yield) of compound 43 as a white solid.

$^1$H NMR (DMSO-d$_6$) δ0.89 (d, J=6.6, 6H), 1.34–1.39 (m, 2H), 1.59–1.65 (m, 1H), 2.81 (t, J=7.1, 2H), 3.01 (s, 2H), 4.08 (t, J=6.8, 2H), 4.28 (t, J=8.0, 2H) 5.35 (s, 2H), 6.95–7.05 (m, 2H), 7.14–7.25 (m, 3H), 7.38 (d, J=6.9, 1H), 7.48 (d, J=7.6, 1H), 7.5 9 (d, J=7.4, 1H); MS m/e 453 (MH$^+$).

Compound 44

Compound 43 (100 mg, 0.22 mmol) was dissolved in acetic acid (7 ml). Sodium perborate tetrahydrate (37.39 mg, 0.24 mmol) was added The mixture was heated at 50° C. overnight. Then the acetic acid was removed. The residue was taken into water and acidified with 1N HCl to pH 5. The product was extracted with EtOAc. The combined organic extracts were dried over Na$_2$SO$_4$, and evaporated to give 63 mg (61% yield) of the compound 44.

$^1$H NMR (DMSO-d$_6$) δ0.88 (d, J=6.6, 6H), 1.23 (t, J=7.1, 2H), 1.32–1.39 (m, 2H), 1.56–1.65 (m, 2H), 3.16 (s, 1H), 3.88–3.95 (m, 1H), 4.25–4.32 (m, 2H), 5.35 (s, 2H), 6.97–7.08 (m, 2H), 7.14–7.29 (m, 4H), 7.48 (d, J=7.4, 1H), 7.59 (d, J=7.0, 1H); MS m/e 469 (MH$^+$).

Compound 45

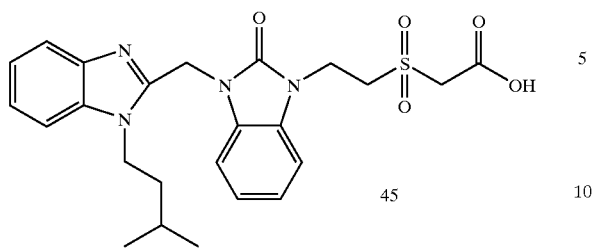

Compound 46

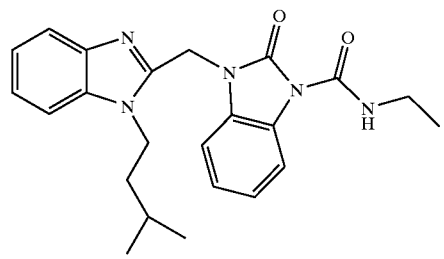

Compound 44 (110 mg, 0.24 mmol) was dissolved in acetic acid (7 ml). Sodium perborate tetrahydrate (149.58 mg, 0.97 mmol) was added and the mixture heated at 55° C. overnight. Acetic acid was removed and the residue taken into water and acidified with 1N HCl to pH 5. The aqueous layer was extracted with EtOAc. The combined organic extracts were dried over $Na_2SO_4$, and evaporated to give 63 mg (53% yield) of compound 45 as a white solid.

$^1$H NMR (DMSO-$d_6$) δ0.90 (d, J=5.0, 6H), 1.35–1.51 (m, 2H), 1.56 (s, 2H), 1.60–1.70 (m, 2H), 3.70–3.75 (m, 2H), 4.28–4.33 (m, 3H), 5.35 (s, 2H), 6.98–7.06 (m, 2H), 7.13–7.26 (m, 4H), 7.47–7.51 (m, 1H), 7.56–7.62 (m, 2H); MS m/e 485 (MH$^+$).

A solution of compound 6 (50 mg, 0.15 mmol) and triethylamine (15 mg, 0.15 mmol) in DMF (2 mL) was cooled to 0° C. To this solution was added ethyl isocyanate (11 mg, 0.15 mmol) and the resulting mixture was stirred at 0° C. for 4 hours. The reaction mixture was diluted with EtOAc, washed with $H_2O$, and dried over $MgSO_4$. Purification by flash column chromatography (straight EtOAc) gave 30 mg (49% yield) of compound 46:

$^1$H NMR (CDCl$_3$) δ0.93 (d, J=6.7Hz, 6H), 1.28 (t, J=7.3Hz, 3H), 1.32–1.40 (m, 2H), 1.63–1.72 (m, 1H), 3.44–3.54 (m, 2H), 4.24–4.30 (m, 2H), 5.46 (s, 2H), 7.13–7.18 (m, 2H), 7.31–7.32 (m, 3H), 7.45–7.54 (m, 1H), 7.80–7.83 (m, 1H), 8.18–8.21 (m, 1H), 8.63–8.70 (m, 1H); MS m/e 406 (MH$^+$).

TABLE 8

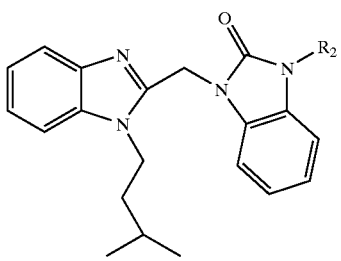

The compounds were prepared from compound 6 and commercially available isocyanates using the method above.

| # | $R_2$ | $^1$H-NMR Data | MS Data |
|---|---|---|---|
| 47a | | (CDCl$_3$)δ0.98(d, J=6.8Hz, 6H), 1.42–1.50(m, 2H), 1.67–1.78(m, 1H), 4.29–4.35(m, 2H), 5.48(s, 2H), 7.18–7.23 (m, 3H), 7.29–7.36(m, 3H), 7.43(t, J=7.9Hz, 2H), 7.52–7.55(m, 1H), 7.63–7.68(m, 2H), 7.80–7.84(m, 1H), 8.27–8.33(m, 1H), 10.88(s, 1H) | No data |
| 47b | | (CDCl$_3$)δ0.87(d, J=6.6Hz, 6H), 1.29–1.38(m, 2H), 1.58–1.69(m, 1H), 4.19–4.25(m, 2H), 4.65(d, J=5.8Hz, 2H), 5.39(s, 2H), 7.12–7.16(m, 2H), 7.27–7.38(m, 8H), 7.42–7.46(m, 1H), 7.77–7.80(m, 1H), 8.20–8.23(m, H), 9.11–9.16(m, 1H) | 468(MH$^+$) |
| 47c | | (CDCl$_3$)δ0.97(d, J=6.7Hz, 6H), 1.42 (t, J=7.1Hz, 3H), 1.43–1.51(m, 2H), 1.68–1.77(m, 1H), 4.28–4.34(m, 2H), 4.40(q, J=7.1Hz, 2H), 5.46(s, 2H), 7.20–7.25(m, 2H), 7.28–7.33(m, 3H), 7.53–7.56(m, 1H), 7.73(d, J=8.7Hz, 2H), 7.78–7.82(m, 1H), 8.10(d, J=8.7 Hz, 2H), 8.26–8.29(m, 1H), 11.14(s, 1H) | 526(MH$^+$) |

TABLE 8-continued

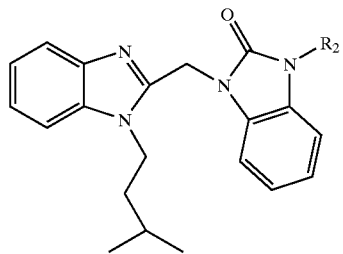

The compounds were prepared from compound 6 and commercially available isocyanates using the method above.

| # | R₂ | ¹H-NMR Data | MS Data |
|---|---|---|---|
| 47d | (acetamido-CH₂-CO₂Et) | (CDCl₃)δ0.96(d, J=6.6Hz, 6H), 1.33 (t, J=7.1Hz, 3H), 1.39–1.47(m, 2H), 1.64–1.75(m, 1H), 4.00(d, J=5.3Hz, 1H), 4.18–4.32(m, 5H), 5.42(s, 2H), 7.13–7.19(m, 2H), 7.28–7.35(m, 3H), 7.46–7.52(m, 1H), 7.77–7.81(m, 1H), 8.14–8.20(m, 1H), 9.30(t, J=5.3Hz, 1H) | 464(MH⁺) |
| 47e | (acetamido-SO₃H) | (DMSO-d₆)δ0.98(d, J=6.2Hz, 6H), 1.67–1.77(m, 3H), 4.51(t, J=7.9Hz, 2H), 5.75(s, 2H), 7.20–7.28(m, 2H), 7.33–7.40(m, 1H), 7.46–7.56(m, 2H), 7.71(d, J=7.3Hz, 1H), 7.88(d, J=8.0 Hz, 1H), 8.09–8.14(m, 1H), 10.18(s, 1H) | 456(MH⁺) |
| 47f | (4-ethylphenyl-NHC(O)NH-phenyl-CO₂H) | (DMSO-d₆)δ0.91(d, J=6.6Hz, 6H), 1.41–1.48(m, 2H), 1.63–1.67(m, 1H), 4.34(t, J=7.7Hz, 2H), 5.05(s, 2H), 5.46(s, 2H), 6.87(s, 1H), 7.01(t, J=3.7 Hz, 2H), 7.15–7.33(m, 5H), 7.42(d, J=8.6Hz, 2H), 7.52–7.64(m, 4H), 7.85(d, J=8.7Hz, 2H), 8.96(s, 1H), 9.20(s, 1H) | 603(MH⁺) |
| 47g[a] | (4-ethylphenyl-NHC(O)NH-phenyl-C(O)NH-CH(CO₂Me)CH₂CO₂Me) | (CD₃OD)δ0.90(d, J=6.6Hz, 6H), 1.36–1.48(m, 2H), 1.57–1.69(m, 1H), 2.73–2.88(m, 2H), 4.27–4.42(m, 2H), 4.61–4.74(m, 1H), 5.11(s, 2H), 5.47(s, 2H), 7.00–7.14(m, 4H), 7.26–7.32(m, 4H), 7.35–7.52(m, 5H), 7.63–7.66(m, 1H), 7.83(d, J=8.7Hz, 2H), | 718(MH⁺) |
| 47h[b] | (4-ethylphenyl-NHC(O)NH-phenyl-C(O)NH-CH(CO₂Me)CH₂CO₂Me) | (DMSO-d₆)δ0.91(d, J=6.5Hz, 6H), 1.41–1.48(m, 2H), 1.60–1.67(m, 1H), 2.77–2.98(m, 2H), 3.61(s, 3H), 3.64(s, 3H), 4.32(t, J=7.8Hz, 2H), 4.78–4.85 (m, 1H), 5.05(s, 2H), 5.42(s, 2H), 6.99–7.02(m, 2H), 7.15–7.24(m, 4H), 7.31 (d, J=8.6Hz, 2H), 7.42(d, J=8.6Hz, 2H), 7.52(d, J=8.9Hz, 3H), 7.60(d, J=7.6Hz, 1H), 7.78(d, J=8.7Hz, 2H), 8.74–8.77(m, 2H), 8.94(s, 1H) | 746(MH⁺) | a, hydrolysis of 47a as described for compound 8; b, amide bond formation as described for compound 9.

TABLE 8-continued

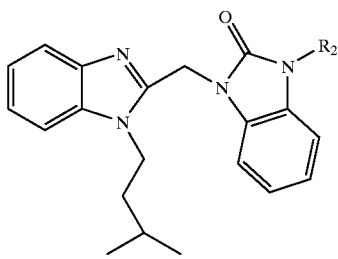

The compounds were prepared from compound 6 and commercially available isocyanates using the method above.

| # | R₂ | ¹H-NMRData | MSData |
|---|----|------------|--------|

Compound 48

Compound 47e (100 mg, 0.22 mmol) was heated at 100° C. for 2 hours in a mixture of DMF (10 ml) and H₂O (30 mL). The aqueous reaction mixture was extracted with EtOAc. The organic extracts were dried over MgSO₄, evaporated, and purified by flash column chromatography (straight EtOAc) to give 18 mg (22% yield) of compound 48:

¹H NMR (CDCl₃) δ0.98 (d, J=6.8 Hz, 6H), 1.38–1.46 (m, 2H), 1.68–1.76 (m, 1H), 4.28–4.33 (m, 2H), 5.49 (m, 2H), 7.17–7.28 (m, 2H), 7.33–7.35 (m, 2H), 7.53–7.56 (m, 1H), 7.82–7.86 (m, 1H), 8.18–8.21 (m, 1H), 8.63 (bs, 1H).

Compound 49

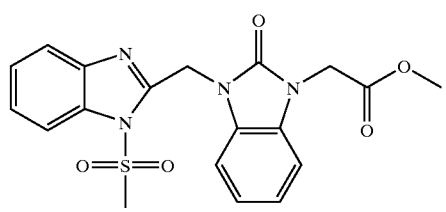

Compound 49 was prepared from compound 2 and (2-Oxo-2,3-dihydro-benzoimidazol-1-yl)-acetic acid methyl ester (Meanwell et al, *J. Org. Chem.* 1995, 60, 1565–1582.) as described for compound 3 without treatment with tetrabutylammonium fluoride hydrate.

¹H NMR (CDCl₃) δ3.41 (s, 3H), .77 (s, 3H), 4.65 (s, 2H), 5.57 (s, 2H), 6.92–7.11 (m, 1H), 7.11–7.27 (m, 3H), 7.32–7.46 (m, 3H), 7.66 (d, J=9.0Hz, 1H), 7.67–7.83 (m, 1H), 7.88 (d, J=9.0Hz, 1H); MS m/e 414 (MH+); Found: C, 55.38;H, 4.58; 13.64.

Compound 49a

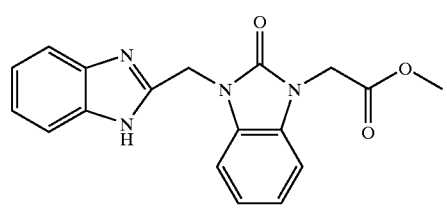

Compound 49 (3 g, 7.23 mmol) and tetrabutylammonium fluoride (1.89 g, 7.23 mmol) were refluxed in THF (300 ml) for 3 hours. After cooling, the solvent was evaporated. The residue was diluted with water and extracted with diethyl ether and EtOAc. The combined organic extracts were dried over Na₂SO₄, and evaporated to give 2.3 g (96% yield) of the desired compound 49a as a yellow solid.

¹H NMR (DMSO-d6) δ3.61 (s, 3H), 4.79 (s, 2H), 5.29 (s, 2H), 7.00–7.21 (m, 6H), 7.43 (d, J=8.3Hz, 1H), 7.53 (d, J=8.3Hz, 1H). MS m/e 336 (MH⁺).

Compound 49a and 49b

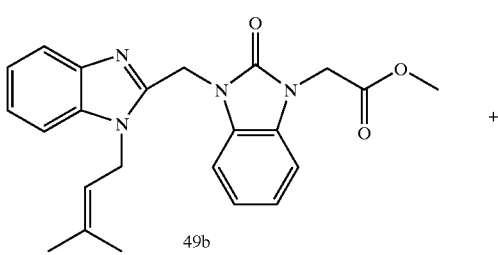

+

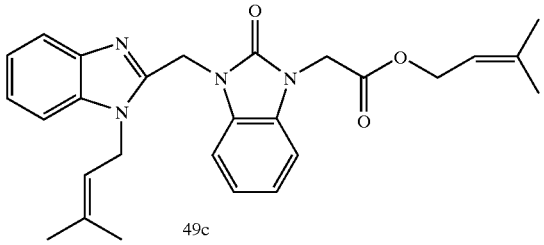

49c

To compound 49a (300 mg, 1.02 mmol) in DMF (10 ml) was added NaH (60% in mineral oil, 45.2 mg, 1.13 mmol) at room temperature. After stirring for 1 hour, 1-bromo-3-methyl-2-butene (168.42 mg, 1.13 mmol) was added and the mixture was stirred overnight. The mixture was diluted with water and extracted with EtOAc. The combined organic extracts were washed with brine, dried over $Na_2SO_4$ and evaporated. The residue was purified by column chromatography (hexane/EtOAc=4:1) to afford 76 mg (18% yield) of compound 49b and 120 mg (25% yield) of compound 49c both as a white solids.

Compound 49b:

$^1$H NMR (DMSO-d6) δ1.65 (s, 3H), 1.86 (s, 3H), 3.70 (s, 3H), 4.80 (s, 2H), 4.95–4.98 (m, 2H), 5.03–5.05 (m, 1H), 5.38 (s, 2H), 7.01–7.08 (m, 2H), 7.15–7.25 (m, 4H), 7.43 (d, J=7.5, 1H), 7.59 (d, J=7.4, 1H); MS m/e 405 (MH$^+$).

Compound 50

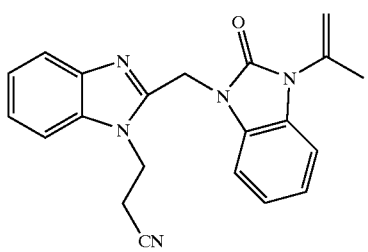

To compound 3 (1.5 g, 4.929 mmol) suspended in $CH_3CN$ (30 ml) was added acrylonitrile (523 mg, 9.858 mmol) followed by MTBD (38 mg, 0.246 mmol). The reaction mixture was heated at 50–60° C. for 16 hours. The solution became transparent. The solvent was stripped. The yellow oil residue was taken up in ether and triturated to give 1.67 g of compound 50 as a pale yellow solid:

$^1$H NMR (CDCl$_3$) δ2.26 (s, 3H), 2.75 (t, J=6.7Hz, 2H), 4.82 (t, J=6.7Hz, 2H), 5.24 (s, 1H), 5.41 (s, 1H), 5.45 (s, 2H), 7.11–7.16 (m, 3H), 7.31–7.37 (m, 3H), 7.57–7.60 (m, 1H), 7.81–7.85 (m, 1H); IR (KBr, cm$^{-1}$) 3005, 1686, 1655, 1615, 1508, 1487, 1427, 1400, 745; MS m/e 358 (MH$^+$); Anal. Calcd for $C_{21}H_{19}N_5O$: C, 70.57;H, 5.36; N, 19.59 Found: C, 70.42;H, 5.51; N, 19.61

Compound 51

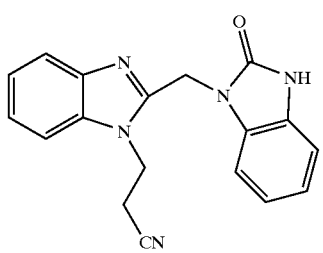

Compound 51 was prepared as described for compound 6.

$^1$H NMR (DMSO-d6) δ3.20 (t, J=6.7Hz, 2H), 4.89 (t, J=6.8 Hz, 2H), 5.60 (s, 2H), 6.97–7.08 (m, 3H), 7.27 (d, J=6.6 Hz, 1H), 7.39–7.50 (m, 2H), 7.69 (d, J=7.5 Hz, 1H), 7.95 (d, J=7.8 Hz, 1H), 11.20 (s, 1H).

Compound 52

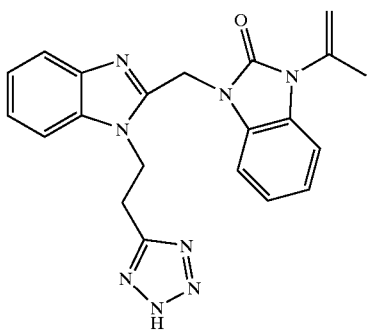

Nitrile 50 (9.19 g, 25.71 mmol), ammonium chloride (4.13 g, 77.13 mmol) and sodium azide (5.01 g, 77.13 mmol) were stirred in DMF (100 mL) at 100° C. for two days. The solvent was evaporated and the residue diluted with water and the pH was adjusted to 5 with concentrated HCl and the solid was filtered. The collected solid was triturated with hot methanol to give 8.85 g (86% yield) of compound 52 as a solid. To the suspension of the tetrazole (6.30 g) in methanol was added 1equivalent of 1 N NaOH. The suspension was then heated to dissolve the solid and solvent was evaporated. The residue was dried in vacuum and triturated in ether to give 6.36 g of the sodium salt of compound 52:

$^1$H NMR (DMSO-d$_6$) δ2.15 (s, 3H), 3.43 (t, J=7.1 Hz, 2H), 4.84 (t, J=7.1 Hz, 2H), 5.20 (s, 1H), 5.38 (s, 2H), 5.40 (d, J=1.2 Hz, 1H), 7.04–7.09 (m, 2H), 7.16–7.26 (m, 4H), 7.53–7.58 (m, 2H); IR (KBr, cm$^{-1}$) 3407, 2484, 2115, 1701, 1656, 1613, 1487, 1396, 1156, 751. MS m/e 401 (MH$^+$); Anal. Calcd for $C_{21}H_{20}N_8O$: C, 62.99;H, 5.03; N, 27.98 Found: C, 59.91;H, 5.20; N, 28.30

Compound 53

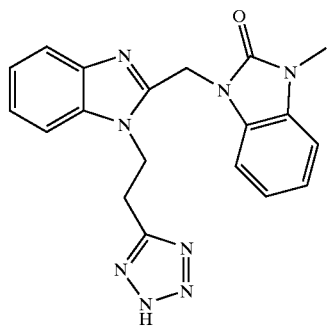

Compound 53 was prepared as described for compound 52 except 1-methyl-2-benzimidazolone was used in the coupling step.

$^1$H NMR (CD$_3$OD) δ3.33 (t, J=6.9 Hz, 2H), 3.46 (s, 3H), 4.79 (t, J=6.9 Hz, 2H), 5.21 (s, 2H), 6.99 (d, J=7.0 Hz , 1H), 7.07–7.31 (m, 5H), 7.50–7.54 (m, 2H); MS m/e 375 (MH$^+$);

Compound 54

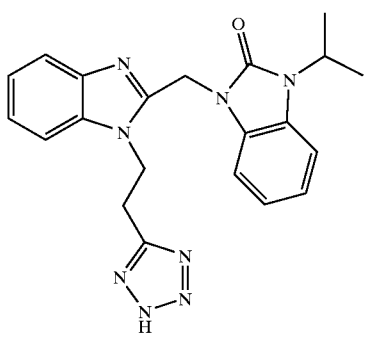

Compound 56

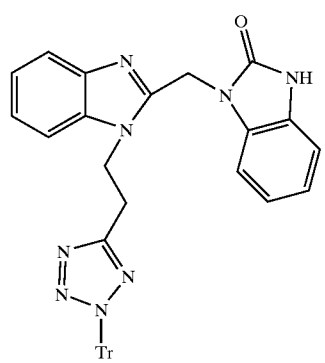

To a solution of compound 52 (2.0 g, 4.99 mmol) and 1 N NaOH (4.99 mmol) in methanol (20 mL) was added 10% Pd/C (0.5 g). The mixture was hydrogenated on a Parr shaker for 3 days. The catalyst was removed by filtration. The filtrate was evaporated, and the residue was purified using C18 column chromatography (H$_2$O: MeOH(1% TFA) =10:1 to 10 :6 as eluant) to give 1.52 g (72% yield) of compound 54 as a white solid:

$^1$H NMR (CDCl$_3$) δ1.46 (d, J=7.0 Hz, 6H), 3.10 (t, J=6.6 Hz, 2H), 4.58–4.71 (m,1 H), 4.68 (t, J=6.6 Hz, 2H), 5.13 (s, 2H), 6.94–7.22 (m, 5H), 7.31 (d, J=7.9 Hz, 1 H), 7.49 (t, J=8.6 Hz, 2H); IR (KBr, cm$^{-1}$) 3384, 1696, 1490, 1410, 751. MS m/e 403 (MH$^+$); Anal. Calcd for C$_{21}$H$_{22}$N$_8$O.H$_2$O C, 57.01;H, 5.24; N, 25.33 Found: C, 56.78;H, 5.62; N, 24.93

Compound 55

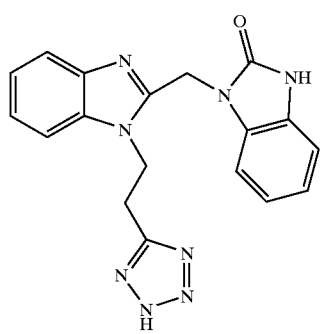

Compound 55 was prepared from compound 52 as described for compound 6.

$^1$H NMR (CD$_3$OD) δ3.78 (t, J=6.6 Hz, 2H), 5.19 (t, J=6.6 Hz, 2H), 5.89 (s, 2H), 7.14–7.21 (m, 3H), 7.31–7.35 (m, 1H), 7.62–7.74 (m, 3H), 7.98 (dd, J=1.6, 7.0 Hz, 1H); MS m/e 361 (MH$^+$).

Compound 55 (31.3 g, 86.85 mmol), triethylamine (13.19 mmol) and trityl chloride (26.64 mmol) were mixed in DMF (0.5 mL) and were stirred at 70° C. for 16 hours. To the mixture additional triethylamine (13.19 g) and trityl chloride (9.52 g) were added and the resulting mixture was stirred for an additional 2 hours. The solvent was evaporated, and the residue was triturated in 1 N NaOH solution and filtered. The solid collected was triturated in hot methanol, cooled to room temperature and filtered to give 44.0 g (84% yield) of compound 56 as a white powder. The filtrate was concentrated to give additional 4.1 g (8% yield) of compound 56.

$^1$H NMR (DMSO-d$_6$) δ3.46 (t, J 6.3Hz, 2H), 4.82 (t, J=6.3 Hz, 2H), 5.15 (s, 2H), 6.81–7.14 (m, 12H), 7.27–7.37 (m, 10H), 7.56 (dd, J=1.5, 6.7 Hz, 1H); MS m/e 625 (MH$^+$); Anal. Calcd for C$_{37}$H$_{30}$N$_8$O: C, 73.74;H, 5.02; N, 18.59 Found: C, 73.46;H, 5.07; N, 18.31.

Compound 57 (General Method)

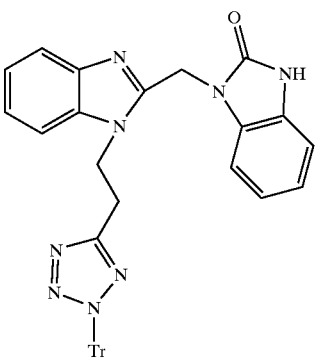 R$_2$X, BTPP →

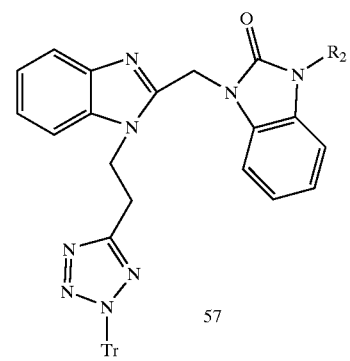

57

Compound 56 (500 mg, 0.83 mmol) was suspended in THF (15 mL) or THF/DMF (10 mL/2 mL) and the base BTPP (518 mg, 1.66 mmol, 2 eq) was added at room temperature. This solution was allowed to stir for 15–30 minutes at which time the alkyl or benzyl halide (0.91 mmol, 1.1 eq) was added. The reaction was stirred 16 hours at room temperature under $N_2$ atmosphere. The solvent was evaporated and the resulting residue was taken up in water and extracted with ether, ethyl acetate, or methylene chloride. The combined organic extracts were dried over $MgSO_4$, filtered, and evaporated. The crude product was purified by flash chromatography on silica gel using a mixture of solvents such as ethyl acetate, hexanes, methylene chloride and methanol.

TABLE 9

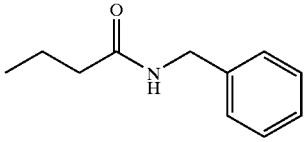

Alkylation of compound 56 with alkyl halide as described above.

| # | $R_2$ | ¹H-NMRData | MSData |
|---|---|---|---|
| 57a | $CH_2CH_2CO_2Et$ | (DMSO-$d_6$)2.56(t, J=6.9Hz, 2H), 3.41(t, J=6.3Hz, 2H), 4.07(t, J=6.6 Hz, 2H), 4.19(d, J=5.9Hz, 2H), 4.79(t, J=6.7Hz, 2H), 5.20(s, 2H), 6.82–6.93(m, 7H), 6.99–7.22(m, 9H), 7.27–7.36(m, 11H), 7.56–7.58(m, 1H), 8.49(t, J=5.8Hz, 1H) | 764(MH+) |
| 57b | 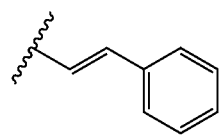 | (DMSO-$d_6$)2.56(t, J=6.9Hz, 2H), 3.41(t, J=6.3Hz, 2H), 4.07(t, J=6.6 Hz, 2H), 4.19(d, J=5.9Hz, 2H), 4.79(t, J=6.7Hz, 2H), 5.20(s, 2H), 6.82–6.93(m, 7H), 6.99–7.22(m, 9H), 7.27–7.36(m, 11H) 7.56–7.58(m, 1 H), 8.49(t, J=5.8Hz, 1H) | 764(MH+) |
| 57c | $CH_2OCH_3$ | (DMSO-$d_6$)3.23(s, 3H) 3.45(t, J= 6.6Hz, 2H), 4.82(t, J=6.6Hz, 2H), 5.22(s, 2H), 5.26(s, 2H) 6.82–6.85 (m, 6H), 6.97(dd, J=1.1, 7.7Hz, 1H), 7.02–7.16(m, 3H) 7.22–7.35(m, 12 H),7.55(dd, J=2.4, 7.6Hz, 1H) | 647(MH+) |
| 57d | 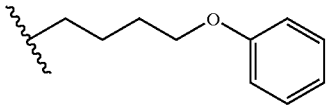 | (CDCl3)3.26(t, J=6.9Hz, 2H), 4.56 (d, J=6.0Hz, 2H) 4.82(t, J=6.9Hz, 2H), 5.27(s, 2H) 6.15–6.25(m, 1H), 6.53, 6.58(bs, 1H) 6.90–6.99(m, 9 H), 7.12–7.39(m, 18H), 7.76(d, J= 7.9Hz, 1H) | 719(MH+) |
| 57e | 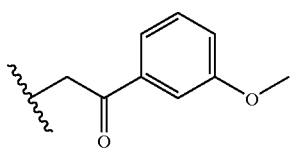 | (CDCl3)1.77–1.94(m, 4H), 3.27(t, J= 6.8Hz, 2H), 3.88(t, J=6.9Hz, 2 H), 3.94(t, J=6.0Hz, 2H), 4.80(t, J= 6.8Hz, 2H), 5.24(s, 2H), 6.83(dd, J= 1.0, 8.7Hz, 2H), 6.90–7.01(m, 11 H), 7.12–7.37(m, 14H), 7.75(d, J= 8.0Hz, 1H) | |
| 57f | | (CDCl3)3.28(t, J=6.8Hz, 2H), 3.83 (s, 3H), 4.76(t, J=6.9Hz, 2H), 5.20 (s, 2H), 5.30(s, 2H), 6.76–6.77(m, 1 H), 6.90–7.00(m, 8H), 7.14–7.38(m, 15H), 7.49–7.60(m, 2H), 7.77(d, J= 8.0Hz, 1H) | 751(MH+) |

TABLE 9-continued

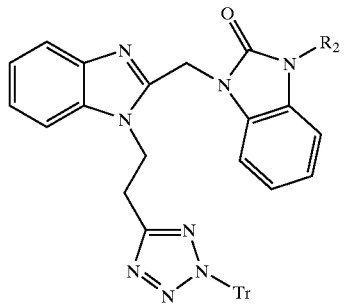

Alkylation of compound 56 with alkyl halide as described above.

| # | R$_2$ | $^1$H-NMRData | MSData |
|---|---|---|---|
| 57g | ~~~-C$_6$H$_4$-NO$_2$ (3-nitrobenzyl) | (CDCl3)3.27(t, J=7.0Hz, 2H), 4.83 (t, J=7.0Hz, 2H), 5.02(s, 2H), 5.30 (s, 2H), 6.77–6.79(m, 1H), 6.94–7.00 (m, 8H), 7.18–7.39(m, 12H), 7.41–7.47(m, 2H), 7.58(d, J=7.4Hz, 1H), 7.77(d, J=7.9Hz, 1H), 8.09–8.12(m, 2H) | 738(MH+) |
| 57h | ~~~-CH$_2$-O-CH$_2$CH$_2$-Si(CH$_3$)$_3$ | (CDCl3)0.02(s, 9H), 0.91(t, J=8.1 Hz, 2H), 3.30(t, J=6.8Hz, 2H), 3.59 (t, J=8.3Hz, 2H), 4.82(t, J=6.9Hz, 2H), 5.22(s, 2H), 5.26(s, 2H), 6.93–6.97(m, 6H), 7.02–7.23(m, 6H), 7.29–7.35(m, 9H), 7.39(d, J=10.5 Hz, 1H), 7.78(d, J=7.8Hz, 1H) | 733(MH+) |
| 57i | ~~~-CH$_2$-C(=O)-O-CH$_2$-C$_6$H$_5$ | (CDCl3)3.42(t, J=6.6Hz, 2H), 4.58 (d, J=5.8Hz, 2H), 4.81(t, J=6.6Hz, 2H), 5.16(s, 2H), 6.93–6.96(m, 6H), 7.11–7.44(m, 20H), 7.75–7.78(m, 1 H), 8.19–8.22(m, 1H), 9.06(t, J=5.9 Hz, 1H) | 736(MH+) |
| 57j | ~~~-CH$_2$-C(=O)-NH-CH$_2$-C$_6$H$_5$ | (DMSO-d6)3.57(t, J=7.0 Hz, 2H), 4.57(d, J=5.9Hz, 2H), 4.94(t, J= 7.0Hz, 2H), 5.56(s, 2H), 7.18–7.41 (m, 10H), 7.61(d, J=7.6Hz, 1H), 7.75(d, J=8.0Hz, 1H), 8.09–8.12(m, 1H), 9.07(t, J=5.9Hz, 1H) | 494(MH+) |
| 57k | ~~~-CH$_2$CH$_2$-CN | (CDCl3)2.74(t, J=6.8Hz, 2H), 3.21 (d, J=7.4Hz, 2H), 4.07(d, J=6.8 Hz, 2H), 4.79(d, J=7.4Hz, 2H), 5.28(s, 2H), 6.07–7.42(m, 22H), 7.79 (d, J=8.2Hz, 1H) | 656(MH+) |
| 57l | CH$_2$OCH$_2$CH$_2$OCH$_3$ | (CDCl3)3.30(t, J=6.9Hz, 2H), 3.31 (s, 3H), 3.45–3.48(m, 2H), 3.64–3.67 (m, 2H), 4.82(t, J=6.9Hz, 2H), 5.27 (s, 2H), 5.31(s, 2H), 6.94–6.97(m, 6 H), 7.02–7.07(m, 2H), 7.14–7.23(m, 4 H), 7.27–7.35(m, 10H), 7.78(d, J= 7.8Hz, 1H) | 691(MH+) |
| 57m | CH$_2$CH$_2$CH$_2$CH$_2$CN | (CD3OD)3.34(t, J=6.9Hz, 2H), 4.80(t, J=6.9Hz, 2H), 5.03(s, 2H), 5.26(s, 2H), 6.73(dd, J=2.0, 6.5Hz, 2H), 6.97–7.01(m, 1H), 7.04–7.05(m, 3H), 7.20–7.31(m, 4H), 7.47(d, J= 7.5Hz, 1H), 7.55(d, J=7.1Hz, 1H) | 467(MH+) |

TABLE 9-continued

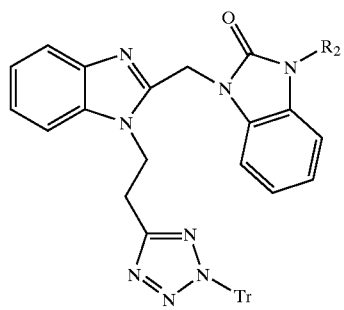

Alkylation of compound 56 with alkyl halide as described above.

| # | R$_2$ | $^1$H-NMRData | MSData |
|---|---|---|---|

Compound 58 (General Method)

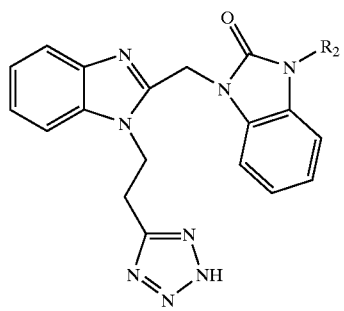

The trityl protected tetrazole (75 mg, 0.12 mmol) compound was suspended in MeOH (5 mL) and to this solution was added conc. HCl (0.25 mL). The reaction was stirred for 1–2 hours at room temperature. The solvent was evaporated and the residue was dried under vacuum. The residue was then triturated with diethyl ether or methylene chloride to give the HCl salts.

The HCl salt was treated with exactly 2 eq 1N NaOH in methanol (one to remove the HCl and one to make the sodium salt of the tetrazole). The solvent was evaporated and the sodium salt was triturated with ether.

Method 2: The trityl protected tetrazole compound was treated with exactly 1 eq 1N NaOH in methanol. The reaction was heated at reflux and monitored by TLC and LC/MS for the completion of deprotection. The solvent was then evaporated and the residue was triturated with ether and/or methylene chloride to remove the trityl side product and filtration gave the final sodium salt product.

TABLE 10

The trityl group was removed as described above for compound 58

| # | R$_2$ | $^1$H-NMRData | MSData |
|---|---|---|---|
| 58a | CH$_2$CH$_2$CO$_2$Me | (CD$_3$OD)δ2.87(t, J=6.9Hz, 2H), 3.65(s, 3H), 3.76(t, J=6.6Hz, 2H), 4.28(t, J=6.9 Hz, 2H), 5.17(t, J=6.6Hz, 2H), 5.89(s, 2H), 7.18–7.29(m, 2H), 7.38(d, J=8.7Hz, 2H), 7.61–7.73(m, 3H), 7.97(dd, J=1.6, 6.9Hz, 1H) | 447(MH+) |

TABLE 10-continued

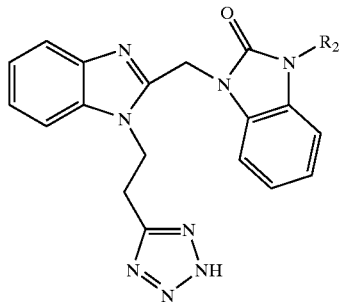

The trityl group was removed as described above for compound 58

| # | R$_2$ | $^1$H-NMRData | MSData |
|---|---|---|---|
| 58b | ![styryl] | (DMSO-d$_6$)δ3.27(tunderDMSO, 2H), 4.66(d, J=5.0Hz, 2H), 4.87(t, J=6.9Hz, 2H), 5.45(s, 2H), 6.35–6.46(m, 1H), 6.60, 6.66(s, 1H), 7.03–7.08(m, 2H), 7.22–7.32 (m, 4H), 7.40(d, J=7.0Hz, 1H), 7.55–7.60 (m, 1H) | 477(MH+) |
| 58c | ![(CH$_2$)$_4$OPh] | (DMSO-d$_6$)δ1.69–1.87(m, 4H), 3.27(t underDMSO, 2H), 3.92–4.00(m, 4H), 4.89 (t, J=6.9Hz, 2H), 5.51(s, 2H), 6.87–6.92 (m, 3H), 7.01–7.12(m, 2H), 7.22–7.33(m, 6H), 7.59(d, J=7.4Hz, 1H), 7.66(d, J=8.2 Hz, 1H) | 509(MH+) |
| 58d | ![CH$_2$C(O)-3-MeOPh] | (DMSO-d$_6$)δ3.27(tunderDMSO, 2H), 3.83(s, 3H), 4.86(t, J=6.9Hz, 2H), 5.49(s, 2H), 5.54(s, 2H), 7.02–7.05(m, 2H), 7.15–7.30(m, 5H), 7.49–7.61(m, 4H), 7.69(d, J=8.0Hz, 1H) | 509(MH+) |
| 58e | ![CH$_2$-3-NO$_2$Ph] | (DMSO-d$_6$)δ3.27(tunderDMSO, 2H), 4.92(t, J=7.1Hz, 2H), 5.27(s, 2H), 5.60(s, 2H), 7.04–7.07(m, 2H), 7.23–7.38(m, 2H), 7.60–7.71 (m, 3H), 7.82(d, J=8.0Hz, 1H), 8.13–8.16(m, 1H), 8.26(s, 1H) | 496(MH+) |
| 58f | CH$_2$OCH$_3$ | (CD$_3$OD)δ3.23(s, 3H), 3.37(t, J=6.9Hz, 2H), 4.80(t, J=6.9Hz, 2H), 5.22(s, 2H), 5.33(s, 2H), 6.99–7.03(m, 1H), 7.09–7.20 (m, 2H), 7.22–7.32(m, 3H), 7.50–7.55(m, 2H) | 405(MH+) |
| 58g | ![CH$_2$CH$_2$OCH$_2$CH$_2$SiMe$_3$] | (DMSO-d$_6$)δ0.08(s, 9H), 0.85(t, J=8.0 Hz, 2H), 3.14(t, J=6.6Hz, 2H), 3.56(t, J= 8.1Hz, 2H),4.67(t,J=6.6Hz, 2H), 5.18(s, 2H), 5.27(s, 2H), 6.98–7.13(m, 4H), 7.16–7.35(m, 2H), 7.42(d, J=7.5Hz, 1H), 7.53 (d, J=7.8Hz, 1H) | 491(MH+) |
| 58h | CH$_2$CO$_2$Me | (DMSO-d$_6$)δ3.40(t, J=6.8Hz, 2H), 3.68 (s, 3H), 4.79(s, 2H), 4.81(t, J=6.8Hz, 2H), 5.39(s, 2H), 7.04–7.07(m, 2H), 7.14–7.24(m, 4H), 7.50(d, J=7.9Hz, 1H), 7.56 (d, J=7.6Hz, 1H) | 433(MH+) |
| 58i | CH$_2$CO$_2$H | (DMSO-d$_6$)δ3.41(t, J=7.2Hz, 2H), 4.65(s, 2H), 4.81(t, J=7.0Hz, 2H), 5.38(s, 2H) 7.01–7.08(m, 2H), 7.14–7.24(m, 4H), 7.49 (d, J=7.5Hz, 1H), 7.56(d, J=7.4Hz, 1H) | 419(MH+) |
| 58j | ![CH$_2$CH$_2$-4-HOPh] | (CD$_3$OD)δ3.34(t, J=6.9Hz, 2H), 4.80(t, J= 6.9Hz, 2H), 5.03(s, 2H), 5.26(s, 2H), 6.73(dd, J=2.0, 6.5Hz, 2H), 6.97–7.01(m, H), 7.04–7.05(m, 3H), 7.20–7.31(m, 4H), 7.47(d, J=7.5Hz, 1H),7.55(d,J=7.1Hz, 1H) | 467(MH+) |

TABLE 10-continued

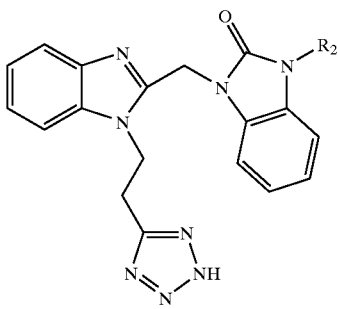

The trityl group was removed as described above for compound 58

| # | R$_2$ | $^1$H-NMRData | MSData |
|---|---|---|---|
| 58k | | (CDCl$_3$)δ3.76(t, J=6.6Hz, 2H), 3.90(s, 3 H), 5.18(t, J=6.6Hz, 2H), 5.27(s, 2H), 5.93(s, 2H), 7.17–7.23(m, 3H), 7.38–7.40 (m, 1H), 7.54(d, J=8.3Hz, 2H), 7.60–7.74 (m, 3H), 7.96(dd, J=6.7, 1.6Hz, 1H), 8.02 (dd, J=6.5, 1.8Hz, 2H) | 509(MH+) |
| 58l | | (DMSO-d$_6$)δ3.45(t, J=7.0Hz, 2H), 4.84 (t, J=7.0Hz, 2H), 5.17(s, 2H), 5.43(s, 2 H), 6.98–7.05(m, 2H), 7.09–7.25(m, 4H), 7.44(d, J=5.3Hz, 2H), 7.53(t, J=6.9Hz, 2 H), 7.89(d, J=5.3Hz, 2H) | 495(MH+) |

Compounds 59 and 60

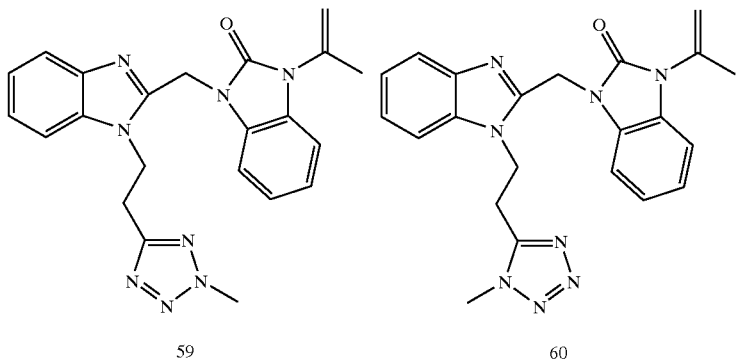

To a solution of compound 52 (2.5 g, 6.24 mmol) and BTPP (2.92 g, 9.36 mmol) in THF (20 mL) was added iodomethane (1.06 g, 1.2 mmol). The reaction mixture was stirred for 3 hours at room temperature. The solvent was evaporated and the residue was purified by flash column chromatography (gradient, EtOAc/hexanes, 2:1 to EtOAc/MeOH, 10:1) to give 2-methyl tetrazole product 59 (1.62 g, 63% yield) and 1-methyltetrazole product 60 (715 mg, 28% yield).

Compound 59

$^1$H NMR (CDCl$_3$) δ2.23 (s, 3H), 3.26 (t, J=7.3 Hz, 2H), 4.16 (s, 3H), 4.88 (t, J=7.3 Hz, 2H), 5.25 (s, 1H), 7.38 (d, J=1.3 Hz, 1H), 5.46 (s, 2H), 7.07–7.10 (m, 3H), 7.29–7.35 (m, 3H), 7.53–7.54 (m, 1H), 7.80–7.83 (m, 1H); MS m/e 415 (MH$^+$); Anal. Calcd for C$_{22}$H$_{22}$N$_8$O: C, 63.75;H, 5.35; N, 27.02 Found: C, 63.46;H, 5.61; N, 26.74.

Compound 60

$^1$H NMR (CDCl$_3$) δ2.21 (s, 3H), 3.22 (t, J=6.8 Hz, 2H), 3.42 (s, 3H), 4.89 (t, J=6.8 Hz, 2H), 5.31 (s, 1H), 5.39 (d, J=1.3 Hz, 1H), 5.44 (s, 2H), 7.06–7.13 (m, 3H), 7.23–7.32 (m, 3H), 7.55–7.61 (m, 1H), 7.80 (d, J=7.2 Hz, 1H); MS m/e 415 (MH$^+$).

Compound 61

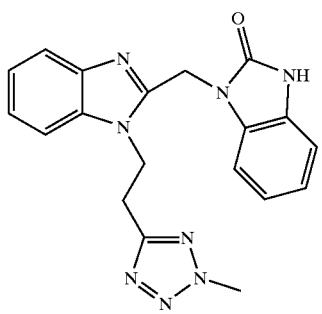

Compound 61 was prepared according to the same procedure as described for compound 6.

$^1$H NMR (DMSO-d6) δ3.34 (t over water, J=6.9 Hz, 2H), 4.24 (s, 3H), 4.79 (t, J=6.9 Hz, 2H), 5.23 (s, 2H), 6.91–7.00

(m, 3H), 7.09–7.23 (m, 3H), 7.48 (d, J=7.6 Hz, 1H), 7.52 (d, J=7.5 Hz, 1H); MS m/e 375 (MH+).

Compound 62

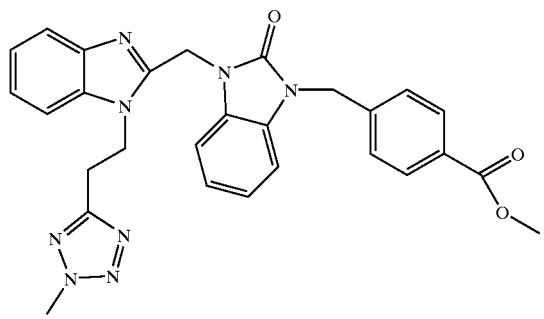

Compound 61 (1.00 g, 2.67 mmol) was suspended in THF/DMF (30 mL/5 mL) and BTPP (1.67 g, 5.32 mmol) was added at room temperature. The solution was allowed to stir for 15–30 minutes at which time methyl 4-(bromomethyl)-benzoate (0.73 g, 3.20 mmol) was added. The reaction was stirred 16 hours at room temperature under nitrogen atmosphere. The solvent was removed and the resulting residue partitioned between water and EtOAc. The combined organic extracts were dried over magnesium sulfate, filtered and evaporated. The crude product was purified by flash chromatography on silica gel using a mixture of ethyl acetate in hexanes to give compound 62.

$^1$H NMR (CDCl$_3$) δ3.24 (t, J=7.3 Hz, 2H), 3.90 (s, 3H), 4.17 (s, 3H), 4.88 (t, J=7.3 Hz, 2H), 5.17 (s, 2H), 5.54 (s, 2H), 6.83 (dd, J=7.7, 1.0 Hz, 1H), 6.99–7.10 (m, 2H), 7.31–7.41 (m, 5H), 7.56 (d, J=6.7 Hz, 1H), 7.82–7.85 (m, 1H), 7.99 (dd, J=6.6, 1.8 Hz, 1H); MS m/e 523 (MH+).

TABLE 11

Prepared as described for compound 62.
Compound 63

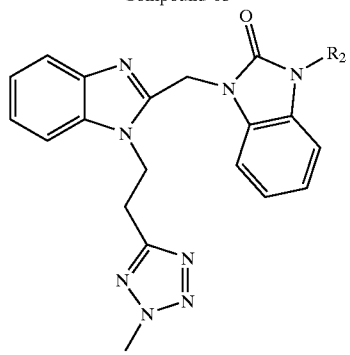

| # | R$_2$ | $^1$H-NMR Data | MS Data |
|---|---|---|---|
| 63a[a] | 4-(CH$_2$)-C$_6$H$_4$-COOH | (DMSO-d6) δ 3.36 (t, J=6.8 Hz, 2 H), 4.25 (s, 3 H), 4.80 (t, J=6.8 Hz, 2 H), 5.14 (s, 2 H), 5.36 (s, 2 H), 6.98-7.03 (m, 2 H), 7.09-7.23 (m, 4 H), 7.39 (d, J=8.2 Hz, 2 H), 7.48-7.55 (m, 2 H), 7.86 (d, J=8.2 Hz, 2 H) | 509 (MH+) |
| 63b | 4-(CH$_2$)-C$_6$H$_4$-NO$_2$ | (CDCl$_3$) δ 3.25 (t, J=7.4 Hz, 2 H), 4.17 (s, 3 H), 4.90 (t, J=7.4 Hz, 2 H), 5.21 (s, 2 H), 5.57 (s, 2 H), 6.84 (d, J=7.5 Hz, 1 H), 7.05-7.14 (m, 2 H), 7.34-7.43 (m, 3 H), 7.50 (d, J=8.9 Hz, 2 H), 7.64 (bd, J=7.5 Hz, 1 H), 7.85-7.88 (m, 1 H), 8.19 (d, J=8.9 Hz, 2 H) | 510 (MH+) |
| 63c[b] | 4-(CH$_2$)-C$_6$H$_4$-NH$_2$ | (DMSO-d6) δ 3.50 (t, J=6.7 Hz, 2 H), 424 (s, 3 H), 4.96 (t, J=6.7 Hz, 2 H), 5.12 (s, 2 H), 5.61 (s, 2 H), 7.04-7.08 (m, 2 H), 7.15-7.19 (m, 1 H), 7.30-7.49 (m, 7 H), 7.69 (d, J= 7.1 Hz, 1 H), 7.83 (d, J=7.7 Hz, 1 H) | 480 (MH+) |
| 63f[c] | 4-(CH$_2$)-C$_6$H$_4$-CH$_2$-pyridyl | (CD$_3$OD) δ 3.37 (t, J=6.8 Hz, 2 H), 4.14 (s, 3 H), 4.87 (t, J=6.9 Hz, 2 H), 5.20 (s, 2 H), 5.44 (s, 2 H), 5.84 (s, 2 H), 7.06-7.09 (m, 3 H), 7.18-7.21 (m, 1 H), 7.24-7.34 (m, 2 H), 7.46-7.53 (m, 5 H), 7.60 (dd, J=1.6, 7.0 Hz, 1 H), 8.12 (t, J=6.8 Hz, 2 H0, 8.62 (t, J=7.9 Hz, 1 H), 9.06 (d, J=5.8 Hz, 2 H) | 556 (MH+) |

TABLE 11-continued

Prepared as described for compound 62.

Compound 63

| # | R₂ | ¹H-NMR Data | MS Data |
|---|----|-----|---------|
| 63g | propyl-morpholine | (CD₃OD) δ .68-3.74 (m, 4 H), 4.02 (bs, 4 H), 4.25 (s, 3 H), 4.49 (t, J=5.7 Hz, 2 H), 5.13 (t, J=6.5 Hz, 2 H), 5.78 (s, 2 H), 7.19-7.31 (m, 3 H), 7.42 (d, J=7.4 Hz, 1 H), 7.61-7.70 (m, 2 H), 7.78 (dd, J=2.4, 6.8 Hz, 1 H), 8.00 (d, J=8.4 Hz, 1 H) | 488 (MH+) |
| 63h | butyl-SO₃H | (CD₃OD) δ 1.86-1.98 (m, 4 H), 2.89 (t, J= 7.3 Hz, 2 H), 3.32 (t, J=7.0 Hz, 2 H), 4.01 (t, J=6.7 Hz, 2 H), 4.17 (s, 3 H), 4.85 (t, J= 7.0 Hz, 2 H), 5.41 (s, 2 H), 7.02-7.20 (m, 3 H), 7.25-7.33 (m, 3 H), 7.50 (dd, J=2.0, 6.7 Hz, 1 H), 7.63 (dd, J=2.0, 6.6 Hz, 1 H) | 511 (MH+) |
| 63i | ethyl pentanoate | (CDCl₃) δ 1.27 (t, J=7.1 Hz, 3 H), 2.05-2.14 (m, 2 H), 2.41 (t, 7.3 Hz, 2 H), 3.18 (t, J=7.6 Hz, 2 H), 3.98 (t, J=8.7 Hz, 2 H), 4.12(q, J=7.1 Hz,2H),4.81 (t,J=7.3 Hz, 2 H), 5.42 (s, 2 H), 7.02-7.12 (m, 3 H), 7.23-7.34 (m, 3 H), 7.43-7.46 (m, 1 H), 7.77-7.80 (m, 1 H) | 489 (MH+) |
| 63j[a] | pentanoic acid | (DMSO-d6) δ 1.70-1.82 (m, 2H), 1.89(t, J= 7.6 Hz,2H), 3.31 (t, J=6.9 Hz, 2 H), 3.83 (t, J=7.3 Hz, 2 H), 4.25 (s, 3 H), 4.79 (t, J=6.9 Hz, 2 H), 5.29 (s, 2 H), 6.97-7.07 (m, 2 H), 7.13-7.23 (m, 3 H), 7.33 (d, J= 7.2 Hz, 1 H), 7.52 (d, J=7.3 Hz, 1 H), 7.55 (d, J=7.4 Hz, 1 H) | 460 (MH+) |
| 63k | methyl hexanoate | (CDCl₃) δ 2.38 (t, J=7.1 Hz, 2 H), 3.20 (t, J=7.3 Hz, 2 H), 3.65 (s, 3 H), 3.93 (t, J= 6.9 Hz, 2 H), 4.18 (s, 3H), 4.83 (t, J=7.4 Hz, 2 H), 5.45 (s, 2 H), 6.98-7.01 (m, 1 H), 7.05-7.09 (m, 2 H), 7.29-7.35 (m, 3 H), 7.48-7.50 (m, 1 H), 7.79-7.82 (m, 1 H) | 489 (MH+) |
| 63l | ethyl hexanoate | (DMSO-d6) δ 1.14 (t, J=7.1 Hz, 3 H), 1.52-1.71 (m, 2 H), 2.34 (t, J=7.4 Hz, 2 H), 3.12 (t over water, 2 H), 3.87 (t, J=6.8 Hz, 2 H), 4.01 (q, J=7.1 Hz, 2 H), 4.79 (t, J=6.8 Hz, 2 H), 5.31 (s, 2 H), 6.99-7.09 (m, 2 H), 7.13-7.24 (m, 4 H), 7.49 (d, J= 7.5 Hz, 1 H), 7.54 (d, J=7.6 Hz, 1 H) | |
| 63m | hexanoic acid | (DMSO-d6) δ 1.35-1.48 (m, 2 H), 1.56-1.64 (m, 2 H), 1.90 (t, J=7.3 Hz, 2 H), 3.31 (t, J= 6.8 Hz, 2 H), 3.81 (t, J=7.1 Hz, 2 H), 4.24 (s, 3 H), 4.78 (t, J=6.8 Hz, 2 H), 5.29 (s, 2 H), 6.96-7.07 (m, 2 H), 7.11-7.22 (m, 4 H), 7.47 (d, J=7.3 Hz, 1 H), 7.53 (d, J= 7.5 Hz, 1 H) | 475 (MH+) |

TABLE 11-continued

Prepared as described for compound 62.
Compound 63

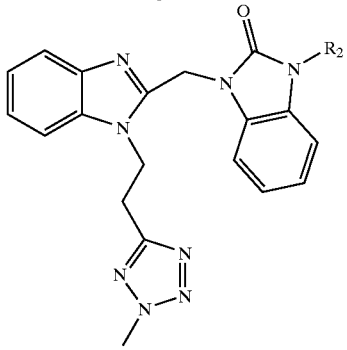

| # | R₂ | ¹H-NMR Data | MS Data |
|---|---|---|---|
| 63n | ethyl heptanoate | (CDCl₃) δ 1.24 (t, J=7.1 Hz, 3 H), 1.37-1.53 (m, 2 H), 1.62-1.93 (m, 4 H), 2.30 (t, J=7.5 Hz, 2 H), 3.42 (t, J=6.8 Hz, 2 H), 4.10 (q, J=7.1 Hz, 2 H), 4.19 (s, 3 H), 4.81 (t, J=7.2 Hz, 2 H), 5.42 (s, 2 H), 6.97-7.12 (m, 3 H), 7.23-7.33 (m, 3 H), 7.43-7.46 (m, 1 H), 7.76-7.82 (m, 1 H) | 517 (MH+) |
| 63o[a] | heptanoic acid | (DMSO-d6) δ 1.20-1.30 (m, 2 H), 1.39-1.48 (m, 2 H), 1.50-1.66 (m, 2 H), 1.82 (t, J=7.2 Hz, 2 H), 3.31 (t, J=6.8 Hz, 2 H), 4.25 (s, 3 H), 4.79 (t, J=7.0 Hz, 2 H), 5.30 (s, 2 H), 6.98-7.23 (m, 6 H), 7.48 (d, J=7.4 Hz, 1 H), 7.55 (d, J=7.4 Hz, 1 H) | 488 (MH+) |
| 63p | butyronitrile | (CDCl₃) δ 2.94 (t, J=7.0 Hz, 2 H), 3.16 (t, J=6.9 Hz, 2 H), 4.16 (s, 3 H), 4.26 (t, J=7.0 Hz, 2 H), 4.77 (t, J=6.9 Hz, 2 H), 5.42 (s, 2 H), 7.06-7.17 (m, 3 H), 7.27-7.33 (m, 2 H), 7.35-7.39 (m, 1 H), 7.44-7.47 (m, 1 H), 7.78-7.83 (m, 1 H) | 428 (MH+) |
| 63q | N,N-dimethylaminopropyl | (CD₃OD) δ 3.08 (s, 6 H), 3.68-3.72 (m, 4 H), 4.23 (s, 2 H), 4.45 (t, J=5.7 Hz, 2 H), 5.11 (t, J=6.5 Hz, 2 H), 5.74 (s, 2 H), 7.19-7.32 (m, 3 H), 7.41 (d, J=7.4 Hz, 1 H), 7.58-7.68 (m, 2 H), 7.74 (d, J=7.4 Hz, 1 H), 7.97 (d, J=7.4 Hz, 1 H) | 446 (MH+) |
| 63r | pentanol | (CDCl₃) δ 1.70-1.80 (m, 2 H), 1.92-2.02 (m, 2 H), 2.46 (t, J=7.0 Hz, 2 H), 3.20 (t, J=7.4 Hz, 2 H), 3.98 (t, J=6.7 Hz, 2 H), 4.18 (s, 3 H), 4.82 (t, J=7.4 Hz, 2 H), 5.44 (s, 2 H), 6.98-7.07 (m, 1 H), 7.07-7.12 (m, 2 H), 7.28-7.37 (m, 3 H), 7.48-7.51 (m, 1 H), 7.78-7.84 (m, 1 H) | 456 (MH+) |
| 63s | butanol | (CDCl₃) δ 2.10-2.24 (m, 2 H), 2.49 (t, J=7.1 Hz, 2 H), 3.22 (t, J=7.4 Hz, 2 H), 4.07 (t, J=6.6 Hz, 2 H), 4.16 (s, 3 H), 4.87 (t, J=7.4 Hz, 2 H), 5.51 (s, 2 H), 7.04-7.07 (m, 1 H), 7.11-7.15 (m, 2 H), 7.34-7.43 (m, 3 H), 7.56-7.64 (m, 1 H), 7.87-7.87 (m, 1 H) | 442 (MH+) |
| 63t[d] | amidoxime | (DMSO-d6) δ 1.82-1.93 (m, 2 H), 2.09 (t, J=7.4 Hz, 2 H), 3.29-3.33 (m, 2 H), 3.85 (t, J=6.9 Hz, 2 H), 4.24 (s, 3 H), 4.78 (t, J=6.9 Hz, 2 H), 5.29 (s, 2 H), 6.16 (bs, 2 H), 6.99-7.08 (m, 2 H), 7.12-7.24 (m, 4 H), 7.48 (d, J=7.5 Hz, 1 H), 7.53 (d, J=7.4 Hz, 1 H), 9.09 (bs, 1 H) | 475 (MH+) |
| 63u | benzyl | (CDCl₃) δ 3.21 (t, J=7.4 Hz, 2 H), 4.14 (s, 3 H), 4.84 (t, J=7.4 Hz, 2 H), 5.12 (s, 2 H), 5.47 (s, 2 H), 6.87-6.92 (m, 1 H), 6.97-7.04 (m, 2 H), 7.24-7.35 (m, 8 H), 7.44-7.47 (m, 1 H), 7.77-7.83 (m, 1 H) | 465 (MH+) |

TABLE 11-continued

Prepared as described for compound 62.
Compound 63

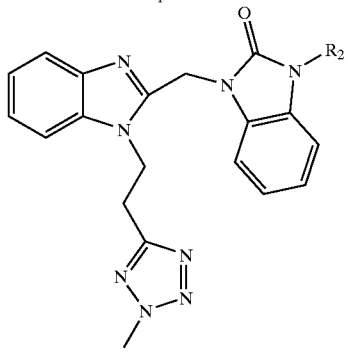

| # | R$_2$ | $^1$H-NMR Data | MS Data |
|---|---|---|---|
| 63v | ![structure] | (DMSO-d6) δ 3.36 (t, J=6.7 Hz, 2 H), 3.66 (s, 3 H), 4.25 (s, 3H), 4.74 (s, 3H), 4.80 (t, J= 6.9 Hz, 2 H), 5.00 (s, 2 H), 5.33 (s, 2 H), 6.87 (d, J=8.7 Hz, 2 H), 6.98-7.01 (m, 2 H), 7.13-7.23 (m, 4 H), 7.30 (d, J=8.7 Hz, 2 H), 7.51 (dd, J=7.7, 12.9 Hz, 2 H) | 553 (MH+) |
| 63w | ![structure] | (DMSO-d6) δ 3.34 (t, J=6.9 Hz, 2 H), 4.01 (s, 2 H), 4.27 (s, 3 H), 4.81 (t, J=6.9 Hz, 2 H), 4.98 (s, 2 H), 5.34 (s, 2 H), 6.73 (d, J= 8.6 Hz, 2 H), 6.98-7.01 (m, 2 H), 7.13-7.25 (m, 6 H), 7.50 (d, J=7.5 Hz, 1 H), 7.55 (d, J=7.3 Hz, 1 H) | 539 (MH+) |

[a]saponification of ester as described for compound 8;
[b]catalytic hydrogenation as described for compound 123;
[c]alkylation with 1,4-di(bromomethyl)benzene followed by addition of pyridine to form a pyridinium salt as described for 37g;
[d]prepared as described for compound 119.

Compound 64

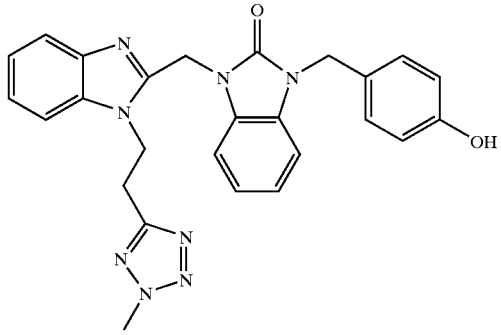

The general coupling method used for compound 63a was applied using 4-benzyloxybenzyl chloride and BTPP in tetrahydrofuran to give the product benzyl ether. The benzyl ether (600 mg, 1.05 mmol) and 10% palladium hydroxide on carbon (160 mg) in 2:1 methanol/tetrahydrofuran (50 mL / 25 mL) was agitated under hydrogen at 55 psi for 48 hours. The reaction mixture was filtered through a pad of Celite and then subjected to column chromatography (2:1 EtOAc/CH$_2$Cl$_2$) to give compound 64 as a white solid (262 mg, 52% yield).

$^1$H NMR (DMSO-d$_6$) δ3.35 (t, J=6.8 Hz, 2H), 4.25 (s, 3H), 4.80 (t, J=6.8 Hz, 2H), 4.94 (s, 2H), 5.33 (s, 2H), 6.68 (d, J=8.5 Hz, 2H), 6.95–7.02 (m, 2H), 7.09–7.23 (m, 6H), 7.47–7.54 (m, 2H), 9.39 (s, 1H); IR (KBr, cm$^{-1}$) 3247, 2944, 1664, 1613, 1597, 1515, 1491, 1445, 1413, 747; MS m/e 481

(MH⁺); Anal. Calcd for $C_{26}H_{24}N_8O_2$: C, 64.99;H, 5.03; N, 23.32 Found: C, 64.79;H, 4.98; N, 23.38.

Compound 65

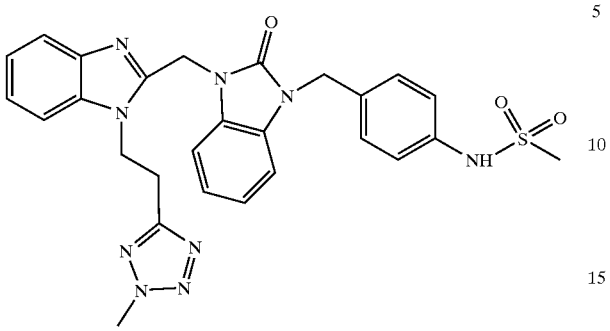

A mixture of compound 63c, (100 mg, 0.18 mmol) and triethylamine (55 mg, 0.54 mmol) in methylene chloride (5 mL) was cooled to 0° C. Methanesulfonyl chloride (21 mg, 0.18 mmol) was added and the reaction mixture was allowed to warm gradually to room temperature. After stirring for 5.5 hours under nitrogen atmosphere, the organic material was washed with dilute aqueous sodium bicarbonate solution (10 mL). The aqueous layer was then extracted with methylene chloride (2×20 mL). The combined organic extracts were dried over magnesium sulfate, filtered and evaporated. Trituration with anhydrous diethyl ether followed by filtration gave compound 65 as a yellow solid (92 mg, 91% yield):

¹H NMR (CD₃OD) δ2.95 (s, 3H), 3.07 (s, 1H), 3.68 (t, J=6.5 Hz, 2H), 4.26 (s, 3H), 5.14 (t, J=6.7 Hz, 2H), 5.15 (s, 2H), 5.81 (s, 2H), 7.16–7.28 (m, 6H), 7.43 (d, J=8.6 Hz, 2H), 7.63–7.75 (m, 3H), 7.99–8.02 (m, 1H); IR (KBr, cm⁻¹): 3435, 2929, 1708, 1615, 1513, 1493, 1404, 1329, 1152, 752. MS m/e 558 (MH⁺).

Compound 66

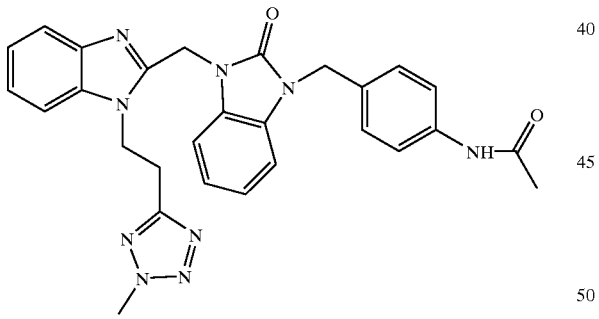

A mixture of compound 63c (100 mg, 0.18 mmol) and triethylamine (55 mg, 0.54 mmol) in methylene chloride (4 mL) was cooled to 0° C. Acetyl chloride (18 mg, 0.23 mmol) was added followed by DMAP (5 mg, catalytic quantity). The reaction mixture was allowed to warm to room temperature gradually and stirring was continued for 16 hours at room temperature under nitrogen atmosphere. A white precipitate was observed. The organic material was washed with dilute aqueous sodium bicarbonate solution (10 mL). The aqueous layer was then extracted with methylene chloride (2×20 mL). The combined organic extracts were dried over magnesium sulfate, filtered and evaporated to give a white solid. The solid was triturated with anhydrous diethyl ether and filtered to give the compound 66 as a white solid (50 mg, 53% yield).

¹H NMR (DMSO-d₆) δ2.00 (s, 3H), 3.36 (t, J=6.9 Hz, 2H), 4.25 (s, 3H), 4.80 (t, J=6.9 Hz, 2H), 5.14 (s, 2H), 5.34 (s, 2H), 6.97–7.02 (m, 2H), 7.07–7.23 (m, 6H), 7.28 (d, J=8.5 Hz, 2H), 7.48–7.54 (m, 4H), 9.92 (s, 1H). IR (KBr, cm⁻¹): 3308, 2929, 1694, 1610, 1516, 1495, 1407, 1311, 749. MS m/e 522 (MH⁺). Anal. Calcd for $C_{28}H_{27}N_9O_2$: C, 64.48;H, 5.22; N, 24.17 Found: C, 64.13;H, 5.32; N, 23.86

Compound 67

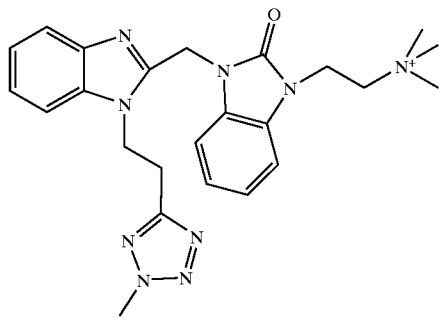

To a solution of compound 63q (32 mg, 0.07 mmol) in acetone (1 mL) was added iodomethane (20 mg, 0.14 mmol). The reaction mixture was stirred at 50° C. for 2 hours and then stirred at room temperature overnight. The resulting precipitate was filtered and triturated with CH₂Cl₂ and Et₂O to give 18 mg (55% yield) of compound 67.

¹H NMR (DMSO-d6) δ3.19 (s, 9H), 3.51 (t, J=7.0 Hz, 2H), 3.74 (t, J=6.7 Hz, 2H), 4.39 (t, J=6.7 Hz, 2H), 4.91 (t, J=7.0 Hz, 2H), 5.57 (bs, 2H), 7.08–7.19 (m, 2H), 7.27–7.28 (m, 3H), 7.41 (d, J=7.2 Hz, 1H), 7.57 (d, J=7.7 Hz, 1H), 7.73 (d, J=7.7 Hz, 1H); MS (m/e) 446 (MH⁺).

Compound 68

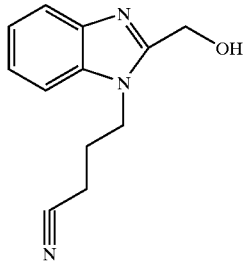

To a solution of 2-hydroxymethylbenzimidazole (29.63 g, 200 mmol) in a mixture of DMF/THF (150 mL, 1:1) was added sodium hydride (60% in mineral oil, 8.4 g, 210 mmol) in several portions at room temperature. After stirring for 1 hour, 4-bromobutyronitrile (29.6 g, 200 mmol) was added and the resulting solution was stirred at 80° C. for 16 hours. The solvent was evaporated and the residue diluted with water and extracted with EtOAc. The combined extracts were dried over MgSO₄ and evaporated. The residue was purified by flash chromatography (gradient, EtOAc/hexane, 1:1 to 2:1, then EtOAc/MeOH, 10:1) to give 22.11 g (51% yield) 4-(2-hydroxymethyl-benzoimidazol-1-yl)-butyronitrile, 68 as a white solid.

¹H NMR (CDCl₃) 2.27–2.32 (m, 2H), 2.41 (t, J=6.0 Hz, 2H), 4.41 (t, J=7.2 Hz, 2H), 7.26–7.38 (m, 3H), 7.67–7.70 (m, 1H); MS m/e 216 (MH⁺).

Compound 69

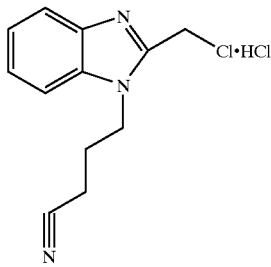

To 4-(2-hydroxymethyl-benzoimidazol-1-yl)-butyronitrile, 68, (22 g, 102.2 mmol) suspended in CH₂Cl₂ (100 mL), thionyl chloride (15.81 g, 132.9 mmol) was slowly added with ice-water bath cooling. The ice bath was removed. The solution was stirred at room temperature for 1 hour and then evaporated. The residue was triturated with EtOAc to give a nearly quantitative yield of 4-(2-chloromethyl-benzoimidazol-1-yl)-butyronitrile, 69, as light gray powder.

¹H NMR (CDCl₃) δ2.32–2.38 (m, 2H), 2.70 (t, J=7.3 Hz, 2H), 4.69 (t, J=7.6 Hz, 2H), 5.33 (s, 2H), 7.69–7.74 (m, 2H), 7.85–7.87 (m, 1H), 8.00–8.02 (m, 1 H); MS m/e 234 (MH⁺). Anal. Calcd for C₁₂H₁₂N₃.HCl.0.25H₂O: C, 52.48;H, 4.95; N, 15.30 Found: C, 52.52;H, 4.88; N, 15.26

Compound 70

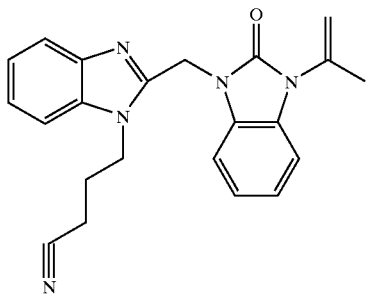

Compound 70 was prepared as described for 4.
¹H NMR (CDCl₃) 1.93–2.06 (m, 2H), 2.29 (s, 3H), 7.65 (t, J=7.6 Hz, 2H), 4.50 (t, J=7.7 Hz, 2H), 5.22 (s, 1H), 5.40 (s, 2H), 5.42 (s, 1H), 7.10–7.17 (m, 3H) 7.30–7.38 (m, 3H), 7.53–7.57 (m, 1H), 7.79–7.83 (m, 1H); MS m/e 372 (MH⁺).

Compound 71

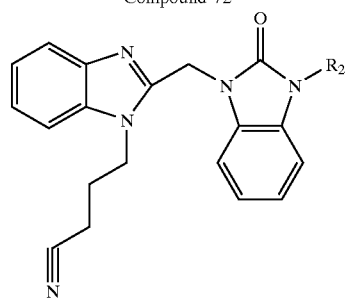

Compound 71 prepared as described for compound 52.
¹H NMR (CD₃OD) δ2.12–2.20 (m, 2H), 2.23 (s, 3H), 2.94 (t, J=7.4 Hz, 2H), 4.46 (t, J=7.8 Hz, 2H), 4.92 (s, 2H), 5.23 (s, 1H), 5.45 (s, 2H), 7.05–7.33 (m, 6H), 7.45 (dd, J=1.3, 6.8 Hz, 1H), 7.61 (dd, J=1.7, 6.9 Hz, 1H); MS m/e 415 (MH⁺).

TABLE 12

Prepared by treatment of compound 71 as described for compound 6 followed by alkylation as described for compound 7 using Cs₂CO₃ instead of BTPP.

Compound 72

| # | R₂ | ¹H-NMR Data | MS Data |
|---|----|----|----|
| 72a | ![structure] | (DMSO-d6) 2.87 (s, 3 H), 2.96 (s, 3 H), 3.13 (t, J=6.7 Hz, 2 H), 4.76 (t, J=6.7 Hz, 2 H), 5.16 (s, 2 H), 5.50 (s, 2 H), 7.02-7.04 (m, 2 H), 7.16-7.21 (m, 2 H), 7.25-7.30 (m, 2 H), 7.37-7.42 (m, 4 H), 7.58 (d, J=7.9 Hz, 1 H), 7.70 (d, J=8.1 Hz, 1 H) | 479 (MH+) |

TABLE 12-continued

Prepared by treatment of compound 71 as described for compound 6 followed by alkylation as described for compound 7 using Cs₂CO₃ instead of BTPP.

Compound 72

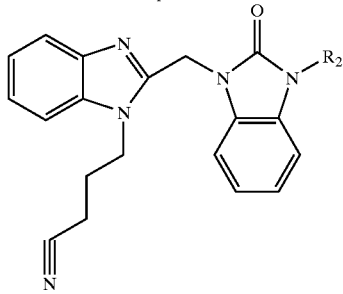

| # | R₂ | ¹H-NMR Data | MS Data |
|---|---|---|---|
| 72b | (structure: 4-ethylbenzoate methyl ester group) | (CDCl3) 2.74 (t, J=6.7 Hz, 2 H), 3.92 (s, 3 H), 4.82 (t, J=6.7 Hz, 2 H), 5.17 (s, 2 H), 5.51 (s, 2 H), 6.87 (d, J=7.3 Hz, 1 H), 7.03-7.12 (m, 1 H), 7.33-7.43 (m, 6 H), 7.60 (d, J=7.2 Hz, 1 H), 7.83-7.86 (m, 1 H), 8.02 (d, J=8.3 Hz, 2 H) | 466 (MH+) |
| 72c | (structure: pentanenitrile group) | (DMSO-d6) δ 1.59-1.62 (m, 2 H), 1.76-1.79 (m, 2 H), 1.99-2.02 (m, 2 H), 2.54-2.63 (m, 4 H), 3.93 (t, J=4.1, 2 H), 4.41 (t, J=4.5, 2 H), 5.41 (s, 2 H), 6.99-7.19 (m, 4 H), 7.24-7.28 (m, 2 H), 7.56-7.60 (m, 2H); | 413 (MH+) |

Compound 73

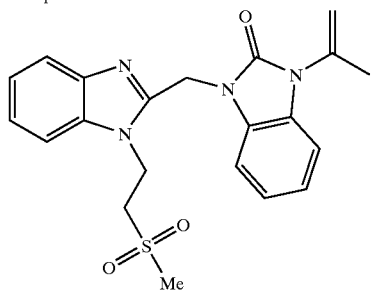

Compound 3 (2.00 g, 6.57 mmol) was suspended in acetonitrile (100 mL) and methyl vinyl sulfone (2.09 g, 19.72 mmol) was added followed by MTBD (50 mg, 0.33 mmol). The reaction mixture was heated at 50–60° C. for 16 hours. The solution became transparent. The solvent was evaporated and the residue was purified by flash column chromatography on silica gel (10:1 ethyl acetate/hexanes) to give 2.50 g (93% yield) of compound 73 as a yellow-orange solid:

¹H NMR (CDCl₃) δ2.25 (s, 3H), 3.07 (s, 3H), 3.39 (t, J=7.6 Hz, 2H), 4.96 (t, J=7.3 Hz, 2H), 5.25 (s, 1H), 5.42 (s, 1H), 5.50 (s, 2H), 7.12–7.28 (m, 3H), 7.36–7.47 (m, 3H), 7.63 (d, J=4.6 Hz, 1H), 7.83–7.86 (m, 1H); IR (KBr, cm⁻¹) 1698, 1489, 1397, 1306, 1137, 745; MS m/e 411 (MH⁺).

Compound 74

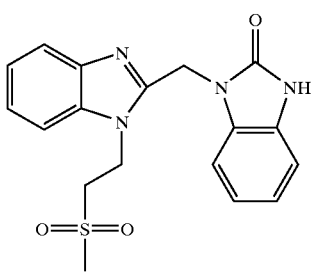

Compound 73 (2.2 g, 5.36 mmol) was suspended in MeOH (100 ml) and concentrated hydrochloric acid (10 mL). The mixture was heated at reflux for 3.5 hours and then stirred overnight at room temperature. The solvent was stripped, repeatedly evaporated with hexanes and/or diethyl ether, and dried under vacuum to give 2.2 g (quantitative yield) compound 74 as a hydrochloride salt:

$^1$H NMR (DMSO-d$_6$) δ3.17 (s, 3H), 4.02 (t, J=6.1 Hz, 2H), 5.24 (t, J=6.1 Hz, 2H), 5.93 (s, 2H), 7.09–7.20 (m, 2H), 7.29 (bd, J=8.0 Hz, 1H), 7.65–7.73 (m, 2H), 8.06 (bd, J=8.0 Hz, 1H); IR (KBr, cm$^{-1}$) 1687,1461, 1399, 1305, 1127,751; MS m/e 317 (MH$^+$).

Compound 75

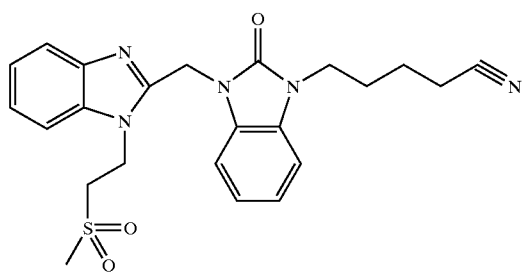

Compound 75 prepared as described for compound 7.

$^1$H NMR (CDCl$_3$) δ1.72–1.78 (m, 2H), 1.92–1.98 (m, 2H), 2.14–2.20 (m, 2H), 2.46 (t, J=7.1 Hz, 2H), 2.85 (s, 3H), 3.07 (t, J=7.6 Hz, 2H), 3.98 (t, J=6.9 Hz, 2H), 4.54 (t, J=7.7 Hz, 2H), 5.42 (s, 2H), 6.98–7.00 (m, 1H), 7.08–7.12 (m, 2H), 7.31–7.34 (m, 2H), 7.39–7.41 (m, 1H), 7.53–7.55 (m, 1H), 7.81 (dd, J 3.1, 5.9 Hz, 1H); MS (m/e) 466 (MH$^+$).

Compound 76

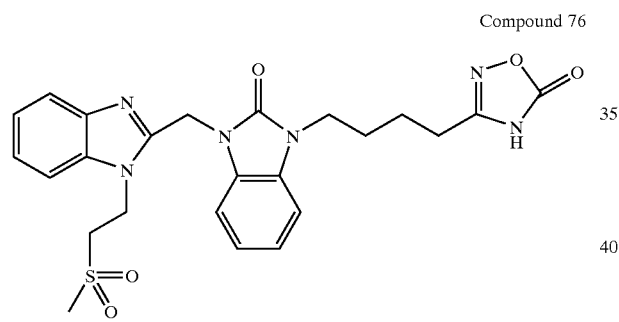

Compound 76 prepared as described for compound 121.

$^1$H NMR (CD$_3$OD) δ1.73–1.78 (m, 2H), 1.86–1.90 (m, 2H), 2.15–2.19 (m, 2H), 2.61 (t, J=7.5 Hz, 2H), 2.94 (s, 3H), 3.20 (t, J=7.6 Hz, 2H), 4.03 (t, J=6.9 Hz, 2H), 4.55 (t, J=7.7 Hz, 2H), 5.47 (s, 2H), 7.07 (t, J=7.7 Hz, 1H), 7.14 (t, J=7.2 Hz, 1H), 7.21–7.34 (m, 4H), 7.59 (d, J=8.0 Hz, 1H), 7.63 (d, J=8.0 Hz, 1H); MS (m/e) 525 (MH$^+$).

Compound 77

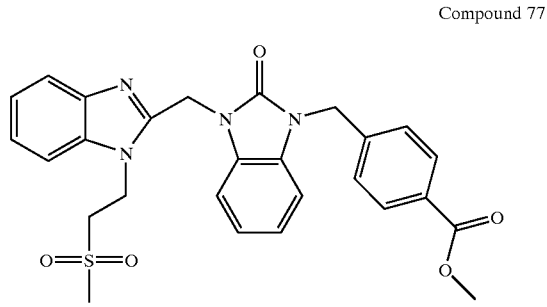

Compound 74 (2.20 g, 5.36 mmol) was suspended in anhydrous THF (70 mL). Upon addition of BTPP (6.70 g, 21.44 mmol), the reaction mixture became a clear solution. After stirring for 20 minutes, methyl 4-(bromomethyl) benzoate (1.47 g, 6.43 mmol) was added and the mixture was allowed to stir at room temperature under a nitrogen atmosphere for 16 hours. The solvent was evaporated. The brown residue was taken up in water (75 mL) and extracted with methylene chloride (3×300 mL). The organic extracts were dried over anhydrous MgSO$_4$, and evaporated. The product was purified by flash column chromatography (gradient with EtOAc/ hexanes 2:1 to 5:1 as eluant to give 1.2 g (43% yield) of compound 77:

$^1$H NMR (CDCl$_3$) δ2.99 (s, 3H), 3.43 (t, J=7.3 Hz, 2H), 3.94 (s, 3H), 4.95 (t, J=7.3 Hz, 2H), 5.17 (s, 2H), 5.55 (s, 2H), 6.86 (d, J=7.7 Hz, 1H), 7.03–7.15 (m, 2H), 7.36–7.7.47 (m, 4H), 7.55 (d, J=4.8 Hz, 1H), 7.65–7.86 (m, 1H), 8.02 (d, J=8.1 Hz, 2H); IR (KBr, cm$^{-1}$) 1707, 1493, 1438, 1408, 1282, 1135, 750; MS m/e 519 (MH$^+$).

Compound 78

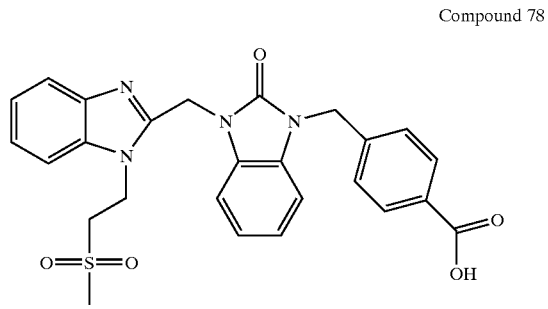

Ester 77 (1.2 g, 2.31 mmol) was suspended in a solution of methanol (75 mL) and 1 N NaOH (4.6 mL, 4.63 mmol). The reaction mixture was heated at reflux for 3 hours. The methanol was evaporated and the residue was taken up in water (75 mL). The aqueous solution was acidified to pH 6 with 1 N HCl. An unfilterable gelatinous precipitate came out of solution. A large amount of sodium chloride was added to the aqueous material to create a saturated solution which was then extracted with THF (400 mL×3 ). The organic extracts were dried over anhydrous magnesium sulfate, filtered, and evaporated to give 894 mg (81% yield) of compound 78 as a free acid.

The acid (500 mg, 0.99 mmol) was suspended in a mixture of methanol and THF (50%, 70 mL), and 1 N NaOH (0.99 mL, 0.99 mmol) was added. The solvent was evaporated and the solid was dried under vacuum. The solid was triturated with diethyl ether to give 464 mg (89% yield) of compound 78 as a sodium salt.

$^1$H NMR (DMSO-d$_6$) δ3.10 (s, 3H), 3.78 (t, J=6.5 Hz, 2H), 4.86 (t, J=6.5 Hz, 2H), 5.09 (s, 2H), 5.52 (s, 2H), 6.97–7.29 (m, 8H), 7.57 (d, J=7.6 Hz, 1H), 7.60 (d, J=7.7 Hz, 1H), 7.79 (d, J=8.1 Hz, 2H); IR (KBr, cm$^{-1}$) 3398, 2926, 1698, 1597, 1554, 1493, 1392, 1293, 1132,750; MS m/e 505 (MH$^+$).

Compound 79

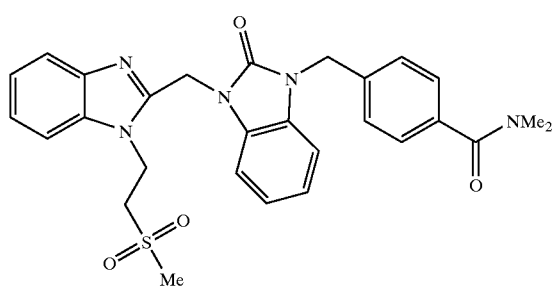

Acid 78 (400 mg, 0.79 mmol), dimethylamine hydrochloric acid salt (97 mg, 1.19 mmol), and N,N-diisopropylethylamine (307 mg, 2.38 mmol) were stirred in DMF (10 mL). To this solution was added PyBroP (433 mg, 0.95 mmol). The reaction was allowed to stir under nitrogen atmosphere at room temperature for 48 hours. The solvent was evaporated. The residue was taken up in water (20 mL) and extracted with ethyl acetate (3×150 mL). The organic extracts were dried over anhydrous MgSO$_4$, and evaporated. Column chromatography (methylene chloride /methanol= 20: 1) followed by preparative high pressure liquid chromatography (reverse phase) gave 110 mg (26% yield) of compound 79:

$^1$H NMR (CD$_3$OD) δ2.96, 3.05, 3.08 (s, 3H each), 3.83(t, J=3.8 Hz, 2H), 5.07 (t, J=3.8 Hz, 2H), 5.21 (s, 2H), 5.77 (s, 2H), 7.08 (bs, 3H), 7.28–7.30 (m, 1H), 7.41 (d, J=4.9 Hz, 2H), 7.44–7.53 (m, 4H), 7.65 (d, J=4.9 Hz, 1H), 7.79 (d, J=4.9 Hz, 1H); IR (KBr, cm$^{-1}$) 3441, 1702,1621, 1493, 1406, 1133, 750; MS m/e 532 (MH$^+$); Anal. Calcd for C$_{28}$H$_{29}$N$_5$O$_4$S .2H$_2$O: C, 59.24;H, 5.86; N, 12.34 Found: C, 59.00;H, 5.15; N, 12.17.

Compound 80

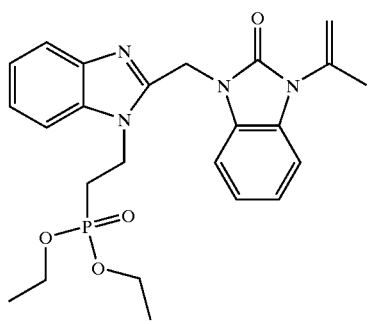

Compound 80 was prepared as described for 50 except ethyl vinylphosphinate was used in place of acrylonitrile.

$^1$H NMR (DMSO-d6) δ1.10 (t, J=7.1, 6H), 2.11 (s, 3H), 2.29–2.40 (m, 2H), 3.85–3.95 (m, 4H), 4.54–4.64 (m, 2H), 5.20 (s, 1H), 5.40 (s, 1H), 5.45 (s, 2H), 7.02–7.09 (m, 2H), 7.14–7.32 (m, 4H), 7.50–7.57 (m, 2H); MS (m/e) 469 (MH$^+$).

Compound 81

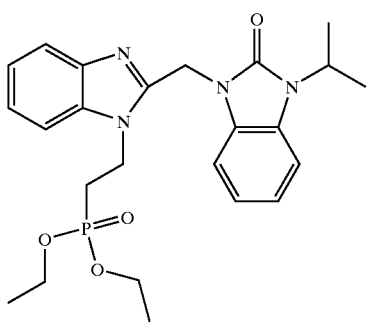

The isopropenyl group of compound 80 was reduced to give compound 81 as described for compound 54.

$^1$H NMR (DMSO-d6) δ1.10 (t, J=7.0, 6H), 1.46 (d, J=7.0, 6H), 2.24–2.35 (m, 2H), 3.85–3.95 (m, 4H), 4.53–4.70 (m, 3H), 5.41 (s, 2H), 6.96–7.06 (m, 2H), 7.14–7.34 (m, 4H), 7.48–7.57 (m, 2H); MS (m/e) 471 (MH$^+$).

Compound 82

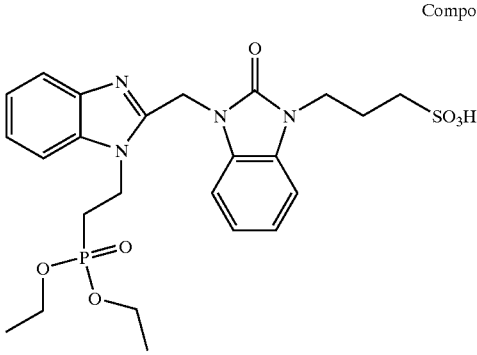

Compound 82 was prepared as described for compound 7 using [1,2]oxathiolane 2,2-dioxide as the alkylating agent.

$^1$H NMR (DMSO-d6) δ1.10 (t, J=7.0, 6H), 1.90–2.0 (m, 2H), 2.28–2.47 (m, 4H), 3.85–3.98 (m, 6H), 4.52–5.62 (m, 2H), 5.44 (s, 2H), 6.96–7.08 (m, 2H), 7.12–7.29 (m, 4H), 7.48–7.57 (m, 2H); MS (m/e) 551 (MH$^+$).

Compound 83

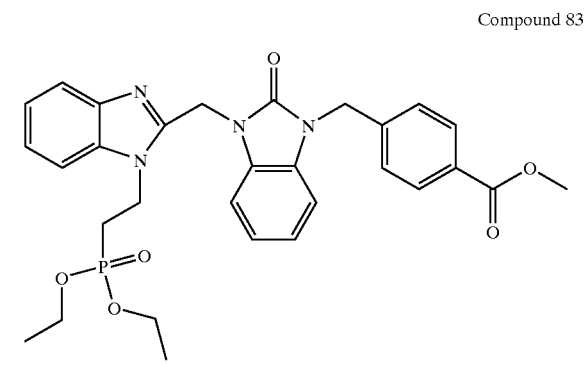

Compound 83 was prepared as described for compound 7.
$^1$H NMR (DMSO-d6) δ1.09 (t, J=7.1, 6H), 2.32–2.43 (m, 2H), 3.82 (s, 3H), 3.84–3.94 (m, 4H), 4.55–4.64 (m, 2H), 5.20 (s, 2H), 5.51 (s, 2H), 6.97–7.04 (m, 2H), 7.09–7.31 (m, 4H), 7.46–7.56 (m, 4H), 7.93 (d, J=8.3, 2H); MS (m/e) 577 (MH$^+$).

Compound 84

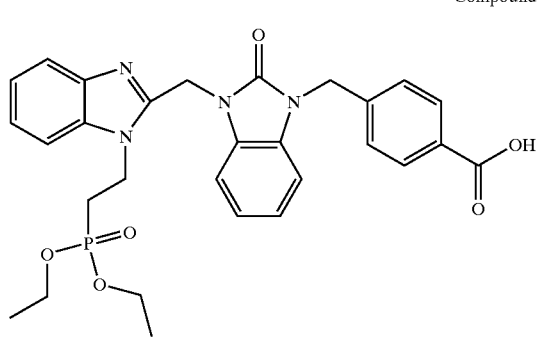

Compound 84 was prepared as described for compound 4.

$^1$H NMR (DMSO-d6) δ1.09 (t, J=7.1, 6H), 7.38–2.44 (m, 2H), 3.86–3.95 (m, 4H), 4.61–4.69 (m, 2H), 5.20 (s, 2H), 5.62 (s, 2H), 7.01–7.04 (m, 2H), 7.25–7.37 (m, 2H), 7.46 (d, J=8.2, 2H), 7.59–7.66 (m, 2H), 7.90 (s, 2H); MS (m/e) 563 (MH$^+$).

Compound 85

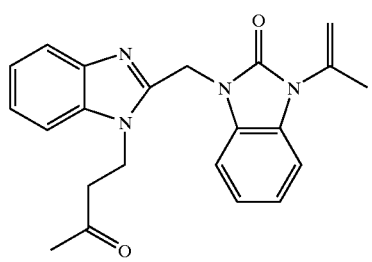

Compound 85 was prepared as described for 50 using methyl vinyl ketone.

$^1$H NMR (CDCl$_3$) δ2.09 (s, 3H), 2.45 (s, 3H), 2.84 (t, J=6.8 Hz, 2H), 4.64 (t, J=6.8 Hz, 2H), 5.21 (s, 1H), 5.38 (d, J=1.3 Hz, 1H), 5.51 (s, 2H), 7.06–7.10 (m, 3H), 7.28–7.31 (m, 2H), 7.34–7.38 (m, 1H), 7.49–7.52 (m, 1H), 7.77–7.80 (m, 1H); MS m/e 375 (MH$^+$).

Compound 86

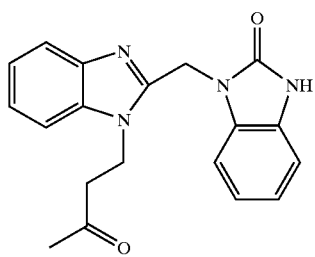

Compound 86 was prepared as described for compound 6.

$^1$H NMR (CDCl$_3$) 2.09 (s, 3H), 2.82 (t, J=6.8 Hz, 2H), 3.50 (s, 1H), 4.63 (t, J=6.9 Hz, 2H), 5.51 (s, 2H), 7.04–7.07 (m, 3H), 7.29–7.37 (m, 2H), 7.44–7.45 (m, 1H), 7.78–7.81 (m, 1H), 8.64 (s, 1H); MS m/e 335 (MH$^+$).

Compound 87

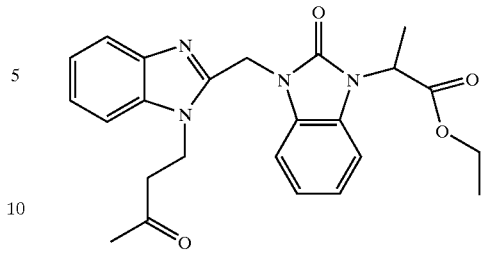

Compound 87 was prepared as described for compound 7 using 2-bromo-propionic acid ethyl ester.

$^1$H NMR (CDCl$_3$) δ1.09 (t, J=7.1 Hz, 3H), 1.57 (d, J=7.4 Hz, 3H), 2.08 (s, 3H), 2.77 (t, J=6.9 Hz, 2H), 4.21 (q, J=7.1 Hz, 2H), 4.60 (t, J=6.9 Hz, 2H), 5.27 (q, J=7.4 Hz, 1H), 5.51 (q, J=12.4 Hz, 2H), 6.93–6.96 (m, 1H), 7.09–7.09 (m, 2H), 7.28–7.32 (m, 2H), 7.34–7.38 (m, 1H), 7.48–7.51 (m, 1H), 7.77–7.81 (m, 1H); MS m/e 435 (MH$^+$).

Compound 88

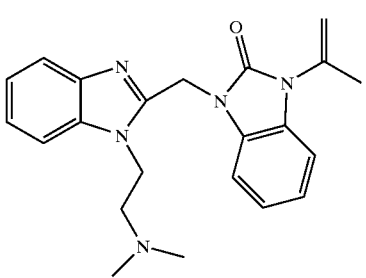

To compound 3 (1.62 g, 5.32 mmol) in anhydrous DMF (20 mL) was added NaH (60% in mineral oil, 510 mg, 12.77 mmol), followed by 2-chloroethyl dimethylamine hydrochloride (843 mg, 5.85 mmol). The mixture was stirred at 65° C. overnight. The solution was poured into saturated sodium bicarbonate and extracted with EtOAc. The combined extracts were dried over MgSO$_4$, and evaporated The residue was purified by chromatography (EtOAc:MeOH, 10:1) to give 1.72g (86% yield) of compound 88 as a solid:

$^1$H NMR (CDCl$_3$) δ2.23 (s, 3H), 2.25 (s, 6H), 2.48 (t, J=6.7 Hz, 2H), 4.45 (t, J=6.7 Hz, 2H), 5.21 (s, 1H), 5.37 (s, 1H), 5.39 (s, 2H), 7.03–7.09 (m, 3H), 7.24–7.34 (m, 3H), 7.49–7.52 (m, 1H), 7.75–7.79 (m, 1H); IR (KBr, cm$^{-1}$) 2941, 2830, 2774, 1693, 1396, 1157, 747, 732; MS m/e 376 (MH$^+$); Anal. Calcd for C$_{22}$H$_{25}$N$_5$O: C, 70.38;H, 6.71; N, 18.65 Found: C, 70.29;H, 6.78; N, 18.76.

Compound 89

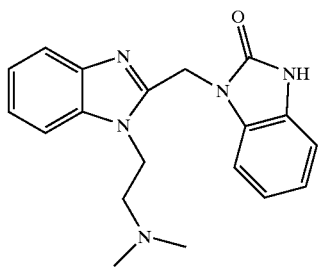

Compound 89 was prepared as described for compound 6.
$^1$H NMR (CDCl$_3$) δ2.29 (s, 6H), 2.50 (t, J=7.2 Hz, 2H), 4.45 (t, J=7.2 Hz, 2H) 5.40 (s, 2H), 7.00–7.05 (m, 3H), 7.27–7.30 (m, 2H), 7.35–7.37 (m, 1H), 7.42–7.44 (m, 1H), 7.77–7.80 (m, 1H), 8.41 (bs, 1H); MS m/e 336 (MH+).

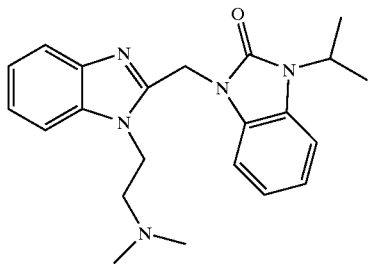

Compound 90

The isopropenyl group of compound 88 was reduced to the isopropyl group as described for compound 115.

¹H NMR (CDCl₃) 1.54 (d, J=7.0 Hz, 6H), 2.27 (s, 6H), 2.47 (t, J=6.8 Hz, 2H), 4.44 (t, J=6.8 Hz, 2H), 4.72–4.82 (m, 1H), 5.39 (s, 2H), 6.98–7.06 (m, 2H), 7.07–7.13 (m, 1H), 7.24–7.33 (m, 3H), 7.48–7.52 (m, 1H), 7.75–7.79 (m, 1H); MS m/e 413 (MH+).

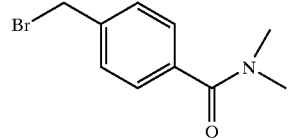

4-Bromomethyl-N,N-dimethyl-benzamide 4-bromomethylbenzoic acid (25 g, 116.25 mmol) was dissolved in CH₂Cl₂ (200 ml) and treated with oxalyl chloride (12.2 ml, 139.5 mmol). DMF (0.45 ml) was added slowly then stirred for 1 h. The solvent was removed to give the 4-bromomethylbenzoyl chloride as a white solid.

A mixture of 4-bromomethyl-benzoyl chloride (7.0 g, 30.24 mmol), polyvinyl pyridine (9.6 g, 90.7 mmol) and dimethyl amine (15.9 ml, 31.8 mmol, 2.0 M in THF) was stirred at 23° C. for 15 h. The solution was filtered and the solvent removed to give 7.3 g (99% yield) of 4-bromomethyl-N,N-dimethyl-benzamide as a yellow solid.

¹H NMR (CDCl₃) δ2.98 (s, 3H), 3.10 (s, 3H), 4.49 (s, 2H), 7.37–7.43 (m, 4H). MS m/e 242 (MH+).

TABLE 13

Compounds in the table below were prepared by alkylation of compound 89 as described for compound 7.

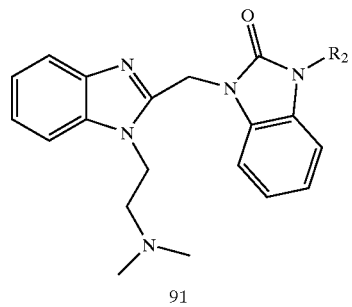

91

| # | R₂ | ¹H-NMR Data | MS Data |
|---|----|-------------|---------|
| 91a | ![structure] | (CD₃OD) 2.36 (s, 3H), 2.39 (s, 3H), 3.10 (s, 6H), 3.87 (t, J=7.9 Hz, 2H), 5.19 (t, J=7.9 Hz, 2H), 5.19 s, 2H), 5.46 (s, 2H), 5.90 (s, 2H), 6.37 (s, 1H), 7.16-7.23 (m, 5H), 7.45 (d, J=8.2 Hz, 3H), 7.68-7.79 (m, 3H), 8.12 (d, J=8.5 Hz, 1H) | 534 (MH+) |
| 91b | ![structure] | (CD₃OD) δ 3.12 (s, 6 H), 3.85 (t, J=7.4 Hz, 2 H), 3.91 (s, 3 H), 5.17-5.24 (m, 2 H), 5.21 (s, 2 H), 5.78 (s, 2 H), 5.90 (s, 2 H), 7.06-7.25 (m, 3 H), 7.38 (d, J=7.9 Hz, 2 H), 7.46 (d, J=8.3 Hz, 3 H), 7.65-7.79 (m, 3 H), 8.10 (d, J=8.3 Hz, 1 H), 8.31 (s, 1 H), 9.23 (s, 1 H) | 564 (MH+) |
| 91c | ![structure] | (DMSO-d6) δ 2.21 (s, 6 H), 2.56 (t, J=6.5 Hz, 2 H), 4.39 (t, J=6.4 Hz, 2 H), 5.08 (s, 2 H), 5.43 (s, 2 H), 5.51 (s, 2 H), 6.98-6.99 (m, 2 H), 7.10 (d, J=8.1 Hz, 2H), 7.14-7.25 (m, 4H), 7.31 (d, J=8.2 Hz, 2 H), 7.54-7.56 (m, 4 H), 8.00 (bs, 1 H) | 550 (MH+) |

TABLE 13-continued

Compounds in the table below were prepared by alkylation of
compound 89 as described for compound 7.

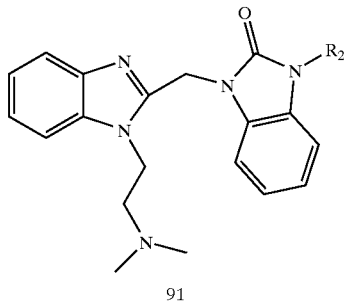

91

| # | R₂ | ¹H-NMR Data | MS Data |
|---|----|-------------|---------|
| 91d | [4-methylbenzyl-substituted uracil with N-CH₂OMe] | (CDCl₃) 2.30 (s, 6H), 2.52-2.63 (m, 2H), 3.38 (s, 3H), 4.47-4.59 (m, 2H), 5.08 (s, 2H), 5.10 (s, 4H), 5.45 (s, 2H), 5.81 (d, J=7.9 Hz, 1H), 6.87-6.90 (m, 1 H), 7.00-7.04 (m, 2H), 7.23-7.30 (m, 5H), 7.42 (d, J=8.0 Hz, 3H), 7.49-7.52 (m, 1H), 7.78-7.81 (m, 1H) | 594 (MH+) |
| 91e | [4-methylbenzyl-substituted uracil with N-CH₂CO₂Me] | (CD₃OD) 3.03 (s, 6H), 3.73 (s, 3H), 3.74-3.80 (m, 2H), 4.56 (s, 2H), 5.07 (s, 2H), 5.12 (s, 2H), 5.12-5.20 (m, 2H), 5.76 (d, J=7.5 Hz, 1H), 5.87 (s, 2H), 7.17-7.20(m, 3H), 7.28-7.33 (m, 4H), 7.44-7.46 (m, 1H), 7.54 (d, J=7.8 Hz, 1H), 7.63-7.78 (m, 3H), 8.11 (d, J=8.1 Hz, 1H) | 622 (MH+) |
| 91f | [4-methylbenzyl-substituted uracil with N-CH₂CO₂tBu] | (DMSO-d6) 1.33 (s, 9H), 2.88 (s, 3H), 2.89 (s, 3H), 3.67-3.41 (m, 2H), 4.44 (s, 2H), 4.94 (s, 2H), 4.96-5.01 (m, 2H), 5.09 (s, 2H), 5.68 (s, 2H), 5.78 (d, J=7.9 Hz, 1H), 7.04-7.07 (m, 2H), 7.16-7.19 (m, 1H), 7.21 (d, J=8.2 Hz, 2H), 7.32 (d, J=8.2 Hz, 2H), 7.39-7.47 (m, 3H), 7.69 (t, J=8.3 Hz, 2H), 7.99 (d, J=8.0 Hz, 1H) | 664 (MH+) |
| 91g | [4-methylbenzyl-substituted uracil with N-CH₂C(O)NH-CH(CO₂Me)CH₂CO₂Me] | (CDCl₃) 2.26 (s, 6H), 2.52 (t, J=6.9 Hz, 2H), 2.82 (dd, J=4.5, 17.4 Hz, 1H), 3.00 (dd, J=4.5, 17.1 Hz, 1H), 3.65 (s, 3H), 3.70 (s, 3H), 4.37 (d, J=5.1 Hz, 2H), 4.47 (t, J=7.1 Hz, 2H), 4.80-4.84 (m, 1H), 5.04 (s, 4H), 5.44 (s, 2H), 5.76 (d, J=7.8 Hz, 1 H), 6.85-6.88 (m, 1H), 6.97-7.00 (m, 2H), 7.14 (d, J=8.1 Hz, 1H), 7.19-7.29 (m, 4H), 7.35-7.47 (m, 4H), 7.75-7.78 (m, 1H) | 751 (MH+) |
| 91h | [ethyl propanoate] | (DMSO-d6) δ1.22 (t, J=7.1 Hz, 3H), 2.36 (s, 6H), 2.71-2.82 (s, 2H), 4.16 (q, J=7.1 Hz, 2H), 4.52 (t, J=6.4 Hz, 2H), 4.79 (s, 2H), 5.43 (s, 2H), 7.00-7.10 (m, 2H), 7.10-7.30 (m, 4H), 7.61-7.72 (m, 2H) | 421 (MH+) |
| 91i | [methyl pentanoate] | (CD₃OD) 1.66-1.72 (m, 2H), 1.83-1.88 (m, 2H), 2.41 (t, J=7.2 Hz, 2H), 3.14 (s, 6H), 3.62 (s, 3H), 3.87 (t, J=8.0 Hz, 2H), 4.02 (t, J=6.8 Hz, 2H), 5.19 (t, J=7.8 Hz, 2H), 5.86 (s, 2H), 7.22-7.34 (m, 3H), 7.45-7.48 (m, 1H), 7.67-7.79 (m, 3H), 8.11 (d, J=8.0 Hz, 1H) | 450 (MH+) |

TABLE 13-continued

Compounds in the table below were prepared by alkylation of compound 89 as described for compound 7.

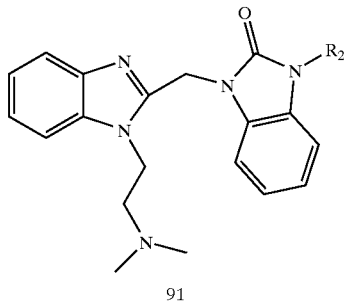

91

| # | R$_2$ | $^1$H-NMR Data | MS Data |
|---|---|---|---|
| 91j | ~~~~~~C(=O)OEt (ethyl octanoate chain) | (CDCl$_3$) 1.21-1.29 (m, 3 H), 1.36-1.46 (m, 2H), 1.64-1.84 (m, 6H), 2.29-2.33 (m, 6 H), 2.52 (m, 2 H), 3.88-3.93 (m, 2 H), 4.07-4.14 (m, 2 H), 4.43-4.48 (m, 2 H), 5.42 (s, 2 H), 6.91-7.50 (m, 6 H), 7.75-7.81 (m, 2 H) | 478 (MH+) |
| 91k | CH$_2$-(4-pyridyl) | (CD$_3$OD) 3.11 (s, 6 H), 3.77 (t, J=7.8 Hz, 2 H), 5.05 (t, J=7.8 Hz, 2 H), 5.53 (s, 2 H), 5.72 (s, 2 H), 7.13-7.25 (m, 3 H), 7.72 (d, J=7.8 Hz, 1 H), 7.85 (d, J=8.1 Hz, 1 H), 8.03-8.06 (m, 2 H), 8.83 (bs, 2 H) | 427 (MH+) |
| 91l | CH$_2$-(3-bromo-4-pyridyl) | (CD$_3$OD) 3.11 (s, 6 H), 3.77 (t, J=7.9 Hz, 2 H), 5.02 (t, J=7.9 Hz, 2 H), 5.52 (s, 2 H), 5.68 (s, 2 H), 7.07 (d, J=8.4 Hz, 1 H), 7.32 (dd, J=1.6, 8.4 Hz, 1 H), 7.43-7.55 (m, 2 H), 7.70-7.73 (m, 2 H), 7.83 (d, J=7.9 Hz, 1 H), 8.03 (d, J=6.3 Hz, 2 H), 8.83 (d, J=6.0 Hz, 2 H) | 505, 507 (MH+) |
| 91m | CH$_2$-(4-bromophenyl) | (CD$_3$OD) 3.09 (s, 6 H), 3.82-3.95 (m, 2 H), 5.13 (s, 2 H), 5.20-5.24 (m, 2 H), 5.94 (s, 2 H), 7.17-7.24 (m, 3 H), 7.30-7.38 (m, 2 H), 7.47-7.52 (m, 3 H), 7.65-7.78 (m, 3 H), 8.18 (d, J=8.0 Hz, 1 H) | 506 (MH+) |
| 91n | CH$_2$-(4-benzyloxyphenyl) | (CDCl$_3$) 2.31 (s, 6 H), 2.57 (t, J=6.6 Hz, 2 H), 4.53 (t, J=6.7 Hz, 2 H), 5.04 (s, 2 H), 5.06 (s, 2 H), 5.46 (s, 2 H), 6.92-6.95 (m, 3 H), 7.01-7.04 (m, 2 H), 7.27-7.43 (m, 10 H), 7.49-7.52 (m, 1 H), 7.79-7.83 (m, 1 H) | 532 (MH+) |
| 91o | CH$_2$-(4-nitrophenyl) | (CD$_3$OD) 3.13 (s, 6 H), 3.87 (t, J=7.9 Hz, 2 H), 5.20 (t, J=7.7 Hz, 2 H), 5.34 (s, 2 H), 5.91 (s, 2 H), 7.19-7.24 (m, 3 H), 7.48-7.52 (m, 1 H), 7.63-7.77 (m, 5 H), 8.09-8.12 (m, 1 H), 8.22-8.26 (m, 2 H) | 505 (M−H−) |
| 91p | CH$_2$-(4-trifluoromethylphenyl) | (CD$_3$OD) 3.12 (s, 6 H), 3.89 (t, J=7.9 Hz, 2 H), 5.24 (t, J=7.9 Hz, 2 H), 5.29 (s, 2 H), 5.96 (s, 2 H), 7.19-7.24 (m, 3 H), 7.50-7.53 (m, 1 H), 7.60 (d, J=8.3 Hz, 1 H), 7.67 (d, J=7.5 Hz, 1 H), 7.71-7.80 (m, 5 H), 8.17 (d, J=8.1 Hz, 1 H) | 494 (MH+) |

TABLE 13-continued

Compounds in the table below were prepared by alkylation of compound 89 as described for compound 7.

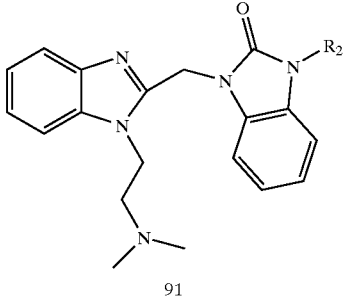

91

| # | R$_2$ | $^1$H-NMR Data | MS Data |
|---|---|---|---|
| 91q | ![4-cyanobenzyl] | (CD$_3$OD) 2.02-2.33 (m, 4 H), 3.22-3.33 (m, 2 H), 3.78-3.89 (m, 2 H), 3.90 (s, 3 H), 3.94 (t, J=7.9 Hz, 2 H), 5.21 (t, J=7.2 Hz, 2 H), 5.27 (s, 2 H), 5.94 (s, 2 H), 7.17-7.25 (m, 3 H), 7.49-7.53 (m, 3 H), 7.69-7.81 (m, 3 H), 8.02 (d, J=8.2 Hz, 2 H), 8.16 (d, J=7.9 Hz, 1 H) | 510 (MH+) |
| 91r | ![diethyl 4-benzylphosphonate] | (DMSO-d6) 1.27 (t, J=6.9 Hz, 6 H), 3.29 (s, 6 H), 3.81 (t, J=7.6 Hz, 2 H), 4.06-4.12 (m, 4 H), 5.19 (t, J=7.6 Hz, 2 H), 5.26 (s, 2 H), 5.88 (s, 2 H), 7.16-7.21 (m, 3 H), 7.46-7.79 (m, 8 H), 8.09 (d, J=7.8 Hz, 1 H) | 562 (MH+) |
| 91s | ![3,4,5-trimethoxybenzyl] | (CDCl$_3$) 2.79 (s, 6 H), 3.41-3.69 (m, 2 H), 3.52 (s, 3 H), 3.62 (s, 6 H), 4.82 (bs, 2 H), 5.22-5.36 (m, 2 H), 5.77 (bs, 2 H), 6.32 (s, 2 H), 6.77 (d, J=7.8 Hz, 1 H), 6.85-7.03 (m, 2 H), 7.18-7.29 (m, 1 H), 7.35-7.51 (m, 2 H), 7.82-7.92 (m, 1 H), 8.10-8.25 (m, 1H) | 516 (MH+) |

Compound 92

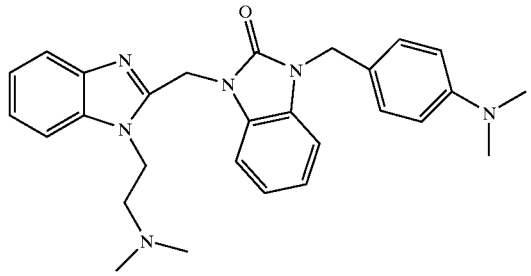

To a solution of compound 89 (502 mg, 1.5 mmol), 4-N,N-dimethylaminobenzyl alcohol (prepared as described by Swami, S. S. et al, Synth Commun., 29(12), 2129–2131, 1999) (272 mg, 1.8 mmol), and 1,1'-(azodicarbonyl) dipiperidine (453 mg, 1.8 mmol) in THF was added tributylphosphine (364 mg, 1.8 mmol) at 0° C. The final solution was allowed to warm to room temperature and stirred for 12 h. The solvent is evaporated the and the residue purified by preparative reverse phase HPLC to yield 420 mg (60%) of compound 92 as a viscous oil.

$^1$H NMR (DMSO-d6) δ3.06 (s, 6H), 3.16 (s, 6H), 3.67 (t, J=7.5 Hz, 2H), 4.99 (t, J=7.5 Hz, 2H), 5.18 (s, 2H), 5.61 (s, 2H), 7.09–7.18 (m, 3H), 7.37–7.53 (m, 7H), 7.66–7.78 (m, 2H); MS m/e 469 (MH+).

Compound 93

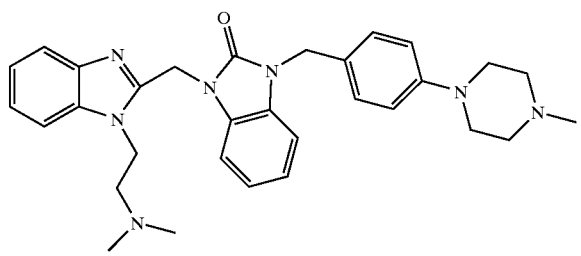

A mixture of compound 91i (50 mg, 0.10 mmol), N-methylpiperidine (12 mg, 0.12 mmol), sodium t-butoxide (14 mg, 0.15 mmol), dipalladium (0) (9 mg, 0.01 mmol) and (R)-(+)-BI NAP (19 mg, 0.03 mmol) in toluene (2 ml) was heated to 100° C. for 2 h. The solvent is evaporated and the residue purified by preparative reverse phase-HPLC to yield 54 mg (100%) of compound 93 as a white solid.

$^1$H NMR (CD$_3$OD) δ2.93 (s, 3H), 3.05 (s, 6H), 3.18–3.24 (m, 2H), 3.57–3.69 (m, 4H), 3.78–3.82 (m, 2H), 4.92–4.98 (m, 2H), 5.09 (s, 2H), 5.56 (s, 2H), 6.98–6.99 (m, 2H), 7.06–7.09 (m, 3H), 7.28–7.34 (m, 2H), 7.38–7.47 (m, 3H), 7.66–7.72 (m, 2H); MS m/e 524 (MH$^+$).

Compound 94

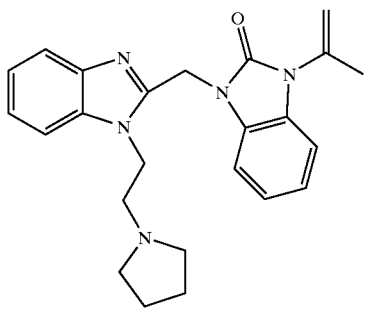

Compound 94 was prepared using the same procedure as compound 88 with N-(2-chloroethyl) pyrrolidine hydrochloride in 82% yield:

$^1$H NMR (CDCl$_3$) δ1.70 (bs, 4H), 2.23 (s, 3H), 2.50 (bs, 4H), 2.66 (t, J=7.0 Hz, 2H), 4.48 (t, J=7.0 Hz, 2H), 5.20 (s, 1H), 5.37 (s, 1H), 5.39 (s, 2H), 7.02–7.09 (m, 3H), 7.24–7.35 (m, 2H), 7.35–7.40 (m, 1H), 7.47–7.50 (m, 1H), 7.75–7.80 (m, 1H); IR (KBr,cm$^{-1}$)2956, 2796, 1701, 1489, 1395, 1332, 1153,743; MS m/e 402 (MH$^+$); Anal. Calcd for C$_{24}$H$_{27}$N$_5$O: C, 71.79;H, 6.78; N, 17.44 Found: C, 71.55;H, 6.84; N, 17.37

Compound 95

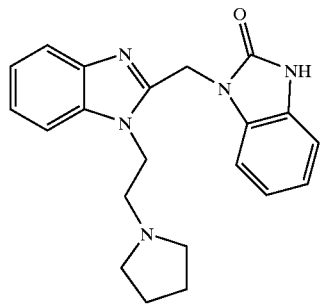

Compound 95 was prepared as described for compound 6.
$^1$H NMR (CDCl$_3$) 1.62–1.80 (m, 4H), 2.46–2.59 (m, 4H), 2.67 (t, J=7.2 Hz, 2H), 4.47 (t, J=7.4 Hz. 2H), 5.40 (s, 2H), 7.00–7.04 (m, 3H), 7.25–7.29 (m, 2H), 7.36–7.43 (m, 2H), 7.76–7.93 (m, 1H), 8.68 (bs, 1H); MS m/e 362 (MH$^+$).

Compound 96

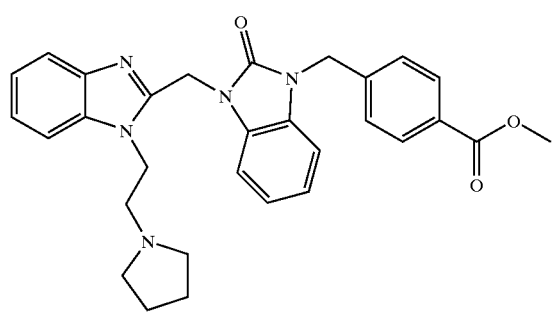

Compound 96 was prepared as described for compound 7.
$^1$H NMR (CD$_3$OD) δ2.02–2.33 (m, 4H), 3.22–3.33 (m, 2H), 3.78–3.89 (m, 2H), 3.90 (s, 3H), 3.94 (t, J=7.9 Hz, 2H), 5.21 (t, J=7.2 Hz, 2H), 5.27 (s, 2H), 5.94 (s, 2H), 7.17–7.25 (m, 3H), 7.49–7.53 (m, 3H), 7.69–7.81 (m, 3H), 8.02 (d, J=8.2 Hz, 2H), 8.16 (d, J=7.9 Hz, 1H); MS m/e 362 (MH$^+$).

Compound 97

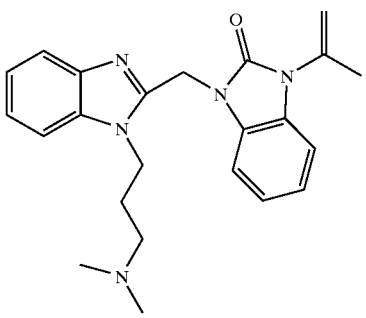

Compound 97 was prepared as described for compound 88 using 2-chloropropyldimethylamine hydrochloride.
$^1$H NMR (CDCl$_3$) 1.74–1.84 (m, 2H), 2.13 (s, 6H), 2.17 (t, J=6.9 Hz, 2H), 2.23 (s, 3H), 4.41 (t, J=7.1 Hz, 2H), 5.20 (s, 1H), 5.37 (d, J=1.4 Hz, 1H), 5.44 (s, 2H), 6.98–7.08 (m, 3H), 7.22–7.28 (m, 2H), 7.35–7.41 (m, 1H), 7.46–7.52 (m, 1H), 7.75–7.80 (m, 1H); MS m/e 390 (MH$^+$).

Compound 98

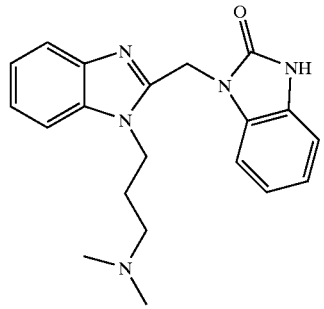

Compound 98 was prepared as described for compound 6.
$^1$H NMR (CDCl$_3$) 1.76–1.85 (m, 2H), 2.23 (s, 6H ), 2.33 (t, J=7.1 Hz, 2H, 4.38 (t, J=7.3 Hz, 2H), 5.43 (s, 28/H), 6.99–7.02 (m, 3H), .25–7.29 (m, 2H), 7.35–7.42 (m, 2H), 7.75–7.80 (m, 1H); MS m/e 350 (MH$^+$).

Compound 99

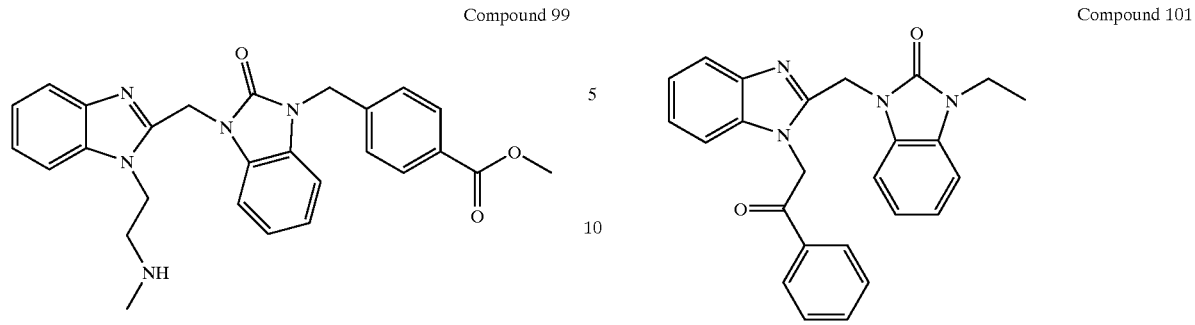

N-methylethanolamine was treated with benzylchloroformate to give (2-hydroxy- ethyl)-methyl-carbamic acid benzyl ester. The product was treated with methanesulfonyl chloride and Et$_3$N in CH$_2$Cl$_2$ to give methanesulfonic acid 2-(benzyloxycarbonyl-methyl-amino)-ethyl ester. The resulting mesylate is used to alklylate 3 as described for the preparation of 4. The isopropenyl group is removed with acid as described for 6. The product is alkylated as described for compound 7 and the benzyloxy group was removed with catalytic hydrogenation (Pd/C) to give compound 99.

$^1$H NMR (CD$_3$OD) δ2.86 (s, 3H), 3.79 (t, J 6.7 Hz, 2H), 3.90 (s, 3H), 5.16 (t, J=6.7 Hz, 2H), 5.26 (s, 2H), 5.96 (s, 2H), 7.19–7.26 (m, 3H), 7.51 (d, J=8.3 Hz, 3H), 7.68–7.80 (m, 3H), 8.01 (d, J 8.3 Hz, 2H), 8.14 (d, J 8.2 Hz, 1H); MS m/e 470 (MH$^+$).

(Scheme I)

Compound 100

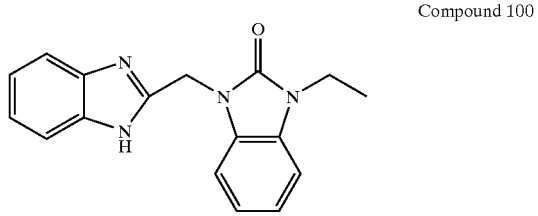

To a solution of 1-ethyl-2-benzimidazolone (0.5 g, 3.39 mmol) in DMF (10 mL) was added to NaH (136 mg, 3.39 mmol) and the mixture was stirred for 1 hr. 1-Methylsulfonyl-2-iodomethylbenzimidazole (2) (1.14 g, 3.39 mmol) was added and the mixture was stirred for 12 h. The reaction was diluted with saturated sodium bicarbonate and extracted with ethyl acetate. The organic extracts were combined, dried over sodium sulfate, filtered and evaporated. The residue was purified by silica gel chromatography, eluted with 50% ethyl acetate in hexanes to give 767 mg (61% yield) of the N-methanesulfonylated derivative of 100a. A mixture of the N-methanesulfonylated derivative of 100 (760 mg, 2.0 mmol) and hydrazine hydrate (0.9 ml) in methanol was heated to reflux for 12 h, then cooled and concentrated. The residue was diluted with water and extracted with ethyl acetate. The combined extracts were dried over sodium sulfate, filtered and concentrated. The residue was purified by chromatography on silica gel with 50% ethyl acetate in hexanes as eluant to give 250 mg (28%) of compound 100 as a white solid.

$^1$H NMR (DMSO-d6) δ1.26 (t, J=7.1 Hz, 3H), 3.93 (q, J=7.1 Hz, 2H), 5.27 (s, 2H), 6.99 (t, J=7.4 Hz, 1H), 7.05–7.06 (m, 2H), 7.07–7.08 (m, 2H), 7.24 (d, J=8.3 Hz, 1H), 7.40–7.60 (m, 2H); MS m/e 292 (MH$^+$).

Compound 101

Compound 100 (500 mg, 1.71 mmol) in DMF (2 mL) was added to a slurry of sodium hydride (60% in mineral oil, 75 mg, 3.14 mmol) in DMF (10 ml) and stirred for 1 h. 2-Bromoacetophenone (375 mg, 1.88 mmol) was added and the mixture was stirred for 48 h. The reaction was diluted with water and extracted with ethyl acetate. The organic extracts were combined, dried over sodium sulfate and concentrated. The residue was purified by silica gel chromatography with 50% ethyl acetate in hexanes as eluant to give 474 mg (68% yield) of compound 101 as a white solid:

$^1$H NMR (DMSO-d$_6$) δ1.05 (t, J=7.1 Hz, 3H), 3.65 (q, J=7.1 Hz, 2H), 5.28 (s, 2H), 6.15 (s, 2H), 7.00–7.05 (m, 2H), 7.13–7.20 (m, 3H), 7.24–7.27 (m, 1 H), 7.44–7.49 (m, 1H), 7.60–7.65 (m, 3H), 7.73–7.95 (m, 1H), 8.03 (d, J=8.4 Hz, 2 H); IR (KBr, cm$^{-1}$) 2956, 1706, 1686, 1497, 1219, 744; MS m/e 411 (MH$^+$); Anal. Calcd for C$_{25}$H$_{22}$N$_4$O$_2$.0.4H$_2$O: C, 72.20;H,5.48; N, 13.47 Found: C, 72.04;H, 5.45; N, 13.66.

Compound 102

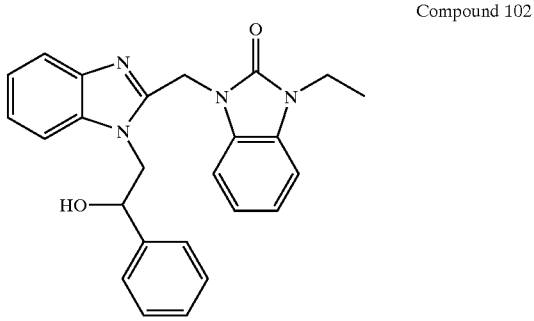

To a 0° C. solution of compound 101 (350 mg, 0.85 mmol) in MeOH (10 ml) was added NaBH$_4$ (323 mg, 8.53 mmol) and the mixture stirred for 2 h. The reaction was warmed to 23° C. and stirred for 12 h. The solvent was evaporated and the residue dissolved in EtOAc and washed with water. The organic layer is dried over Na$_2$SO$_4$ and concentrated. The residue was purified by flash chromatography with 50% EtOAc in hexanes to give 264 mg (75%) of compound 102 as a white solid.

$^1$H NMR (DMSO-d$_6$) δ1.22 (t, J 7.1 Hz, 3H), 3.91 (q, J=6.9 Hz, 2H), 4.42–4.61 (m, 2H), 4.90–4.91 (m, 1H), 5.26–5.31 (m, 1H), 5.40–5.46 (m, 1H), 5.82–5.83 (m, 2H), 6.97–7.08 (m, 2H), 7.15–7.29 (m, 4H), 7.32–7.42 (m, 3H), 7.39–7.61 (m, 4H); IR (KBr, cm$^{-1}$) 3200, 1701, 733; MS m/e 412 (MH$^+$); Anal. Calcd for C$_{25}$H$_{24}$N$_4$O$_2$.0.16H$_2$O: C, 72.29;H,5.90; N, 13.49 Found: C, 72.27;H, 5.72; N, 13.33.

Compound 103

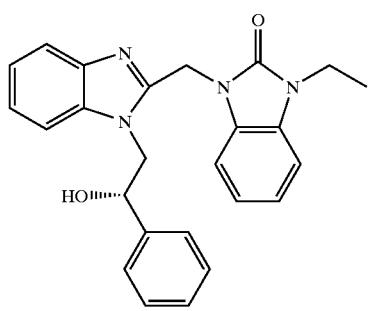

To a stirred solution of compound 100 (150 mg, 0.51 mmol) in DMF (10 ml) was added sodium hydride (22.6 mg, 0.55 mmol) and the mixture stirred for I hour. R-(+)-styrene oxide (123 mg, 1.02 mmol) was added and the mixture heated to 110° C. for 2 h. The mixture was cooled, diluted with water and extracted with EtOAc. The combined organic extracts are dried over $Na_2SO_4$ and concentrated. The residue is purified by flash chromatography to give compound 103 (34 mg, 16%) as a white solid.

$^1$H NMR (DMSO-$d_6$) δ1.22 (t, J 7.1 Hz, 3H), 3.91 (q, J 6.9 Hz, 2H), 4.43–4.61 (m, 2H), 4.90–4.93 (m, 1H), 5.16–5.31 (m, 1H), 5.33–5.46 (m, 1H), 5.82–5.83 (m, 2H), 6.97–7.08 (m, 2H), 7.15–7.29 (m, 4H), 7.32–7.42 (m, 3H), 7.39–7.61 (m, 4H); $[a]_D^{25}$=−44.76 (25° C., C=0.714, $CH_2Cl_2$) MS m/e 412 (MH$^+$); Anal. Calcd for $C_{25}H_{24}N_4O_2$: C, 72.80;H,5.86; N, 13.58 Found: C, 72.50;H, 6.21; N, 12.52.

Compound 104

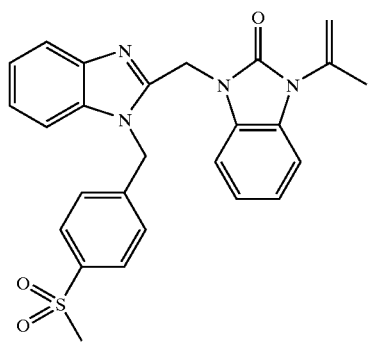

Compound 104 was prepared by alklylation of compound 100 with 1-methanesulfonyl-4-chloromethyl-benzene as previously described for compound 101.

$^1$H NMR (DMSO-d6) δ1.96 (s, 3H), 3.12 (s, 3H), 4.94 (s, 1H), 5.19 (s, 1H), 5.42 (s, 2H), 5.77 (s, 2H), 6.95 (d, J=5.0, 2H), 7.02–7.07 (m, 3H), 7.20–7.25 (m, 3H), 7.61–7.63 (m, 2H), 7.68–7.71 (m, 1H), 7.90–7.98 (m, 1H); MS m/e 473 (MH$^+$).

Compound 105

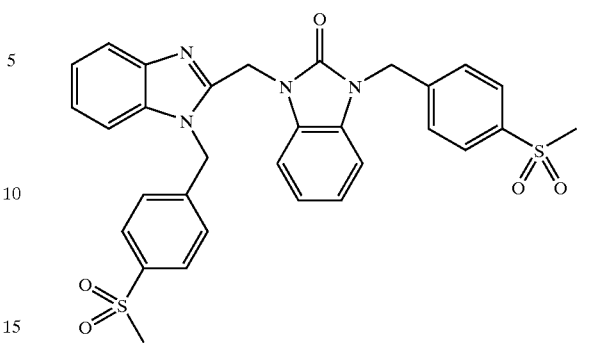

The isopropenyl group of compound 104 was removed as described for compound 6 and converted to compound 105 as described for compound 7 using 1-methanesulfonyl-4-chloromethylbenzene.

$^1$H NMR (DMSO-d6) δ3.17 (s, 6H), 4.99 (s, 2H), 5.47 (s, 2H), 5.79 (s, 2H), 6.98–7.03 (m, 3H), 7.07 (d, J=5.0, 2H), 7.17 (d, J=5.5, 1H), 7.25–7.27 (m, 2H), 7.47–7.53 (m, 1H), 7.51 (d, J=4.1, 2H), 7.69–7.72 (m, 2H), 7.88 (d, J=5.0, 2H); MS m/e 600 (MH$^+$).

Scheme II

Compound 106

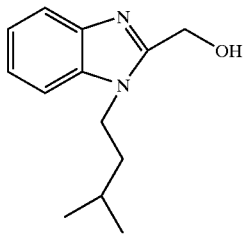

To a solution of 2-hydroxymethylbenzimidazole (27.1 g, 182.9 mmol) in 1:1 mixture of DMF/THF (200 mL) was added NaH (60% in mineral oil, 8.05 g, 201.2 mmol) at room temperature. After stirring for 1.5 h, 1-bromo-3-methylbutane (29 g, 192 mmol) was added and the mixture was stirred at 75° C. overnight. The mixture was adjusted to neutral pH with concentrated HCl and the solvent was evaporated. The residue was diluted with EtOAc, washed with water, dried over $MgSO_4$, and evaporated. The residue was crystallized from EtOAc/hexane to give 29 g of compound 106 as white solid. The mother liquor was purified by flash chromatography (EtOAc:hexane=1:1 to 2:1 and then EtOAc:MeOH=10:0 to 10:1) to give additional 5.24 g (total 86% yield) of compound 106.

Compound 107

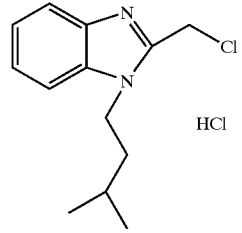

To a solution of compound 106 (34.24g, 156.9 mmol) in CH$_2$Cl$_2$ (100 mL) was slowly added SOCl$_2$ (28 g, 235.4 mmol) with an ice-bath cooling. The resulting solution was stirred at room temperature for 1 h and evaporated. The residue was dried in vacuum and then triturated in a mixture of CH$_2$Cl$_2$/Et$_2$O to give 41.25 g (96% yield) of compound 107 as a white solid:

$^1$H NMR (DMSO-d$_6$) δ0.99 (d, J=6.3 Hz, 6H), 1.72–1.79 (m, 3H), 4.47–4.52 (m, 2H), 5.36 (s, 2H), 7.52–7.61 (m, 2H), 7.82–7.92 (m, 2H); MS m/e 237 (MH$^+$).

Compound 108

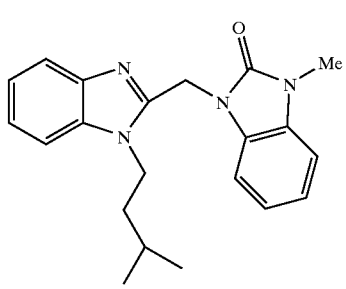

A mixture of 107 (200 mg, 0.84 mmol), N-methylbenzimidazole (128 mg, 0.76 mmol) and NaH (33.6 mg, 0.84 mmol) were stirred in acetonitrile (10 mL) for 1 h. The solvent was evaporated. The residue was diluted with water and extracted with CH$_2$Cl$_2$. The combined extracts were washed with water, brine, and dried over MgSO$_4$. The solvent was evaporated, and the residue was purified by chromatography to give 65.9 mg (25% yield) of compound 108:

$^1$H NMR (CDCl$_3$) δ0.92 (d, J=6.6 Hz, 6H), 1.28–1.36 (m, 2H), 1.61–1.74 (m, 1H), 3.45 (s, 3H), 4.26–4.32 (m, 2H), 5.42 (s, 2H), 6.93–7.10 (m, 3H), 7.27–7.32 (m, 3H), 7.40 (d, J=7.4 Hz, 1H), 7.79–7.81 (m, 1H); IR (KBr, cm$^{-1}$) 3425, 3054, 1706, 1499, 1399, 743; MS m/e 349 (MH$^+$); Anal. Calcd for C$_{21}$H$_{24}$N$_4$O$_1$.0.65H$_2$O: C, 70.03;H, 7.08; N, 15.56. Found: C, 70.05;H, 6.83; N, 15.45.

Compound 109

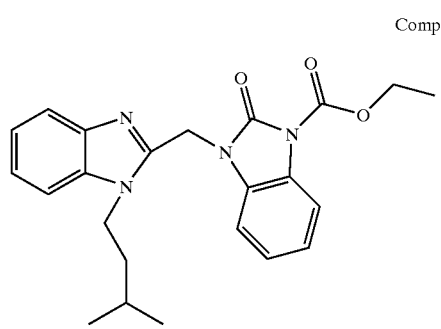

Compound 109 was prepared from the known 1-carboethoxy-benzimidazolone (Meanwell et al J. Org. Chem. 1995, 60, 1565–1582) and 107 as described above for the preparation of 108.

$^1$H NMR CDCl$_3$) δ0.95 (d, J=6.6 Hz, 6H), 1.37–1.45 (m, 2H), 1.50 (t, J=7.1 Hz, 3H), 1.67–1.74 (m, 1H), 4.29–4.35 (m, 2H), 5.38 (s, 2H), 7.10–7.19 (m, 2H), 7.29–7.33 (m, 3H), 7.47–7.50 (m, 1H), 7.77–7.80 (m, 1H), 7.83–7.86 (m, 1H); MS m/e 407 (MH$^+$).

Compound 110

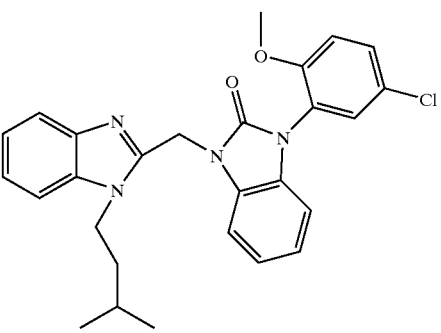

$^1$H NMR (CDCl$_3$) δ0.94 (dd, J=1.3, 6.6 Hz, 6H), 1.44–1.74 (m, 3H), 3.76 (s, 3H), 4.32–4.38 (m, 2H), 5.46 (s, 2H), 6.67 (d, J=7.5 Hz, 1H), 6.97–7.09 (m, 3H), 7.27–7.43 (m, 5H), 7.54 (d, J=7.6 Hz, 1H), 7.78–7.83 (m, 1H).

Compound 111

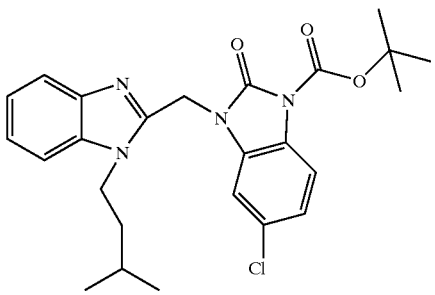

Compound 111 was prepared in 49% yield by the same procedure as described for compound 108 with chloride 107 and N-t-butoxycarbonyl-5-chlorobenzimidazolone (Meanwell et al J. Org. Chem. 1995, 60, 1565–1582):

$^1$H NMR (CDCl$_3$) δ0.95 (d, J=6.7 Hz, 6H), 1.39–1.45 (m, 2H), 1.66 (s, 9H), 1.64–1.77 (m, 1H), 4.29–4.35 (m, 2H), 5.37 (s, 2H), 7.07 (dd, J=2.0, 8.,6 Hz, 1H), 7.28–7.33 (m, 3H), 7.56 (bs, 1H), 7.69 (d, J=8.6 Hz, 1H), 7.80–7.82 (m, 1H); IR(KBr, cm$^{-1}$) 2871, 1791, 1752, 1489, 1378, 1323, 1253, 1149, 1113, 742. MS m/e 469 (MH$^+$); Anal. Calcd for C$_{25}$H$_{29}$ClN$_4$O$_3$: C, 64.03;H, 6.23; N, 11.95 Found: C, 64.29;H1 6.02; N, 11.55.

Compound 112

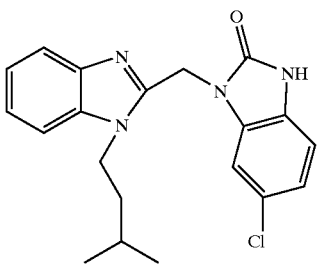

Compound 111 (200 mg, 0.43 mmol) was dissolved in a mixture of CH$_2$Cl$_2$:TFA (3:1, 4 mL). The mixture was stirred at ambient temperature for 5 minutes and then evaporated. The residue was dissolved in CH$_2$Cl$_2$, washed with saturated NaHCO$_3$, water, and dried over MgSO$_4$. The residue was purified by chromatography (EtOAc: hexane 1:1 to 2:1) to give compound 18 mg of the compound 112 as a light yellow solid:

¹H NMR (DMSO-d₆) δ0.94 (d, J=6.6 Hz, 6H), 1.41–1.48 (m, 2H), 1.63–1.72 (m, 1H), 4.30 (bt, J=8.1 Hz, 2H), 5.34 (s, 2H), 7.04 (s, 2H), 7.12–7.27 (m, 3H), 7.52 (d, J=7.9 Hz, 1H), 7.60 (d, J=7.5 Hz, 1H); IR (KBr, cm⁻¹)2956, 1705, 1489, 1458, 1386,741; MS m/e 369 (MH⁺); Anal. Calcd for $C_{20}H_{21}ClN_4O.4$ $CF_3COOH$: C, 60.28;H,5.20; N, 13.52. Found: C, 60.49;H, 5.58; N, 13.41.

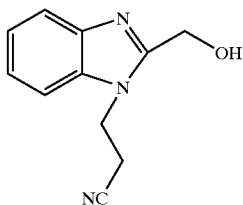

Compound 113

Compound 113 was prepared using Michael addition conditions described by Popov, I. I. in Khim Geterotskl. Soedin. 1996 (6), 781–792.

¹H NMR (CDCl3) δ3.08 (t, J=6.8 Hz, 2H), 4.63 (t, J=6.8 Hz, 2H), 4.77 (d, J=5.7 Hz, 2H), 5.73 (t, J=5.7 Hz, 1H), 7.17–7.28 (m, 2H), 7.64 (d, J=1.2 Hz, 1H), 7.70 (d, J=1.2 Hz, 1H); MS m/e 202 (MH⁺); Anal. Calcd for $C_{11}H_{11}N_3O$: C 65.66;H, 5.51; N, 20.88. Found: C, 65.94;H, 5.57; N, 21.08.

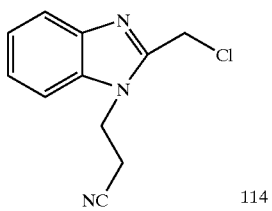

Compound 114

To a solution of alcohol 113 (20g, 99.4 mmol) in methylene chloride (50 mL) was slowly added $SOCl_2$ (15.4 g, 129.2 mmol). The solution was stirred at room temperature for 3 hours. The solvent was evaporated. The residue was diluted with water and neutralized with saturated aqueous sodium bicarbonate solution, and extracted with ethyl acetate. The combined extracts were washed with water, dried over magnesium sulfate, and evaporated. The residue was triturated with $Et_2O$ and hexane to give 19.78 g (91% yield) of compound 114 as a white solid:

¹H NMR (CDCl₃) δ3.02 (t, J=7.0 Hz, 2H), 4.65 (t, J=7.0 Hz, 2H), 4.99 (s, 2H), 7.34–7.44 (m, 3H), 7.79–7.82 (m, 1H); MS m/e 220 (MH⁺); Anal. Calcd for $C_{11}H_{10}ClN_3$: C, 60.09;H, 4.65; N, 19.13. Found: C, 60.09;H, 4.65; N, 19.1 1.

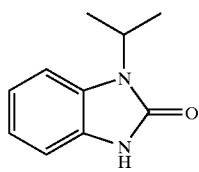

Compound 115

A mixture of N-isopropenyl-2-benzimidazolone (6.90 g, 39.6 mmol) and 1 g of 10% palladium on carbon in 30 mL of methanol was hydrogenated at 45–55 psi for one hour. The catalyst was filtered and the filtrate was evaporated to give quantitative yield of compound 115 as a white solid:

¹H NMR (CDCl₃) δ1.57 (d, J=7.1 Hz, 6H), 4.70–4.81 (m, 1H), 7.02–7.10 (m, 2H), 7.10–7.20 (m, 2H); MS m/e 177 (MH⁺); Anal. Calcd for $C_{10}H_{12}N_2O$: C, 68.16; H, 6.86; N, 15.90 Found: C, 68.05; H, 6.63; N, 15.77.

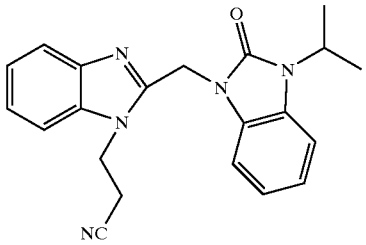

Compound 116

To compound 115 (5.0 g, 28.37 mmol) and chloride 114 (6.23 g, 28.37 mmol) in THF (50 mL) was added BTPP (7.39 g, 42.6 mmol) at room temperature and stirred for 30 minutes. The solvent was evaporated and the residue was purified by flash chromatography (EtOAc: hexane 1:2 to 2:1) to give 7.62 g (75%) of compound 116 as a white solid:

¹H NMR (CDCl₃) δ1.58 (d, J=7.0 Hz, 6H), 2.68 (t, J=6.8 Hz, 2H), 4.71–4.83 (m, 1H), 4.81 (t, J=6.8 Hz, 2H), 5.40 (s, 2H), 7.06–7.27 (m, 3H), 7.34–7.40 (m 3H), 7.57–7.61 (m, 1H), 7.82–7.87 (m, 1H); IR (KBr, cm⁻¹) 2250, 1694, 1493, 1396, 745; MS m/e 360 (MH⁺); Anal. Calcd for $C_{21}H_{21}N_5O.0.3$ $H_2O$: C, 69.14; H, 5.97; N, 19.20 Found: C, 69.07; H, 5.92; N, 19.40.

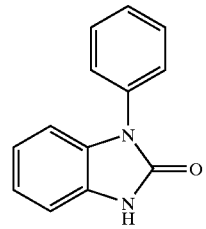

Compound 117

2-fluoronitrobenzene was treated with aniline in the presence of $K_2CO_3$ in $CH_3CN$ and heated to reflux for 12 h. The solution is cooled, filtered and the solvent removed. The nitro group is reduced with catalytic hydrogenation and the diamine treated with CDI to give 1-phenyl-1,3-dihydrobenzoimidazol-2-one.

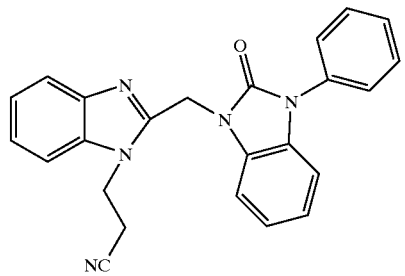

Compound 118

Compound 118 was prepared by alkylation of compound 117 with compound 114 as described for compound 7.

¹H NMR (CDCl₃) δ2.82 (t, J=6.5 Hz, 2H), 4.86 (t, J=6.5 Hz, 2H), 5.56 (s, 2H), 7.08–7.21 (m, 3H), 7.34–7.39 (m, 3H), 7.44–7.47 (m, 1H), 7.54–7.57 (m, 4H), 7.72 (d, J=7.8 Hz, 1H), 7.85–7.89 (m, 1H); MS m/e 393 (MH⁺).

Compound 119

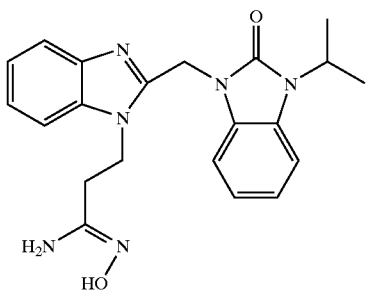

Nitrile 116 (4.6 g, 12.80 mmol), hydroxylamine hydrochloride (3.2 g, 46.07 mmol), and potassium carbonate (3.5 g, 25.60 mmol) were suspended in ethanol/water (100 mL/50 mL). This mixture was stirred at near reflux (60–80° C.) for 16 hours. The solvent was evaporated. To the residue, water was added to dissolve any inorganic salts. The white solid was filtered and washed with water. The solid was triturated with EtOAc to give 5.0 g (quantitative yield) of compound 119 as a white solid.

$^1$H NMR (DMSO-$d_6$) δ1.47 (d, J=6.9 Hz, 6H), 2.39 (t, J=6.8 Hz, 2H), 4.56 (t, J=6.8 Hz, 2H), 4.61–4.70 (m, 1H), 5.35 (s, 2H), 6.61 (s, 2H),6.98–7.06 (m, 2H 7.12–7.24 (m, 3H), 7.33 (d, J=7.1 Hz, 1H), 7.54 (t, J=8.4 Hz, 2H), 8.96 (s, 1H); IR (KBr, cm$^{-1}$) 3470, 3332, 1698, 1680, 1663, 1491, 1430, 750; MS m/e 393 (MH$^+$); Anal. Calcd for $C_{21}H_{24}N_6O_2\cdot2.75\ H_2O$: C, 57.07; H, 6.73; N, 19.01 Found: C, 57.43; H, 6.43; N, 18.79.

Compound 120

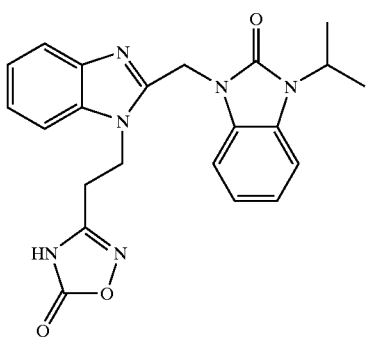

Amidoxime 119 (4.0 g, 10.19 mmol) was suspended in a toluene solution of phosgene (1.92M, 53 mL, 101.92 mmol). The reaction mixture was heated to reflux (120° C.) for 8 hours under nitrogen. The solvent was evaporated. The residue was taken up in water and the pH was adjusted to 5 by addition of saturated sodium bicarbonate. The aqueous mixture was then extracted with $CH_2Cl_2$ The combined organic extracts were dried over $MgSO_4$, filtered and evaporated. Recrystallization of 4 g of the crude product in hot EtOAc (400–500 mL) gave compound 120 as fine white needles (3.0 g, 75% recovery, 71% yield from 119):

To a solution of compound 120 (1.58 g, 3.77 mmol) in MeOH (10 mL) was added 1N NaOH (3.77 mL, 3.77 mmol) and evaporated. The residue was taken up in water and filtered. The filtrate was lyophilized to give the sodium salt of compound 120 as an amorphous fluffy white solid (1.56 g, 94% yield):

$^1$H NMR (DMSO-$d_6$) δ1.46 (d, J=7.0 Hz, 6H), 2.67 (t, J=6.7 Hz, 2H), 4.59–4.68 (m, 3H), 5.35 (s, 2H), 6.94–7.05 (m, 2H), 7.14–7.23 (m, 3H), 7.32 (d, J=7.9 Hz, 1H), 7.52 (t, J=6.8 Hz, 2H); IR (KBr, cm$^{-1}$) 3406, 2978, 1686, 1490, 1408, 750; MS m/e 511 (MH$^+$); Anal. Calcd for $C_{22}H_{22}N_6NaO_3$: C, 59.86; H, 5.02; N, 19.04 Found: C, 59.68; H, 5.00; N, 18.78

Scheme II

Compound 121

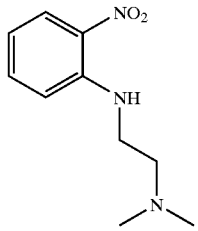

To a mixture of 2-fluoronitrobenzene (16.8 g, 119 mmol) and sodium acetate (300 mg) was added N,N-dimethylethylenediamine (12.5 mL, 113 mmol). After heating to 80° C. for 1 h, the mixture was poured into water, and extracted with EtOAc. The combined organic layers were dried over $MgSO_4$ and evaporated. The crude material was purified by silica gel chromatography (gradient, 1:1 EtOAc:Hexanes to 5% MeOH in EtOAc) to provide 12.0 g (50% yield) of compound 121 as an orange oil.

$^1$H NMR (CDCl$_3$) δ2.31 (s, 6H), 2.64 (t, J=6.3 Hz, 2H), 3.35 (t, J=6.3 Hz, 2H), 6.63 (t, J=7.0 Hz, 1H), 6.83 (d, J=8.5 Hz, 1H), 7.40–7.45 (m, 1H), 8.17 (d, J=8.6 Hz, 1H), 8.29–8.39 (m, 1H); MS m/e 209 (MH$^+$).

Compound 122

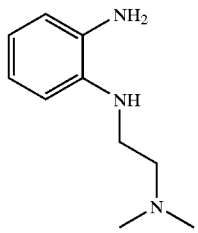

A mixture of compound 121 (10.0 g, 47.7 mmol) and 10% Pd/C (500 mg) in ethanol (100 mL) was hydrogenated at 50 psi for 1 h. The mixture was filtered through a pad of celite and the filtrate was evaporated. The residue was recrystallized from hexanes to give 7.52 g (88%) of a flaky brown solid of compound 122.

$^1$H NMR (CDCl$_3$) δ2.26 (s, 6H), 2.59 (t, J=6.0 Hz, 2H), 3.15 (t, J=6.0 Hz, 2H), 6.65–6.72 (m, 3H), 6.79–6.82 (m, 1H); MS m/e 179 (MH$^+$).

Compound 123

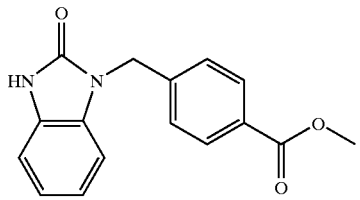

A mixture of ethyl 2,3-dihydro-2-oxo-1H-benzimidazole-1-carboxylate (5 g, 24.3 mmol), $K_2CO_3$ (3.35 g, 24.3 mmol) and methyl 4-bromomethyl-benzoate (5.56 g, 24.3 mmol) was stirred in acetonitrile (100 mL) at reflux for 3 h. The mixture was filtered and the filtrate was concentrated. The oily residue was dissolved in methanol (50 mL), treated with sodium methoxide in methanol (1.0 mL, 0.5 M) and stirred for 12 h. The product precipitated from the solution was filtered to give 5.88 g (99% yield) of compound 123 as white solid:

$^1$H NMR (DMSO-d$_6$) δ3.82 (s, 3H), 5.09 (s, 2H), 6.95–6.99 (m, 4H), 7.42 (d, J=8.4 Hz, 2H), 7.92 (d, J=8.4 Hz, 2H); IR (KBr, cm$^{-1}$) 3464(br), 1718, 1696; MS m/e 283 (MH$^+$); Anal. Calcd for C$_{16}$H$_{14}$N$_2$O$_3$: C, 68.08; H, 5.00; N, 9.92. Found: C, 67.85; H, 5.01; N, 9.84.

Compound 124

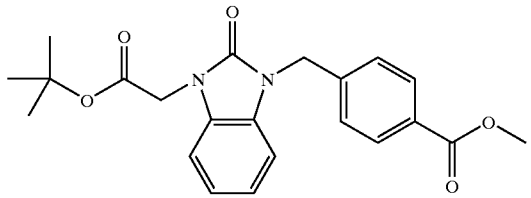

A mixture of 123 (5.8 g, 27.6 mmol), t-butyl bromoacetate (4.1 mL, 27.6 mmol) and potassium carbonate (3.8 g, 27.6 mmol) in acetonitrile (100 mL) was heated to reflux for 3 h. The mixture was cooled to room temperature, filtered and concentrated to give 9.58 g (88% yield) of compound 124 as a white solid:

$^1$H NMR (DMSO-d$_6$) δ1.41 (s, 9H), 3.83 (s, 3H), 4.66 (s, 2H), 5.17 (s, 2H), 7.02–7.18 (m, 4H), 7.42 (d, J=8.1 Hz, 2H), 7.92 (d, J=8.1 Hz, 2H); IR (KBr, cm$^{-1}$) 1742, 1721, 1715; MS m/e 397 (MH$^+$).

4-(3-Isopropenyl-2-oxo-2,3-dihydro-benzoimidazol-1-ylmethyl)-N,N-dimethyl-benzamide

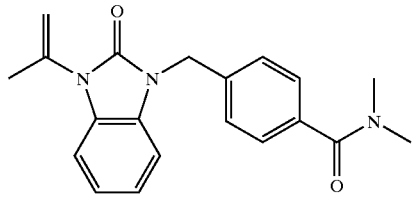

4-(3-Isopropenyl-2-oxo-2,3-dihydro-benzoimidazol-1-ylmethyl)-N,N-dimethyl-benzamide was prepared from 1-isopropenyl- 1,3-dihydro-benzoimidazol-2-one and compound 90 as described for compound 7.

$^1$H NMR (CD$_3$OD) δ2.21 (s, 3H), 2.96 (s, 3H), 3.07 (s, 3H), 5.15 (s, 2H), 5.23 (s, 1H), 5.45–5.46 (m, 1H), 7.05–7.12 (m, 3H), 7.17–7.18 (m, 1H), 7.39–7.43 (m, 4H); MS m/e 336 (MH$^+$).

N,N-Dimethyl-4-(2-oxo-2,3-dihydro-benzoimidazol-1-ylmethyl)-benzamide

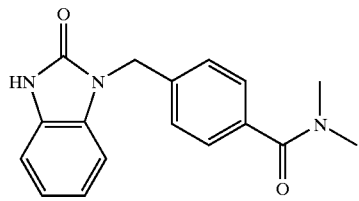

N,N-Dimethyl4-(2-oxo-2,3-dihydro-benzoimidazol-1-ylmethyl)-benzamide was prepared as described for compound 6.

$^1$H NMR (DMSO-d6) δ2.86 (s, 3 H), 2.95 (s, 3H), 5.04 (s, 2H), 6.94–7.05 (m, 4H), 7.33–7.37 (m, 4H); MS m/e 296 (MH$^+$).

Compound 125

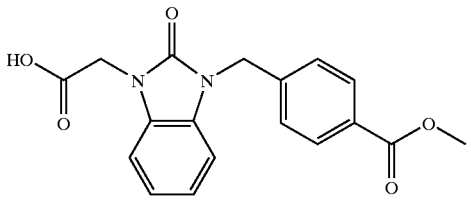

Ester 124 (5.4 g, 13.6 mmol) was stirred in trifluoroacetic acid (50 mL) at room temperature for 12 h. The mixture was evaporated to give 4.0 g (87% yield) of compound 125 as a light yellow solid:

$^1$H NMR (DMSO-d$_6$) δ3.88 (s, 3H), 4.72 (s, 2H), 5.22 (s, 2H)., 7.06–7.24 (m, 3H), 7.17–7.27 (m, 1H), 7.48 (d, J=8.1 Hz, 2H), 7.97 (d, J=8.4 Hz, 2H); IR (KBr, cm$^{-1}$) 3464(br), 1738, 1720, 1666; MS m/e 341 (MH$^+$); Anal. Calcd for C$_{18}$H$_{16}$N$_5$O.0.86 H$_2$O: C, 57.67; H, 4.69; N, 7.26. Found: C, 57.67; H, 4.29; N, 6.95.

Compound 126

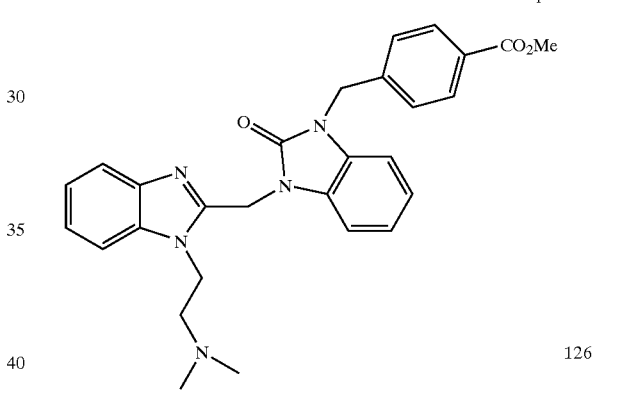

126

Compound 122 (1.32 g, 7.35 mmol) and benzimidazolone 125 (2.5 g, 7.35 mmol) were dissolved in DMF (8 mL). To the solution EDC (3.18 g, 16.2 mmol) was added and the resulting mixture was stirred for 18 h under nitrogen. The mixture was poured into water and extracted into EtOAc. The extracts were dried over MgSO$_4$ and evaporated. The gummy residue was dissolved in 20 mL of acetic acid and the solution was heated to reflux for 6 h. The mixture was evaporated and the residue was diluted with EtOAc, washed with water, dried over MgSO$_4$ and evaporated. The gummy residue was triturated with EtOAc to produce 255 mg (7% yield) of compound 126. A portion of the material was converted to the HCl salt with excess HCl in dioxane and the volatile components were removed in vacuo:

$^1$H NMR (DMSO-d$_6$) δ3.12, 3.33 (s, 6H), 4.00 (m, 2H), 4.25 (s, 3H), 5.39 (m, 2H), 5.65 (s, 2H), 6.10 (s, 2H), 7.49 (m, 2H), 7.57 (m, 1H), 7.81 (m, 4H), 7.92 (d, J=8.1 Hz, 2H), 8.08 (d, J=7.8 Hz, 1H), 8.36 (d, J=8.1 Hz, 2H), 11.67 (s, 1H); IR (KBr, cm$^{-1}$) 3421, 2952, 1708, 1491, 1407, 1280, 750; MS m/e 484 (MH$^+$); Anal. Calcd for C$_{28}$H$_{29}$N$_5$O$_3$.2.25 HCl: C, 59.22; H, 5.56; N, 12.33. Found: C, 59.22; H, 5.42; N, 12.01.

Compound 131

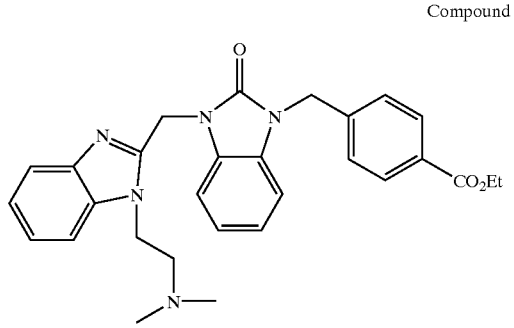

Sodium ethoxide was prepared by dissolving fresh cut sodium (0.2 g, 8.40 mmol) in anhydrous EtOH (10 mL). To a solution of methyl ester, compound 126, (1.2 g, 2.48 mmol) in anhydrous EtOH (300 mL) was added the ethanolic sodium ethoxide solution. The reaction mixture was stirred at reflux for 1 hour and the solution was adjusted to pH 1 with 4 N HCl in dioxane. The solvent was evaporated. The residue was purified by flash column chromatography (gradient, straight EtOAc to EtOAc/MeOH, 10:1) and treated with excess 4 N HCl in dioxane to give 1.07 g (87% yield) of compound 131 as the HCl salt:

$^1$H NMR (CDCl$_3$) δ1.37 (t, J=7.2Hz, 3H), 2.26 (s, 6H), 2.51 (t, J=6.9Hz, 2H), 4.36 (q, J=7.2Hz, 2H), 4.45 (t, J=6.9Hz, 2H), 5.16 (s, 2H), 5.47 (s, 2H), 6.80 (d, J=7.5Hz, 1H), 6.98–7.04 (m, 2H), 7.28–7.35 (m, 2H), 7.28–7.35 (m, 4H), 7.38 (d, J=8.4Hz, 1H), 7.52 (d, J=7.2Hz, 1H), 7.78–7.81 (m, 1H), 8.00 (d, J=8.1Hz, 2H); MS m/e 498 (MH$^+$).

Compound 132

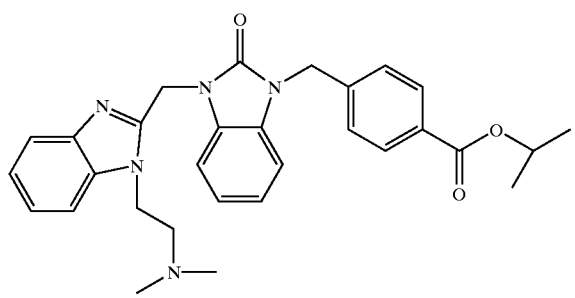

As described for compound 131, the isopropyl derivative 132 was prepared from compound 126 using sodium isopropoxide.

$^1$H NMR (DMSO-d6) δ1.29 (d, J=6.2Hz, 6H), 2.89 (s, 3H), 2.91 (s, 3H), 4.93 (t, J=7.8Hz, 2H), 5.07–5.15 (m, 1H), 5.22 (s, 2H), 5.63 (s, 2H), 7.02–7.14 (m, 3H), 7.32–7.40 (m, 3H), 7.48 (d, J=8.3Hz, 2H), 7.65 (d, J=8.0 Hz, 1H), 7.87–7.93 (m, 3H); MS m/e 512 (MH$^+$).

Compound 133

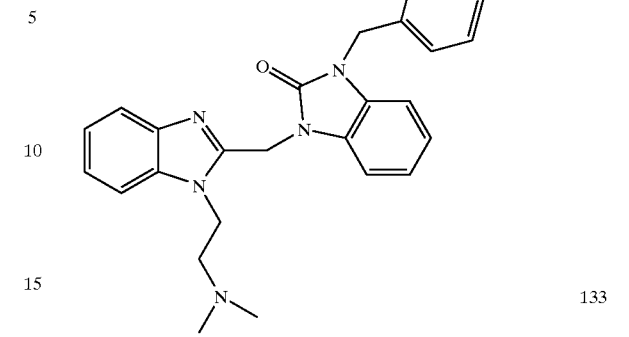

Compound 133 was prepared as a white powder in 71% yield using the same procedure as compound 8:
$^1$H NMR (DMSO-d$_6$) δ2.18 (s, 6H), 3.30–3.50 (m, 2H), 4.43 (t, J=6.3 Hz, 2H), 5.09 (s, 2H), 5.44 (s, 2H), 6.95–7.00 (m, 2H), 7.08–7.25 (m, 1H), 7.52–7.57 (m, 5H), 7.54 (t, J=8.0 Hz, 2H), 7.78 (d, J=8.0 Hz, 2H). IR (KBr, cm$^{-1}$) 3422, 1702, 1599, 1557, 1395, 750; MS m/e 470 (MH$^+$); Anal. Calcd for C$_{27}$H$_{26}$N$_5$O$_3$Na.2.1NaOH.2.0 H$_2$O: C, 52.88; H, 5.28; N, 11.42. Found: C, 53.10; H, 4.88; N, 11.02.

Compound 134

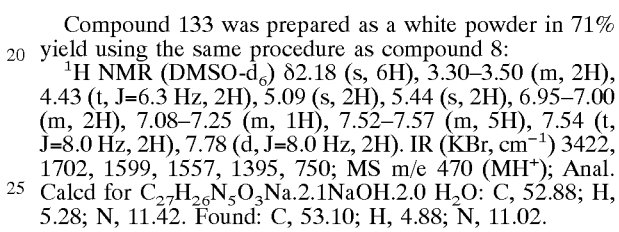

Compound 134 was prepared from compound 133 using PyBroP and 2-aziridin-1-yl-ethanol. The aziridine ring was opened during preparative HPLC with MeOH/H$_2$O with 1% TFA as buffer.
$^1$H NMR (DMSO-d6) 2.90–2.92 (m, 6H), 3.08–3.08 (m, 2H), 3.37 (s, 2H), 3.63 (s, 2H), 3.71–3.76 (m, 2H), 4.54 (t, J=4.8Hz, 2H), 5.02 (t, J=7.4Hz, 2H), 5.25 (s, 2H), 5.72–5.77 (m, 2H), 7.06–7.15 (m, 3H), 7.38–7.70 (m, 5H), 7.70 (d, J=8.0Hz, 1H), 8.00 (d, J=8.0 Hz, 1H), 8.10 (d, J=8.1Hz, 2H), 9.79 (m, 1H), 11.59 (m, 1H); MS m/e 557 (MH$^+$).

Compound 135

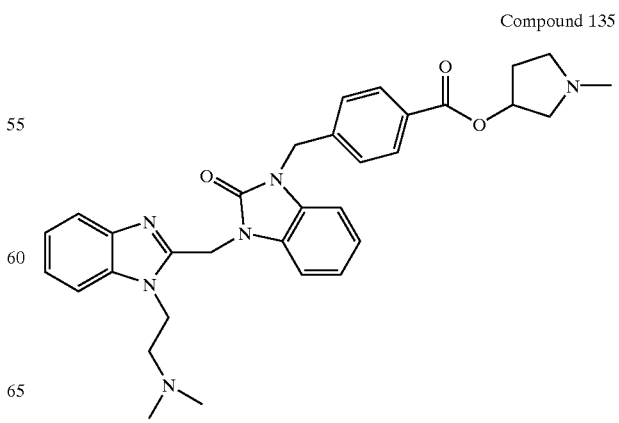

Compound 135 was prepared from compound 133 using PyBroP 1-methyl-3-hydroxylpyyrolidine.

$^1$H NMR (CD$_3$OD) δ2.28–2.81 (m, 2H), 3.02 (s, 2H), 3.07 (s, 1H), 3.12 (s, 6H), 3.86–3.91 (m, 4H), 5.23 (t, J=8.2Hz, 2H), 5.29 (s, 2H), 5.64–5.69 (m, 1H), 5.94 (s, 2H), 7.16–7.23 (m, 3H), 7.49–7.55 (m, 3H), 7.69–7.82 (m, 3H), 8.07–8.17 (m, 3H); MS m/e 553 (MH$^+$).

Compound 136

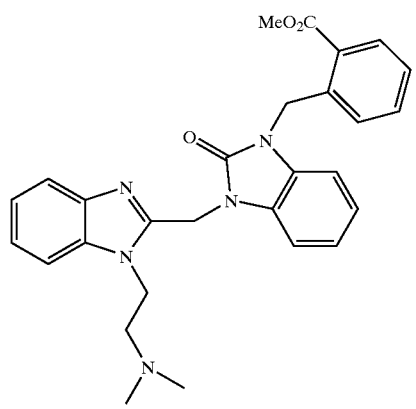

Compound 136 was prepared using the same procedure as compound 126:

$^1$H NMR (CDCl$_3$) δ2.31 (bs, 6H), 2.58 (bs, 2H), 3.97 (s, 3H), 4.52 (bs, 2H), 5.50 (s, 2H), 5.60 (s, 2H), 6.81 (d, J=6.8 Hz, 1H), 6.98–7.09 (m, 3H), 7.28–7.42 (m, 5H), 7.80–7.83 (m, 1H), 8.07 (dd, J=1.4, 7.4 Hz, 1H); IR (KBr, cm$^{-1}$) 1717,1702, 1497,1417, 1261, 742; MS m/e 484(MH$^+$).

Compound 137

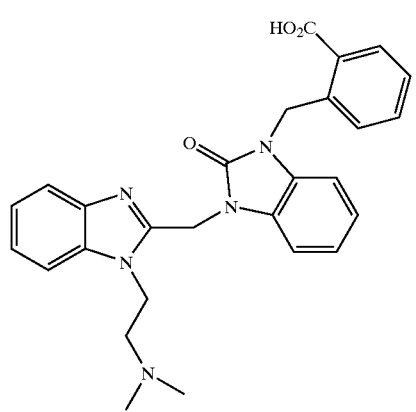

Compound 137 was prepared using the same procedure as compound 133:

$^1$H NMR (CD$_3$OD) δ2.28 (s, 6 H), 2.59 (t, J=6.9 Hz, 2 H), 4.50 (t, J=6.9 Hz, 2 H), 5.20 (s, 2 H), 5.30 (s, 2 H), 6.98–7.08 (m, 4 H), 7.18–7.32 (m, 5 H), 7.64–7.68 (m, 2 H); IR (KBr, cm$^{-1}$) 1699, 168, 1586, 1560, 1492, 1395, 742; MS m/e 470 (MH$^+$); Anal. Calcd for C$_{27}$H$_{27}$N$_5$NaO$_3$.0.75H$_2$O: C, 64.09; H, 5.68; N, 13.84 Found: C, 63.96; H, 5.49; N, 13.74

Compound 138

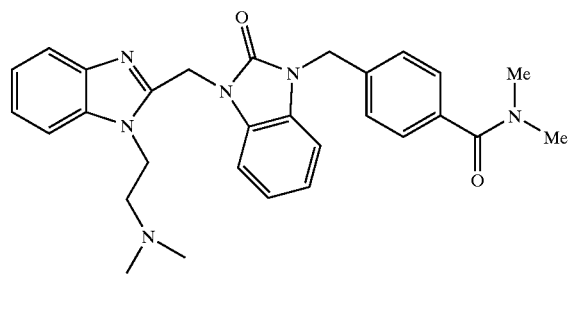

To a solution of acid 133 (704 mg, 1.5 mmol), N,N-dimethylamine hydrochloride salt (183 mg, 2.25 mmol), and diisopropylethylamine (386 mg, 3.0 mmol) in DMF (10 mL) was added PyBroP (769 mg, 1.65 mmol) in one portion at the ambient temperature. After stirring overnight, the resulting solution was concentrated. The residue was purified by prep-HPLC to furnish 660 mg (89% yield) of compound 138 as white solid. To a solution of this solid (660 mg, 1.33 mmol) in methanol (20 mL) was added 4 N HCl in 1,4-dioxane (0.66 mL, 2.66 mmol). The resulting hydrochloride salt precipitated out of solution and was collected by filtration to yield 650 mg (92% yield) of dihydrochloride salt of compound 138 as white crystals:

$^1$HNMR (CD$_3$OD) δ2.99 (s, 3H), 3.10 (s, 3H), 3.12 (s, 6H), 3.87 (t, J=7.5 Hz, 2H), 5.23 (t, J=7.5 Hz, 2H), 5.24 (s, 2H), 5.94 (s, 2 H), 7.20–7.23 (m, 3 H), 7.43 (d, J=8.2 Hz, 2H), 7.48–7.52 (m, 3H), 7.70–7.81 (m, 3H), 8.16 (d, J=8.3 Hz, 1H); IR(KBr, cm$^{-1}$) 3422, 1702, 1614, 1493, 1406, 1181, 753; MS m/e 497 (MH$^+$); Anal. calcd for C$_{29}$H$_{33}$ClN$_6$O$_2$.2.0HCl.1.0TFA.1.5H$_2$O: C, 52.40; H, 5.39; N, 11.83%; Found: C, 52.21; H, 5.34; N, 11.83%

Compound 139

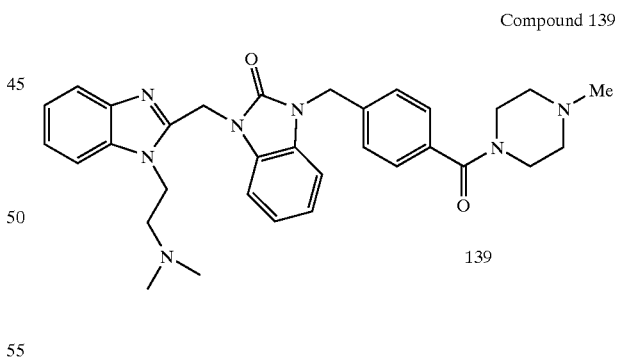

Compound 139 was prepared by the same procedure as compound 138 using N-methylpiperazine and acid 133:

$^1$HNMR (CD$_3$OD) δ2.92 (s, 3H), 3.06 (s, 6H), 3.65 (t, J=8.0 Hz, 2H), 4.92 (t, J=7.9 Hz, 2H), 5.22 (s, 2H), 5.54 (s, 2H), 7.09–7.14 (m, 3H), 7.34 (t, J=8.0 Hz 1H), 7.39–7.47 (m, 6H), 7.66–7.68 (m, 2H); MS m/e 552 (MH$^+$); IR (KBr, cm$^{-1}$) 3442, 1685, 1638, 1494, 1412, 1202, 1131; Anal. Calcd for C$_{32}$H$_{37}$N$_7$O$_2$.3TFA.2.5H$_2$O: C, 48.62; H, 4.83; N, 10.44 Found: C, 48.51; H, 4.44; N, 10.21.

Compound 140

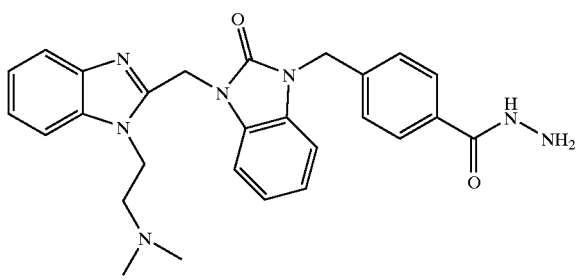

A solution of the methyl ester 126 (484 mg, 1.0 mmol) and hydrazine (250 mg, 5.0 mmol) in MeOH (5 ml) was heated in a sealed tube at 90° C. for 4 h. After cooling, the precipitate formed was collected and washed with cold MeOH and dried to yield compound 140 (84 mg, 17%) as a white solid.

$^1$H NMR (CD$_3$OD) δ3.08 (s, 6H), 3.71–3.78 (m, 2H), 5.01–5.08 (m, 2H), 5.17 (s, 2H), 5.68 (s, 2H), 7.06–7.19 (m, 3H), 7.42–7.57 (m, 5H), 7.70–7.73 (m, 1H), 7.85–7.91 (m, 3H); MS m/e 484 (MH$^+$).

TABLE 13A

Compounds were prepared as described for compound 138 using acid 133 and a commercially available amine.

Compound 141

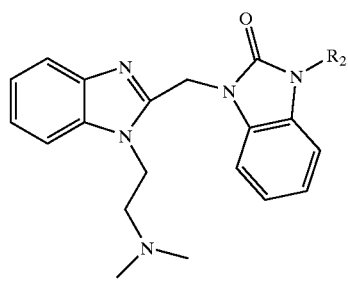

| # | R$_2$ | $^1$H-NMR Data | MS Data |
|---|---|---|---|
| 141a | ![structure: 4-methyl-N-methylbenzamide] | (DMSO-d6) δ 2.76 (d, J=4.6 Hz, 3H), 2.95 (s, 6H), 3.56-3.59 (m, 2H), 4.80 (t, J=7.8 Hz, 2H), 5.18 (s, 2H), 5.52 (s, 2H), 7.02-7.08 (m, 2H), 7.14-7.16 (m, 1H), 7.24-7.27 (m, 1H), 7.32-7.35 (m, 1H), 7.41 (d, J=8.4 Hz, 2H), 7.62 (d, J=8.0 Hz, 1 H), 7.69 (d, J=8.2 Hz, 1 H), 7.78-7.80 (m, 2H), 8.39-8.41 (m, 1H), 9.99(6, 1H) | 483 (MH+) |
| 141b | ![structure: 4-methyl-N-(methylsulfonyl)benzamide] | (CD$_3$OD) δ 3.09 (s, 6H), 3.80-3.84 (m, 5H), 5.16-5.26 (m, 4H), 5.82 (s, 2H), 7.05-7.13 (m, 3H), 7.38-7.42 (m, 3H), 7.53-7.618 (m, 2H), 7.72-7.78 (m, 1H), 7.91-7.99 (m, 3H) | 547 (MH+) |
| 141c | ![structure: N-(2-hydroxyethyl)-N,4-dimethylbenzamide] | (CD$_3$OD) δ 3.03-3.13 (m, 9H), 3.38-3.91 (m, 6H), 5.24-5.29 (m, 4H), 5.97 (s, 2H), 7.16-7.26 (m, 3H), 7.44-7.52 (m, 5H), 7.67-7.80 (m, 3H), 8.19 (d, J=8.2 Hz, 1H) | 527 (MH+) |
| 141d | ![structure: N-(2-(dimethylamino)ethyl)-N,4-dimethylbenzamide] | (CD$_3$OD) δ 2.99 (s, 6H), 3.12 (s, 6H), 3.40 (t, J=9.6 Hz, 2H), 3.74-3.79 (m, 2H), 3.88 (t, J=8.0 Hz, 2H), 5.21-5.27 (m, 4H), 5.97 (s, 2H), 7.15-7.25 (m, 3H), 7.49-7.54 (m, 3H), 7.67-7.82 (m, 3H), 7.91 (d, J=8.3 Hz, 2H), 8.17 (d, J=8.3 Hz, 1H) | 540 (MH+) |

TABLE 13A-continued

Compounds were prepared as described for compound 138 using acid 133 and a commercially available amine.

Compound 141

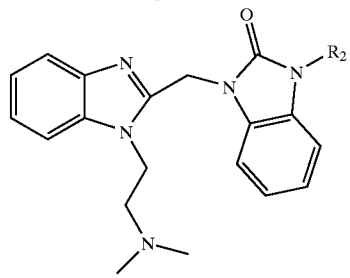

| # | R₂ | ¹H-NMR Data | MS Data |
|---|---|---|---|
| 141e | ![R2 structure with benzamide-N-methyl-polyol chain with multiple OH groups] | (CD₃OD) δ 3.06-3.14 (m, 9H), 3.47-3.88 (m, 10H), 5.21-5.28 (m, 4H), 5.95-5.98 (m, 2H), 7.20-7.22 (m, 3H), 7.44-7.52 (m, 5H), 7.66-7.80 (m, 3H), 8.17 (d, J=8.2 Hz, 1H) | 647 (MH+) |
| 141f | ![R2 structure: benzamide-N-thiazole] | (CD₃OD) δ 3.10 (s, 6H), 3.88 (t, J=7.9 Hz, 2H), 5.24 (t, J=7.9 Hz, 2H), 5.31 (s, 2H), 5.97 (s, 2H), 7.17-7.24 (m, 3H), 7.44 (d, J=4.0 Hz, 1H), 7.49 (d, J=7.3 Hz, 1 H), 7.62 (d, J=8.3 Hz, 2H), 7.68-7.80 (m, 4H), 8.07 (d, J=8.3 Hz, 2H), 8.16 (d, J=8.3 Hz, 2H) | 552 (MH+) |
| 141g | ![R2 structure: benzamide-N-pyrazole] | (CD₃OD) δ 1.75 (s, 6H), 2.24 (t, J=7.8 Hz, 2H), 3.58 (t, J=7.5 Hz, 2H), 3.72 (s, 2H), 4.26 (s, 2H), 5.60-5.64 (m, 4H), 5.91 (d, J=7.5 Hz, 2H), 5.98 (d, J=8.0 Hz, 2H), 6.00-6.06 (m, 1H), 6.06-6.13 (m, 1H), 6.19 (d, J=8.0 Hz, 1H), 6.40-6.46 (m, 3H) | 535 (MH+) |
| 141h | ![R2 structure: benzamide-N-tetrazole] | (DMSO-d6) δ 2.35 (s, 6H), 2.74 (t, J=6.2 Hz, 2H), 4.52 (t, J=6.4 Hz, 2H), 5.23 (s, 2H), 5.76 (s, 2H), 7.01-7.04 (m, 2H), 7.14-7.27 (m, 4H), 7.52 (d, J=8.1 Hz, 2H), 7.57 (d, J=8.6 Hz, 2H), 8.06 (d, J=8.0 Hz, 2H) | 537 (MH+) |
| 141i | ![R2 structure: benzamide-N-pyridine] | (CD₃OD) δ 3.10 (s, 6H), 3.84 (t, J=8.2 Hz, 2H), 5.18 (t, J=7.9 Hz, 2H), 5.30 (s, 2H), 5.90 (s, 2H), 7.15-7.22 (m, 3H), 7.48 (d, J=7.6 Hz, 1H), 7.59 (d, J=8.9 Hz, 2H), 7.63 (t, J=7.3 Hz, 1H), 7.69 (t, J=7.3 Hz, 1H), 7.77 (d, J=8.2 Hz, 1H), 8.04 (d, J=8.9 Hz, 2H), 8.07 (d, J=8.2 Hz, 1H), 8.39 (d, J=7.6 Hz, 2H), 8.66 (d, J=7.6 Hz, 2H) | 546 (MH+) |
| 141j | ![R2 structure: benzamide-N-pyrimidine] | (CD₃OD) δ 2.29 (s, 6H), 2.64 (t, J=6.9 Hz, 2H), 4.51 (t, J=6.9 Hz, 2H), 5.27 (s, 2H), 5.53 (s, 2H), 7.04-7.07 (m, 3H), 7.22-7.34 (m, 3H), 7.52-7.55 (m, 3H), 7.96 (d, J=8.3 Hz, 2H), 8.32 (dd, J=1.1, 5.8 Hz, 1H), 8.64 (d, J=5.9 Hz, 1H), 8.86 (s, 1H) | 547 (MH+) |

TABLE 13A-continued

Compounds were prepared as described for compound 138 using acid 133 and a commercially available amine.

Compound 141

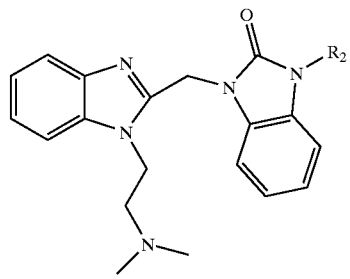

| # | R₂ | ¹H-NMR Data | MS Data |
|---|---|---|---|
| 141k | (4-ethylbenzamido-N-methyl-pyridin-4-yl) | (CD₃OD) δ 3.04 (s, 6H), 3.74-3.79 (m, 2H), 5.08-5.13 (m, 2H), 5.21 (s, 2H), 5.81 (s, 2H), 7.08-7.15 (m, 4H), 7.40 (d, J=6.6 Hz, 1H), 7.47 (d, J=8.4 Hz, 1 H), 7.53-7.64 (m, 2H), 7.70 (d, J=8.1 Hz, 1H), 7.86 (d, J=8.4 Hz, 2H), 7.98 (d, J=6.6 Hz, 3H), 8.73 (d, J=6.9 Hz, 2H) | 561 (MH+) |
| 141l | (4-ethylbenzamido-N-methyl-pyridoxine) | (CD₃OD) δ 2.65 (s, 3H), 3.08 (s, 6H), 3.67-3.85 (m, 2H), 4.70 (s, 2H), 4.96 (s, 2H), 5.14-5.19 (m, 2H), 5.24 (s, 2H), 5.87 (s, 2H), 7.10-7.19 (m, 3H), 7.45-7.50 (m, 3H), 7.60-7.64 (m, 2H), 7.75 (d, J=7.8 Hz, 1 H), 7.88 (d, J=8.4 Hz, 2H), 8.08 (d, J=8.1 Hz, 1H), 8.18 (s, 1H) | 620 (MH+) |

Compound 142

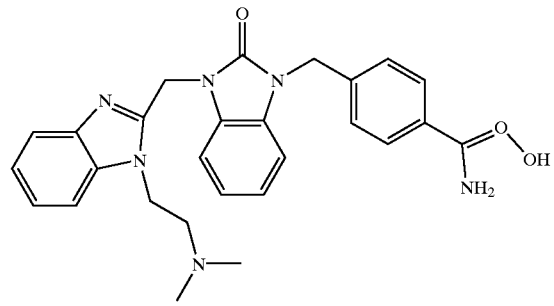

Carbon disulfide (0.5 mL) was added dropwise to ethylenediamine (5 g, 83.20 mmol). To this solution was added the nitrile (0.55 g, 1.22 mmol) and the resulting solution was stirred at 110° C. for 4 hours (Pharmazie, 1992, (47), 11–14). The excess ethylenediamine was evaporated and the residue was purified by preparative HPLC to compound 142:

¹H NMR (CD₃OD) δ3.09 (s, 6H), 3.77 (t, J=7.9Hz, 2H), 4.08 (s, 4H), 5.09 (t, J=7.7 Hz, 2H), 5.29 (s, 2H), 5.75 (s, 2H), 7.07–7.18 (m, 3H), 7.42 (d, J=7.7 Hz, 1H), 7.51 (t, J=7.6 Hz, 1H), 7.57 (t, J=7.8 Hz, 1H), 7.61 (d, J=7.9 Hz, 2H), 7.72 (d, J=8.1 Hz, 1H), 7.85 (d, J=8.2 Hz, 2H), 7.91 (d, J=8.0 Hz, 1H) MS m/e 494 (MH⁺);

Compound 143

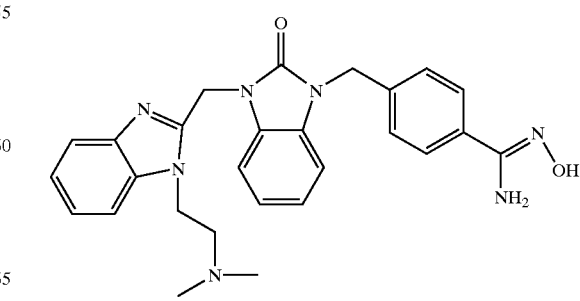

A mixture of compound 91m (840 mg, 1.87 mmol), hydroxylamine hydrochloride (195 mg, 2.80 mmol) and triethylamine (321 mg, 3.18 mmol) in ethanol (20 ml) was heated to reflux for 12 h. After cooling, the product precipitated and was collected by filtration. The cake was washed with $H_2O$ and cold MeOH. After drying, 610 mg (67%) of compound 143 was obtained as a white solid.

$^1$H NMR ($CD_3OD$) δ3.11–3.12 (m, 6H), 3.89–3.93 (m, 2H), 5.22–5.25 (m, 2H), 5.30 (s, 2H), 5.98 (s, 2H), 7.13–7.24 (m, 4H), 7.51–7.54 (m, 2H), 7.61–7.79 (m, 5H), 8.17–8.19 (m, 1H); MS m/e 413 (MH$^+$).

Compound 144

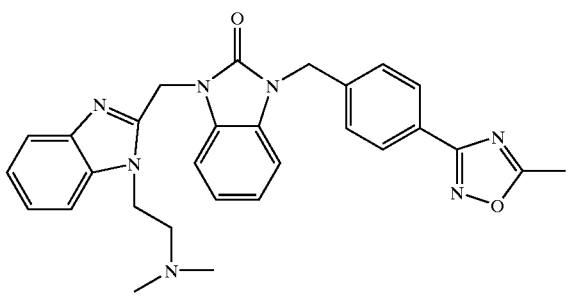

A solution of compound 143 (48 mg, 0.10 mmol) in $Ac_2O$ (1 ml) was heated to 120° C. for 4 h. The solvent was evaporated and the residue purified by prep-HPLC to yield 45 mg (88%) of compound 144 as a white solid.

$^1$H NMR ($CDCl_3$) δ3.07 (s, 9H), 3.79 (t, J=7.6 Hz, 2H), 5.08 (t, J=7.9 Hz, 2H), 5.19 (s, 2H), 5.74 (s, 2H), 7.10–7.18 (m, 3H), 7.40–7.58 (m, 5H), 7.74 (d, J=7.5 Hz, 1H), 7.89–7.99 (m, 3H); MS m/e 508 (MH$^+$).

Compound 145

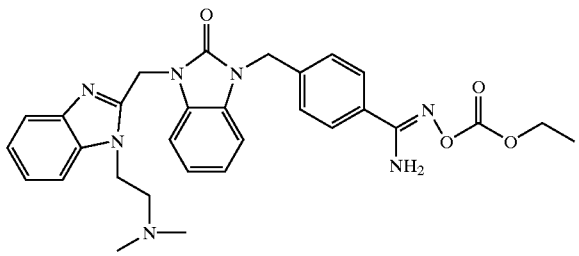

To a suspension of compound 143 (976 mg, 2.0 mmol), TEA (404 mg, 5.0 mmol) and DMAP (50 mg, 0.41 mmol) in $CH_2Cl_2$ (100 ml) was added ethyl chloroformate (259 mg, 2.4 mmol). After stirring for 12 h, the solution was concentrated and the residue purified by preparative reverse phase HPLC to yield 980 mg (88%) of compound 145 as a white solid.

$^1$H NMR (DMSO-d6) δ1.25 (t, J=7.2 Hz, 3H), 2.95 (s, 6H), 3.55–3.58 (m, 2H), 4.16–4.20 (m, 2H), 4.80 (t, J=7.6 Hz, 2H), 5.18 (s, 2H), 5.52 (s, 2H), 6.82 (b, 1H), 7.02–7.08 (m, 2H), 7.16–7.17 (m, 1H), 7.23–7.26 (m, 1H), 7.31–7.35 (m, 2H), 7.41 (d, J=8.4 Hz, 2H), 7.61–7.70 (m, 4H), 9.99 (b, 1H); MS m/e 556 (MH$^+$).

Compound 146

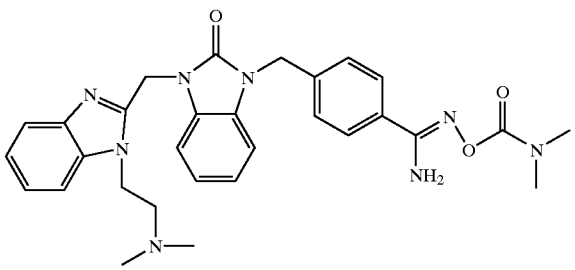

Compound 146 was prepared as described for compound 145 using N,N-dimethylcarbamoyl chloride.

$^1$H NMR ($CD_3OD$) 2.97–3.05 (m, 12H), 3.62–3.66 (m, 2H), 4.92–4.95 (m, 2H), 5.22 (s, 2H), 5.60 (s, 2H), 7.11–7.15 (m, 3H), 7.41–7.44 (m, 4H), 7.46–7.48 (m, 1H), 7.70–7.75 (m, 4H); MS m/e 555 (MH$^+$).

Compound 147

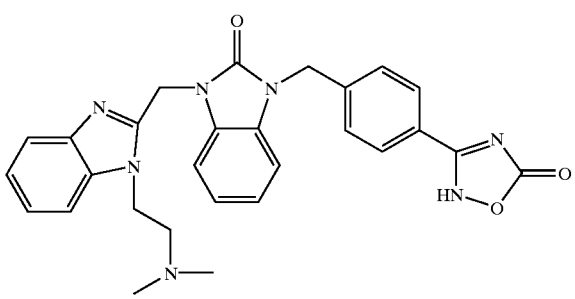

A solution of compound 145 (110 mg, 0.20 mmol) and DBU (110 mg, 0.74 mmol) in THF (10 ml) was heated to 80° C. in sealed tube for 3h. Evaporated the solvent. The residue was purified by prep-HPLC to yield 94 mg (92%) of compound 147 as a white solid.

$^1$H NMR ($CD_3OD$) δ3.08 (s, 6H), 3.71–3.78 (m, 2H), 5.00–5.08 (m, 2H), 5.25 (s, 2H), 5.68 (s, 2H), 7.08–7.18 (m, 3H), 7.41–7.58 (m, 5H), 7.69–7.78 (m, 3H), 7.82 (d, J=7.9 Hz, 1H); MS m/e 510 (MH$^+$).

Compound 148

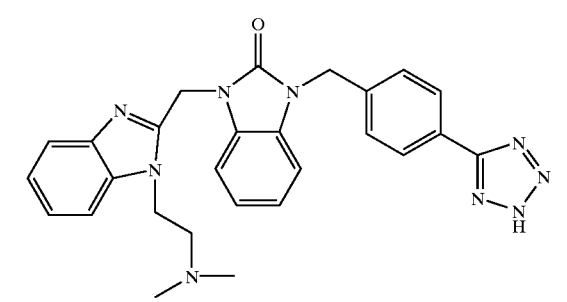

Compound 91m was converted to the tetrazole as described for compound 52.

$^1$H NMR ($CD_3OD$) δ3.13 (s, 6H), 3.87 (t, J 8.0 Hz, 2H), 5.23 (t, J 7.1 Hz, 2H), 5.30 (s, 2H), 5.94 (s, 2H), 7.22–7.24 (m, 3H), 7.49–7.52 (m, 1H), 7.63 (d, J=8.4 Hz, 2H), 7.68–7.81 (m, 3H), 8.03 (d, J=8.3 Hz, 2H), 8.12–8.15 (m, 1H).

Compound 149

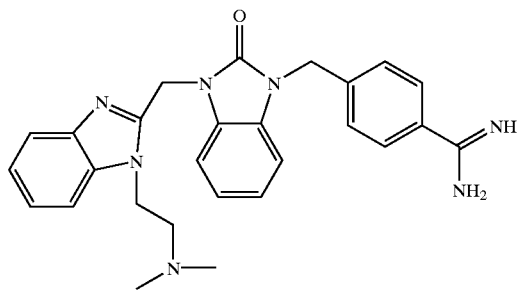

Compound 149 was prepared by hydrogenation of compound 146 as described for the hydrogenation of compound 115.

$^1$H NMR (CD$_3$OD) δ3.07 (s, 6H), 3.72 (t, J=7.5 Hz, 2H), 4.95–4.99 (m, 2H), 5.28 (s, 2H), 5.60 (s, 2H), 7.04–7.15 (m, 3H), 7.37–7.44 (m, 3H), 7.58–7.79 (m, 6H); MS m/e 468 (MH$^+$).

Compound 150

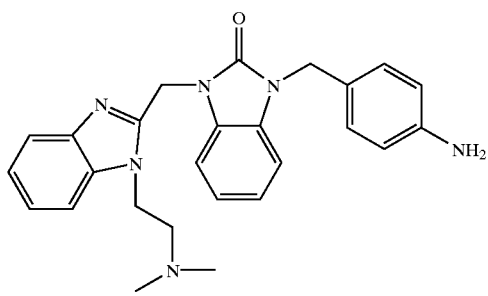

Compound 150 was prepared by catalytic hydrogenation of compound 91k as described for compound 149 above.

$^1$H NMR (CD$_3$OD) δ3.13 (s, 6H), 3.90 (t, J=7.9 Hz, 2H), 5.21–5.26 (m, 4H), 5.97 (s, 2H), 7.16–7.26 (m, 3H), 7.42–7.52 (m, 3H), 7.61 (d, J=8.5 Hz, 2H), 7.66–7.81 (m, 3H), 8.16 (d, J 7.9 Hz, 2H); MS m/e 441 (MH$^+$).

Compound 151

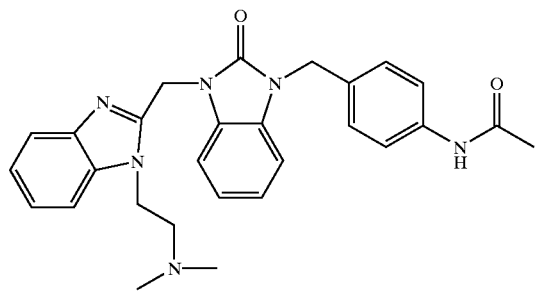

A mixture of compound 150 (100 mg, 0.18 mmol) and Et$_3$N (55 mg, 0.54 mmol) in methylene chloride (4 mL) was cooled to 0° C. Acetyl chloride (18 mg, 0.23 mmol) was added followed by DMAP (5 mg, catalytic quantity). The reaction mixture was allowed to warm to room temperature gradually and stirring was continued for 16 hours at room temperature under nitrogen atmosphere. A white precipitate was observed. The organic material was washed with dilute aqueous sodium bicarbonate solution (10 mL). The aqueous layer was then extracted with methylene chloride (2×20 mL). The combined organic extracts were dried over magnesium sulfate, filtered and evaporated to give a white solid. The solid was triturated with anhydrous diethyl ether and filtered to give compound 151 as a white solid (50 mg, 53% yield).

$^1$H NMR (DMSO-d$_6$) δ2.00 (s, 3 H), 3.36 (t, J=6.9 Hz, 2 H), 4.25 (s, 3 H), 4.80 (t, J=6.9 Hz, 2 H), 5.14 (s, 2 H), 5.34 (s, 2 H), 6.97–7.02 (m, 2 H), 7.07–7.23 (m, 6 H), 7.28 (d, J=8.5 Hz, 2 H), 7.48–7.54 (m, 4 H), 9.92 (s, 1H); IR (KBr, cm$^{-1}$): 3308, 2929, 1694, 1610, 1516, 1495, 1407, 1311, 749. MS m/e 522 (MH$^+$). Anal. Calcd for C$_{28}$H$_{27}$N$_9$O$_2$: C, 64.48; H, 5.22; N, 24.17 Found: C, 64.13; H, 5.32; N, 23.86.

Compound 152

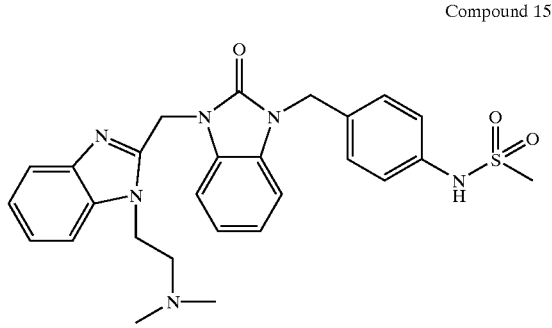

A mixture of compound 150 (100 mg, 0.18 mmol) and Et$_3$N (55 mg, 0.54 mmol) in CH$_2$Cl$_2$ (5 mL) was cooled to 0° C. Methanesulfonyl chloride (21 mg, 0.18 mmol) was added and the reaction mixture was allowed to warm gradually to room temperature. After stirring for 5.5 h under nitrogen atmosphere, the organic material was washed with dilute aqueous sodium bicarbonate solution (10 mL). The aqueous layer was then extracted with CH$_2$Cl$_2$ (2×20 mL). The combined organic extracts were dried over MgSO$_4$, filtered and evaporated. Trituration with anhydrous diethyl ether followed by filtration gave compound 152 as a yellow solid (92 mg, 91% yield).

$^1$H NMR (CD$_3$OD) δ2.95 (s, 3 H), 3.07 (s, 1H), 3.68 (t, J=6.5 Hz, 2H), 4.26 (s, 3H), 5.14 (t, J=6.7 Hz, 2H), 5.15 (s, 2H), 5.81 (s, 2H), 7.16–7.28 (m, 6H), 7.43 (d, J=8.6 Hz, 2H), 7.63–7.75 (m, 3H), 7.99–8.02 (m, 1H); IR (KBr, cm$^{-1}$): 3435, 2929, 1708, 1615, 1513, 1493, 1404, 1329, 1152, 752; MS m/e 558 (MH$^+$).

Compound 153

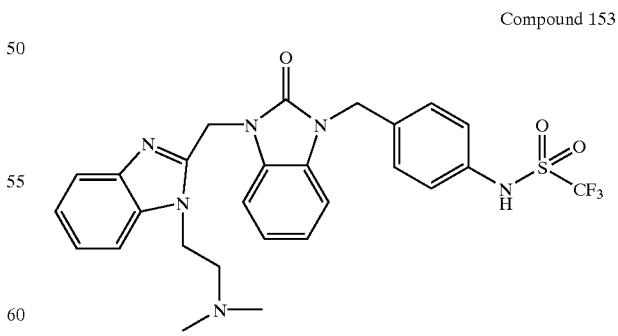

To a solution of compound 150 (600 mg, 1.36 mmol) and Et$_3$N (413 mg, 4.08 mmol) in CH$_2$Cl$_2$ (10 ml) at 0° C. was triflic anhydride (460 mg, 1.63 mmol) dropwise. The solution was warmed to room temperature and stirred for 12 h, washed with sat. NH$_4$Cl, dried, evaporated, and purified by preparative reverse phase HPLC to yield compound 153 (522 mg, 67%) as white solid.

$^1$H NMR (CD$_3$OD) δ3.11 (s, 6H), 3.85 (t, J=8.1 Hz, 2H), 5.18–5.23 (m, 4H), 5.89 (s, 2H), 7.20–7.29 (m, 5H), 7.43–7.50 (m, 3H), 7.67–7.79 (m, 3H), 8.12 (d, J=8.0 Hz, 1H); MS m/e 573 (MH$^+$).

Compound 154

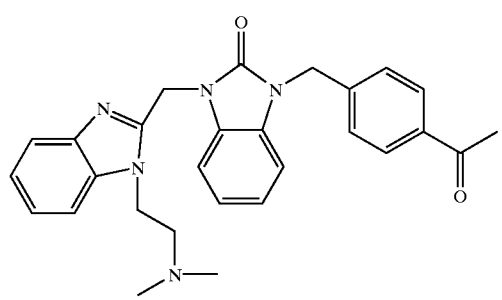

A mixture of compound 91 m (50 mg, 0.1 mmol), ethoxyvinyltributyltin (50 mg, 0.12 mmol) and palladium tetrakis(triphenylphosphine) (12 mg, 0.01 mmol) in toluene (1 ml) was heated to reflux under nitrogen. Diluted with CH$_2$Cl$_2$ (20 ml) and washed with sat. NaHCO$_3$, dried and concentrated. The residue was purified by prep-HPLC to yield 35 mg (67%) of compound 154 as a white solid.

$^1$H NMR (CD$_3$OD) δ2.55 (s, 3H), 3.06 (s, 6H), 3.76 (t, J=7.5 Hz, 2H), 5.02 (t, J=7.5 Hz, 2H), 5.23 (s, 2H), 5.67 (s, 2H), 7.07–7.18 (m, 3H), 7.41–7.57 (m, 5H), 7.72 (d, J=7.4 Hz, 1H), 7.81–7.83 (m, 1H), 7.96 (d, J=8.0 Hz, 2H); MS m/e 468 (MH$^+$).

Compound 155

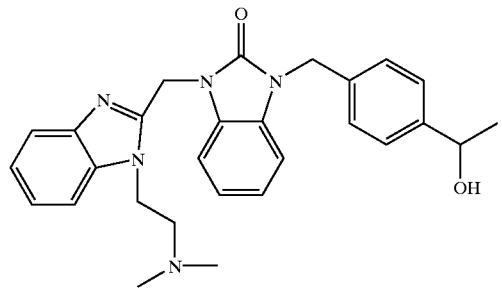

To a solution of compound 154 (24 mg, 0.05 mmol) in ethanol was added NaBH$_4$(14 mg, 0.37 mmol) at 0° C. After stirring at this temperature for 30 min, the reaction mixture was quenched with 1 M HCl then extracted with EtOAc. The organic layer was washed with sat. NaHCO$_3$, dried, and concentrated. The residue was purified by preparative HPLC to yield 18 mg (75%) of compound 155 as a white solid.

$^1$H NMR (CD$_3$OD) δ1.38 (d, J=6.6 Hz, 3H), 3.03 (s, 6H), 3.67 (t, J=7.8 Hz, 2H), 4.77–4.80 (m, 1H), 5.01 (t, J=7.5 Hz, 2H), 5.14 (s, 2H), 5.64 (s, 2H), 7.11–7.14 (m, 3H), 7.32–7.55 (m, 7H), 7.72 (d, J=7.2 Hz, 1H), 7.81 (d, J=7.5 Hz, 1H); MS m/e 470 (MH$^+$).

Compounds 156 and 157

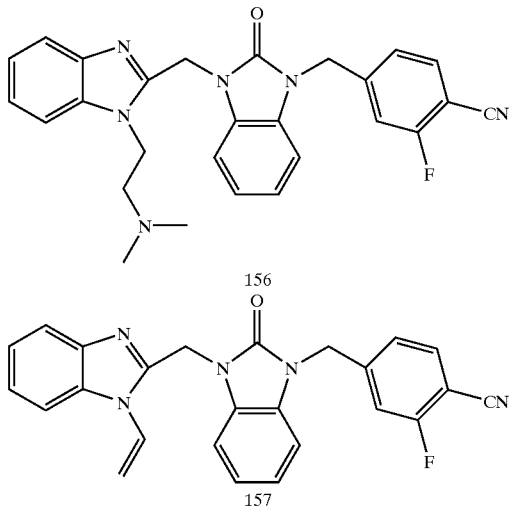

A mixture of 2-fluoro-4-methylbenzonitrile (5.0 g, 37 mmol), N-bromosuccinimide (6.4 g, 37 mmol) and AIBN (100 mg) was heated to reflux in CCl$_4$ (50 ml) for 12 h. The mixture was filtered and concentrated to give a 3:2 mixture of 2-fluoro-4-bromomethylbenzonitrile and starting material. A mixture of compound 128 (1.0 g, 2.98 mmol) and 2-fluoro-4-bromomethylbenzonitrile (0.91, 2.98 mmol) and Cs$_2$CO$_3$ (0.97 g, 2.98 mmol) in CH$_3$CN (50 ml) was heated to reflux for 30 minutes. The mixture was cooled, filtered and concentrated. The residue was purified by column chromatography (EtOAc to 3% MeOH/EtOAc as eluant) to give (10 mg, 1%) of the first eluting vinyl compound 157 and (432 mg, 31%) of compound 156 product.

$^1$H NMR (DMSO-d6): δ2.20 (s, 6H), 2.49–2.55 (m, 2H), 4.44 (t, J=5.7 Hz, 2H), 5.18 (s, 2H), 5.45 (s, 2H), 7.01–7.14 (m, 2H), 7.16–7.25 (m, 5H), 7.51–7.58 (m, 4H), 7.77–7.81 (m, 1H), 7.92–7.95 (m, 1H); MS m/e 468 (MH$^+$).

Compound 158

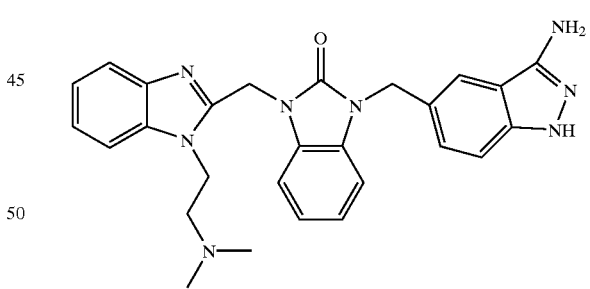

A mixture of compound 156 (210 mg, 0.45 mmol) and hydrazine (14 ml, 0.45 mmol) was heated to reflux in butanol for 12 h as described by R. F. Kaltenbach III, R. M. Klabe, B. C. Cordova and S. P. Seitz in *Biorg. Med Chem. Lett.* 1999, 15, 2259–2262. The reaction was incomplete as judged by thin layer chromatography. Additional hydrazine (0.2 ml) was added and stirring continued at reflux for 12 h. The solvent was removed and the residue purified by flash column chromatography (3% MeOH/CH$_2$Cl$_2$ to 3% MeOH/CH$_2$Cl$_2$/0.1% NH$_4$OH to give compound 158 (200 mg, 92%) as a white solid.

$^1$H NMR (DMSO-d6) δ2.19 (s, 6 H), 4.41–4.52 (m, 2 H), 5.13 (s, 2 H), 5.21–5.40 (m, 2 H), 5.45 (s, 2 H), 5.76 (s, 1

H), 6.95–7.08 (m, 2 H), 7.10–7.31 (m, 6 H), 7.52–7.59 (m, 2 H), 7.72 (s, 1 H), 11.40 (s, 1 H); MS m/e 480 (MH+).

Compounds 159 and 160

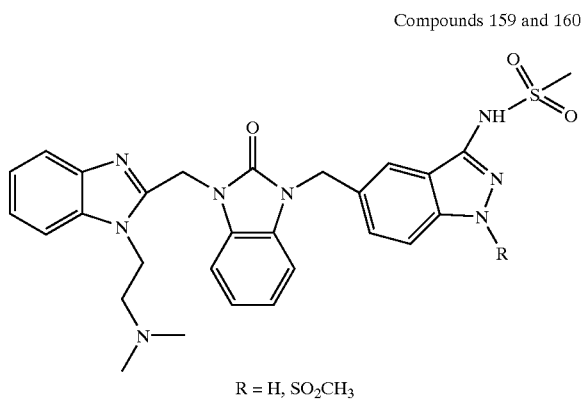

R = H, SO₂CH₃

Compound 158 was treated with methanesulfonyl chloride as described for compound 152 to give a mixture of monomethanesulfonamide compound 160 and dimethanesulfonamide compound 159.

Compound 159; R=H

¹H NMR (DMSO-d6) δ2.33 (s, 6H), 3.36 (s, 3H), 3.50–3.60 (m, 2H), 4.84–4.90 (m, 2H), 5.27 (s, 2H), 5.57 (s, 3H), 7.00–7.15 (m, 2H), 7.18–7.25 (m, 2H), 7.25–7.40 (m, 2H), 7.40–7.50 (m, 3H), 7.59–7.65 (m, 1H), 7.78–7.81 (m, 2H); MS dime 558 (MH+).

Compound 160; R=Ms (DMSO-d6) δ2.96 (s, 6H), 3.32 (s, 3H), 3.36 (s, 3H), 3.25–3.65 (m, 2H), 4.80–4.95 (m, 2H), 5.27 (s, 2H), 5.55 (s, 2H), 7.00–7.18 (m, 2H), 7.19–7.40 (m, 3H), 7.60–7.65 (m, 2H), 7.65–7.78 (m, 2H), 7.85–7.95 (m, 1H), 8.01 (s, 1H); MS m/e 636 (MH+).

Compound 162

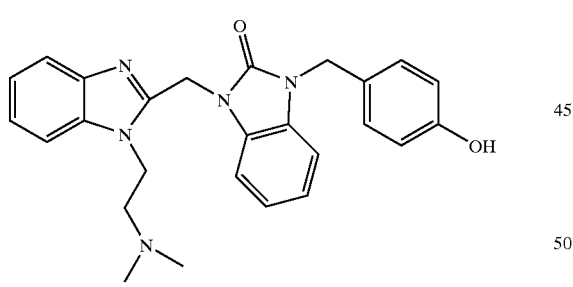

A mixture compound 91 n (600 mg, 1.05 mmol) and 10% palladium hydroxide on carbon (160 mg) in 2:1 MeOH/THF (50 mL /25 mL) was agitated under hydrogen at 55 psi for 48 hours. The reaction mixture was filtered through a pad of Celite and then subjected to column chromatography (2:1 EtOAc/CH₂Cl₂) to give compound 162 as a white solid (262 mg, 52% yield).

¹H NMR (DMSO-d₆) δ3.35 (t, J=6.8 Hz, 2H), 4.25 (s, 3H), 4.80 (t, J=6.8 Hz, 2H), 4.94 (s, 2H), 5.33 (s, 2H), 6.68 (d, J=8.5 Hz, 2H), 6.95–7.02 (m, 2H), 7.09–7.23 (m, 6H), 7.47–7.54 (m, 2H), 9.39 (s, 1 H); IR (KBr, cm⁻¹) 3247, 2944, 1664, 1613, 1597, 1515, 1491, 1445, 1413, 747; MS m/e 481 (MH+); Anal. Calcd for C₂₆H₂₄N₈O₂: C, 64.99; H, 5.03; N, 23.32 Found: C, 64.79; H, 4.98; N, 23.38.

Compound 163

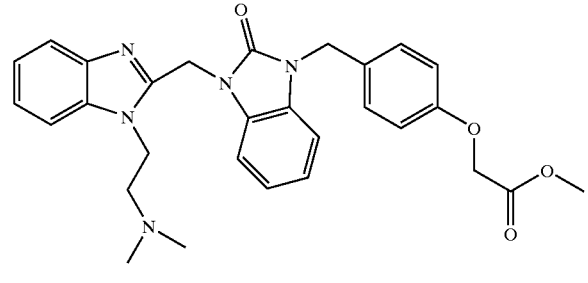

To the compound 162 (127 mg, 0.26 mmol) DMF (5 mL) was added NaH (60% suspension in mineral oil, 13 mg, 0.32 mmol) while stirring under nitrogen atmosphere. After stirring for 15 minutes, methyl bromoacetate (48 mg, 0.32 mmol) was added. The reaction was stirred at room temperature for 16 hours. Column chromatography on silica gel (gradient, CH₂Cl₂ to 1% MeOH in CH₂Cl₂) gave compound 163 as a solid (142 mg, 97% yield).

¹H NMR (DMSO-d₆) δ3.36 (t, J=6.7 Hz, 2 H), 3.66 (s, 3 H), 4.25 (s, 3H), 4.74 (s, 3H), 4.80 (t, J=6.9 Hz, 2 H), 5.00 (s, 2 H), 5.33 (s, 2 H), 6.87 (d, J=8.7 Hz, 2 H), 6.98–7.01 (m, 2 H), 7.13–7.23 (m, 4 H), 7.30 (d, J=8.7 Hz, 2 H), 7.51 (dd, J=12.9, 7.4 Hz, 2 H); IR (KBr, cm⁻¹: 2922, 1745, 1698, 1611, 1509, 1498, 1438, 1230, 742. MS m/e 553 (MH+). Anal. Calcd for C₂₉H₂₈N₈O₄: C, 63.03; H, 5.11; N, 20.28 Found: C, 63.20; H, 5.14; N, 18.48

Compound 164

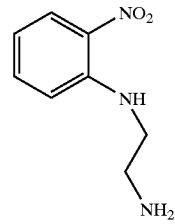

A solution of 2-fluoronitrobenzene (30 mL, 2.84 mmol) in acetonitrile (30 mL) was added to a solution of ethylenediamine (76 mL, 1.14 mmol) in acetonitrile (50 mL). The mixture was stirred at room temperature for 12 h then concentrated to give 51 g (99% yield) of compound 164 as an orange oil.

¹H NMR (DMSO-d₆) δ2.82 (t, J=6.0 Hz, 2 H), 3.30 (t, J=6.0 Hz, 2 H), 6.66 (t, J=8.4 Hz, 1 H), 7.05 (d, J=8.7 Hz, 1 H), 7.53 (d, J=8.4 Hz, 1 H), 8.30–8.34 (m, 1 H); IR (film, cm⁻¹) 1621, 1514, 1347, 740; MS m/e 182 (MH+); Anal. Calcd for C₈H₁₁N₃O₂.0.20 H₂O: C, 51.99; H, 6.22; N, 22.74 Found: C, 51.99; H, 6.29; N, 22.46.

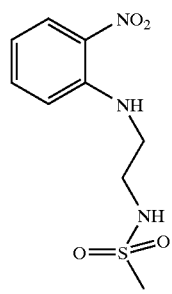

Compound 165

To a mixture of amine 164 (2.0 g, 11 mmol) in CH$_2$Cl$_2$ (50 mL) was added triethyl amine (1.53 mL, 11 mol) and the mixture was cooled to 0° C. Methanesulfonyl chloride (0.85 mL, 11 mmol) was added slowly. Once the addition was complete, the reaction mixture was warmed to room temperature and stirred for 12 h. The mixture was poured into water and the aqueous layer separated, dried over MgSO$_4$, and evaporated. The residue was chromatographed with 3% methanol in dichloromethane to give 2.55 g (89%) of compound 165 as an orange oil:

$^1$H NMR (DMSO-d$_6$) δ2.91 (s, 3H), 3.18 (dd, J=6.1, 11.6 Hz, 2H), 3.39–3.42 (m, 2H), 6.70 (t, J=9.0 Hz, 1H), 7.08 (d, J=8.5 Hz, 1H), 7.28 (t, J=6.1 Hz, exchanges with D$_2$O , 1H), 7.55 (td, J=1.0, 6.0, Hz, 1H); 8.07 (dd, J=1.0, 8.7 Hz, 1H); 8.23 (br s, 1H exchanges with D$_2$O); IR (film, cm$^{-1}$) 1511, 1354, 1317, 1151; MS m/e 260 (MH$^+$); Anal. Calcd for C$_9$H$_{13}$N$_3$O$_4$S.0.5 H$_2$O.0.08 EtOAc: C, 40.66; H, 5.36; N, 15.26. Found: C,40.58; H, 5.29; N, 14.88.

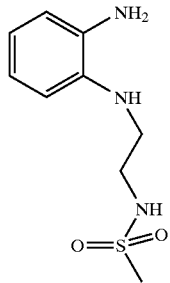

Compound 166

A mixture of compound 165 (1.0 g, 3.9 mmol) and 10% Pd/C (100 mg) in ethanol (50 mL) was hydrogenated at 50 psi for 12 h. The mixture was filtered and the filtrate was evaporated to give an orange oil. The residue was chromatographed (1% MeOH in CH$_2$Cl$_2$) to give 0.55 g (62% yield) of compound 166 as a dark oil:

$^1$H NMR (DMSO-d$_6$) δ2.91 (s, 3H), 3.17 (br s, 2H), 4.45 (br s, 3H, 1H exchanges with D$_2$O), 6.40–6.56 (m, 4H), 7.11 (br s, 1 H, exchanges with D$_2$O); IR (film, cm$^{-1}$) 3326, 1625, 1510, 1315, 1148, 738; MS m/e 230 (MH$^+$); Anal. Calcd for C$_9$H$_{15}$N$_3$O$_2$S: C, 46.78; H, 6.63; N, 18.18 Found: C, 46.81; H, 6.79; N, 17.81.

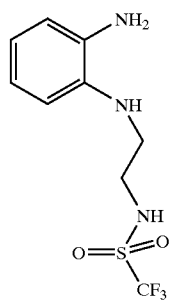

Compound 167

Compound 167 was prepared as described for 166 above. $^1$H NMR (DMSO-d$_6$) δ3.17–3.21 (m, 2H), 3.31–3.35 (m, 4H, 2H exchange with D$_2$O), 6.42–6.57 (m, 4H); IR (film, cm$^{-1}$) 1365, 1143; MS m/e 283 (MH$^+$).

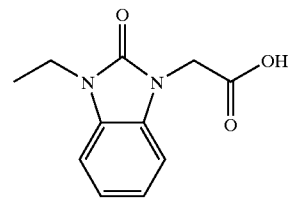

Compound 168

A mixture of 1,3 dihydro-2-H-1-ethylbenzimidazol-2-one (5.0 g, 30.8 mmol), ethyl bromoacetate (3.4 mL, 30.8 mmol) and potassium carbonate (4.25 g, 30.8 mmol) in acetonitrile (50 mL) was heated to reflux for 12h, and then evaporated. To the residue was added 6 N HCl (100 mL) and the resulting mixture was heated to reflux for 4 h. The solution was cooled to room temperature and precipitate was filtered to give 6.2 g (99% yield) of compound 168 as white needles: mp 225–227° C.;

$^1$H NMR (DMSO-d$_6$) δ1.20 (t, J=7.1 Hz, 3H), 3.87 (q, J=7.1, 14.1 Hz, 2H), 4.60 (s, 2H), 7.00–7.10 (m, 2H), 7.13–7.16 (m, 1H), 7.21–7.24 ( m, 2H); IR (KBr, cm$^{-1}$) 3000, 1750, 1655, 752; MS m/e 230 (MH$^+$); Anal. Calcd for C$_{11}$H$_{12}$N$_2$O$_3$: C, 59.99; H, 5.49; N, 12.72. Found: C, 59.82; H, 5.43; N, 12.64.

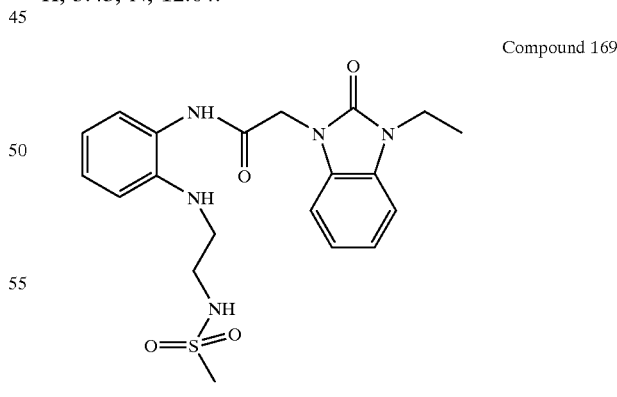

Compound 169

Acid 168 (0.48 g, 2.2 mmol) was refluxed with thionyl chloride (2 mL) for 30 minutes and then evaporated to dryness. To the residue was added a solution of diamine 166 (0.5 g, 2.2 mmol) and triethylamine (0.55 mL, 4.0 mmol) in CH$_2$Cl$_2$ (10 mL). The reaction mixture was stirred for 12 h and then poured into water. The organic layer was separated, dried over magnesium sulfate, and evaporated. The residue was chromatographed on silica gel eluted with 3% methanol in methylene chloride to give 810 mg (86% yield) of 169 as a light green solid: mp 82–85° C.;

$^1$H NMR (DMSO-d$_6$) δ1.23 (t, J=7.1 Hz, 3H), 2.90 (s, 3H), 3.13–3.17 (m, 2H), 3.18–24 (m, 2H), 3.90 (q, J=7.1, 14.1 Hz, 2H), 4.71 (s, 2H), 5.18 (t, J=7.1 Hz, 1H, exchanges with D$_2$O), 6.58 (t, J=7.6 Hz, 1H), 6.67 (d, J=7.5 Hz, 1H), 7.03–7.24 (m, 6H), 9.44 (s, 1 H, exchanges with D$_2$O); IR (KBr, cm$^{-1}$) 1686, 1522, 1317, 1149; MS m/e 432 (MH$^+$). Anal. Calcd for C$_{20}$H$_{25}$N$_5$O$_4$.0.3 H$_2$O: C, 54.98; H, 5.91; N, 16.03 Found: C, 55.07; H, 5.97; N, 15.65.

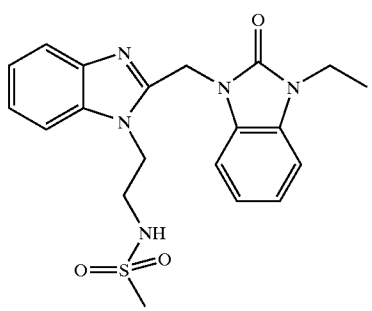

Compound 170

Amide 169 (0.72g, 1.67 mmol) was heated to reflux in acetic acid for 12 h and evaporated. The residue was purified by chromatography (3% MeOH in CH$_2$Cl$_2$) to give 0.37 g (53% yield) of compound 170 as a white solid: mp 57–60° C.;

$^1$H NMR (DMSO-d$_6$) δ1.24 (t, J=7.1 Hz, 3H), 1.90 (s, 3H), 3.38–3.34 (m, 2H), 3.92 (q, J=7.1, 14.7 Hz, 2H); 4.49 (t, J=6.0 Hz, 2H); 5.41 (s, 2H); 6.98–7.28 (m, 6H); 7.40 (t, J=6.0, 1H, exchanged with D$_2$O), 7.54 (d, J=7.7Hz, 1H), 7.58 (d, J=8.1 Hz, 1H); IR (KBr cm$^{-1}$) 1693, 1317, 1140, 744; MS m/e 414 (MH$^+$). Anal. Calcd for C$_{20}$H$_{25}$N$_5$O$_4$S.1.1 H$_2$O: C, 55.65; H, 5.76; N, 14.75. Found: C, 55.65; H, 5.74; N, 14.72.

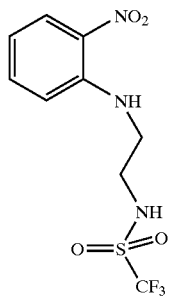

Compound 171

To a mixture of amine 164 (3.0 g, 13.8 mmol) in CH$_2$Cl$_2$ (50 mL) was added triethyl amine (3.8 mL, 28 mol) and the mixture was cooled to 0° C. Trifluoromethanesulfonic anhydride (2.32 mL, 13.8 mmol) was added slowly. Once the addition was complete the reaction mixture was warmed to room temperature and stirred for 12 h. The mixture was poured into water and the aqueous layer separated, dried over MgSO$_4$, and evaporated. The residue was was dissolved in MeOH and treated with 25% NaOH (1 mL) and stirred for 6 h. The mixture is acidified and extracted with EtOAc. The organic layer was dried and concentrated to give 1.07 g (71%) of compound 171.

$^1$H NMR (DMSO-d6) d 3.38 (t, J=5.8 Hz, 2H), 3.52–3.58 (m, 2H), 6.72 (t, J=6.8 Hz, 1H), 7.07 (d, J=8.6 Hz, 1H), 7.55 (t, J=7.1 Hz, 1H), 8.08 (d, J=8.6 Hz, 1H), 8.22 (t, J=3.06 Hz, 1H, exchanges with D$_2$O) MS m/e 313 (MH$^+$); Anal. Calcd for C$_9$H$_{10}$F$_3$N$_3$O$_4$S: C, 34.51; H, 3.22; N, 13.41 Found: C, 34.39 ; H, 3.20; N, 13.24.

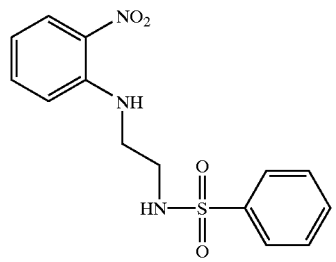

Compound 172

To a solution of compound 164 (2 g, 9.2 mmol) in CH$_2$Cl$_2$ (70 ml) was added Triethylamine (2.32 g, 22.9 mmol) at 0° C. Benzenesulfonyl chloride(1.95 g, 11.04 mmol) was added slowly and the mixture was stirred overnight at room temperature. The mixture was diluted with CH$_2$Cl$_2$ and washed with water, 1N HCl, and brine. The organic layer was dried over Na$_2$SO$_4$ and concentrated to give 3.06 g (97% yield) of the compound 172 as a yellow solid.

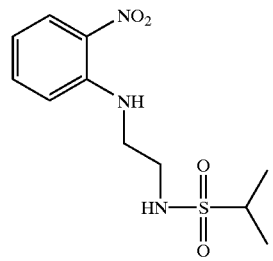

Compound 173

To a solution of compound 164 (2 g, 9.2 mmol) in CH$_2$Cl$_2$ (70 ml) was added Triethylamine (2.32 g, 22.9 mmol) at 0 C. Isopropylsulfonyl chloride (1.57 g, 11.0 mmol) was added slowly and the mixture was stirred overnight at room temperature. The mixture was diluted with CH$_2$Cl$_2$ and washed with water, 1N HCl, and brine. The organic layer was dried over Na$_2$SO$_4$ and concentrated to give 830 mg (31% yield) of the compound 173 as a yellow oil.

TABLE 14

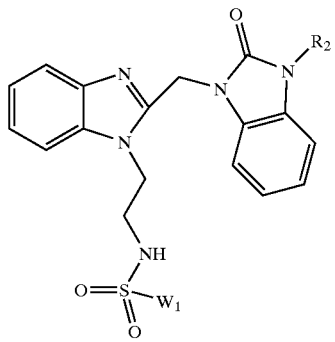

Compounds were prepared as described for compound 170.

| # | $R_2$ | $W_1$ | $^1$H-NMR Data | MS Data |
|---|---|---|---|---|
| 174a | $CH_2CO_2Et$ | Me | (DMSO-d6) δ 1.20 (t, J = 7.1 Hz, 3H), 2.81 (s, 3H), 3.25 (t, J = 5.9 Hz, 2H), 4.07 (q, J = 7.1 Hz, 2H), 4.39 (t, J = 5.8 Hz, 2H), 4.69 (s, 2H), 5.34 (s, 2H), 6.94–6.98 (m, 2H), 7.08–7.16 (m, 4H), 7.45 (d, J = 7.7 Hz, 1H), 7.49 (d, J = 7.9 Hz, 1H) | 471 (MH+) |
| 174b | $CH_2CO_2Et$ | $CF_3$ | (DMSO-d6) δ 1.22 (t, J = 6.3 Hz, 3H), 3.51–3.62 (m, 2H), 4.17 (q, J = 7.2 Hz, 2H), 4.45–4.58 (m, 2H), 4.76 (s, 2H), 5.43 (s, 2H), 7.05–7.10 (m, 2H), 7.16–7.29 (m, 4H), 7.57 (d, J = 7.8 Hz, 2H), 9.81 (s, 1H, exchanges with $D_2O$) | 525 (MH+) |
| 174c | $CH_2CO_2Et$ | Ph | 1H NMR(DMSO-d6) d 1.21 (t, J = 7.1, 3H), 3.09–3.13 (m, 2H), 4.15 (q, J = 7.1, 2H), 4.45–4.4.67 (m, 2H), 4.78 (s, 2 H), 5.43 (s, 2H), 7.01–7.26 (m, 6H), 7.50–7.65 (m, 5H), 7.73 (d, J = 7.1, 2H), 8.03 (t, J = 6.2, 1H); | MS m/e 534 (MH+); |

TABLE 15

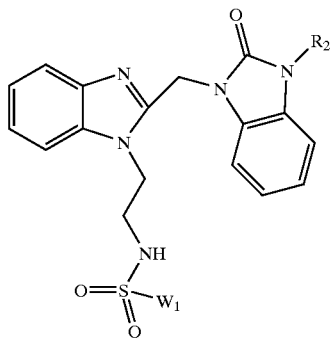

Prepared as described for compound 8.

| # | $R_2$ | $W_1$ | $^1$H-NMR Data | MS Data |
|---|---|---|---|---|
| 175a | $CH_2CO_2H$ | $CF_3$ | (DMSO-d6) δ 3.48–3.60 (m, 2H), 4.43–4.58 (m, 2H), 4.67 (s, 2H), 5.41 (s, 2H), 7.03–7.10 (m, 2H), 7.14–7.27 (m, 5H), 7.54 (d, J = 7.8 Hz, 2H) | 497 (MH+) |
| 175b | $CH_2CO_2H$ | $CH_3$ | (DMSO-d6 δ 2.78 (s, 3H), 3.32 (t, J = 5.2 Hz, 2H), 4.45 (t, J = 5.8 Hz, 2H), 4.65 (s, 3H), 5.41 (s, 2H), 6.99–7.10 (m, 2 H), 7.10–7.22 (m, 4H), 7.52–7.58 (m, 2H) | 443 (MH+) |

TABLE 15-continued

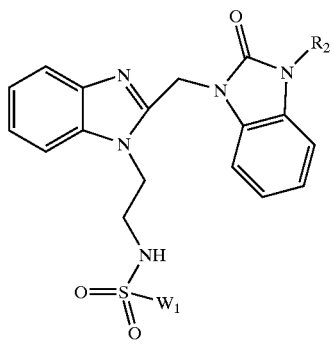

Prepared as described for compound 8.

| # | R₂ | W₁ | ¹H-NMR Data | MS Data |
|---|---|---|---|---|
| 175c | 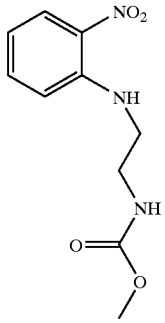 | $CH_3$ | (DMSO-d6) δ 2.84 (s, 3H), 6.38–6.46 (m, 2H), 4.55–4.61 (m, 2H), 5.60 (s, 2H), 5.76 (s, 2H), 7.02–7.06 (m, 2H), 7.14–7.16 (m, 1H), 7.27–7.31 (m, 2H), 7.36–7.39 (m, 1H), 7.44–7.46 (m, 1H), 7.49 (d, J = 8.1 Hz, 2H), 7.61 (d, J = 7.9 Hz, 1H), 7.74 (d, J = 7.8 Hz, 1H), 7.92(d, J = 8.1 Hz, 2H) | 520 (MH+) |
| 175d | $CH_2CO_2H$ | iPr | (DMSO-d6) δ 1.11 (d, J = 6.8, 6H), 1.22 (t, J = 7.1, 3 H), 3.07–3.16 (m, 2H), 4.16 (q, J = 7.1, 2H), 4.31–4.33 (m, 2H), 4.78 (s, 2H), 5.44 (s, 2H), 7.00–7.08 (m, 2H), 7.13–7.27 (m, 3H), 7.35 (t, J = 6.3, 1H), 7.53–7.59 (m, 2H); | 500 (MH+) |
| Compound 176 | 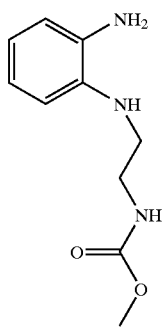 | | | |

To a slurry of compound 164 (2.0 g, 9.2 mmol) and KHCO₃ (2.3 g, 23.0 mmol) was added methyl chloroformate (1.42 ml, 18.4 mmol) and the mixture stirred at 23° C. for 12 h. The reaction mixture is extracted with EtOAc. The organic extracts are combined, dried over MgSO₄ and concentrated to give 1.82 g (83%) of compound 176 as a yellow solid.

¹H NMR (DMSO-d₆) δ3.19–3.25 (m, 2H), 3.39–3.45 (m, 2H), 3.52 (s, 3H), 6.67 (t, J=7.3 Hz, 1 H), 7.12 (d, J=8. 7 Hz, 1H), 7.37 (br t, 1 H, exchanges with D₂O), 7.53 (t, 7.2 Hz, 1H), 8.04 (d, J=8.7 Hz, 1H), 8.20 (br t, 1H, exchanges with D₂O) IR (film, cm⁻¹) 1736, 1515, 1353; MS m/e 239 (MH⁺); Anal. Calcd for $C_{10}H_{135}N_3O_4$: C, 50.21; H, 5.48; N, 17.56 Found: C, 50.15 ; H, 5.61; N, 17.58.

Compound 177

Compound 177 was prepared as described for compound 166 above.

¹H NMR (DMSO-d₆) δ3.03–3.10 (m, 2H), 3.16–3.22 (m, 2H), 3.53 (s, 3H), 4.40–4.45 (m, 2H, exchanges with D₂O), 6.38–6.55 (m, 4H), 7.21 (t, J=5.3 Hz, 1H, exchanges with D₂O); IR (film, cm⁻¹) 1702, 1565, 733; MS m/e 209 (MH).

TABLE 16

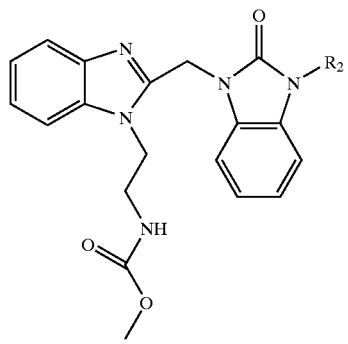

178

Compounds were prepared as described for compound 170 using 177.

| # | $R_2$ | $^1$H-NMR Data | MS Data |
|---|---|---|---|
| 178a | Et | 1H NMR (DMSO-d6) d 1.23 (t, J = 7.1, 3H), 3.32–3.38 (m, 2H), 3.47 (s, 3H), 3.91 (q, J = 7.2, 2H), 4.43 (t, J = 6.0, 2H), 5.33 (s, 2H), 6.97–7.09 (m, 2H), 7.13–7.24 (m, 4H), 7.46–7.55 (m, 2H); | MS m/e 394 (MH+); |
| 178b | $CH_2CO_2Et$ | DMSO-d6: 1.22 (t, J = 7.10 Hz, 3H), 3.33 (s, 3H), 3.32–3.42 (m, 2H), 4.17 (q, J = 7.10 Hz, 2H), 4.40–4.48 (m, 2H), 4.79 (s, 2H), 5.37 (s, 2H), 7.01–7.16 (m, 2H), 7.21–29 (m, 3H), 7.32–7.39 (m, 1H), 7.55–7.65 (m, 2H) | 451 (MH+) |
| 178c[a] | $CH_2CO_2H$ | (DMSO-d6) 3.25-3.34 (m, 2H), 3.48 (s, 3H), 4.41–4.45 (m, 2H), 4.68 (s, 2H), 5.37 (s, 2H), 7.03–7.10 (m, 2H), 7.05–7.30 (m, 4H), 7.30–7.38 (m, 2H), 7.43–7.58 (m, 2H) | 423 (MH+) |

Compound 179

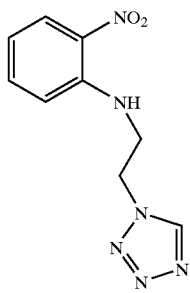

[a]ester hydrolyzed as described for compound 8.

A mixture of amine 164 (40 g, 220 mmol), trimethyl ortho formate (38.5 mL, 352 mmol) and sodium azide (15.7 g, 242 mmol) in acetic acid (400 mL) was heated to reflux for 12 h. The resulting mixture was cooled to room temperature and poured into 1N HCl in ice (300 mL). The precipitate was filtered and recrystallized from ethyl acetate to give 19.2 g (37% yield) of compound 179 as bright yellow needles:

$^1$H NMR (DMSO-d$_6$) δ3.90 (J=6.6 Hz, 2H), 4.73 (t, J=6.6 Hz, 2H), 6.72 (t, J=6.9 Hz, 1H), 7.07 (d, J=10.2 Hz, 1H), 7.53 (d, J=6.3 Hz, 1H), 8.06 (d, J=10.1 Hz, 1 H), 8.18 (t, J=6.6 Hz, 1 H); 9.40 (s, 1 H); IR (KBr, cm$^{-1}$) 1621, 1514, 1347, 740; MS m/e 235 (MH$^+$); Anal. Calcd for $C_9H_{10}N_6O_2$: C, 46.15; H, 4.30; N, 35.88. Found: C, 46.17; H, 4.35; N, 35.85.

Compound 180

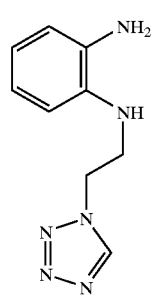

A solution of nitroaniline 179 (3.5 g, 14.95 mmol) in ethanol (50 mL) containing 10% Pd/C (200 mg) was hydrogenated at 50 psi for 4 h. The reaction mixture was filtered and concentrated to give 2.8 g (93% yield) of compound 180 as a black solid:

¹H NMR (DMSO-d₆) δ3.52 (q, J=6.0, 2H), 4.46 (s, 3H), 4.63–4.69 (m, 3H), 6.45–6.57 (m, 4H), 9.4 (s, 1H); MS m/e 205 (MH⁺).

Compound 181

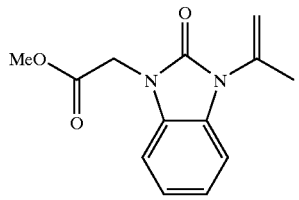

N-isopropenyl-2-benzimidazolone (1 5.0g, 86.10 mmol), methyl bromoacetate (13.2 g, 86.1 mmol) and potassium carbonate (14.25 g, 103.26 mmol) were stirred in acetonitrile (300 ml) at room temperature overnight. The next day the reaction mixture was filtered and concentrated to give 21.0 g (99% yield) of product 181 as a clear oil:

¹H NMR (DMSO) δ2.13 (s, 3H), 3.69 (s, 3H), 4.74 (s, 2H), 5.17 (s, 1H), 5.38 (s, 1H), 7.05–7.23 (m, 4H); IR (KBr, cm⁻¹) 2955, 1755, 1714, 1493, 757; MS m/e 247 (MH⁺).

Compound 182

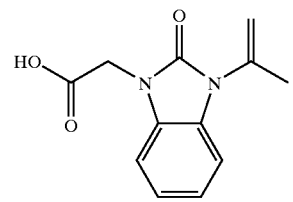

The solution of ester 181 (3.33g, 17.79 mmol) in methanol (20 mL) was stirred with 1N NaOH (19.19 ml, 19.18 mmol) at room temperature overnight. The solvent was evaporated and the residue dissolved in water and acidified with 1N HCl. The precipitate was filtered off, washed with water and dried under vacuum to give 2.7 g (91% yield) of compound 182 as a white solid:

¹H NMR (DMSO-d₆) δ2.15 (s, 3H), 4.62 (s, 2H), 5.18 (s, 1H), 5.4 (s, 1H), 7.07–7.21 (m, 4H); IR (KBr, cm⁻¹) 2967, 1751 1675, 1206, 752; MS m/e 233 (MH⁺); Anal. Calcd for C₁₂H₁₂N₂O₃: C, 62.06; H, 5.21; N, 12.06 Found: C, 61.69; H, 5.33; N, 11.98

Compound 183

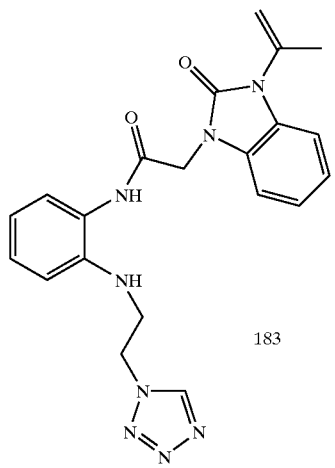

183

To a mixture of acid 182 (1.35 g, 6.61 mmol) and 2-chloro-1-methylpyridinium iodide (2.02 g, 7.92 mmol) in acetonitrile (30 mL) was added triethylamine (3.21 mL, 23.13 mmol), followed by diamine 180 (1.53 g, 6.61 mmol). The reaction mixture was stirred at room temperature overnight. The precipitate was filtered and dried under vacuum to give compound 183 (1.281 g, 46% yield): mp 184–186° C.

¹H NMR (DMSO-d₆) δ2.15 (s, 3H), 3.59 (q, J=6.5 Hz, 2H), 4.64 (t, J=6.6 Hz, 2H), 4.71 (s, 2H), 5.17 (s, 1H), 5.36–5.39 (m, 2H), 6.60 (t, J=7.5 Hz, 1H), 6.70 (d, J=7.4 Hz, 2H), 7.02–7.19 (m, 6H), 9.34 (s, 1H), 9.48 (s, 1H); IR (KBr, cm⁻¹) 3400, 1710, 1680, 1493, 1426, 742; MS m/e 419 (MH⁺); Anal. Calcd for C₂₁H₂₂N₈O₂: C, 60.28; H, 5.30; N, 26.78 Found: C, 59.92; H, 5.31; N, 26.41.

Compound 184

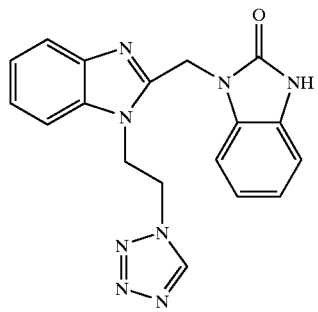

A solution of compound 183 (1.25 g, 2.98 mmol) in acetic acid (40 ml) was refluxed overnight. The solvent was evaporated to give compound 184 as an off-white solid (850mg, 79% yield): mp>200° C.

¹H NMR (DMSO-d₆) δ4.91–4.98 (m, 4H), 5.14 (s, 2H), 6.95–7.0 (m, 3H), 7.10–7.17 (m, 3H), 7.25–7.27 (m, 1H), 7.50–7.54 (m, 1H), 9.28 (s, 1H), 11.03 (s, 1H); IR (KBr, cm⁻¹) 3429, 3256, 1694, 1489, 738; MS m/e 361 (MH⁺); Anal. Calcd for C₁₈H₁₆N₈O·0.33 H₂O·0.35 EtOAc: C, 58.67; H, 4.94; N, 28.21 Found: C, 58.55; H, 4.69; N, 27.83

Compound 185

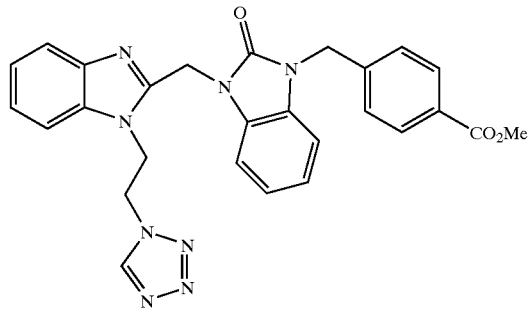

A mixture of compound 184 (1.0 g, 2.77 mmol) and Cs₂CO₃ (904 mg, 2.77 mmol) in CH₃CN (40 mL) was heated to reflux for 10 minutes, and then methyl 4-(bromomethyl)benzoate (636 mg, 2.77 mmol) in CH₃CN (5 mL) was added. The resulting mixture was refluxed for 30 minutes and cooled to room temperature. The mixture was filtered and the filtrate was evaporated. Flash chromatography (MeOH:CH₂Cl₂=5:95) gave 700 mg (50% yield) of compound 185 as a white solid: mp 144–147° C.;

¹H NMR (DMSO-d₆) δ3.83 (s, 3H), 4.94–5.01 (m, 4H), 5.21 (s, 2H), 5.27 (s, 2H), 6.7–7.07 (m, 2H), 7.11–7.19 (m,

3H), 7.22–7.31 (m, 2H), 7.48 (d, J=8.3 Hz, 2H), 7.54–7.56 (m, 1H), 7.93 (d, J=8.3 Hz, 2H), 9.31 (s, 1H); IR (KBr, cm$^{-1}$) 3423, 1714,1437,1284, 1110,748; MS m/e 509 (MH$^+$); HRMS calcd for $C_{27}H_{24}N_8O_3$, 509.2049; found, 509.2046

Compound 186

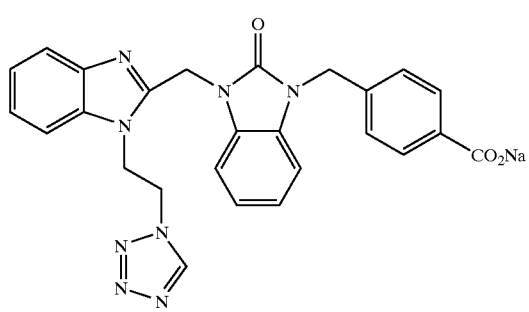

To a solution of compound 185 (1.82 g, 3.57 mmol) in methanol (110 mL) was added lithium hydroxide monohydrate (0.90 g, 21.47 mmol) in water (20 mL). The resulting mixture was stirred overnight at room temperature and evaporated. The residue was diluted with water and acidified with 1N HCl. The white precipitate was filtered and dried under vacuum. To the solid in methanol (120 mL) was added one equivalent of 0.5 M NaOMe (5.5 mL) at room temperature under nitrogen and the solution was stirred for 3 hours. The solvent was evaporated and dried under vacuum to give 1.38 g (74% yield) of compound 186 as a white solid:

$^1$H NMR (DMSO-d$_6$) δ4.92–5.05 (m, 4H), 5.18 (s, 2H), 5.26 (s, 2H), 7.01–7.03 (m, 2H), 7.1–7.29 (m, 3H), 7.38–7.45 (m, 2H), 7.51–7.54 (m, 1H), 7.89 (d, J=8.3, 4H), 9.29 (s, 1H); IR (KBr, cm$^{-1}$) 3406, 1695, 1599,1556, 1396, 750; MS m/e 495 (MH$^+$).

Compound 187

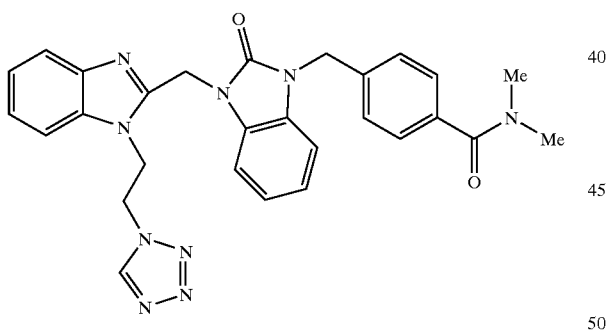

To a mixture of acid 186 (250 mg, 0.5 mmol), dimethylamine hydrochloride (62 mg, 0.75 mmol) and diisopropyl ethylamine (131 mg, 1.0 mmol) in DMF (10 mL) was added PyBroP (283 mg, 0.60 mmol) in one portion. The reaction was stirred at room temperature overnight, quenched with MeOH (1 mL), and evaporated. The residue was taken into ethyl acetate and washed with 5% KHSO$_4$, 5% NaHCO$_3$, brine, dried over Na$_2$SO$_4$, and evaporated. The crude solid was washed with ethyl acetate and large portions of water to give 181 mg (69% yield) of compound 187 as a white solid: mp>200° C.

$^1$H NMR (DMSO-d$_6$) δ2.86 (s, 3H), 2.95 (s, 3H), 4.93–4.95 (m, 2H), 5.0–5.02 (m, 2 H), 5.15 (s, 2H), 5.26 (s, 2H), 7.02–7.04 (m, 2H), 7.14–7.17 (m, 3H), 7.23–7.24 (m, 1H), 7.28–7.3 (m, 1H), 7.38 (q, J=5.0 Hz, 4H), 7.53 (d, J=5.3 Hz, 1H), 9.31 (s, 1H); MS m/e 521(MH$^+$).

Compound 188

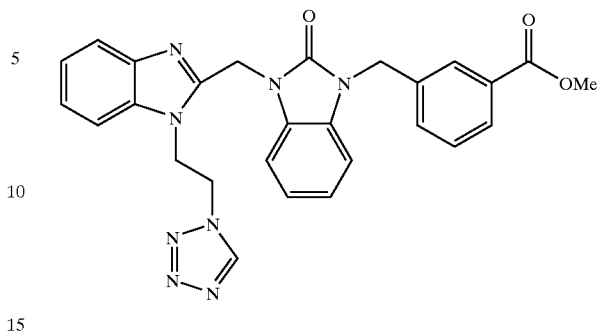

Compound 184 (300mg, 0.83 mmol) in THF (5 mL) was added BTPP (0.51 mL, 1.82 mmol) under nitrogen at 0° C. After stirring for 15 minutes, methyl 3-(bromomethyl) benzoate (190.7 mg, 0.83 mmol) was added. The reaction mixture was allowed to warm up to room temperature overnight under nitrogen and evaporated. The residue was diluted with water and extracted with ether and ethyl acetate. The combined extracts were dried over Na$_2$SO$_4$ and evaporated. The crude product was purified by flash chromatography on silica gel using CH$_2$Cl$_2$:MeOH:NH$_4$OH=90:10:1 to give 196 mg (46% yield) of compound 188 as a white solid: mp 162–164° C.;

$^1$H NMR (DMSO-d$_6$) δ3.85 (s, 3H), 4.92–5.05 (m, 4H), 5.19 (s, 2H), 5.27 (s, 2H), 6.99–7.05 (m, 2H), 7.11–7.17 (m, 3H), 7.20–7.28 (m, 2H), 7.48–7.55(m, 2H), 7.63 (d, J=7.9 Hz, 1H), 7.85 (d, J=6.5 Hz, 1H), 7.97 (s, 1 H), 9.29 (s, 1H); IR (KBr, cm$^{-1}$) 3424, 1701, 1494, 1434, 1289, 748; MS m/e 509 (MH$^+$); Anal. Calcd for $C_{27}H_{24}N_8O_3$.0.55 EtOAc: C, 62.97; H, 5.14; N, 20.12 Found: C, 63.22; H, 4.75; N, 19.73.

Compound 189

Compound 188 (100 mg, 0.19 mmol) in methanol (10 mL) was stirred with 1N NaOH (0.3 mL) at room temperature for 2 days, and then refluxed for 3 hours. The solvent was removed. The residue was diluted with water and acidified to pH 5 with 1N HCl. The white precipitate was filtered and dried under vacuum. The solid in methanol (5 mL) was stirred with 0.5M NaOMe (0.34 mL) at room temperature under nitrogen for 3 hours. The solvent was evaporated and the residue was dried under vacuum to give 87 mg (86% yield) of the sodium salt of compound 189 as a white solid:

$^1$H NMR (DMSO-d$_6$) δ4.92–5.0 (m, 4H), 5.09 (s, 2H), 5.27 (s, 2H), 6.99–7.29 (m, 9H), 7.53–7.56 (m, 1H), 7.72 (d, J=7.2 Hz, 1H), 7.81 (s, 1H), 9.34 (s, 1H); IR (KBr, cm$^{-1}$) 3412, 1698, 1566, 1492, 1390, 750; MS m/e 495 (MH$^+$).

Compound 190

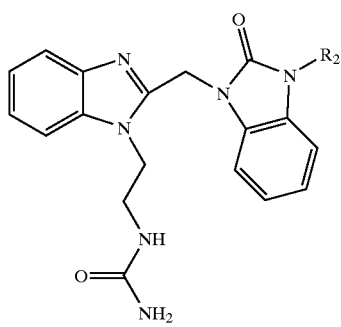

The tetrazole was dissolved in MeOH (30 ml) and NaOH (1N, 2 eq) was added and the mixture stirred for 12 h. The solvent removed and the resulting mixture was adjusted to pH 7 with 1N HCl. The product was extracted with EtOAc and the organic extracts were combined, dried over $Na_2SO_4$ and concentrated to give the products in the table below.

Compound 191 was prepared using the same procedure described for compound 4, except that 3-methylbromobutane was replaced with 4-bromobutyl acetate.

$^1$H NMR (CDCl$_3$) δ1.68–1.72 (m, 2H), 1.91–1.94 (m, 2H), 2.03 (s, 3H), 4.07 (t, J=6.4 Hz, 2H), 4.26 (t, J=7.5 Hz, 2H), 4.86 (s, 2H), 6.86 (bs, 1H), 7.20–7.29 (m 3H), 7.65 (dd, J=1.8, 6.7 Hz, 1 H); MS m/e 263 (MH$^+$).

Compound 192

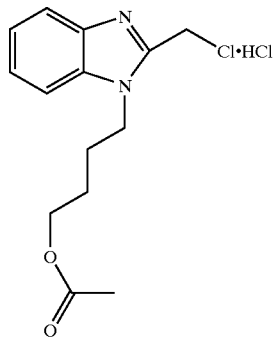

TABLE 16

Compound prepared as described for 190.

| # | R$_2$ | $^1$ H-NMR Data | MS Data |
|---|---|---|---|
| 190a | CH$_2$CH$_2$CH$_2$CO$_2$H | 1H NMR (DMSO-d6) d 1.86–1.90 (m, 2H), 2.29 (t, J = 7.2, 2H), 3.90 (t, J = 7.0, 2H), 4.39 (t, J = 6.3, 2H), 5.19 (s, 2H), 5.36 (s, 2H), 6.13 (t, J = 5.9, 1H), 6.98–7.13 (m, 6H), 7.19–7.24 (m, 2H), 7.49–7.57 (m, 2H), 12.06 (s, 1H); | MS m/e 437 (MH+); |
| 190b | 4-(HOOC)C$_6$H$_4$-CH$_2$- | 1H NMR (DMSO-d6) d 3.34 (t, J = 6.0, 2H), 4.41 (t, J = 6.0, 2H), 5.19 (s, 2H), 5.42 (s, 2H), 5.60 (s, 2H), 6.16 (t, J = 5.9, 1H), 6.99–7.02 (m, 2H), 7.10–7.26 (m, 4H), 7.45 (d, J = 8.2, 2), 7.50–7.58 (m, 2H), 7.90 (d, J = 8.2, 2H); | MS m/e 485 (MH+); |
| 190c | 2-methyl-C$_6$H$_4$-SO$_3$H | 1H NMR (DMSO-d6) d 3.35–3.40 (m, 2H), 4.44 (t, J = 6.9 Hz, 2H), 5.47 (s, 2H), 5.56 (s, 2H), 5.62 (s, 2H), 6.85–7.02 (m, 4H), 7.15–7.30 (m, 5H), 7.52–7.61 (m, 2H), 7.81–7.88 (m, 1H); | MS m/e 521 (MH+); |

Compound 191

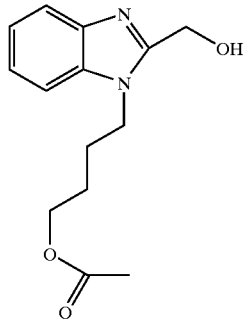

Compound 192 was prepared according to the same procedure described for compound 6.

¹H NMR (CDCl₃) δ1.80–1.86 (m, 2H), 2.03 (s, 3H), 2.06–2.12 (m, 2H), 4.14 (t, J=6.1 Hz, 2H), 4.55 (t, J=8.1 Hz, 2H), 5.42 (s, 2H), 7.48 (t, J=7.3 Hz, 1H), 7.55 (t, J=7.3 Hz, 1H), 7.64 (d, J=8.5 Hz, 1H), 7.78 (d, J=8.2 Hz, 1H); MS m/e 281 (MH⁺).

Compound 193

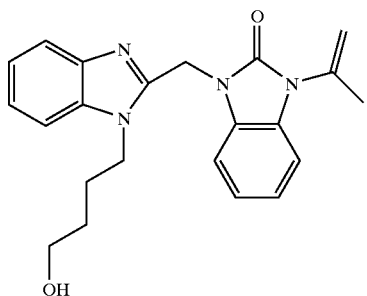

Compound 193 was prepared as described for compound 4. The acetate group was removed by stirring with MeOH for 1 hour before work-up as previously described.

¹H NMR (DMSO-d6) δ1.38–1.45 (m, 2H), 1.46–1.65 (m, 2H), 2.19 (s, 3H), 3.15–3.21 (m, 2H), 4.32–4.40 (t, J=7.5 Hz, 2H), 4.40–4.46 (m, 1 H), 5.20 (s, 1H), 5.38 (s, 2H), 5.43 (s, 1H), 7.02–7.16 (m, 2H), 7.16–7.36 (m, 3H), 7.50–7.62 (m, 2H), 8.55 (s, 1H); MS m/e 376 (MH⁺).

Compound 194

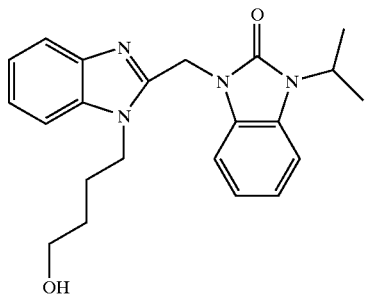

Compound 194 was prepared as described for compound 115.

¹NMR (DMSO-d6) δ1.39–1.45 (m, 2H), 1.46 (d, J=6.9 Hz, 6H), 1.54–1.59 (m, 2H), 3.33–3.37 (m, 2H), 4.33 (t, J=7.5 Hz, 2H), 4.45 (t, J=5.1 Hz, 1 H), 4.6–4.68 (m, 1H), 5.35 (s, 2H), 6.98–7.05 (m, 2H), 7.17 (t, J=7.6 Hz, 1H), 7.23 (t, J=8.8 Hz, 2H), 7.33 (d, J=8.4 Hz, 1H), 7.54 (d, J=8.0 Hz, 1H), 7.60 (d, J=7.9 Hz, 1H); MS m/e 378 (MH⁺).

Compound 195

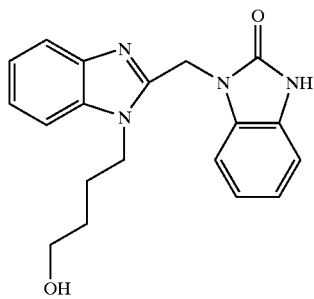

Compound 195 was prepared from compound 193 as described for compound 6.

¹H NMR (DMSO-d6) δ1.42–1.47 (m, 2H), 1.59–1.62 (m, 2 H), 3.36–3.40 (m, 2H), 4.33 (t, J=7.5 Hz, 2H), 4.46 (t, J=5.1 Hz, 2H), 5.32 (s, 2 H), 6.93–7.02 (m, 3H), 7.14–7.19 (m, 2H), 7.22–7.25 (m, 1H), 7.54 (d, J=8.0 Hz, 1H), 7.59 (d, J=7.9Hz, 1H); MS m/e 336 (MH⁺).

Compound 196

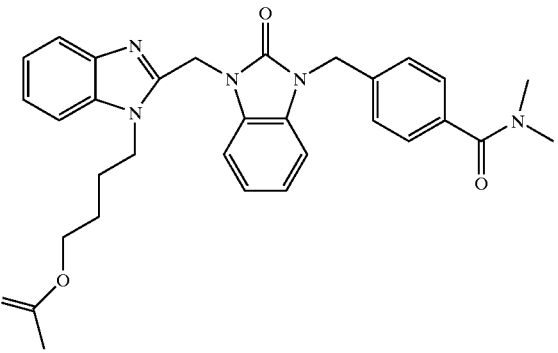

Compound 196 was prepared by alkylation of compound 195 with compound 90.

¹H NMR (DMSO-d6) δ1.60–1.68 (m, 2H), 1.69–1.79 (m, 2H), 1.96 (s, 3H), 2.86 (s, 3 H), 2.95 (s, 3H), 3.97 (t, J=6.4 Hz, 2H), 4.37 (t, J=7.15 Hz, 2H), 5.47 (s, 2H), 6.98–7.03 (m, 2H), 7.14–7.18 (m, 2H), 7.19–7.28 (m, 2H), 7.35–7.42 (m, 4H), 7.58 (dd, J=2.9, 8.2 Hz, 2H); MS m/e 539 (MH⁺).

Compound 197

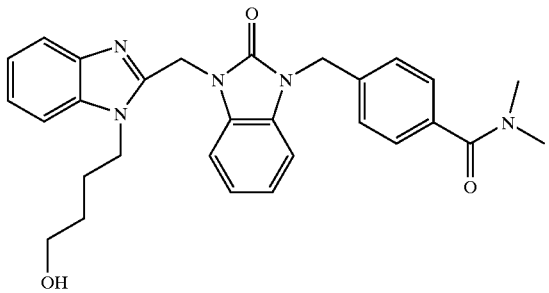

Compound 197 was prepared as described for compound 8.

¹H NMR (DMSO-d6) δ1.30–1.45 (m, 2H), 1.47–1.70 (m, 2H), 2.86–2.95 (m, 6H), 3.33–3.39 (m, 2H), 4.34–4.36 (m, 2H), 4.464.48 (m, 1H), 5.16 (s, 2 H), 5.43 (s, 2H), 6.95–7.11 (m, 2H), 7.14–7.19 (m, 2H), 7.22–7.26 (m, 2H), 7.36–7.47 (m, 3), 7.49–7.59 (m, 3H); MS m/e 496 (MH⁺).

Compound 198

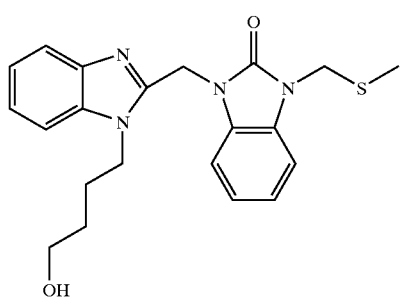

Compound 198 was prepared by alkylation of compound 195.

$^1$H NMR (DMSO-d6) δ1.59–1.62 (m, 2H), 1.76–1.79 (m, 2H), 1.99–2.02 (m, 2H), 2.54–2.63 (m, 4H), 3.93 (t, J=4.1, 2H), 4.41 (t, J=4.5, 2H), 5.41 (s, 2H), 6.99–7.19 (m, 4H), 7.24–7.28 (m, 2H), 7.56–7.60 (m, 2H); MS m/e 413 (MH$^+$).

Compound 199

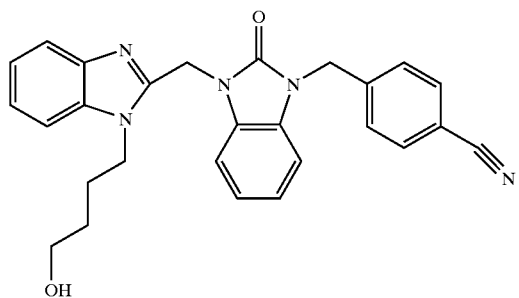

Compound 199 was prepared as described for compound 7 using Cs$_2$CO$_3$ as base.

$^1$H NMR (DMSO-d6) δ1.41–1.48 (m, 2H), 1.64–1.71 (m, 2H), 3.36–3.38 (m, 2H), 4.35 (t, J=7.8 Hz, 2H), 4.48 (t, J=5.6 Hz, 1H), 5.23 (s, 2H), 5.43 (s, 2H), 7.01–7.04 (m, 2H), 7.14–7.28 (m, 4H), 7.52–7.60 (m, 4H), 7.84 (d, J=8.2 Hz, 2H); MS m/s 452 (MH$^+$).

Compound 200

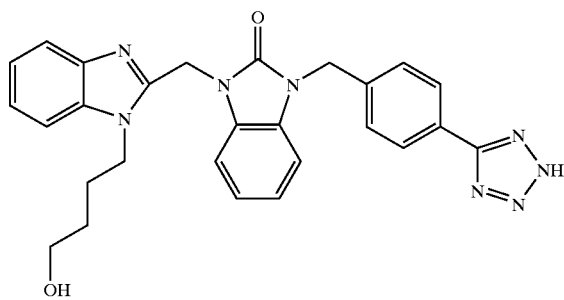

Compound 200 was prepared as described for compound 22.

$^1$H NMR (DMSO-d6) δ1.45–1.50 (m, 2H), 1.69–1.75 (m, 2H), 3.39 (t, J=6.4 Hz, 2H), 4.44 (t, J=7.4 Hz, 2H), 5.22 (s, 2H), 5.55 (s, 2H), 7.03–7.07 (m, 2H), 7.17–7.21 (m, 1 H), 7.27–7.30 (m, 2H), 7.34–7.37 (m, 1H), 7.59 (d, J=8.3 Hz, 2H), 7.65 (d, J=8.0 Hz, 1H), 7.71 (d, J=7.4 Hz, 1H), 8.04 (d, J=8.3 Hz, 2H); MS m/e 495 (MH$^+$).

Compound 201

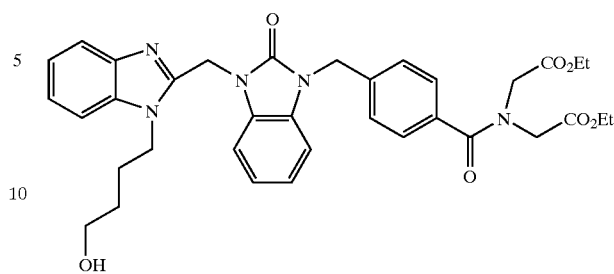

Compound 201 was prepared as described for compound 9 except EDC was used as coupling reagent.

$^1$H NMR (DMSO-d6) δ1.11 (t, J=6.9 Hz, 3H), 1.22 (t, J=6.9 Hz, 3H), 1.20–1.38 (m, 2H), 1.65–1.80 (m, 2H), 3.41 (t, J=6.3 Hz, 2H), 4.04–4.18 (m, 4H), 4.17 (s, 2 H), 4.40–4.52 (m, 2H), 5.17 (s, 2 H), 5.58 (s, 2H), 7.01–7.11 (m, 2H), 7.17–7.21 (m, 1H), 7.24–7.50 (m, 6H), 7.67 (d, J=7.8 Hz, 1H), 7.75 (d, J=6.9 Hz, 1H); MS m/e 598 (MH$^{30}$).

Compound 202

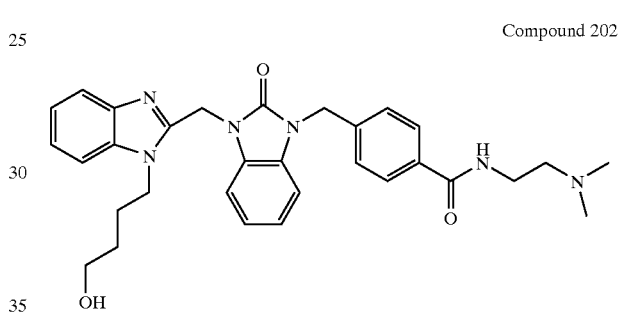

Compound 202 was prepared as described for compound 201.

$^1$H NMR (DMSO-d6) δ1.43–1.50 (m, 2H), 1.60–1.78 (m, 2H), 2.13 (s, 6H), 3.32–3.41 (m, 4H), 4.36 (t, J=7.5 Hz, 2H), 4.61–4.68 (m, 2H), 5.17 (s, 2H), 5.43 (s, 2H), 6.99–7.05 (m, 2H), 7.09–7.26 (m, 3 H), 7.43 (d, J=8.4 Hz, 2H), 7.57 (t, J=7.2 Hz, 2H), 7.79 (d, J=8.1 Hz, 2H), 8.35 (t, J=5,7 Hz, 1 H); MS m/e 540 (MH$^+$).

Compound 203

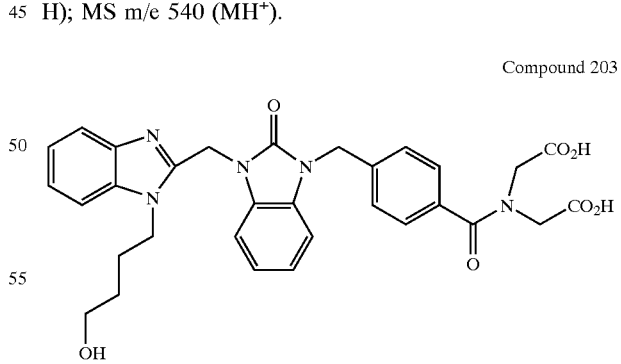

Compound 203 was prepared as described for compound 12.

$^1$H NMR (DMSO-d6) δ1.25–1.42 (m, 2H), 1.43–1.63 (m, 2H) 3.20–3.40 (m, 2H), 3.62–3.82 (m, 2H), 4.21–4.39 (m, 2H), 4.72–4.92 (bs, 1H), 5.13 (s, 2H), 5.43 (s, 2H), 6.92–7.10 (m, 2H), 7.10–7.36 (m, 6H), 7.37–7.43 (m, 2H), 7.54–7.62 (m, 2H), MS m/e 585 (MH$^+$).

Compound 204

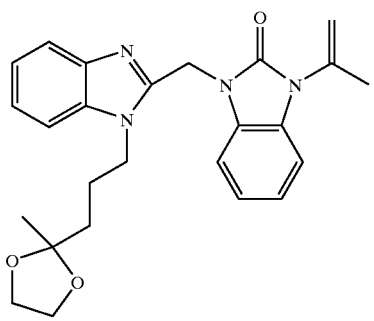

Compound 204 was prepared as described for compound 88 using 2-(3-chloro-propyl)-2-methyl-[1,3]dioxolane.

$^1$H NMR (CDCl3) δ1.18 (s, 3H), 1.55–1.72 (m, 4H), 2.25 (s, 3H), 3.67–3.71 (m, 2H), 3.81–3.84 (m, 2H), 4.33–4.36 (m, 2H), 5.27 (s, 1 H), 5.38 (s, 1 H), 5.42 (s, 2 H), 7.02–7.09 (m, 3H), 7.25–7.36 (m, 2H), 7.35–7.36 (m, 1H), 7.45–7.47 (m, 1H), 7.80–7.81 (m, 1H); MS m/e 432 (MH$^+$).

Compound 205

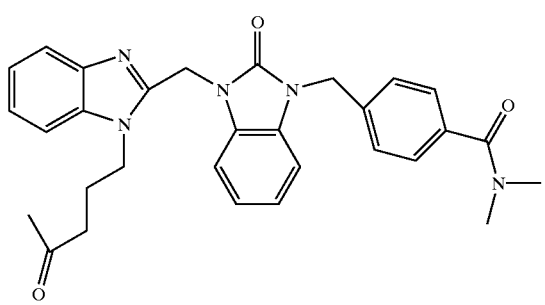

Compound 205 was prepared by deprotection of compound 204 as described for compound 6 followed by alkylation of the intermediate as described for compound 7.

$^1$H NMR (DMSO-d6) δ1.86–1.91 (m, 2H), 2.05 (s, 3H), 2.41–2.56 (m, 2H), 2.72–2.87 (m, 6H), 4.30–4.45 (m, 2H), 5.16 (s, 2H), 5.56 (s, 2H), 7.04–7.19 (m, 3H), 7.18–7.21 (m, 1H), 7.23–7.45 (m, 6H), 7.64 (d, J=7.5 Hz, 1H), 7.75 (d, J=7.5 Hz, 1H); MS m/s 509 (MH$^+$).

Compound 206

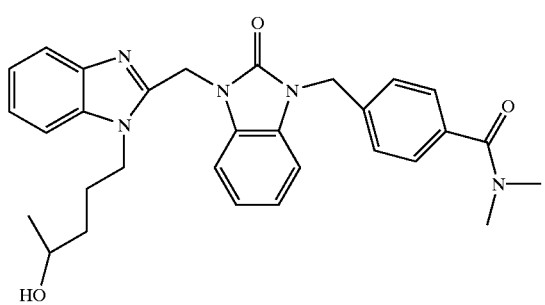

Compound 206 was prepared by NaBH$_4$ reduction of compound 205.

$^1$H NMR (DMSO-d6) δ0.96 (d, J=6.1 Hz, 3H), 1.28–1.32 (m, 2H), 1.60–1.63 (m, 1H), 1.72–1.75 (m, 1H), 2.86 (s, 3H), 2.96 (s, 3H), 3.50–3.59 (m, 1H), 4.34 (t, J=7.4 Hz, 2H), 4.41–4.48 (m, 1H), 5.16 (s, 2H), 5.43 (s, 2H), 7.0–7.02 (m, 2H), 7.15–7.18 (m, 2H), 7.22–7.26 (m, 2H), 7.36–7.42 (m, 4H), 7.55 (d, J=8.0 Hz, 1H), 7.59 (d, J=7.9 Hz, 1H); MS m/e 511 (MH$^+$).

Compound 207

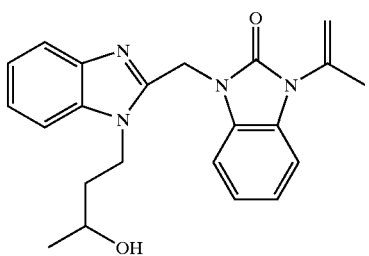

Compound 207 was prepared from compound 85 as described for compound 206.

$^1$H NMR (CDCl$_3$) δ1.19 (d, J=6.18Hz, 3 H), 1.67–1.78 (m, 1 H), 1.83–1.92 (m, 1 H), 2.25 (s, 3 H), 2.76 (d, J=5.6 Hz, 1 H), 3.84–3.87 (m, 1 H), 4.43–4.52 (m, 2 H), 5.22 (s, 1 H), 5.40 (d, J=1.4 Hz, 1 H), 5.46 (d, J=4.5 Hz, 2 H), 7.08–7.12 (m, 3 H), 7.28–7.32 (m, 2 H), 7.37–7.40 (m, 1 H), 7.56–7.59 (m, 1 H), 7.79–7.82 (m, 1 H); MS m/e 377 (MH$^+$).

Compound 208

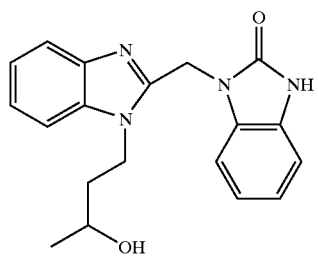

Compound 208 was prepared as described for compound 6.

$^1$H NMR (DMSO-d6) δ1.08 (d, J=6.1 Hz, 3H), 1.77–1.82 (m, 2H), 3.62–3.74 (m, 1H), 4.56 (t, J=7.1 Hz, 2H), 5.55–5.62 (m, 2H), 6.99–7.08 (m, 3H), 7.19 (d, J=7.2 Hz, 1H), 7.43–7.53 (m, 2H), 7.69 (d, J=7.4 Hz, 1H), 7.85 (d, J=7.6 Hz, 1H); MS m/e 337 (MH$^+$).

Compound 209

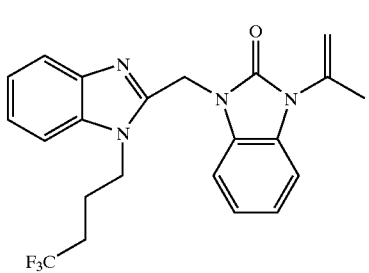

Compound 209 was prepared by alkylation of compound 3.

$^1$H NMR (CDCl$_3$) δ1.81–1.91 (m, 2H), 2.07–2.22 (m, 2H), 2.25 (s, 3H), 4.44 (t, J=7.8 Hz, 2H), 5.21 (s, 1H), 5.40 (s, 3H), 7.06–7.10 (m, 3H), 7.27–7.33 (m, 3H), 7.52–7.62 (m, 1H), 7.80–7.84 (m, 1H); MS m/e 415 (MH$^+$).

Compound 210

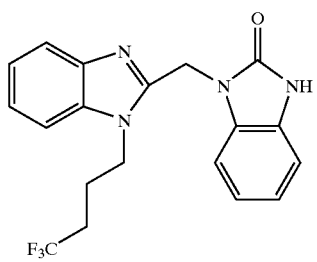

Compound 210 was prepared as described for compound 6.

¹H NMR (CDCl₃) δ1.76–1.86 (m, 2H), 2.10–2.27 (m, 2H), 4.41 (t, J=8.0 Hz, 2H), 5.42 (s, 2H), 7.02–7.09 (m, 3H), 7.29–7.32 (m, 3H), 7.45–7.48 (m, 1H), 7.80–7.84 (m, 1H), 8.48 (s, 1H); MS m/e 375 (MH⁺).

Compound 211

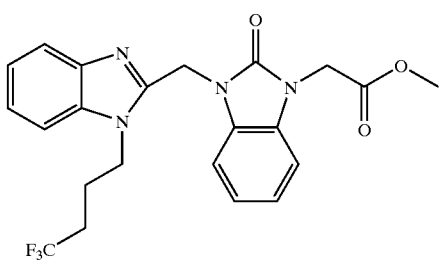

Compound 211 was prepared by alkylation of compound 210 as described for compound 7.

¹H NMR (CDCl₃) δ81.78–1.89 (m, 2H), 2.09–2.25 (m, 2H), 3.79 (s, 3H), 4.38 (t, J==8.0 Hz, 2H), 4.67 (s, 2H), 6.87–6.92 (m, 1H), 7.05–7.12 (m, 1H), 7.29–7.32 (m, 3H), 7.47–7.50 (m, 1H), 7.81–7.84 (m, 1H); MS m/e 447 (MH⁺).

Compound 212

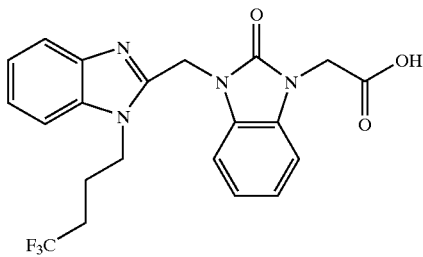

Compound 212 was prepared as described for compound 8.

¹H NMR (DMSO-d6) δ1.71–1.82 (m, 2H), 2.24–2.38 (m, 2 H), 4.05 (s, 2H), 4.39 (t, J=7.7 Hz, 2H), 5.37 (s, 2H), 6.90–7.00 (m, 3H), 7.16–7.28 (m, 3H), 7.58 (d, J=7.8 Hz, 1H), 7.62 (d, J=7.5 Hz, 1H); MS m/e 433 (MH⁺).

Compound 213

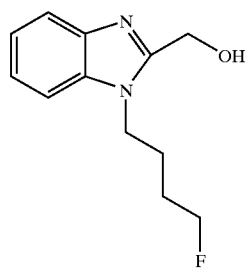

Compound 213 was prepared according to the same procedure described for compound 106 except that 3-methylbutylbromide was replaced with 1-bromo-4-fluorobutane.

¹H NMR (DMSO-d₆) δ1.65–1.75 (m, 2H), 1.85–1.90 (m, 2H), 4.32 (t, J=7.5 Hz, 2H), 4.41 (t, J=6.0 Hz, 1H), 4.51 (t, J=6.0 Hz, 1H), 4.71 (d, J=5.8 Hz, 2H), 5.62 (t, J=5.8 Hz, 1H), 7.18 (t, J=7.0 Hz, 1H), 7.23 (t, J=6.3 Hz, 1H), 7.56–7.60 (m, 2H); MS m/e 222 (MH⁺).

Compound 214

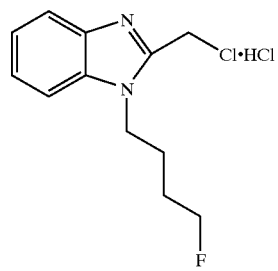

Compound 214 was prepared according to the same procedure described for chloride 107 and was used immediately upon isolation.

Compound 215

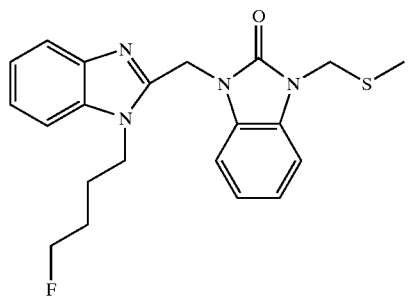

Compound 215 was prepared as described for compound 4, followed by deprotection and alkylation as described for compound 7.

¹H NMR (DMSO-d6) δ1.71–1.84 (m, 4 H), 2.15 (s, 3 H), 4.12 (t, J=3.5, 1 H), 4.50–4.54 (m, 3 H), 5.11 (s, 2 H), 5.65 (s, 2 H), 7.10–7.17 (m, 2 H), 7.34–7.38 (m, 2 H), 7.45–7.50 (m, 2 H), 7.71 (d, J=4.8, 1 H), 7.89 (d, J=4.6, 1 H); MS m/e 399 (MH⁺).

Compound 216

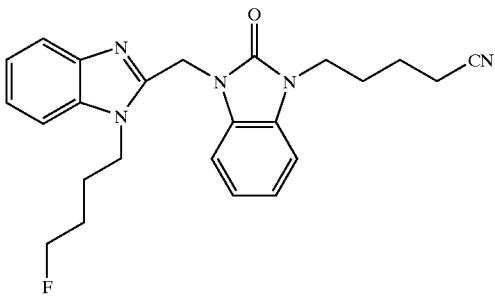

Compound 216 was prepared as described for compound 215 except 4-bromo-1-fluorobutane was used as the alkylating agent.

$^1$H NMR (DMSO-d6) δ1.22–1.28 (m, 2H), 1.54–1.85 (m, 8H), 2.54–2.58 (m, 2H), 3.93 (t, J=4.1, 2H), 4.35–4.40 (m, 2H), 5.39 (s, 2 H), 6.98–7.09 (m, 2H), 7.14–7.27 (m, 4H), 7.58 (t, J=4.9, 2H); MS m/e 420 (MH$^+$).

Compound 217

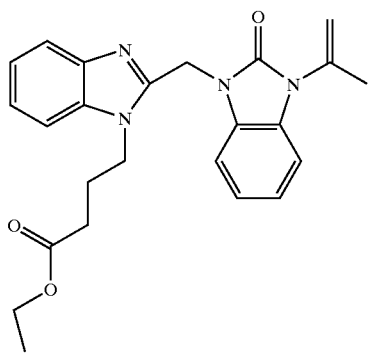

Compound 217 was prepared as described for compound 4.

$^1$H NMR (DMSO-d6) δ1.13 (t, J=6.9 Hz, 3H), 1.80–1.95 (m, 2H), 2.17 (s, 3H), 2.37 (t, J=7.2 Hz, 2H), 4.02 (q, J=7.2 Hz, 2H), 4.36 (t, J=6.6 Hz, 2H), 5.19 (s, 1H), 5.39 (s, 1H), 5.42 (s, 1H), 7.06–7.10 (m, 2H), 7.11–7.28 (m, 4H), 7.58–7.71 (m, 2H); MS m/e 418 (MH$^+$).

Compound 218

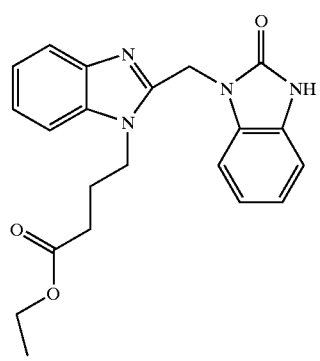

Compound 218 was prepared was described for compound 6.

$^1$H NMR (DMSO-d6) δ1.15 (t, J=7.2 Hz, 3H), 1.81–1.98 (m, 2H), 4.02 (q, J=7.2 Hz, 2H), 4.36 (t, J=7.5 Hz, 2H), 5.32 (s, 2H), 6.91–7.08 (m, 3H), 7.15–7.30 (m, 3H), 7.58 (d, J=8.1 Hz, 2H); MS m/e 378 (MH$^+$).

Compound 219

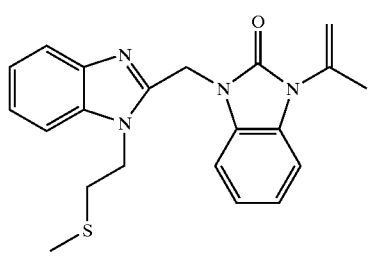

Compound 219 was prepared as described for compound 4 using 2-chloroethyl thiomethyl ether as the alkylating agent.

$^1$H NMR (CDCl$_3$) δ2.07 (s, 3H), 2.25 (s, 3H), 2.75 (t, J=6.9 Hz, 2 H), 4.62 (t, J=6.9 Hz, 2H), 5.23 (d, J=0.5 Hz, 1H), 5.40 (d, J=1.4 Hz, 1H), 5.48 (s, 2H), 7.05–7.09 (m, 3H), 7.28–7.37 (m, 3H), 7.53–7.57 (m, 1H), 7.79–7.84 (m, 1H); MS m/e 379 (MH$^+$).

Compound 220

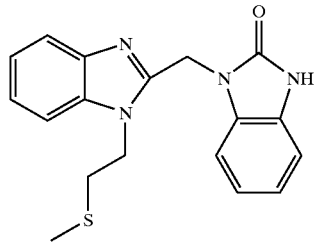

Compound 220 was prepared as described for compound 6.

$^1$H NMR CDCl$_3$) δ1.61 (s, 3H), 2.09 (s, 3H), 2.74 (t, J=7.1 Hz, 2H), 4.59 (t, J=7.1 Hz, 2H), 5.47 (s, 2H), 7.04–7.08 (m, 3H), 7.28–7.37 (m, 3H), 7.46–7.50 (m, 1H), 7.79–7.84 (m, 1H), 8.65 (bs, 1 H); MS m/e 339 (MH$^+$).

Compound 221

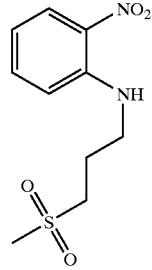

2-fluoronitrobenzene (35.4 g, 250.9 mmol), 3-)methylthio)propylamine (24.0 g, 228.1 mmol) and potassium carbonate (47.3 g, 342 mmol) were stirred in CH$_3$CN (100 mL) at room temperature overnight. After stirring for an additional hour at reflux, the mixture was cooled to room temperature and filtered. The filtrate was evaporated. To the residue in DMF (150 mL), magnesium monoperoxyphthalate hexahydrate (MMPP, 168 g, 340 mmol) was added in several portions with ice-water cooling. The mixture was stirred at room temperature for 3 hours and the solvent was evaporated. The residue was dissolved in CH$_2$Cl$_2$ and washed with I N NaOH, water, brine, dried over MgSO$_4$ and evaporated. The residue was triturated with hot EtOAc to give compound 221 (48.7 g, 75% yield) as an orange solid.

$^1$H NMR (CDCl$_3$) δ2.25–2.35 (m, 2H), 2.97 (s, 3H), 3.17 (t, J=7.2 Hz, 2H), 3.59 (t, J=6.9 Hz, 2H), 6.68–6.74 (m, 1H), 6.89 (d, J=8.1 Hz, 1H), 7.45–7.51 (m, 1H), 8.20 (dd, J=1.5, 8.7 Hz, 1H); MS m/e 259 (MH$^+$); Anal. Calcd for C$_{10}$H$_{14}$N$_2$O$_4$S: C, 46.50; H, 5.46; N, 10.84 Found: C, 46.53; H, 5.54; N, 10.90.

Compound 222

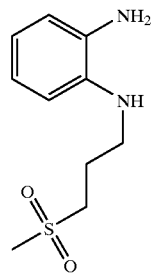

To a suspension of compound 221 (48.5 g, 187.8 mmol) in a mixture of CHCl₃ and MeOH (150 mL, 1:3) was added 10% palladium on carbon (6 g) under nitrogen. The reduction was carried out in a Parr shaker with hydrogen pressure maintained between 40 and 60 psi for 25 minutes. The catalyst was removed by filtration through a pad of Celite and the filtrate was evaporated to give crude 222.

¹H NMR (CD₃OD) δ2.11–2.21 (m, 2H), 2.98 (s, 3H), 3.28–3.36 (m, 4H), 6.75 (dt, J=0.9, 7.2 Hz, 1H), 6.85 (d, J=7.5 Hz, 1H), 7.06–7.12 (m, 2H); MS m/e 229 (MH⁺).

Compound 223

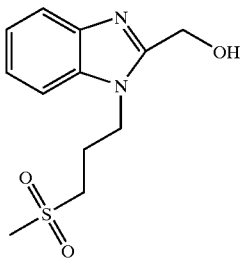

The crude diamine 222 obtained above was stirred at reflux overnight with glycolic acid (15.7 g, 207 mmol) in 6 N HCl (150 mL). The solution was cooled in an ice bath and neutralized with concentrated NH₄OH solution, extracted with EtOAc, dried over MgSO₄ and evaporated. The residue was purified by chromatography (gradient, EtOAc/hexane, 1:1 to EtOAc/MeOH, 10:1) to give a product which crystallized from EtOAc/MeOH to afford 25.7 g (51% yield in two steps) of 223.

¹H NMR (CD₃OD) δ2.38–2.44 (m, 2H), 2.97 (s, 3H), 3.24 (t, J=7.6 Hz, 2H), 4.54 (t, J=7.6Hz, 2H), 7.27 (t, J=1.1, 8.1 Hz, 1H), 7.33 (dt, J1.1,8.0Hz, 1H), 7.62 (d, J=8.1 Hz, 1H), 7.64 (dd, J=1.0, 8.0 Hz, 1H); MS m/e 269 (MH⁺).

Compound 224

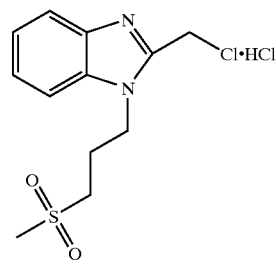

Compound 224 was prepared according to the same procedure described for compound 6.

¹H NMR (CD₃OD) δ2.46–2.52 (m, 2H), 3.03 (s, 3H), 3.37 (t, J=7.1 Hz, 2H), 4.77 (t, J=7.8 Hz, 2H), 5.31 (s, 2H), 7.68–7.73 (m, 2H), 7.86 (dd, J=2.8, 6.9 Hz, 1H), 8.03 (dd, J=1.7, 6.1 Hz, 1H); MS m/e 287 (MH⁺).

Compound 224a

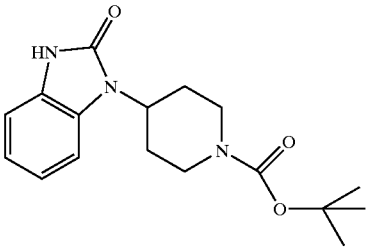

To a solution of 4-(2-keto-1-benzimidazolinyl)piperidine (3.0 g, 13.8 mmol), triethylamine (2.79 g, 27.6 mmol) and DMAP (17 mg, 0.1 mmol) in CH₂Cl₂ (50 ml) was added di-tert butyldicarbonate (3.31 g, 15.2 mmol) at 0° C. and stirred for 2 h. The reaction mixture was washed with NaHCO₃, dried and evaporated. The residue was purified by flash chromatography using hexanes:EtOAc (2:1 to 1:1) as eluant to give 2.68 g (61%) of compound 224a as a white solid.

¹H NMR (CD₃OD) δ1.49 (s, 9H), 1.75–2.02 (m, 2H), 2.29–2.43 (m, 2H), 2.89–2.99 (m, 2H), 4.23–4.29 (m, 2H), 4.37–4.46 (m, 1H), 7.02–7.07 (m, 3H), 7.19–7.22 (m, 1H); MS m/e 318 (MH⁺).

TABLE 17

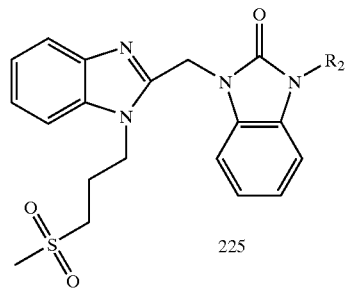

225

Sulfones were prepared as described for compound 7 using chloride 224 and a benzimidazolone such as 224a with Cs₂CO₃ as base.
Compound 225d was prepared from compound 225c as described for compound 6.

| # | R₂ | ¹H-NMR Data | MS Data |
|---|---|---|---|
| 225a | CH₃ | (CDCl₃) δ 1.61–1.67 (m, 2H), 1.85–1.91 (m, 2H), 2.13–2.19 (m, 2H), 2.83 (s, 3H), 3.05 (t, J = 7.2 Hz, 2H), 3.70 (t, J = 6.2 Hz, 2H), 3.99 (t, J = 7.0 Hz, 2H), 4.57 (t, J = 7.2 Hz, 2H), 5.48 (s, 2H), 7.01–7.05 (m, 1H), 7.07–7.14 (m, 2H), 7.32–7.35 | 457 (MH+) |

TABLE 17-continued

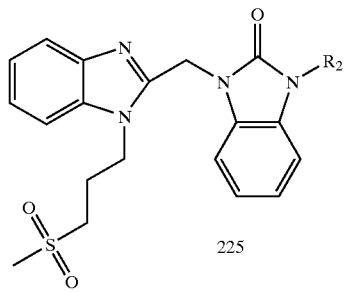

225

Sulfones were prepared as described for compound 7 using chloride 224 and a benzimidazolone such as 224a with Cs$_2$CO$_3$ as base.

Compound 225d was prepared from compound 225c as described for compound 6.

| # | R$_2$ | $^1$H-NMR Data | MS Data |
|---|---|---|---|
| | | (m, 2H), 7.42–7.43 (m, 1H), 7.55–7.58 (m, 1H), 7.83–7.85 (m, 1H) | |
| 225b |  | (DMSO-d6) δ 2.07–2.15 (m, 2H), 2.18 (s, 3H), 2.98 (s, 3H), 3.21 (t, J = 7.4 Hz, 2H), 4.50 (t, J = 7.4 Hz, 2H), 5.22 (s, 1H), 5.40–5.41 (m, 3H), 7.06–7.09 (m, 2H), 7.16–7.32 (m, 4H), 7.38–7.64 (m, 2H) | 425 (MH+) |
| 225c | 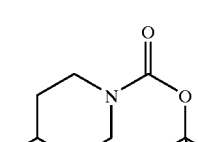 | (CDCl$_3$) δ 1.52 (s, 9H), 1.82–1.88 (m, 2H), 2.18–2.38 (m, 4H), 2.85 (s, 3H), 2.86–2.94 (m, 2H), 3.04 (t, J = 7.3 Hz, 2H), 4.27–4.38 (m, 2H), 4.40–4.49 (m, 1H), 4.62 (t, J = 7.5 Hz, 2H), 5.49 (s, 2H), 7.07–7.15 (m, 2H), 7.36–7.39 (m, 2H), 7.44–7.49 (m, 1H), 7.63–7.66 (m, 1H), 7.84–7.88 (m, 1H) | 568 (MH+) |
| 225d | 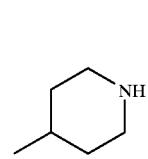 | (CD$_3$OD) δ 2.12–2.16 (m, 2H), 2.44–2.48 (m, 2H), 2.76–2.80 (m, 2H), 3.02 (s, 3H), 3.22–3.28 (m, 2H), 3.32–3.35 (m, 2H), 3.58–3.65 (m, 2H), 4.64–4.69 (m, 1H), 4.83 (t, J = 7.9 Hz, 2H), 5.79 (s, 2H), 7.20–7.28 (m, 2H), 7.35 (d, J = 7.9 Hz, 1H), 7.49 (d, J = 7.8 Hz, 1H), 7.65–7.72 (m, 2H), 7.75 (d, J = 8.2 Hz, 1H), 8.05 (d, J = 8.2 Hz, 1H) | 463 (MH+) |

Compound 226

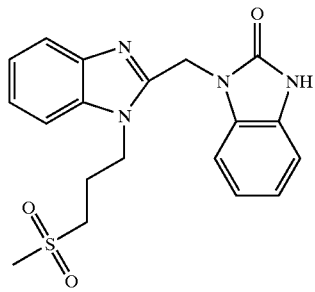

Compound 226 was prepared as described for compound 6.

¹H NMR (DMSO-d6) δ2.03–2.14 (m, 2H), 2.97 (s, 3H), 3.21 (t, J=8.0 Hz, 2H), 4.48 (t, J=7.4 Hz, 2H), 5.34 (s, 2H), 6.95–7.02 (m, 3H), 7.16–7.29 (m, 3H), 7.57–7.63 (m, 2H); MS m/e 385 (MH⁺).

mixture was quenched with 1 M NaOH (2 ml) and 30% H₂O₂ (1 ml) and the mixture was stirred for 2 h then extracted with EtOAc. The organic layer was washed with brine, dried, evaporated. The residue was purified by preparative reverse phase HPLC to yield 28 mg (63%) of 228 as a hygroscopic solid.

TABLE 18

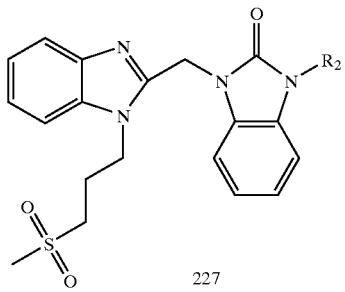

227

Compounds were prepared by alkylation of 226 as described for compound 7.

| # | R₂ | ¹H-NMR Data | MS Data |
|---|---|---|---|
| 227a | (isopropyl with two F) | (CDCl₃) δ 2.16–2.26 (m, 2H), 2.90 (s, 3H), 3.08 (t, J = 7.3 Hz, 2H), 4.58 (t, J = 77 Hz, 2H), 5.45 (s, 2H), 7.18–7.23 (m, 2H), 7.35–7.45 (m, 4H), 7.62–7.66 (m, 1H), 7.81–7.86 (m, 1H) | 435 (MH+) |
| 227b[a] | (CH₂)₄CH₂OH | (CDCl₃) δ 1.61–1.67 (m, 2H), 1.85–1.91 (m, 2H), 2.13–2.19 (m, 2H), 2.83 (s, 3H), 3.05 (t, J = 7.2 Hz, 2H), 3.70 (t, J = 6.2 Hz, 2H), 3.99 (t, J = 7.0 Hz, 2H), 4.57 (t, J = 7.2 Hz, 2H), 5.48 (s, 2H), 7.01–7.05 (m, 1H), 7.07–7.14 (m, 2H), 7.32–7.35 (m, 2H), 7.42–7.43 (m, 1H), 7.55–7.58 (m, 1H), 7.83–7.85 (m, 1H) | 457 (MH+) |
| 227c[a] | CH₂-(4-CN-C₆H₄) | (DMSO-d6) δ 2.12–2.17 (m, 2H), 3.00 (s, 3H), 3.22 (t, J = 7.9 Hz, 2H), 4.50 (t, J = 8.0 Hz, 2H), 5.23 (s, 2H), 5.47 (s, 2H), 7.01–7.06 (m, 2H), 7.13–7.22 (m, 2H), 7.28–7.31 (m, 2H), 7.53 (d, J = 8.2 Hz, 2H), 7.58–7.65 (m, 2H), 7.83 (d, J = 8.2 Hz, 2H) | 500 (MH+) |

Compound 228

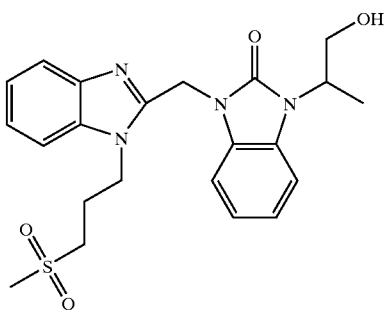

[a]Cs₂CO₃ was used as base instead of BTPP.

To a solution of 225b (42 mg, 0.1 mmol) in THF (1 ml) was added 9-BBN (0.5 M in THF) (1.0 ml, 0.5 mmol) at 0° C and the final solution was stirred for 12 h. The reaction ¹H NMR (CD₃OD) δ1.54 (d, J=7.1 Hz, 3H), 2.41–2.47 (m, 2H), 3.00 (s, 3H), 3.31–3.32 (m, 2H), 3.82–3.86 (m, 1H), 4.14–4.18 (m, 1H), 4.61–4.66 (m, 1), 4.76 (t, J=7.6 Hz, 2H), 5.70 (s, 2H), 7.13–7.21 (m, 2H), 7.27 (d, J=7.7 Hz, 1H), 7.39 (d, J=8.0 Hz, 1H), 7.53–7.62 (m, 2 H), 7.69 (d, J=8.0 Hz, 1H), 7.92 (d, J=8.3 Hz, 1H); MS m/e 443 (MH⁺).

Compound 229

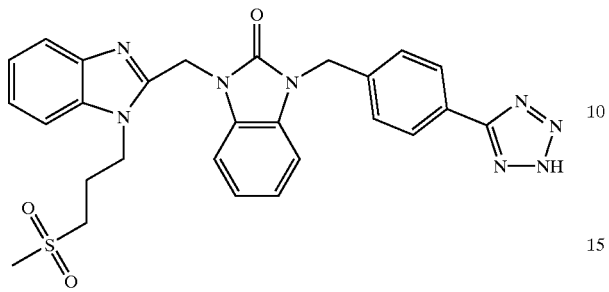

Compound 229 was prepared as described for compound 52.

¹H NMR (DMSO-d6) δ2.12–2.17 (m, 2H), 3.00 (s, 3H), 3.24 (t, J=7.7 Hz, 2H), 4.52 (t, J=7.4 Hz, 2H), 5.22 (s, 2H), 5.48 (s, 2H), 7.031–7.06 (m, 2H), 7.16–7.22 (m, 2H), 7.26–7.31 (m, 2H), 7.57–7.60 (m, 3H), 7.64 (d, J=8.0 Hz, 1H), 8.01 (d, J=8.3 Hz, 2H); MS m/e 543 (MH⁺).

Compound 230

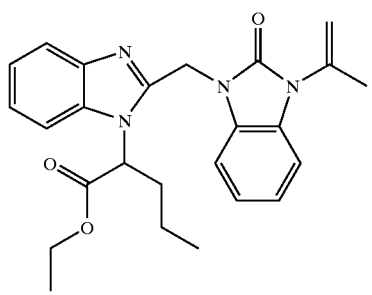

Compound 230 was prepared as described compound 4.
¹H NMR (CDCl₃) δ0.77 (t, J=7.1 Hz, 3H), 0.83 (t, J=7.1 Hz, 3H), 0.90–0.98 (m, 1H), 1.20–1.29 (m, 1H), 2.13–2.35 (m, 2H), 2.24 (s, 3H), 3.78–3.94 (m, 2H), 5.19 (s, 1H), 5.36 (d, J=15.8 Hz, 1H), 5.39 (d, J=1.4Hz, 1H), 5.51 (d, J=15.7 Hz, 1H), 5.52–5.57 (m, 1H), 7.01–7.09 (m, 3H), 7.21–7.31 (m, 2H), 7.37 (d, J=7.3 Hz, 1H), 7.44–7.46 (m, 1H), 7.82 (d, J=7.4 Hz, 1H); MS m/e 433 (MH⁺).

Compound 231

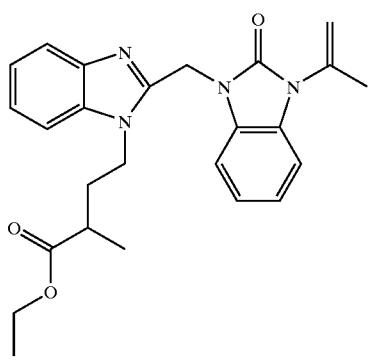

Compound 231 was prepared as described for compound 4.
¹H NMR (CDCl₃) δ1.19 (d, J=7.1 Hz, 3H), 1.52–1.64 (m, 1H), 2.03–2.15 (m, 1H), 2.25 (s, 3 H), 2.53–2.62 (m, 1H), 3.67 (s, 3H), 4.29–4.50 (m, 2H), 5.21 (s, 1H), 5.39 (d, J=1.1 Hz, 1H), 5.34–5.48 (m 2H), 7.04–7.12 (m, 3H), 7.25–7.34 (m, 2H), 7.40–7.44 (m, 1H), 7.49–7.53 (m, 1H), 7.77–7.83 (m, 1H); MS m/e 405 (MH⁺).

Compound 232

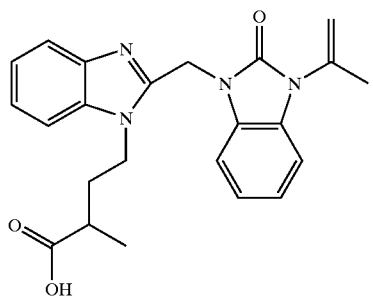

Compound 232 was prepared as described for compound 8.
¹H NMR(CD₃OD) δ1.15 (d, J=7.1 Hz, 3 H), 1.50–1.64 (m, 1 H), 1.99–2.11 (m, 1 H), 2.27 (s, 3 H), 2.29–2.43 (m, 1 H), 4.35–4.44 (m, 2 H), 5.29 (s, 1 H), 5.40–5.59 (m, 3 H), 7.04–7.34 (m, 5 H), 7.59 (d, J=8.2 Hz, 1 H), 7.66 (d, J=7.5 Hz, 1 H); MS m/e 405 (MH⁺).

(Scheme III)

Compound 233

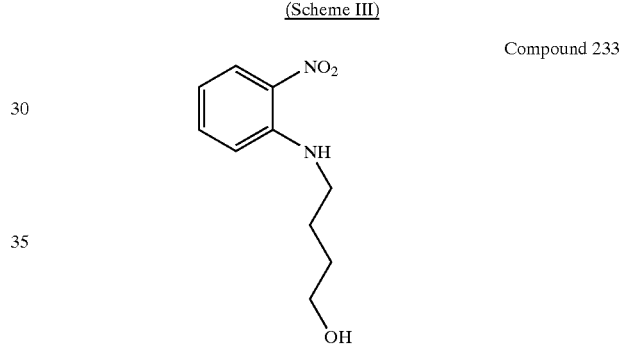

A solution of 2-fluoronitrobenzene (5.0 g, 35.5 mmol) and 1-amino-4-butanol (3.2 g, 35.5 mmol) in CH₃CN (100 mL) and triethylamine (3.80 g, 35.5 mmol) was heated to reflux for 12 h, and evaporated. The residue was dissolved in ethyl acetate and washed with 1N HCl, dried over magnesium sulfate and evaporated to give 7.21 g (97% yield) of compound 233 as a dark orange solid:

¹H NMR (DMSO-d₆) δ1.45–1.56 (m, 2H), 1.58–1.69 (m, 2H), 3.35 (t, J=6.7 Hz, 2H), 3.43 (t, J=6.4 Hz, 2H), 3.90–4.0 (br, 1H, exchanges with D₂O), 6.66 (t, J=6.0 Hz, 1H); 7.04 (d, J=9.0 Hz, 1H);.7.52 (t, J=7, 2 Hz, 1H); 8.04 (d, J=7.2 Hz, 1H); 8.13 (br s, 1H, exchanges with D₂O); IR (KBr cm⁻¹) 1350, 1154; MS m/e 211 (MH⁺); Anal. Calcd for C₁₀H₁₄N₂O₃.0.28 H₂O: C, 55.80; H, 6.82; N, 13.01 Found: C, 55.80; H, 6.62; N, 12.97.

Compound 234

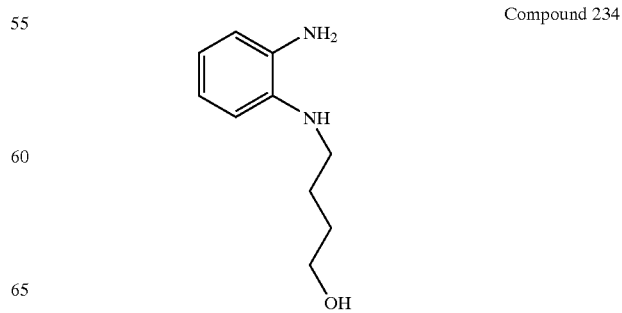

A mixture of nitro compound 233 (5.0 g, 23.8 mmol) and 10% Pd/C (100 mg) in ethanol (50 mL) was hydrogenated at 40 psi for 4 h. The catalyst was removed by filtration and the filtrate was evaporated to give 4.3 g (99% yield) of compound 234 as a dark oil:

$^1$H NMR(DMSO-d$_6$) δ1.47–1.66 (m, 4 H), 2.99 (t, J=6.6 Hz, 2 H), 3.43 (t, J=6.6 Hz, 2 H), 4.31–4.5(br, 4 H, exchange with D$_2$O), 6.36–6.42 (m, 2 H) 6.54–6.82 (m, 2 H); IR (film, cm$^{-1}$) 1055, 739; MS m/e 181 (MH$^+$); Anal. Calcd for C$_{10}$H$_{16}$N$_2$O.0.71 H$_2$O: C, 62.23; H, 9.10; N, 14.51 Found: C, 62.23; H, 8.78; N, 14.41.

Compound 235

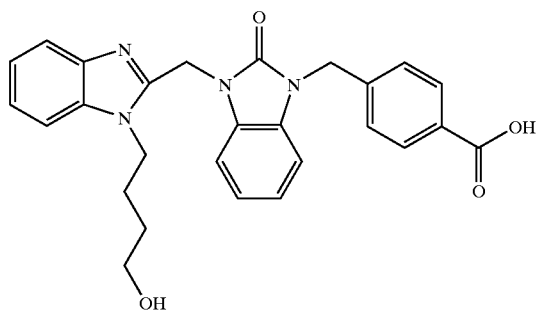

To a solution of diamine 234 (1.0 g, 6.0 mmol) in methylene chloride (50 mL) at −78° C. was added a solution of an acid chloride which was prepared from the acid 125 (2.05 g, 6.02 mmol) with excess SOCl$_2$, followed by addition of triethylamine (0.97 mL, 7.0 mmol). The mixture was stirred at −78° C. for 1 hr then at room temperature for 12 h. The solvent was evaporated and the black residue (2.7 g) was dissolved in acetic acid and heated to reflux for 4 h. The solvent was evaporated. The black residue was purified by chromatography on silica gel and eluted with 3% methanol in methylene chloride to give 2.3 g of a mixture of esters as a yellow oil. The mixture in methanol (20 mL) was treated with 1N sodium hydroxide (10 mL, 10 mmol) and heated to reflux for 1 h, and concentrated under reduced pressure. The precipitate was filtered to give 0.65 g (31% yield) of the sodium salt of compound 235 as a white solid: mp>240° C.;

$^1$H NMR (DMSO-d6) δ1.47–1.40 (m, 2 H), 1.68–1.60 (m, 2 H), 3.37 (t, J=6.3 Hz, 2 H), 4.35 (t, J=7.5 Hz, 2 H), 5.15 (s, 2 H), 5.43 (s, 2 H), 7.03–6.99 (m, 2H), 7.38–7.15 (m, 3 H), 7.35 (d, J=8.1 Hz, 2 H), 7.57 (d, J=7.2 Hz, 1 H), 7.87 (d, J=8.1 Hz, 2 H); IR (KBr cm$^{-1}$) 1701, 750; MS m/e 471 (MH$^+$); HRMS m/e (M$^+$) calcd for C$_{27}$H$_{26}$N$_4$O$_4$: 470.1954, found 470.2039.

Compound 236

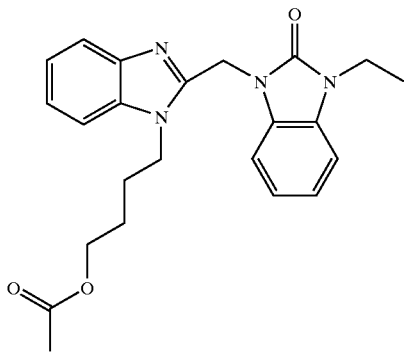

Compound 236 was prepared as described for compound 235 using compound 169.

$^1$H NMR (DMSO-d6) δ1.23 (t, J=7.1 Hz, 3H), 1.45–1.55 (m, 4H), 19.2 (s, 3H), 3.50–3.61 (m, 2H), 3.81–3.90 (m, 4H), 4.25–4.35 (m, 1H), 5.35 (s, 2H), 6.97–7.15 (m, 2H), 7.15–7.25 (m, 4H), 7.53–7.60 (m, 2H); MS m/e 406 (MH$^+$)

Compound 237

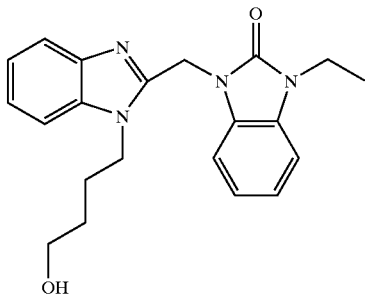

Compound 237 was prepared from compound 236 as described for compound 8.

$^1$H NMR (DMSO-d6) δ1.23 (t, J=7.1 Hz, 3H), 1.30–1.45 (m, 2H), 3.20–3.40 (m, 2H), 1.45–1.60 (m, 2H), 3.20–3.40 (m, 2H), 3.92 (q, J=7.2 Hz, 2H), 4.33 (t, J=7.3 Hz, 2 H), 4.46(t, J=5.0 Hz, 1H), 5.36 (s, 2H), 6.97–7.12 (m, 2H), 7.12–7.25 m, 4H), 7.52–7.59 (m, 2H); MS m/e 364 (MH$^+$).

Compound 238

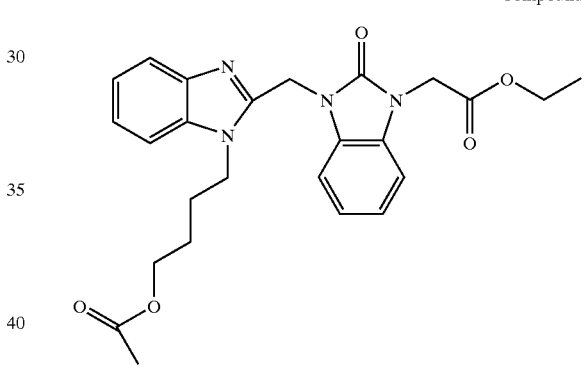

Compound 238 was prepared as described for compound 235 before the hydrolysis step.

$^1$H NMR (DMSO-d6) δ1.22 (t, J=6.2 Hz, 3H), 1.53–1.78 (m, 4H), 1.97 (s, 3H), 3.99 (t, J=6.0 Hz, 2H), 4.17 (q, J=7.2 Hz, 2H), 4.35 (t, J=6.6 Hz, 2H), 4.79 (s, 2H), 5.40 (s, 2H), 7.04–7.07 (m, 2H), 7.08–7.31 (m, 4H), 7.56 (t, J=8.1 Hz, 2H); MS m/e 464 (MH$^+$).

Compound 239

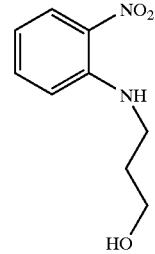

Compound 239 was prepared from 1-aminopropanol and 2-fluoronitrobenzene as previously described for compound 233.

$^1$H NMR (CDCl$_3$) δ1.97–2.02 (m, 2H), 3.46–3.50 (m, 2H), 3.84–3.87 (m, 2H), 6.64 (t, J=8.0 Hz, 1H), 6.89 (d, J=8.6 Hz, 1H), 7.43 (t, J=7.05 , 1H), 8.17 (d, J=7.2 Hz, 1H); MS m/e 166 (MH$^+$).

TABLE 20

[Structure 240: benzimidazole-CH2-benzimidazolone with R2 on one N and propyl-O-W1 chain on the other benzimidazole N]

Compounds were prepared as described for compound 235. The acetates were removed by mild acid hydroylsis.

| # | W₁ | R₂ | ¹H-NMR Data | MS Data |
|---|---|---|---|---|
| 240a | OAc[a] | Et | (DMSO-d6) 1.23 (t, J = 7.3 Hz, 3H), 1.90–2.10 (m, 2H), 1.97 (s, 3H), 3.92 (q, J = 7.2 Hz, 2H), 3.99–4.06 (m, 2H), 4.42 (t, J = 7.3 Hz, 2H), 5.37 (s, 2H), 6.98–7.08 (m, 2H), 7.14–7.25 (m, 4H), 7.53–7.60 (m, 2H) | 392 (MH+) |
| 240b | H[b] | Et | DMSO-d6: 1.24(t,J = 7.0 Hz, 3H), 1.76–1.82 (m, 2H), 3.39–3.42 (m, 2H), 3.92 (q, J = 7.0 Hz, 2H), 4.40 (t, J = 7.1 Hz, 2H), 4.71 (t, J = 4.8 Hz, 1H), 5.39 (s, 2H), 7.01–7.14 (m, 2H), 7.15–7.26 (m, 4H), 7.55 (t, J = 8.6 Hz, 2H) | 350 (MH+) |
| 240c | OAc | CH₂CO₂Et | DMSO-d6: 1.21 (t, J = 7.1 Hz, 3H), 1.89–2.02 (m, 2H), 1.98 (s, 3H), 4.10 (t, J = 6.1 Hz, 2H), 4.16 (q, J = 7.1 Hz, 2H), 4.15 (t, J = 7.4 Hz, 2H), 4.79 (q, J = 7.1 Hz, 2H), 5.40 (s, 2H), 7.01–7.08 (m, 2H), 7.15–7.28 (m, 4H), 7.55 (d, J = 7.7 Hz, 1H), 7.60 (d, J = 7.5 Hz, 1H) | 450 (MH+) |
| 240d | H | CH₂CO₂H | (DMSO-d6) 1.59–1.65 (m, 2H), 3.35 (t, J = 6.2 Hz, 2H), 4.12 (s, 2H), 4.33 (t, 7.2 Hz, 2H), 5.35–5.38 (m, 2H), 6.89–7.01 (m, 3H), 7.11–7.25 (m, 3H), 7.52 (d, J = 7.4 Hz, 1H), 7.58 (d, J = 7.3 Hz, 1H) | 380 (MH+) |
| 240e[c] | H | 4-methylbenzoyloxymethyl (p-tolyl-C(O)-O-CH₃) | (DMSO-d6) 1.80–1.94 (m, 2H), 3.42 (t, J = 7.2 Hz, 2H), 3.82 (s, 3H), 4.51 (t, J = 6.8 Hz, 2H), 5.20 (s, 2H), 5.60 (s, 2H), 7.01–7.07 (m, 2H), 7.12–7.16 (m, 1H), 7.23–7.26 (m, 1H), 7.25–7.40 (m, 2H), 7.48 (d, J = 7.3 Hz, 2H), 7.63 (d, J = 7.3 Hz, 1H), 7.73 (d, J = 7.9 Hz, 1H), 7.93 (d, J = 7.3 Hz, 2H) | 470 (MH+) |
| 240f | H | 4-methylbenzoic acid (p-tolyl-C(O)-OH) | (DMSO-d6) 1.84 (m, 2H), 3.31–3.45 (m, 2H), 4.35–4.45 (m, 2H), 4.78–4.91 (m, 1H), 5.10 (s, 2H), 5.46 (s, 2H), 6.92–7.09 (m, 2H), 7.10–7.38 (m, 6H), 7.56 (d, J = 7.8 Hz, 2H), 7.81 (d, J = 7.5 Hz, 2H) | 456 (MH+) |

TABLE 20-continued

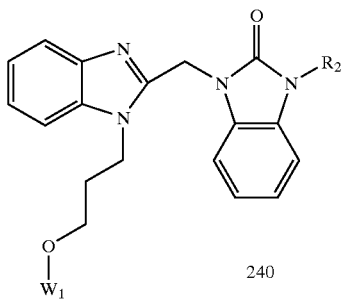

240

Compounds were prepared as described for compound 235. The acetates were removed by mild acid hydroylsis.

| # | $W_1$ | $R_2$ | $^1$H-NMR Data | MS Data |
|---|---|---|---|---|

Compound 241

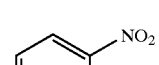

$^a$acetate is isolated by silica gel chromatography prior to hydrolysis;
$^b$hydrolysis carried out as described for compound 4;
$^c$cyclization step carried using TFA instead of AcOH.

Compound 241 was prepared by addition of ethanolamine to 2-fluoronitrobenzene as previously described for compound 233.

$^1$H NMR (CDCl$_3$) δ3.39–3.43 (m, 2H), 3.63–3.69 (m, 2H), 6.68 (t, J=7.2 Hz, 1H), 7.07 (d, J=8.7 Hz, 1H), 7.53 (t, J=6.9 Hz, 1H), 8.06 (d, 8.7 Hz, 1H), 8.23–8.35 (m, 1H); MS m/e 196 (MH$^+$).

Compound 242

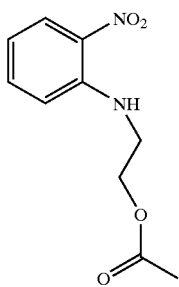

To a solution of 2-(2-nitro-phenylamino)-ethanol (2 g, 10.97 mmol) in CH$_2$Cl$_2$ (70 ml) were added triethylamine (2.77 g, 27.37 mmol) and acetic anhydride (1.68 g, 16.45 mmol). The mixture was refluxed overnight. The next day it was diluted with CH$_2$Cl$_2$ and washed with 1N HCl, and brine. The organic layer was dried over Na$_2$SO$_4$ and concentrated to give 2.40 g (98% yield) of compound 242 as yellow solid.

Compound 243

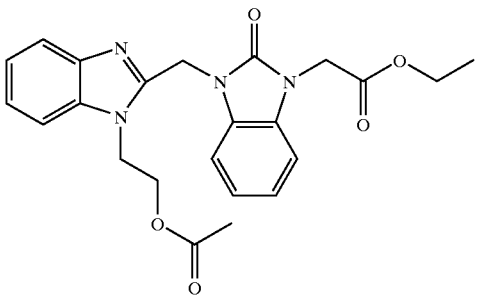

Compound 243 was prepared as described for compound 170 using acetic acid 2-(2-amino-phenylamino)-ethyl ester and (3-ethoxycarbonylmethyl-2-oxo-2,3-dihydro-benzoimidazol-1-yl)-acetic acid as described for compound 170.

$^1$H NMR (DMSO-d6) δ1.22 (t, J=7.1, 3H), 1.90 (s, 3H), 4.16 (q, J=7.1, 2H), 4.35 (t, J=5.0, 2H), 4.68 (t, J=5.1, H), 4.79 (s, 2H), 5.45 (s, 2H), 7.03–7.10 (m, 2H), 7.15–7.27 (m, 4H), 7.55–7.62 (m, 2H); MS m/e 437 (MH$^+$).

Compound 244

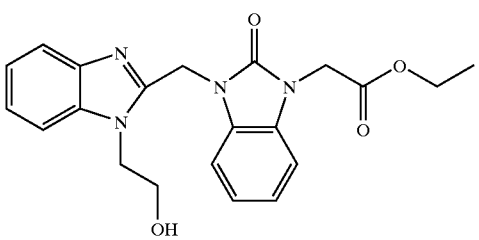

To a solution of compound 243 (570 mg, 1.30 mmol) in EtOH (40 ml) was added 3 drops of $H_2SO_4$ and the solution was refluxed overnight. The solvent was evaporated. The residue was diluted with EtOAc and washed with saturated aqueous sodium bicarbonate solution. The organic layer was dried over $Na_2SO_4$, and evaporated to give 473 mg (92% yield) of compound 244 as a white solid.

$^1$H NMR (DMSO-d6) δ1.22 (t, J=7.1, 3 H), 3.71 (t, J=4.8, 2 H), 4.17 (q, J=7.1, 2 H), 4.46 (t, J=4.9, 2 H), 4.78 (s, 2 H), 5.11 (s, 1 H), 5.45 (s, 2 H), 7.00–7.08 (m, 2 H), 7.12–7.24 (m, 4 H), 7.53–7.57 (m, 2 H); MS m/e 395 (MH$^+$)

Compound 245

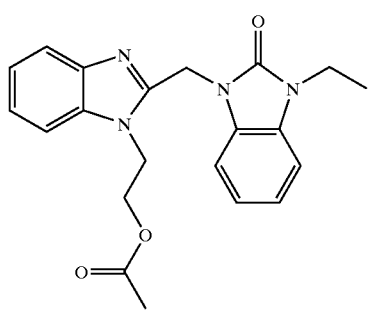

Compound 245 was prepared as described for compound 236.

$^1$H NMR (DMSO-d6) δ1.24 (t, J=7.2 Hz, 3H), 1.87 (s, 3H), 3.93 (t, J=7.6 Hz, 2H), 4.32 (t, J=4.8 Hz, 2 H), 4.69 (t, J=5.1 Hz, 2H), 5.42 (s, 2H), 7.03–7.18 (m, 2H), 7.19–7.31 (m, 2 H), 7.55–7.61 (m, 2H); MS m/e 378 (MH$^+$).

Compound 246

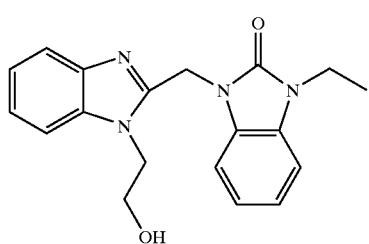

Compound 246 was prepared as described for compound 240b.

$^1$H NMR (DMSO-d6) δ1.25 (t, J=6.6 Hz, 3H), 3.60–3.70 (m, 2H), 3.93 (q, J=7.2 Hz, 2H), 4.47 (t, J=5.1 Hz, 2H), 5.09 (t, J=5.1 Hz, 1H), 5.42 (s, 2H), 7.00–7.11 (m, 2H), 7.11–7.27 (m, 4H), 7.52–7.57 (m, 2H); MS m/e 336 (MH$^+$).

Compound 247

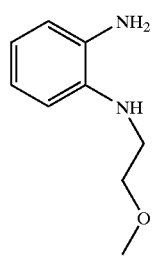

Compound 247 was prepared as previously described for compound 234 using 2-methoxyethylamine.

$^1$H NMR (CDCl$_3$) δ3.18 (dt, 5.7, 6.0 Hz, 2H), 3.21 (s, 3H), 3.53 (t, J=5.7 Hz, 2H), 4.3–24.40 (m, 1H), 4.40–4.49 (s, 2H), 6.42–6.56 (m, 4H); MS m/e 166 (MH$^+$).

Compound 248

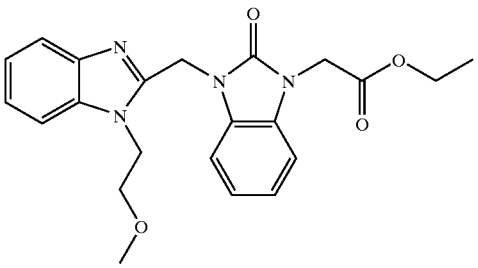

Compound 248 was prepared as described for compound 235 using N-(2-methoxy-ethyl)-benzene-1,2-diamine and (3-ethoxycarbonylmethyl-2-oxo-2,3-dihydro-benzoimidazol-1-yl)-acetic acid.

$^1$H NMR (DMSO-d6) δ1.23 (t, J=6.9 Hz, 3H), 3.19 (s, 3H), 3.28–3.72 (m, 2H), 4.17 (q, J=7.2 Hz, 2H), 4.5–14.62 (m, 2H), 4.79 (s, 2H), 5.42 (s, 2H), 7.01–7.06 (m, 2H), 7.19–7.25 (m, 4H), 7.56 (d, J=8.1 Hz, 2H); MS m/e 408 (MH$^+$).

Compound 249

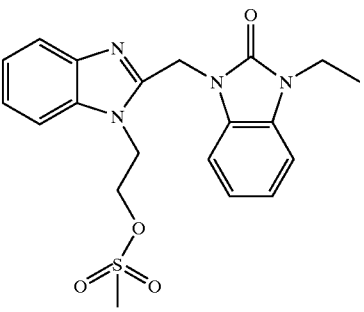

To a 0° C. solution of compound 246 (2.38 g, 0.71 mmol) in $CH_2Cl_2$ (100 ml) was added Et$_3$N (0.12 ml, 0.9 mmol) followed by methanesulfonyl chloride (0.085 ml, 0.75 mmol). The mixture was warmed to room temperature, stirred for 12 h then poured into 1N HCl. The organic layer was separated and dried over MgSO$_4$ and concentrated to give 0.196 mg (67%) of compound 249 as a white solid.

$^1$NMR (DMSO-d6) δ1.25 (t, J=7.2 Hz, 3H), 3.01 (s, 3H), 3.82–3.99 (m, 2H), 4.54 (t, J=5.4 Hz, 2H), 4.76 (m, J=5.4 Hz, 2H), 5.41 (s, 2H), 7.02–7.12 (m, 3H), 7.15–7.34 (m, 3H), 7.51–7.65 (m, 2H); MS (m/e) 414 (MH$^+$)

Compound 250

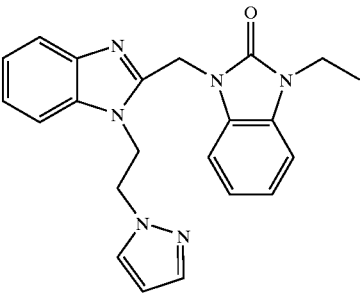

To a slurry of NaH (38 mg, 0.95 mml) in DMF (5 ml) was added pyrazine (63 mg, 0.92 mmol) followed by a solution of mesylate prepared above. The mixture was stirred at 23° C. for 12 h. The solvent was removed and the residue dissolved in EtOAc and washed with water. The organic layers was dried over MgSO₄ concentrated and the residue chromatographed (3% MeOH/CH₂Cl₂ as eluant to give compound 250 as a clear glass (120 mg, 85% yield).

¹H NMR (DMSO-d6) δ1.23 (t, J=6.9 Hz, 3H), 3.92 (q, J=7.2 Hz, 2H), 4.55 (t, J=5.3 Hz, 2H), 4.80 (t, J=4.8 Hz, 2H), 4.94 (s, 2H), 6.17–6.19 (m, 1H), 7.00–7.25 (m, 6H), 7.27–7.58 (m, 3H); MS (m/e) 386 (MH⁺).

Compound 251

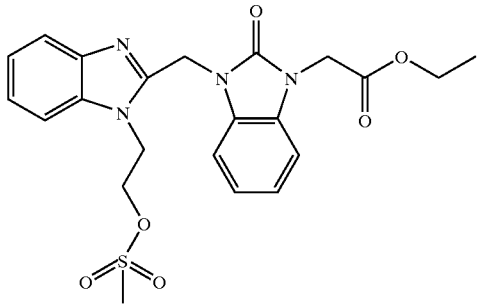

Compound 251 was prepared from compound 244 as described for compound 249 above.

¹H NMR (DMSO-d6) δ1.18–1.23 (m, 3H), 3.06 (s, 3H), 4.11–4.20 (m, 3H), 4.56–4.59 (m, 2H), 4.59–4.84 (m, 3H), 5.52 (s, 2H), 7.05–7.11 (m, 2H), 7.16–7.35 (m, 4H), 7.62 (d, J=7.4 Hz, 1H), 7.72 (d, J=8.0, 1H); MS (m/e) 473 (MH⁺)

Compound 252

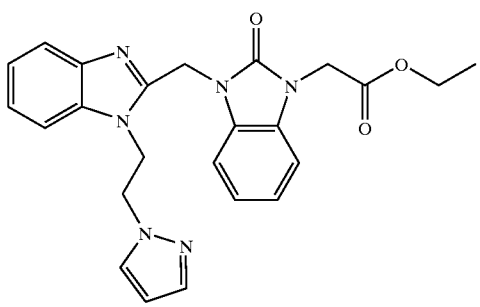

Compound 252 was prepared from compound 251 as described for compound 250 above.

¹H NMR (DMSO-d6) δ1.19 (t, J=7.1, 3H), 4.14 (q, J=7.1, 2H), 4.50–4.54 (m, 2H), 4.75–4.79 (m, 3H), 5.00 (s, 2H), 6.17 (s, 1H), 7.00–7.07 (m, 2H), 7.10–7.20 (m, 3H), 7.34–7.41 (m, 2H), 7.46–7.53 (m, 2H); MS (m/e) 445 (MH⁺).

Compound 253

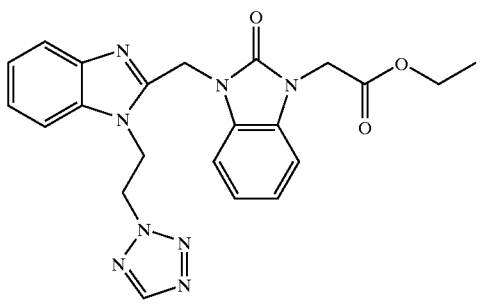

Compound 253 was prepared as described for compound 252 using tetrazole instead of pyrazole.

¹H NMR (DMSO-d6) δ1.21 (t, J=7.1 Hz, 3H), 2.09 (s, 2H), 4.15 (q, J=7.1 Hz, 2H), 4.77 (s, 2H), 5.00–5.03 (m, 1H), 5.19–5.22 (m, 3H), 7.04–7.07 (m, 1H), 7.13–7.16 (m, 1H), 7.18–7.23 (m, 2H), 7.51–7.65 (m, 3H), 8.91 (s, 1H); MS (m/e) 447 (MH⁺).

Compound 254

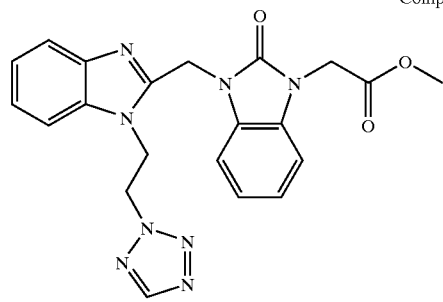

Compound 254 was prepared by transesterification using NaOMe as previously described for compound 131.

¹H NMR (DMSO-d6) δ3.34 (bs, 2H), 4.08 (s, 2H), 4.86 (bs, 2H), 5.26 (s, 2H), 6.93–7.02 (m, 3H), 7.14–7.24 (m, 3H), 7.24–7.31 (m, 1H), 7.61–7.63 (m, 1H), 9.33 (s, 1H); MS (m/e) 431 (MH⁺).

(Scheme III)

Compound 255

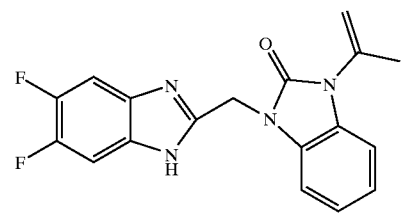

A mixture of 6-amino-3,4-difluoroaniline (1.2 g, 8.33 mmol, from Specs), acid 182 (2.13 g, 8.33 mmol), and EEDQ (2.06 g, 8.33 mmol) were stirred in THF (40 mL) at reflux for 12 h. The mixture was evaporated and the residue was purified by chromatography on silica gel to give 850 mg of compound 255:

¹H NMR (CD₃OD) δ2.26 (s, 3H), 5.28 (s, 1H), 5.37 (s, 2H), 5.49 (s, 1H), 7.03–7.24 (m, 4H), 7.37–7.43 (m, 2H); IR (KBr, cm⁻¹) 1686, 1655, 1491, 1471, 1405, 1346, 1157, 883, 859, 634, 600; MS m/e 339 (MH⁺); Anal. Calcd for C₁₈H₁₄F₂N₄O: C, 63.53; H,4.15; N, 16.46 Found: C, 63.28; H, 4.37; N, 16.21.

Compound 256

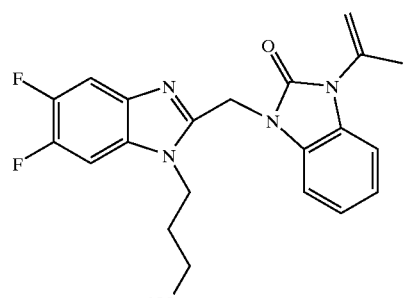

Compound 256 was prepared from 255 and 4-bromobutyronitrile in the same manner as compound 4.

$^1$H NMR (CDCl$_3$) δ1.60 (s, 3H), 1.92–2.02 (m, 2H), 2.25 (s, 3H), 2.47 (t, J=7.3 Hz, 2H), 4.44–4.49 (m, 2H), 5.22 (s, 1H), 5.35 (s, 2H), 5.42 (s, 1H), 7.11–7.13 (m, 3H), 7.17 (dd, J=6.7, 9.5 Hz, 1H), 7.49–7.53 (m, 1H), 7.58 (dd, J=7.2, 10.2 Hz, 1H); IR (KBr, cm$^{-1}$) 1686, 1487,1471, 1401, 1155, 753; MS m/e 408 (MH$^+$); Anal. Calcd for C$_{22}$H$_{19}$F$_2$N$_5$O.0.25 H$_2$O C, 64.14; H,4.77; N, 17.00 Found: C, 64.03; H, 4.97; N, 17.18.

Compound 257

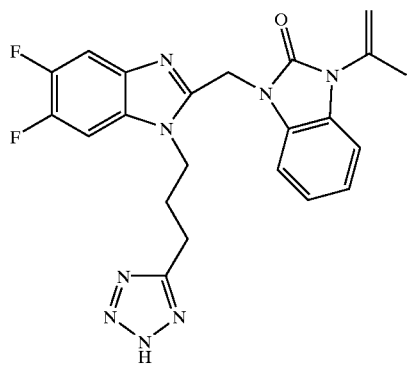

Compound 257 was prepared in the same manner as compound 52.

$^1$H NMR (CD$_3$OD) δ2.13–2.23 (m, 2H), 2.21 (s, 3H), 2.94 (t, J=7.6 Hz, 2H), 4.44 (t, J=7.6 Hz, 2H), 5.37 (s, 1H), 5.43 (s, 2H), 5.45 (s, 1H), 7.06–7.23 (m, 4H), 7.41–7.52 (m, 2H); IR (KBr, cm$^{-1}$) 3411, 1698, 1681, 1654, 1487, 1470, 1407, 1157, 753; MS m/e 451 (MH$^+$).

Compound 258

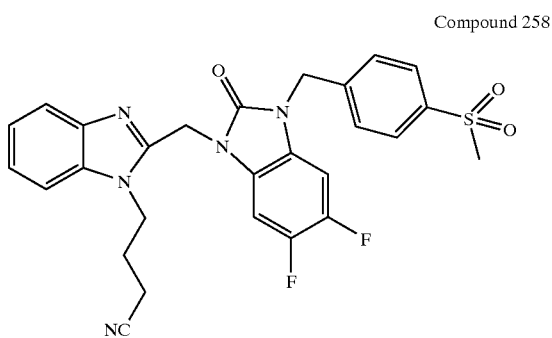

Compound 258 was prepared as described for compound 105.

$^1$H NMR (DMSO-d6) δ2.07–2.13 (m, 2H), 2.63 (t, J=7.4 Hz, 2H), 3.20 (s, 3H), 4.42 (t, J=7.4 Hz, 2H), 5.24 (s, 2H), 5.46 (s, 2H), 7.19 (t, J=7.5 Hz, 1H), 7.27 (t, J=7.5 Hz, 1H), 7.50–7.54 (m, 1H), 7.56 (d, J=7.8 Hz, 1H), 7.61 (d, J=8.3 Hz, 2H), 7.92 (d, J=8.3 Hz, 2H); MS m/e 535 (MH$^+$).

Compound 259

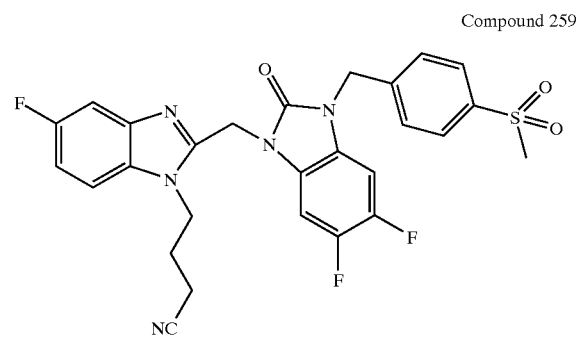

Compound 259 was prepared described for compound 105.

$^1$H NMR (DMSO-d6) δ2.07–2.15 (m, 2H), 2.64 (t, J=7.5 Hz, 2H), 3.20 (s, 3H), 4.42 (t, J=7.5Hz, 2H), 5.23 (s, 2H), 5.45 (s, 2H), 7.15 (td, J=2.5, 9.3Hz, 1H), 7.40 (dd, 2.4, 9.8 Hz, 1H), 7.45–7.53 (m, 2H), 7.60 (d, J=8.3 Hz, 2H), 7.63–7.65 (m, 1H), 7.92 (d, J=8.3 Hz, 2H); MS m/e 553 (MH$^+$).

Compound 260

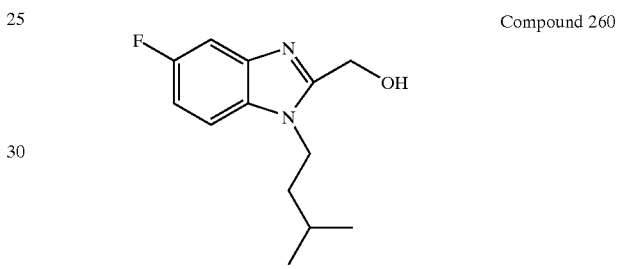

Compound 260 was prepared as described for compound 266.

Compounds 261 and 262

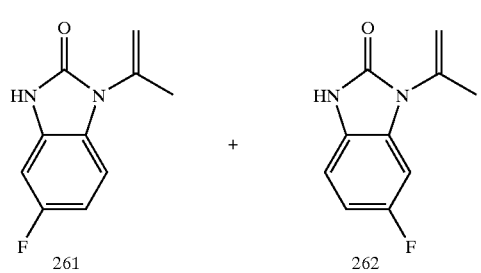

A mixture of 3-fluorobenzenediamine (6.3 g, 50.0 mmol) and ethyl acetoacetate (6.50 g, 50.0 mmol) and DBU (0.76 g, 5.0 mmol) in p-xylene (50 mL) was heated to reflux for 2 h. Water formed during reaction was removed with a Dean-Stark trap. After cooling, the solvent was removed in vacuo. The residue was purified by flash chromatography (gradient, hexanes:EtOAc 4:1 to 1:1) to give 0.76 mg (8%) of 5-fluoro-1-isopropenyl-1,3-dihydro-benzoimidazol-2-one, 261 and 1.10 (11%) of 6-fluoro-1-isopropenyl-1,3-dihydro-benzoimidazol-2-one 262 as white solids.

261: 5-Fluoro-1-isopropenyl-1,3-dihydro-benzoimidazol-2-one $^1$H NMR (CDCl$_3$) δ2.24 (s, 3H), 5.24 (d, J=0.4 Hz, 1H), 5.41–5.43 (m, 1H), 6.77–6.81 (m, 1H), 6.89–6.91 (m, 1H), 6.98–7.00 (m, 1H); MS m/e 193 (MH$^+$);

262: 6-Fluoro-1-isopropenyl-1,3-dihydro-benzoimidazol-2-one $^1$H NMR (CDCl$_3$) δ2.24 (s, 3H), 5.24 (s, 1H), 5.42 (d, J=1.2 Hz, 1H), 6.78–6.85 (m, 2H), 7.03–7.06 (m, 1H); MS m/e 193 (MH$^+$).

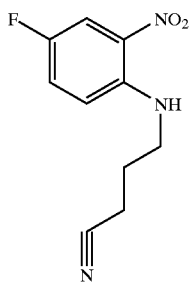

Compound 263

A solution of 2,5-difluoronitrobenzene (15.4 g, 96.8 mmol), 4-aminobutyronitrile (7.4 g, 88 mmol) and diisopropylethylamine (23 ml, 132 mmol) in DMF (250 ml) was stirred at room temperature for 32 hours. After filtration, the solvent was evaporated and the orange solid was recrystallized from MeOH (250 ml) to afford 263 (14 g, 65% yield) as orange crystals.

$^1$H NMR (CDCl$_3$) δ2.06–2.12 (m, 2H), 2.54 (t, J=7.0 Hz, 2H), 3.48–3.53 (m, 2H), 6.85–6.88 (m, 1H), 7.27–7.31 (m, 1H), 7.89–7.92 (m, 1H); MS m/e 224 (MH$^+$).

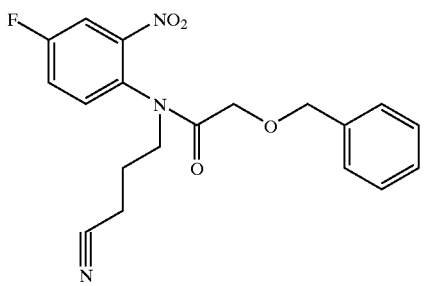

Compound 264

To a suspension of nitrile 263 (10.8 g, 48.4 mmol) and potassium carbonate (20.1 g, 145 mmol) in CH$_3$CN (200 ml) was added benzyloxyacetyl chloride (7.64 ml, 48.4 mmol) dropwise. After stirring at room temperature for 12 hours, the mixture was diluted with EtOAc (500 ml) and filtered. The filtrate was washed with 1 N HCl, brine, dried over MgSO$_4$ and evaporated. The residue was purified by flash chromatography (gradient, EtOAc/hexane, 1:2 to 1:1) to yield 264 (7.5 g, 42% yield) as a viscous pale yellow oil.

$^1$H NMR (CDCl$_3$) δ1.86–1.98 (m, 2H), 2.38–2.51 (m, 2H), 3.34–3.39 (m, 1H), 3.80–3.87 (m, 2H), 4.06–4.14 (m, 1H), 4.40–4.48 (m, 2H), 7.18–7.19 (m, 1H), 7.26–7.40 (m, 5H), 7.72–7.74 (m, 1H); MS m/e 394 (MH$^+$).

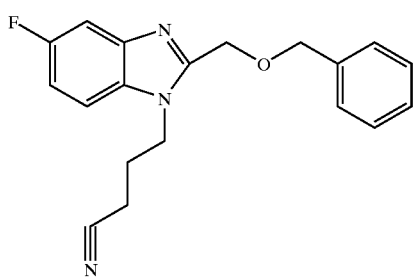

Compound 265

In a flask equipped with a mechanical stirrer, a suspension of compound 264 (6.40 g, 17.25 mmol), iron powder (2.89 g, 51.8 mmol) and ammonium chloride (4.61 g, 86.2 mmol) in a mixture of MeOH and H$_2$O (200 ml, 1:1) was stirred at reflux for 4 hours. The mixture was filtered through a pad of Celite and washed with MeOH. The filtrate was evaporated and the residue was taken up in EtOAc (500 ml), washed with brine, dried over MgSO$_4$, and evaporated. To the residue was added CH$_3$CN (100 ml) and acetic acid (1 ml), and the mixture was stirred at reflux for 4 hours. The solvent was evaporated and the residue was purified by flash chromatography (gradient, EtOAc/hexane, 1:2 to 2:1) to give 265 (4.42 g, 75% yield) as a viscous oil which solidified upon standing.

$^1$H NMR (CDCl$_3$) δ2.15–2.20 (m, 2H), 2.31 (t, J=7.0 Hz, 2H), 4.35 (t, J=7.2 Hz, 2H), 4.62 (s, 2H), 4.83 (s, 2H), 7.07–7.11 (m, 1H), 7.29–7.38 (m, 6H), 7.43–7.46 (dd, J=2.4, 9.2 Hz, 1H); MS m/e 324 (MH$^+$).

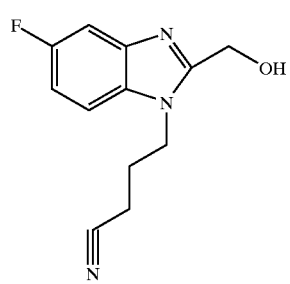

Compound 266

To a solution of 265 (3.23 g, 10 mmol) in CH$_2$Cl$_2$ (100 ml) at 0° C. was added boron tribromide (2.84 ml, 30 mmol). After stirring for 1 hour, the mixture was quenched with saturated NaHCO$_3$ solution with ice bath cooling and extracted with EtOAc. The combined extracts were dried over MgSO$_4$ and evaporated. The residue was purified by flash chromatography (gradient, CH$_2$Cl$_2$/MeOH, 40:1 to 20:1) to give 266 (1.68 g, 72% yield) as an off-white solid.

$^1$H NMR (CDCl$_3$) δ2.25–2.30 (m, 2H), 2.43 (t, J=7.1 Hz, 2H), 4.41 (t, J=7.1 Hz, 2H), 4.85 (s, 2H), 7.04–7.081 (m, 1H), 7.29–7.34 (m, 2H); MS m/e 234 (MH$^+$).

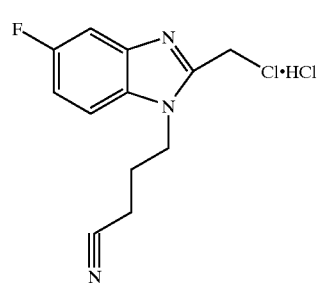

Compound 267

Compound 267 was prepared according to the same procedure described for compound 6.

$^1$H NMR (CD$_3$OD) δ2.30–2.36 (m, 2H), 2.70 (t, J=7.2 Hz, 2H), 4.67 (t, J=7.6 Hz, 2H), 5.30 (s, 2H), 7.49–7.54 (dt, J=2.4, 9.2 Hz, 1H), 7.62–7.64 (dd, J=2.4, 8.0 Hz, 1H), 8.01–8.04 (dd, J=2.0, 9.2 Hz, 1H); MS m/e 252 (MH$^+$).

Compound 268

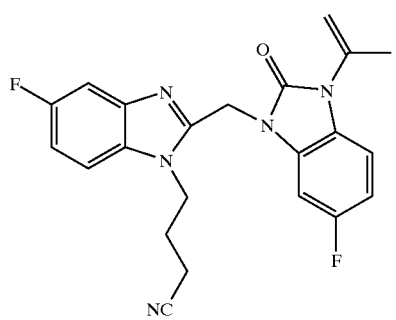

Compound 268 was prepared as described for compound 106 using intermediates 267 and 261.

$^1$H NMR (CDCl$_3$) δ1.90–1.95 (m, 2H), 2.16 (s, 3H), 2.37–2.40 (m, 2H), 4.43 (t, J=7.6Hz, 2H), 5.12 (s, 1H), 5.26 (s, 2H), 5.33 (s, 1H), 6.71–6.75 (m, 1H), 6.92–6.95 (m, 1H), 7.00–7.04 (m, 1H), 7.22–7.40 (m, 2H), 7.40–7.42 (m, 1H).

Compound 269

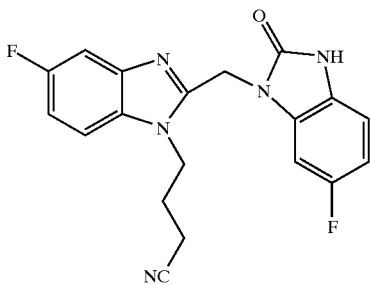

Prepared from compound 268 as described for compound 6.

$^1$H NMR (DMSO-d6) δ2.09–2.16 (m, 2H), 2.67 (t, J=7.5 Hz, 2H), 4.51 (t, J=7.5 Hz, 2H), 5.50 (s, 2H), 6.84–6.88 (m, 1H), 7.01–7.04 (m, 1H), 7.21–7.23 (m, 1H), 7.30–7.34 (m, 1H), 7.49–7.52 (m, 1H), 7.83–7.86 (m, 1H); MS m/e 368 (MH$^+$).

Compound 270

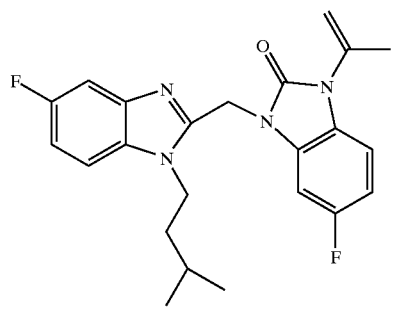

Compound 270 was prepared as described for compound 106 using 262 and 267.

$^1$H NMR (CDCl$_3$) δ0.95 (d, J=6.6 Hz, 6H), 1.42–1.46 (m, 2H), 1.67–1.71 (m, 1H), 2.23 (s, 3H), 4.29–4.32 (m, 2H), 5.19 (s, 1H), 5.34 (s, 2H), 5.39 (s, 1H), 6.75–6.85 (m, 2H), 7.02–7.07 (m, 1H), 7.21–7.24 (m, 1H), 7.36–7.46 (m, 2H); MS m/e 411 (MH$^+$).

Compound 271

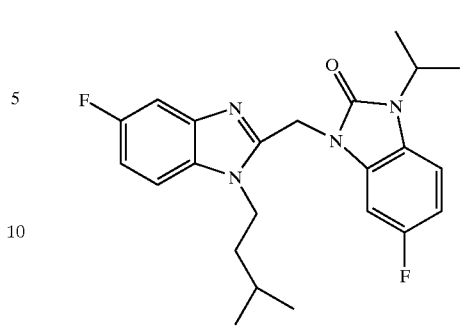

Compound 271 was prepared from compound 270 as described for compound 115.

$^1$H NMR (CDCl$_3$) δ0.95 (d, J=6.6 Hz, 6H), 1.41–1.45 (m, 2H), 1.53 (d, J=7.0 Hz, 6H), 1.66–1.72 (m, 1H), 4.28–4.31 (m, 2H), 4.70–4.74 (m, 1H), 5.32 (s, 2H), 6.72–6.76 (m, 1H), 6.85–6.87 (m, 1H), 7.02–7.06 (m, 1H), 7.20–7.23 (m, 1H), 7.34–7.36 (m, 1H), 7.43–7.46 (m, 1H); MS m/e 411 (MH$^+$).

Compound 272

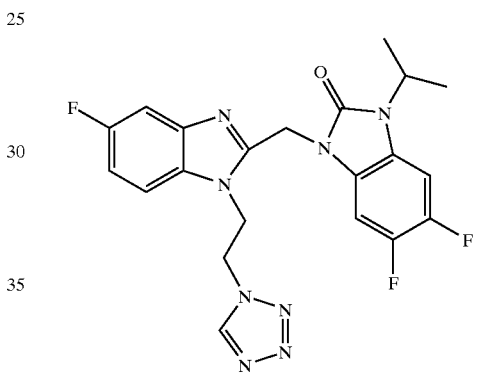

Compound 272 was prepared as described for compound 115.

$^1$H NMR (DMSO-d6) δ1.45 (d, J=5.2 Hz, 6H), 3.21–3.33 (m, 2H), 4.51–4.71 (m, 2H), 4.81–5.10 (m, 4H), 5.41 (s, 2H), 6.91–7.15 (m, 1H), 7.21–7.51 (m, 3H), 7.52–7.62 (m, 1H), 9.30 (s, 1H); MS m/e 456 (MH$^+$).

Compound 273

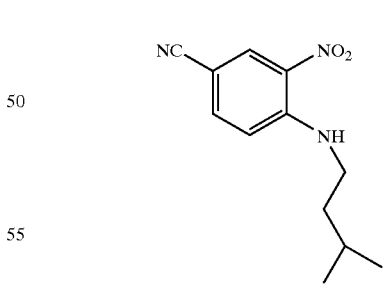

Compound 273 was prepared by addition of 3-methyl-butylamine to 3-chloro-4-nitro benzonitrile as described for compound 233.

$^1$H NMR (CDCl$_3$) δ1.01 (d, J=6.5 Hz, 6H), 1.63–1.70 (m, 2H), 1.74–1.83 (m, 1H), 3.34–3.41 (m, 2H), 6.93 (d, J=9.0 Hz, 1H), 7.62 (dd, J=1.9, 8.9 Hz, 1H), 8.35–8.40 (m, 1H), 8.53 (d, J=2.0 Hz, 1H); MS m/e 321 (M$^+$NH$_4^+$). Calcd for C$_{12}$H$_{15}$N$_3$O$_2$: C 61.69; H 6.48; N 18.01; Found: C 61.75; H 6.39; N 17.94.

Compound 274

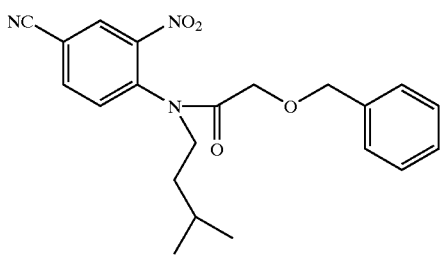

To a mixture of compound 273 (10.8 g, 48.4 mmol) and K$_2$CO$_3$ (20.1 g, 145 mmol) in CH$_3$CN (200 ml) was added benzyloxyacetic chloride and stirred for 12 h. Diluted with EtOAc, filtered. The filtrate was washed with NaHCO$_3$ and brine, dried, evaporated. The residue was recrystallized from MeOH to yield 7.5 g (42%) of compound 274 as a pale yellow solid.

$^1$H NMR (CDCl$_3$) δ0.94 (d, J=6.6 Hz, 6H), 1.58 (q, J=6.8 Hz, 2H), 1.66–1.77 (m, 1 H), 2.26 (s, 3H), 3.18 (t, J=7.3 Hz, 2H), 4.73 (s, 2H), 6.76–6.78 (m, 1H), 7.46–7.53 (m, 3H); MS m/e 315 (MH). Anal. Calcd for C$_{21}$H$_{25}$N$_3$O$_2$ C: 63.35; H 6.98; N 13.85.

Found: C, 63.37; H 6.87; N 13.72.

Compound 274a

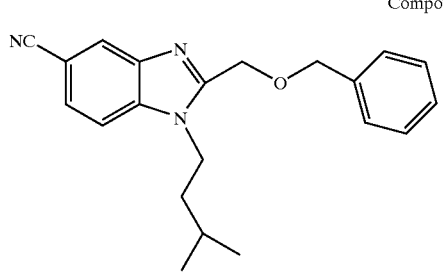

A mixture of compound 274 (6.4 g, 17.2 mmol), iron powder (2.89 g, 51.8 mmol) and ammonium chloride (4.61 g, 86.2 mmol) in MeOH (100 ml) and H$_2$O (100 ml) was heated to reflux for 4 h. The reaction mixture was filtered while hot through celite and the aqueous layer extracted with EtOAc. The organic layer was washed with brine, dried and evaporated. The residue was dissolved in CH$_3$CN (100 ml) and acetic acid (1 ml) and heated to reflux 4 h. The solvent was removed and the residue purified by flash chromatography eluting with hexanes-EtOAc (2:1 to 1:2) to yield 4.17 g (75%) of compound 274a as a viscous oil.

$^1$H NMR (CDCl$_3$) δ1.86–1.98 (m, 2 H), 2.38–2.51 (m, 2 H), 3.34–3.39 (m, 1 H), 3.80–3.87 (m, 2 H), 4.06–4.14 (m, 1 H), 4.38–4.66 (m, 2 H), 7.18–7.19 (m, 1 H), 7.26–7.40 (m, 6 H), 7.72–7.74 (m, 1 H); MS m/e 372 (MH$^+$).

Compound 275

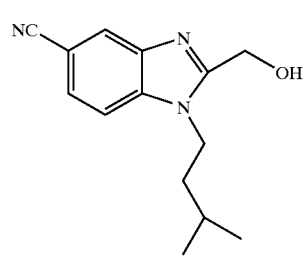

To a solution of compound 274a (3.23 g, 10 mmol) in CH$_2$Cl$_2$ at 0° C. was added BBr$_3$ (7.50 g, 30 mmol) and the reaction mixture stirred for 1 h. The reaction mixture was quenched with aqueous NaHCO$_3$ and extracted with EtOAc. The organic layer was washed with brine, dried and evaporated. The residue was purified by flash chromatography eluting with CH$_2$Cl$_2$-MeOH (40:1 to 20:1) to yield 1.68 g (72%) of compound 275 as an off-white solid.

$^1$H NMR (CDCl$_3$) 2.25–2.31 (m, 2H), 2.43 (t, J=7.1 Hz, 2H), 4.41 (t, J=7.1 Hz, 2H), 4.85 (s, 2H), 6.09 (b, 1H), 7.04–7.08 (m, 1H), 7.29–7.34 (m, 2H) MS m/e 234 (MH$^+$).

Compound 276

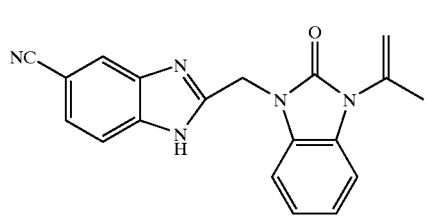

Compound 276 was prepared as described for compound 3.

$^1$H NMR (DMSO-d6) δ2.18 (s, 3H), 5.21 (s, 1H), 5.35 (s, 2H), 5.42 (d, J=1.3 Hz, 1H), 7.02–7.13 (m, 3H), 7.17–7.20 (m, 1H), 7.55–7.71 (m, 2H), 8.12 (bs, 1H), 13.08 (bs, 1H); MS m/e 329 (MH$^+$).

Compound 277

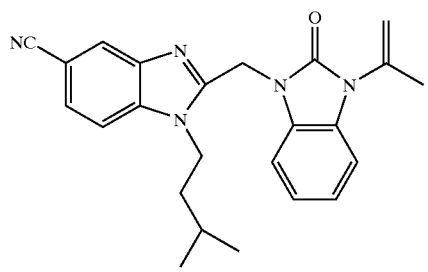

Compound 277 was prepared as described for compound 4.

$^1$H NMR (CDCl$_3$) δ0.96 (d, J=6.6 Hz, 6H), 1.41–1.49 (m, 2H), 1.67–1.76 (m, 1H), 2.23 (s, 3H), 4.43 (t, J=8.1 Hz, 2H), 5.20 (s, 1H), 5.39 (s, J=1.3 Hz, 1H), 5.50 (s, 2H), 7.09–7.10 (m, 3H), 7.43 (d, J=8.5 Hz, 1H), 7.55–7.61 (m, 2H), 8.19 (s, 1H); MS m/e 400 (MH$^+$).

Compound 278

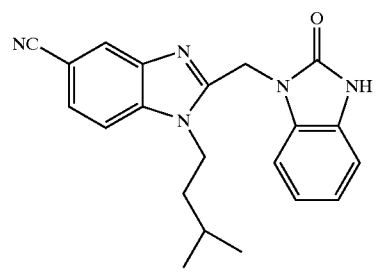

Compound 278 was prepared as described for compound 62.

¹H NMR (CD₃OD) δ1.921 (d, J=6.6 Hz, 6H), 1.635–1.66 (m, 2H), 1.91–2.05 (m, 1H), 4.45 (t, J=8.3 Hz, 2H), 5.70 (s, 2H), 7.28–7.39 (m, 4H), 7.88–7.90 (m, 2H), 8.29 (s, 1H); MS m/e 360 (MH⁺).

Compound 279

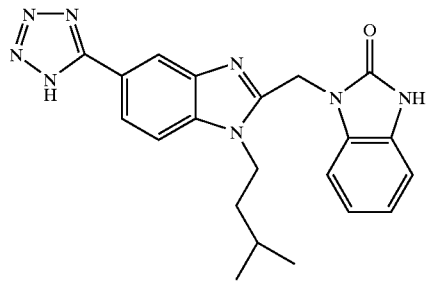

Compound 279 was prepared as described for compound 52.

¹H NMR (DMSO-d₆) 0.92 (d, J=6.6 Hz, 6H), 1.35–1.43 (m, 2H), 1.63–1.72 (m, 1H), 4.35 (t, J=8.0 Hz, 2H), 5.37 (s, 2H), 6.91–7.03 (m, 3H), 7.12–7.15 (m, 1H), 7.75 (d, J=8.5 Hz, 1H), 7.95 (dd, J=1.6, 8.5 Hz, 1H), 8.26 (d, J=1.2 Hz, 1H), 11.11 (s, 1H); MS m/e 403 (MH⁺).

Compound 280

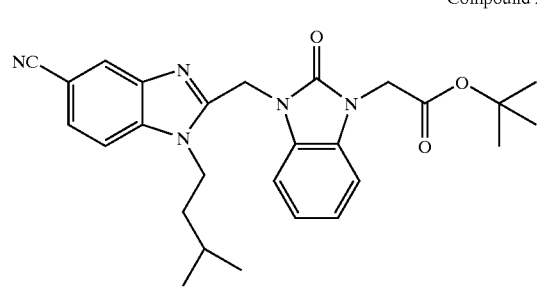

Compound 280 was prepared as described for compound 7 using tert-butylbromoacetate.

¹H NMR (CDCl₃) δ0.97 (d, J=6.6 Hz, 6H), 1.45–1.57 (m, 2H), 1.48 (s, 9H), 1.68–1.77 (m, 1H), 4.34 (t, J=8.3 Hz, 2H), 5.43 (s, 2H), 6.86–6.89 (m, 1H), 7.40–7.12 (m, 2H), 7.36–7.39 (m, 2H), 7.54 (dd, J=1.2, 8.4 Hz, 1H), 8.13 (s, 1H); MS m/e 474 (MH⁺).

Compound 281

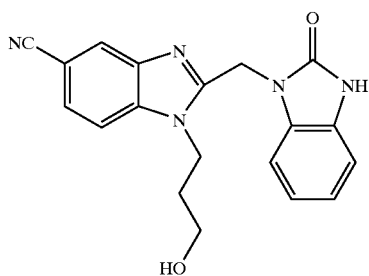

Compound 281 was prepared as described for 6.

¹H NMR (CDCl₃) δ2.07–2.14 (m, 2H), 4.43 (t, J=6.1 Hz, 2H), 4.55 (t, J=7.6 Hz, 2H), 5.41 (s, 2H), 7.05–7.14 (m, 3H), 7.38–7.45 (m, 2H), 7.58 (dd, J=1.4, 8.4 Hz, 1H), 8.00 (s, 1H), 8.15 (d, J=5.4 Hz, 1H); MS m/e 347 (MH⁺).

Compound 282

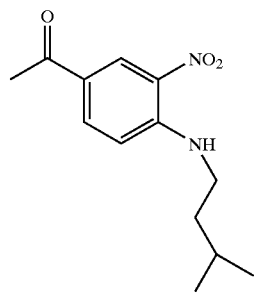

4-chloro-3-nitroacetophenone was treated with 3-methylbutyl amine to give 1-[4-(3-methyl-butylamino)-3-nitro-phenyl]-ethanone, compound 282.

¹H NMR (CDCl₃) δ0.99 (d, J=6.6 Hz, 6H), 1.37–1.67 (m, 2H), 1.72–1.83 (m, 1H), 2.55 (s, 3H), 3.36–3.42 (m, 2H), 6.90 (d, J=9.3 Hz, 1H), 8.07 (dq, J=0.6, 9.3 Hz, 1H), 8.39–8.44 (s, 1H), 8.79 (d, J=2 Hz, 1H); MS m/e 250 (MH⁺).

Compound 283

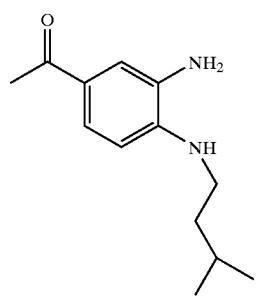

1-[4-(3-methyl-butylamino)-3-nitro-phenyl]-ethanone was reduced with catalytic hydrogenation as previously described for compound 164.

¹H NMR (CDCl₃) δ0.97 (d, J=6.6 Hz, 6H), 1.58 (q, J=7.2 Hz, 2H), 1.73–1.78 (m, 1H), 2.50 (s, 3H), 3.20 (t, J=7.5 Hz, 2H), 6.58 (d, J=8.1 Hz, 1H), 7.39 (d, J=1.8 Hz, 1H), 7.52 (dd, J=1.8, 8.2 Hz, 1H); MS m/e 220 (MH⁺).

Compound 284

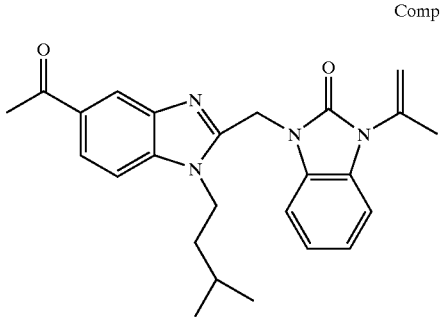

1-[3-Amino-4-(3-methyl-butylamino)-phenyl]-ethanone was coupled with compound 182 to give the final product using EEDQ as shown in Scheme IV.

¹H NMR (CDCl₃) δ0.96 (d, J=6.6 Hz, 6H), 1.42–1.50 (m, 2H), 1.65–1.76 (m, 1H), 2.69 (s, 3H), 4.35–4.40 (m, 2H), 5.22 (s, 1H), 5.40 (d, J=1.4 Hz, 1H), 5.43 (s, 2H), 7.05–7.12 (m, 3H), 7.36 (d, J=8.6 Hz, 1H), 7.45–7.48 (m, 1H), 7.99 (dd, J=1.5, 8.6 Hz, 1H), 8.43 (s, 1H); MS m/e 417 (MH⁺).

Compound 285

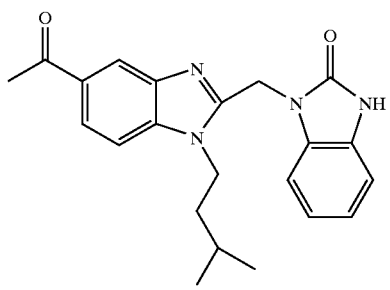

Compound 285 was prepared as previously described for compound 6.

$^1$H NMR (DMSO-d$_6$) δ0.92 (d, J=6.6 Hz, 6H), 1.36–1.44 (m, 2H), 1.62–1.70 (m, 1H), 2.61 (s, 3H), 4.34 (t, J=8.1 Hz, 2H), 5.37 (s, 2H), 6.91–7.03 (m, 3H), 7.10–7.14 (m, 1H), 7.61 (d, J=8.6 Hz, 1H), 7.86 (dd, J=1.6, 8.5 Hz, 1H), 8.29 (d, J=1.0 Hz, 1H), 11.09 (s, 1H); MS m/e 377 (MH+).

Compound 286

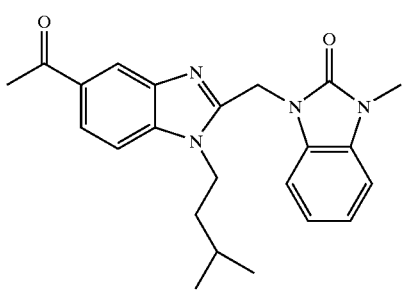

Compound 286 was alkylated with methyl iodide with sodium hydride as base as described for compound 7.

$^1$H NMR (CDCl$_3$) δ0.96 (d, J=6.6 Hz, 6H), 1.34–1.42 (m, 2H), 1.66–1.75 (m, 1H), 2.68 (s, 3H), 3.47 (s, 3H), 4.31–4.37 (m, 2H), 5.43 (s, 2H), 6.92–7.14 (m, 3H), 7.35 (d, J=8.6 Hz, 1H), 7.38–7.41 (m, 1H), 7.98 (dd, J=1.5, 8.6 Hz, 1H), 8.42 (d, J=1.3 Hz, 1H); MS m/e 391 (MH$^+$).

Compound 287

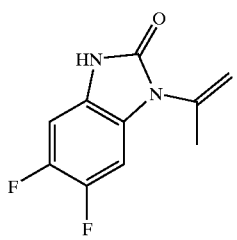

Compound 287 was prepared using the procedure of J. Davoll, J. Chem. Soc. 1960, p 308) using 2-amino-4,5-difluoroaniline.

$^1$H NMR (DMSO-d6) δ2.21 (s, 3H), 5.20 (s, 1H), 5.36 (s, 1H), 7.03–7.12 (m, 2H).

(5,6-Difluoro-3-isopropyl-2-oxo-2,3-dihydro-benzoimidazol-1-yl)-acetic acid

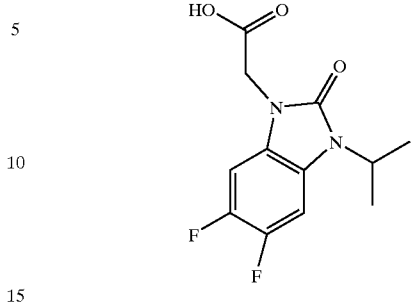

Compound 287 was alkylated with methyl bromo acetate as described for compound 181. The isopropenyl group was reduced as described for compound 155 and the ester hydrolyzed as described for compound 182.

$^1$H NMR CDCl$_3$: 1.52 (d, J=7.0 Hz, 6H), 4.61 (s, 2H), 4.60–4.71 (m, 1H), 6.79–6.85 (m, 1H), 6.99–7.04 (m, 1H).

Compound 288

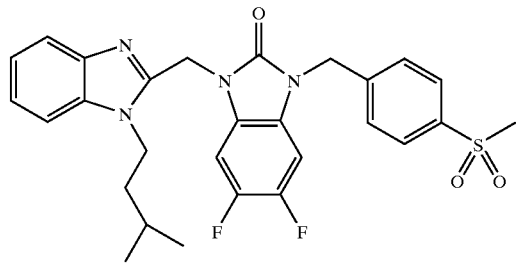

Compound 288 was prepared using the procedure shown in Scheme IV.

$^1$H NMR (DMSO-d$_6$) δ0.93 (d, J=6.6 Hz, 6H), 1.52–1.57 (m, 2H), 1.64–1.69 (m, 1H), 3.19 (s, 3H), 4.32 (t, J=7.8 Hz, 2H), 5.23 (s, 2H), 5.43 (s, 2H), 7.18 (t J=7.6 Hz, 1H), 7.25 (t, J=7.3 Hz, 1H), 7.46–7.50 (m, 1H), 7.53 (d, J=7.9 Hz, 1H), 7.58–7.62 (m, 4H), 7.91 (d, J=8.2 Hz, 2H); MS m/e 538 (MH$^+$).

Compound 289

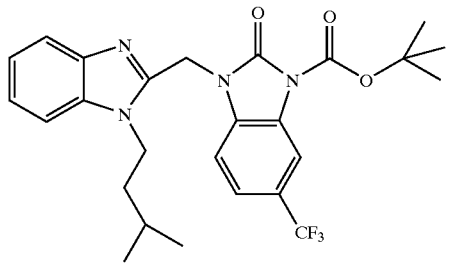

Prepared from compound 107 and 2-oxo-6-trifluoromethyl-2,3-dihydro-benzoimidazole-1-carboxylic acid tert-butyl ester [mixture of 5 and 6 regioisomers 2-oxo-trifluoromethyl-2,3-dihydro-benzoimidazole (Meanwell et al. J. Org. Chem. 1995, 60, 1565–1582) were separated by column chromatography and alkylated with methyl bromoacetate] as previously described for compound 108.

$^1$H NMR (CDCl$_3$) δ0.91 (d, J=6.6 Hz, 6H), 1.36–1.43 (m, 2H), 1.61 (s, 9H), 1.64–1.73 (m, 1H), 4.23–4.29 (m, 2H), 5.32 (s, 2H), 7.19–7.25 (m, 4H), 7.31–7.34 (m, 1H), 7.70–7.76 (m, 2H), 7.82 (d, J=8.5 Hz, 1H); MS m/e 503 (MH$^+$).

Compound 290

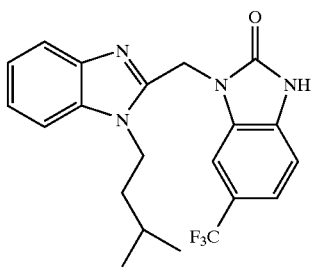

The t-butylcarbamate was removed as previously described for compound 6.

$^1$H NMR (CD$_3$OD) δ0.96 (d, J=6.6 Hz, 6H), 1.39–1.47 (m, 2H), 1.67–1.75 (m, 1H), 4.35 (t, J=8.3 Hz, 2H), 5.44 (s, 2H), 7.19–7.38 (m, 4H), 7.45–7.47 (m, 2H), 7.46 (d, J=7.3 Hz, 1H); MS m/e 403 (MH$^+$).

Compound 291

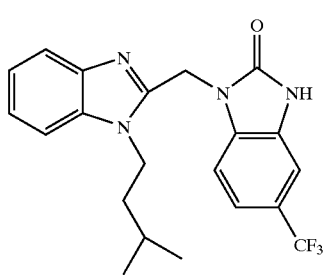

Compound 291 was prepared in a similar manner as for compound 290 above.

$^1$H NMR (DMSO-d$_6$) δ0.92 (d, J=6.6 Hz, 6H), 1.39–1.46 (m, 2H), 1.61–1.70 (m, 1H), 4.29 (t, J=8.1 Hz, 2H), 5.37 (s, 2H), 7.05–7.25 (m, 3H), 7.29–7.36 (m, 2H), 7.49 (d, J=7.7 Hz, 1H), 7.56 (d, J=7.5 Hz, 1H), 11.44 (s, 1H).

(5,6-Difluoro-3-isopropyl-2-oxo-2,3-dihydro-benzoimidazol-1-yl)-acetic acid

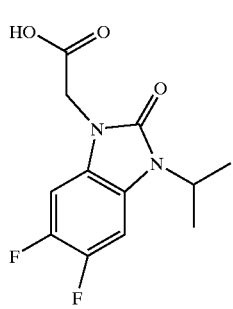

(5,6-Difluoro-3-isopropyl-2-oxo-2,3-dihydro-benzoimidazol-1-yl)-acetic acid was prepared by hydrogenation of (5,6-Difluoro-3-isopropenyl-2-oxo-2,3-dihydro-benzoimidazol-1-yl)-acetic acid as described for compound 115 then alkylated as described for compound 181 and hydrolysis to the acid as described for 182.

$^1$H NMR (CDCl$_3$) δ1.52 (d, J=7.0 Hz, 6H), 4.61 (s, 2H), 4.60–4.71 (m, 1H), 6.79–6.85 (m, 1H), 6.99–7.04 (m, 1H).

Biological Activity

The antiviral activity of these compounds against respiratory syncytial virus was determined in HEp-2 (ATCC CCL 23) cells that were seeded in 96 well microtiter plates at 1.5×10$^4$ cells/100 μL/well in DMEM (Dulbecco's Modified Eagle's Medium) supplemented with penicillin, streptomycin, glutamine, and 10% fetal bovine serum. The cells were incubated overnight at 37° C., the culture medium was removed, and cells were infected (100 μL volume in medium containing 2% fetal bovine serum) with respiratory syncytial virus Long strain at 5000 plaque forming units/mL. The compounds, 100 μL at appropriate dilution, were added to the cells 1 hour post infection. After incubation for 4 days at 37° C., the plates were stained with MTT solution (3-[4,5-dimethlythiazol-2-yl]-2,5-diphenyltetrazolium bromide) and incubated for 4 hours at 37° C. The media was aspirated from the cells and 100 μL/well of acidified isopropanol (per liter: 900 mL isopropanol, 100 mL Tritonx 100, and 4 mL conc. HCl) was added. Plates were incubated for 15 minutes at room temperature with shaking, and an optical density (OD 540) reading at 540 nanometer (nm) was obtained. The optical density reading is proportional to the number of viable cells. The increase in the number of viable cells reflects the protective, antiviral activity of the compound. Assays comparing MTT staining in uninfected cells containing compound with uninfected cells in the absence of compound provide a measure of cellular toxicity. The control compound in this assay is Ribavirin which exhibits 100% cell protection at 2.5 μg/mL (corresponding to 10.2 μM).

The antiviral activity of compounds, designated as EC$_{50}$, is presented as a concentration that produces 50% cell protection in the assay. The compounds disclosed in this application show antiviral activity with EC$_{50}$.s between 50 μM and 0.001 μM. Ribavirin has an EC$_{50}$ of 3 μM in this assay.

What is claimed is:

1. A compound having the Formula I, and pharmaceutically acceptable salts thereof,

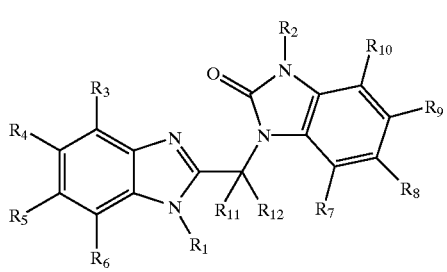

Formula I wherein:
R$_1$ is —(CR$^v$R$^w$)$_n$—X;
R$^v$ and R$^w$ are independently selected from the group consisting of H, C$_{1-6}$ alkyl, and C$_{2-6}$ alkenyl; each of said C$_{1-6}$ alkyl and C$_{2-6}$ alkenyl being optionally substituted with 1–6 of the same or different halogen;
X is H, C$_{1-6}$ alkyl, C$_{2-6}$ alkenyl; each of said C$_{1-6}$ alkyl, C$_{2-6}$ alkenyl being optionally substituted with (1) one to six same or different halogen or hydroxy; (2) a member selected from the group consisting of phenyl, —C(=NOH)NH$_2$, —CH(OH)-Ph, -Ph-S(O)$_2$C$_{1-6}$ alkyl,

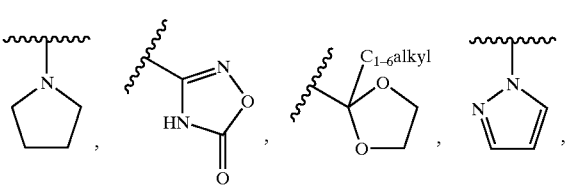

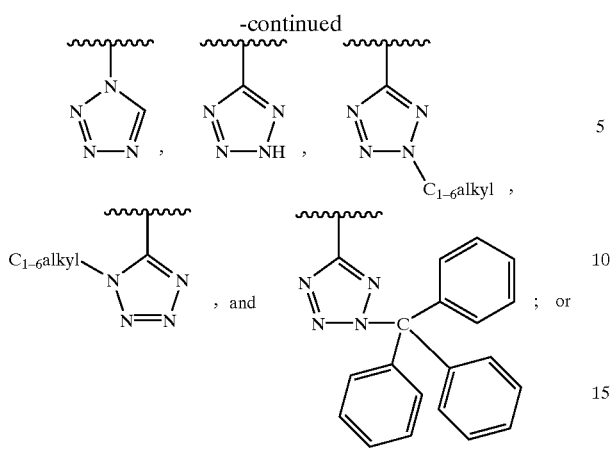

(3) a member from Group A1;
Group A1 is CN, OR', NR'R", N(R')COR", NR'CONR"R'", NR'SO$_2$R" NR'COOR", COR', COOR',OS(O)$_2$R', S(O)$_t$R' or PO(OR')$_2$;
n is 1–6;
t is 0–2;
$R_2$ is
(i) H, $C_{1-6}$ alkyl, $C_{2-6}$ alkenyl, phenyl, or a functionality selected from Group A2 or Group B; each of said $C_{1-6}$ alkyl, $C_{2-6}$ alkenyl, and phenyl being optionally substituted with (1) one to six same or different halogen or hydroxy or (2) one to two same or different members of Group A or Group B;
(ii) —(CR$^x$R$^y$)$_{n'}$—(CO)$_p$—C$_6$H$_3$—(Z$_1$)(Z$_2$), wherein Z$_1$ and Z$_2$ are each independently selected from the group consisting of Group A, Group B, and —(CH$_2$)$_{n'}$—Z'; wherein said Z' is heterocycle or —(NR$_d$R$_e$R$_f$)+(halogen)—; and the Z$_1$ and Z$_2$ groups may each be in the ortho, meta or para position relative to the —(CR$^x$R$^y$)$_{n'}$—(CO)$_p$— group; wherein R$_d$, R$_e$ and R$_f$ are independently $C_{1-6}$ alkyl, $C_{2-6}$ alkenyl, OH or $C_{1-6}$ alkyl COOH;
p is 0 or 1;
n' is 1–6; or
(iii) —(CR$^x$R$^y$)$_{n''}$-heterocycle;
n" is 0–6;
$R_3$, $R_6$, $R_7$ and $R_{10}$ are each independently H;
$R_5$, $R_8$ and $R_9$ are each independently H, halogen or CF$_3$;
$R_4$ is selected from the group consisting of H, halogen, CN, —C(O)C$_{1-6}$ alkyl and

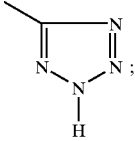

$R_{11}$, $R_{12}$ are each independently H;
$R^x$, $R^y$ are each independently H or $C_{1-6}$ alkyl;
Group A2 is COR', COOR', CONR'R" or CONR'SO$_2$R";
Group A3 is H, halogen, CN, NO$_2$, OR', OCONR'R", NR'R", N(R') COR", N(R')CONR"R'", NR'SO$_2$R", NR'COOR", SO$_m$R', SO$_2$NR'R", SO$_2$NR'COR" or PO(OR')$_2$;
Group A is a member selected from Group A2 and Group A3;
R', R", R'" are each independently selected from the group consisting of H, $C_{1-6}$ alkyl, phenyl and heterocycle; and each of said $C_{1-6}$ alkyl, phenyl and heterocycle being optionally substituted with (1) one to six of same or different halogen or hydroxy; (2) one to two of the same or different members of Group A' or Group B; or (3) heterocycle; or R' and R" taken together form a 5 to 6 membered aromatic or non-aromatic ring which consists of carbon atoms and from one to four of the same or different heteroatoms selected from the group consisting of N, S and O;
Group A' is halogen, CN, NO$_2$, OR$^a$, OCONR$^a$R$^b$, NR$^a$R$^b$, R$^a$NCOR$^b$, NR$^a$CONR$^b$R$^c$, NR$^a$SO$_2$R$^b$, NR$^a$COOR$^b$, COR', CR$^c$NNR$^a$R$^b$, CR$^a$NOR$^b$, COOR$^a$, CONR$^a$R$^b$, CONR$^a$ SO$_2$R$^b$, SO$_m$·R$^a$, SO$_2$NR$^a$R$^b$, SO$_2$NR$^a$COR$^b$ or PO(OR$^a$)$_2$;
R$^a$, R$^b$, R$^c$ are each independently selected from the group consisting of H and $C_{1-6}$ alkyl;
Group B is —(CH$_2$)$_{n'''}$Q, —(CH$_2$)$_{n'''}$SO$_{m''}$—R$_{13}$ or —COQ;
Q is an N-linked amino acid selected from the group consisting of alanine, asparagine, aspartic acid, glutamic acid, glutamine, glycine, pipecolic acid, α-amino-butyric acid, α-amino-propanoic acid, 2-amino-3-phosphonopropionic acid and iminodiacetic acid; wherein Q is linked to the adjacent carbon atom in Group B through a nitrogen atom of said N-linked amino acid; wherein said N-linked amino acid consists of D- or L-enantiomers or mixtures thereof;
$R_{13}$ is selected from a group consisting of H and $C_{1-6}$ alkyl; said $C_{1-6}$ alkyl being optionally substituted with (1) one to five hydroxy groups or (2) two of the same or different functionalities selected from the group consisting of COOR$^x$ and CONR$^x$R$^y$;
m, m' and m" are independently 0–2;
n'" is 1–6;
heterocycle is a 5–6 membered aromatic or non-aromatic ring which consists of carbon atoms and from one to four heteroatoms independently selected from the group consisting of O, N and S; wherein said aromatic or non-aromatic ring is optionally fused to a phenyl ring; wherein the aromatic or non-aromatic ring is optionally substituted with one to five of the same or different substituents selected from the group consisting of $C_{1-6}$ alkyl, Group A and Group B; and halogen is bromine, chlorine, fluorine or iodine.

2. A compound of claim 1 wherein heterocycle is an aromatic ring selected from the group consisting of furyl, thienyl, pyridyl, pyrrolyl, oxazolyl, thiazolyl, imidazolyl, pyrazolyl, isoxazolyl, isothiazolyl, 1,2,3-oxadiazolyl, 1,2,4-oxadiazolyl, 1,2,4-oxadiazolyl-5-one, 1,2,3-triazolyl, 1,3,4-thiadiazolyl, pyridazinyl, pyrimidinyl, pyrazinyl, 1,3,5-triazinyl, indolizinyl, indolyl, isoindolyl, 3H-indolyl, indolinyl, benzo[b]furanyl, benzo[b]thiophenyl, 1H-indazolyl, benzimidazolyl, tetrazolyl, uridinyl and cytosinyl.

3. A compound of claim 1 wherein the heterocycle is a non-aromatic ring selected from the group consisting of pyrrolidinyl, imidazolinyl, 2-imidazolidonyl, 2-pyrrolidonyl, pyrrolin-2-onyl, tetrahydrofuranyl, 1,3-dioxolanyl, piperidinyl, tetrahydropyranyl, oxazolinyl, 1,3-dioxanyl, piperazinyl, morpholinyl and thiomorpholinyl.

4. A compound of claim 1 wherein:

$R_1$ is —(CH$_2$)$_n$—X.

5. A compound of claim 1 wherein in $R_2$, substituents $R^x$ and $R^y$ are each hydrogen.

6. A compound of claim 1 wherein in $R_1$, n is 1–4.

7. A compound of claim 5 wherein in $R_2$, n' is 1; and n" is 3–4.

8. A compound of claim 1 wherein:
R₁ is vinyl, allyl, 3-methyl-2-butene or —(CH₂)n-X, wherein n is 2–4, and X is a functionality selected from the group consisting of
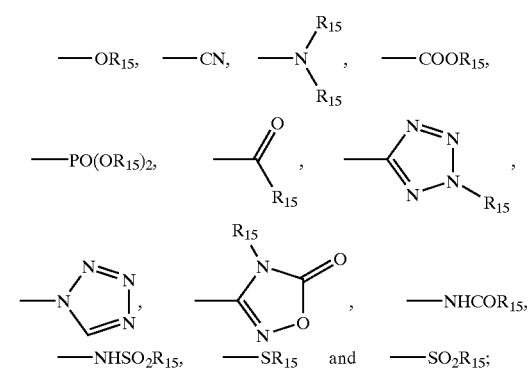
R₂ is
(i)
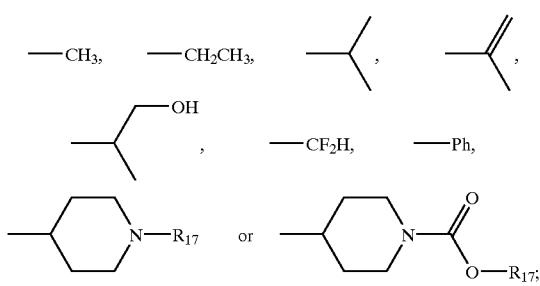
wherein R₁₇ is H or C₁₋₄ alkyl;
(ii) —CH₂—C₆H₄—Z₁;
(iii) —(CH₂)ₖ—Z″; wherein k is 1–6; wherein Z₁ and Z″ are each independently selected from the group consisting of:
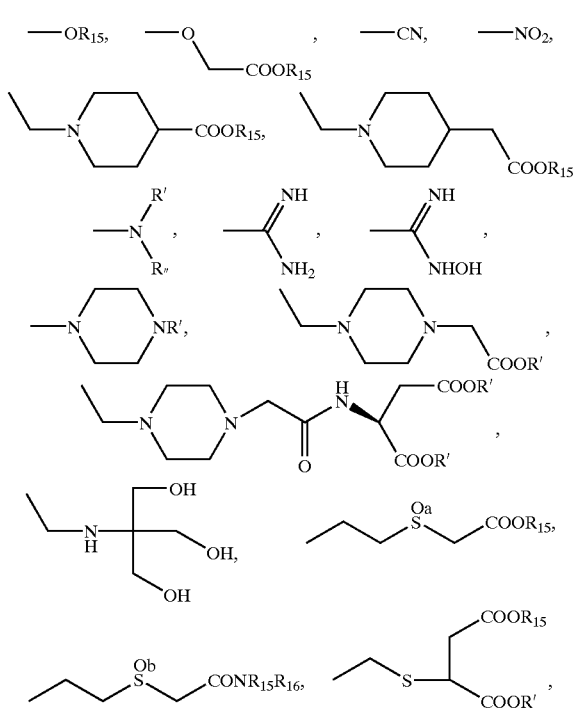
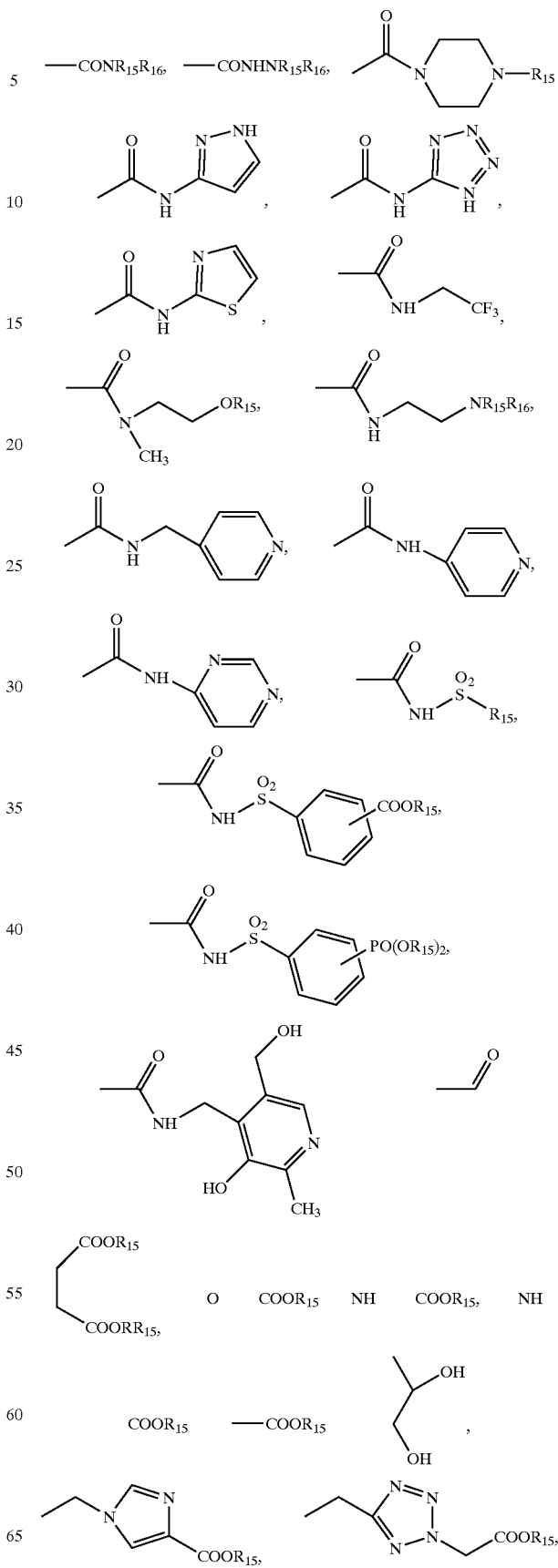

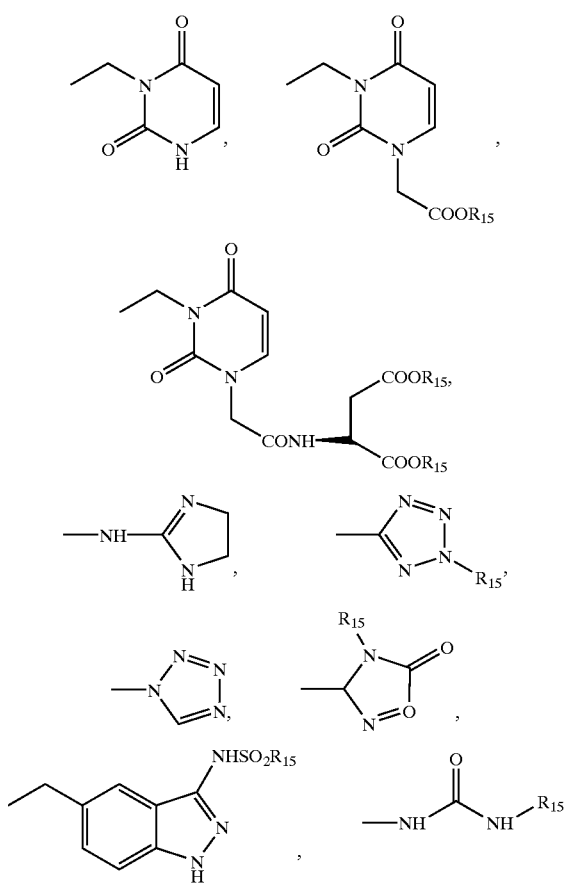

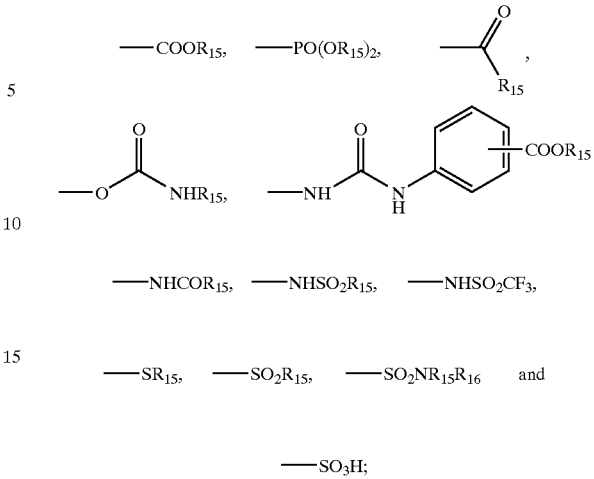

—SO₃H;

a and b are each independently 0–2; and $R_{15}$ and $R_{16}$ are each independently H, $C_{1-4}$ alkyl, wherein said $C_{1-4}$ alkyl is optionally substituted with 1–3 same or different halogens.

9. A method for treating a mammal infected with RSV which comprises administering to said mammal a therapeutically effective amount of one or more of the compounds as claimed in any one of claims 1–8.

10. A pharmaceutical composition which comprises a therapeutically effective amount of one or more of the compounds as claimed in any one of claims 1–8 and a pharmaceutically acceptable carrier.

* * * * *